(12) United States Patent
Eisenreich et al.

(10) Patent No.: US 7,534,742 B2
(45) Date of Patent: May 19, 2009

(54) ISOPRENOID BIOSYNTHESIS

(76) Inventors: Wolfgang Eisenreich, Prälat-Michael-Höck-Str. 27, D-85354 Freising (DE); Monika Fellermeier, Eichenweg 6, D-83556 Griesstaett (DE); Markus Fischer, Rupperstr. 10, D-80337 München (DE); Stefan Hecht, Ganghofer Str. 4a, D-83043 Bad Aibling (DE); Stefan Herz, Albrechtsstr. 32, D-80636 München (DE); Klaus Kis, Beustweg 3, CH-8032 Zürich (CH); Holger Lüttgen, Fritz-von-Briesen-Str. 22, D-69151 Neckargemünd (DE); Felix Rohdich, Moosburger Str. 16, D-85406 Zolling (DE); Silvia Sagner, Hess Str. 41, D-80798 München (DE); Christoph A. Schuhr, Carl-Benz-Str. 39 A, D-68167 Mannheim (DE); Jurathip Wungsintaweekul, Department of Pharmacognosy and Pharmaceutical Botany, Faculty of Pharmaceutical Sciences, Prince of Songkla University, Hat Yai, Songkhla (TH) 90112; Adelbert Bacher, Köigsberger Str. 74, D-85748 Garching (DE); Meinhart H. Zenk, Carl-von-Ossietzky-Str. 14, D-Halle/Saale (DE)

( * ) Notice: Subject to any disclaimer, the term of this patent is extended or adjusted under 35 U.S.C. 154(b) by 247 days.

(21) Appl. No.: 11/526,318

(22) Filed: Sep. 25, 2006

(65) Prior Publication Data
US 2007/0015216 A1    Jan. 18, 2007

Related U.S. Application Data

(62) Division of application No. 10/048,874, filed as application No. PCT/EP00/07548 on Aug. 3, 2000, now Pat. No. 7,122,331.

(30) Foreign Application Priority Data

| Aug. 4, 1999 | (DE) | 199 36 663 |
| Sep. 21, 1999 | (DE) | 199 45 174 |
| Sep. 21, 1999 | (DE) | 199 45 175 |
| Oct. 11, 1999 | (DE) | 199 48 887 |
| Nov. 5, 1999 | (DE) | 199 53 309 |
| Apr. 28, 2000 | (DE) | 100 20 996 |

(51) Int. Cl.
*C40B 30/04* (2006.01)
(52) U.S. Cl. .............................. 506/9; 435/7.4; 506/12; 506/23
(58) Field of Classification Search ...................... None
See application file for complete search history.

(56) References Cited

OTHER PUBLICATIONS

Herz et al., PNAS, 97(6):2486-2490 (2000).*

* cited by examiner

*Primary Examiner*—Christopher Low
*Assistant Examiner*—Jeffrey S. Lundgren
(74) *Attorney, Agent, or Firm*—Myers Bigel Sibley & Sajovec, P.A.

(57) ABSTRACT

The present invention relates to enzymatic activity involved in isoprenoid biosynthesis as well as to inhibitors, notably herbicides, for enzymes in the biosynthesis of isoprenoids. More specifically, the present invention relates to screening methods for detecting such inhibitors, and to enzymatically active proteins for performing said methods as well as purified isolated DNA coding for such proteins. Moreover, the present invention relates to novel inhibitors detectable by said screening methods as well as compositions and processes for inhibiting the synthesis of isoprenoids and for controlling the growth of organisms based on said inhibitors. The invention relates also to the development of inhibitor-resistant plant enzymes and plants, plant tissues, plant seeds and plant cells.

6 Claims, 40 Drawing Sheets

Alignment of amino acid sequences orthologous to YgbP and YgbB of E. coli

```
            *         20         *         40         *         60       (SEQ ID NO:)
A.T.    : MAMLQTNLGFITSPTFLCPKLKVKLNSYLWFSYRSQGNFSYSLYTFKPMNLWFVQKLDF :  59        2

*         80         *        100         *        120
E.C.    :                                       MATTHLDVCAVVPAAGFGRRM---- :  21       67
H.I.    :                                       MARSIIAVLPAAGVGSRM----   :  18       68
B.S.    :                                       MSYDVVIPAAGQGKRMK---     :  17       69
S.S.    :                                         MHLLIPAAGSGKRM----     :  14       70
M.T.    :                                       MVREAGEVVAIVPAAGSGERL---- :  21       71
A.E.    :                                         MYTAIILAAGRGSRI----    :  15       72
C.T.    :                                       MNLSCSLVLLGGGKGERF----   :  18       73
C.P.    :                                       MIKSSLILLSGGQGTRF----    :  17       74
T.M.    :                                         MNVAILLAAGKGERM----    :  15       75
P.H.    :                                         MVTLILLAGGSGTRA----    :  15       76
S.T.    :                                       MAATLLDVCAVVPAAGFGRRM---- :  21       79
Y.P.    :                                         <EVIAVLPAAGIGSRM----   :  15       80
A.A.    :                                       <TSTRKIIAVVPAAGIGSRM---- :  19       81
V.C.    :                                         <NMTAIVPAAGVGSRM----   :  15       82
S.P.    :                                         <NVVAIVPAAGIGSRM----   :  15       83
P.M.    :                                          <IVAVVPAAGIGSRM----   :  14       84
P.A.    :                                             <VIPAAGVGSRM----  :  11       85
N.G.    :                                            <ALIPAAGIGVRF----  :  12       86
B.P.    :                                           <AIVPAAGIGARASLPG   :  16       87
N.M.SA  :                                            <ALIPAAGIGARF----  :  12       88
D.R.    :                                            <ALIPAAGSGTRL----  :  12       90
C.A.    :                                           <CAIIMAAGRGSRMK---  :  14       91
M.A.    :                                            <VAAVVPAAGSGERL----:  14       92
M.B.    :                                           <EVVAIVPAAGSGERL----:  15       93
C.T.    :                                       MKTVVIIAASGVGKRMKL--     :  18       94
P.G.    :                                            <ALIVAGGHGLRM----  :  12       95
E.F.    :                                           <ITALIIAGGVGKRM----  :  14       96
S.Pn.   :                                          <IYAGILAGGTGTRM---G  :  15       97
S.A.    :                                             <ILAGGIGSRM---G   :  11       98
A.T.    : SKRVNRSYKRDALLLSIKCSSSTGFDNSNAVNSNVVVKEKSVSVILLAGGQGKRM---- : 114        2
H.P.    :         MSLIRVNGEAFKLSLESLEEDPFETKETLETLIKQTSVVLLAAGESRRF---- :  49       77
T.P.    :                                              MRRGGACVQK----   :  10       78
R.C.    :                                         MTVAVIIVAAGRGTRA----   :  16      100
C.C.    :                                         MTFSVVIVAAGSGTRA----   :  16      101
C.J.    :                                          MSLIMLAAGNSTRF----    :  14      102
```

FIG. 4

Alignment of amino acid sequences orthologous to YgbP and YgbB of *E. coli*, continued

```
            120         *         140         *         160         *              (SEQ ID NO:)
E.C.   : QTECPKQYLSIGNQTILEHSVHALLAHPRVKRVVIAISPG-D----SRFAQLPLA----  :  71      67
H.I.   : QADKPKQYLTLLGKTLLEHTLDVMLSYPAVSKIILAVSKD-D----PYISTLSL-----  :  67      68
B.S.   : -AGRNKLFIELKGDPVIIHTLRVFDSHRQCDKIIILVINEQ-DRE-HFQQLLSDYP----  :  69      69
S.S.   : GSGHNKLLLNVLGQPLLSWTVQAALASQSIEWIGIMGQPY-DFP-AFEALLTPLH----  :  67      70
M.T.   : AVGVPKAFYQLDGQTLIERAVDGLLDSGVVDTVVV------AVP-ADRTDEARQI----  :  69      71
A.E.   : --GFRKQFATLCGKPLFMHSLEKVLD--IFEEVILVLPE---------DFLDKVK----  :  57      72
C.T.   : NSLQPKQYTHLCGEPLILHALHAYQRLPFVQEVVVVCEEQYRELFLPY----------  :  66      73
C.P.   : GSKIPKQYLPLNGTPLVLHSLKILSSLPQIAEVIVVCDPSYQETFQEY-----------  :  65      74
T.M.   : SENVPKQFLEIEGRMLFEYPLSTFLKSEAIDGVVIVTRREWFE---VV--EKRVF----  :  65      75
P.H.   : SLNLPKQYYRIEEKMVIEYTLENVSRVKGVDNIILVSNPRFMDT--AL--ELKES----  :  66      76
S.T.   : QTECPXQYLSIGNKTILEHSVHALLAHPRVTRVVIAISPG-D----HRFAQLPLA----  :  71      79
Y.P.   : LVDCPKQYLTVGGKTIIEHAIFSLLHHPRIQRVIVVIHPQ-D----TQFSRLSVA----  :  65      80
A.A.   : QADKPKQYLHIHGQPILQHTLNVLLAYPHISRIVLAVAAD-D----PYIDQLKLS----  :  69      81
V.C.   : QADRPKQYLTLLDKTVLEHTVEHLLEHPLIEHVVVAVSAD-D----PYFANLPLA----  :  65      82
S.P.   : GAGKPKQYLPLLGQSILAHTLDKLLSHPLISQVIVALHPE-D----ADFYALPQA----  :  65      83
P.M.   : QMDKPKQYLHIHGKTILEHTLSVLLGYPLIEKII*AVAAN-D----PYISTCPLL----  :  63      84
P.A.   : RADRPKQYLDLAGRTVIERTLDCFLEHPMLRGLVVCLAED-D----PYWPGLDCA----  :  61      85
N.G.   : GADKPKQYVEIGSKTVLEHVLGIFERHEAVDLTVVVVSPE-D----TFADKVQTA----  :  62      86
B.P.   : EAAVPKQYRPLAGQPMLRHAVRALLADPRIVQVRVAVSAG-D----GXVEQALAG----  :  66      87
N.M.SA : GADKPKQYVEIGSKTVLEHTIGIFERHEAVDLTVVVVSPE-D----TFADKVQTA----  :  62      88
T.F.   : -----------DRPVIAHTLAAFLGEPRIAGIQLVLPGE-DIATGAWRELLGPM----  :  42      89
D.R.   : GLG-PKAFVEVAGRSLLARSVAAL--APFVDEVVV-----ALP-AGMDLPA-------  :  54      90
C.A.   : -VNKNKQFILIQGKPILAYTIDKFQRSPLIDEIIIVAAES-EINFCMQEIVYKYK---  :  67      91
M.A.   : AAGIPKAFCEIDGASMLARAVAGLLDSKVVDHVVV------AVP-ADRVDEAKRL----  :  62      92
M.B.   : AVGVPKAFYQLDGQTLIERAVDGLLDSGVVDTVVV------AVP-ADRTDEARQI----  :  63      93
C.T.   : DGGRSKQMLEIGGQPVIWHTMKAFQEASTVESV-YIATLP-DSIPVFKEIAKANG----  :  71      94
P.G.   : GADRPKQFLLLAGLPVLMHTLNRF--APHVDAIVLVLP-T-DHHAYWQELCRKYD----  :  63      95
E.F.   : GQEIPKQFIMVEEKPIIIYTLESFQKHPLIDRILVVCKKGWEQTLDAY--AKEYH----  :  67      96
S.Pn.  : ISNLPKQFLELGDRPILIHTIEKFVLEPSIEKIVVGHGDWVSHAEDLVDKYLPL----  :  70      97
S.A.   : NVPLPKQFLDIDNKPILIHTIEKFILVSEFNEIIIATPAQWISHTQDILKKY-NI----  :  65      98
P.F.   :                           <DEVVIVVAPGEDARAVDVLAGLSNWRS---  :  27      99
A.T.   : -----KLCFWLRDVPKISLSLFLFCGVLEYEESIDV---------------------- : 145       2
H.P.   : SQTIKKQWLRSNHTPLWLSVYESFKEALDFKEIILVVSELDYIYIK------------ :  95      77
T.P.   : KEYLPLTSRQPGVCLLSEILVRALEARSFFLVVVTVPAGEVAYAESQVACDSRLSAFPS :  69      78
R.C.   : GEGLPKQWRDLAGRPVLAQTVAAFAGLGRILVVLHPDDMGLGMDLLGGS--------- :  65     100
C.C.   : GPGQAKQWRVLAGRPVLRWSVEAFLAAGAAEVVVVTTADGEAFLPRMLEGLQGWRS--- :  72     101
C.J.   : NTKVKKQFLRLGNDPLWLYATKNLSSFYPFKKIVVTSSNI--TYMK------------ :  58     102
```

FIG. 4 (CONT'D.)

Alignment of amino acid sequences orthologous to YgbP and YgbB of *E. coli*, continued

```
           180         *         200         *         220         *                  (SEQ ID NO:)
E.C.   : -NHPQITVVDGGDERADSVLAGLKAAGD---AQ-----WVLVHDAARPCLHQDDLARLL : 121         67
H.I.   : --DPKIQLVEGGTTRAESVLNGLNAIAE-----K--NAWVLVHDAARPCLQHADIDKLL : 117         68
B.S.   : -FQTSIELVAGGDERQHSVYKGLKAVKQE--------KIVLVHDGARPFIKHEQIDELI : 119         69
S.S.   : -SPKPVQLIVGGDTRQQSVFNGIQALP--PGAK-----FVLIHDGARCLATPDLFDRCT : 118         70
M.T.   : -LGHRAMIVAGGSNRTDTVNLALTVLSGTAEPE-----FVLVHDAARALTPPALVARVV : 122         71
A.E.   : -VHPKVKKVAGGPERQDSVFNALLQAT-G--------DIVVIHDSARPLATKKMFLE-V : 105         72
C.T.   : ----SVKFASPGTLRQDSVFSGLQ--Q--------VSTPWVCIHDGVRPFVYADEVIEVC : 112         73
C.P.   : ----PVSFAIPGERRQDSVFSGLQ--Q--------VSYPWIIHDGARPFIYPDEIHDLL : 111         74
T.M.   : -HEKVLGIVEGGDTRSQSVRSALEFLEKFS--P----SYVLVHDSARPFLRKKHVSEVL : 117         75
P.H.   : -FPKIKDVAKGGRTRNESIYNGFMKVPQ-K--E----SKILVHDAVRPFTPRWVFERII : 117         76
S.T.   : -NHPQITVVDGGNERADSVLAGLQAVAK---AQ-----WVLXHDAARPCLHQDDLARLL : 121         79
Y.P.   : -QDPRISTVYGGDQRANSVMAGLQLAGQ---AE-----FVLVHDAARPCLHLDDLSRLL : 115         80
A.A.   : -QNPKIQLVEGGETRADSVLNGLNAVQDA---GA--DVWVMVHDAARPCLTHGDLEKLL : 122         81
V.C.   : -HHPRVIRVDGGKERADSVLSALEYVCQHRLSE-----WVLVHDAARPCVTHADITQLI : 118         82
S.P.   : -KHPKLKTVIGGSERANSVLAALDKAPDN---S-----WALVHDAARPCLMASDIDKLL : 115         83
P.M.   : -THPKIQLVEGGSSRADSVLNGLNAVKSAVQNSE--DFWVMVHDAARPCLTHQDLDKLV : 119         84
P.A.   : -ASRHVQRAAGGAERAGSVLNGLLRLLE-LGAQA--DDWVLVHDAARPNLTRGDLDRLL : 116         85
N.G.   : -FPQVRVWKNGGQTRAETVRNGVAKLLETGLAAE--TDNILVHDAARCCLPSEALARLI : 118         86
B.P.   : -LPRTVWRPCGGPNRADTVAXALADSG----AAA--DDWIXVHDAARPGLPAAAXARLI : 118         87
N.M.SA : -FPQVRVWKNGGQTRAETVRNGVAKLLETGLAAE--TDNILVHDAARCCLPSEALTRLI : 118         88
T.F.   : -PAPLLPPVVGGGLRADSVRLGLEALLRQG-AVP--SDWVLVHDAARPCLRREDLLRLL :  97         89
D.R.   : --GVPARAIVGGETRQGSVRRLLEA----TEAG-----TVLIHDAARPFVPPPVILALL : 102         90
C.A.   : -FNKVKNIVSGGSERQQSVMNGLKAVKSA--------NIVLIHDGARPFVDNKIIENGI : 117         91
M.A.   : -LAAQATVVAGGADRTASVRLALAAVPG--NPA-----FVLVHDAARALTPPALIARVV : 113         92
M.B.   : -LGHRAMIVAGGSNRTDTVNLALAVLSGTAEPE-----FVLVHDAARALTPPALVARVV : 116         93
C.T.   : -FTKITAIIEGGKERQDSIGNCMKLIEQEIENSGVMPDAILVHDGARPFIQPEEIDDIA : 129         94
P.G.   : -FSVSHRVVAGGNTRFASVRNGLQVVPDGV--------LVAVHDGVRPLVSAETIDACF : 113         95
E.F.   : -IDKLQWIIPGGNSGQESINNGVNFLKEHSNPE----DTIVIHDGIRPLVDELVLSDVI : 121         96
S.Pn.  : -YKERIIITKGGADRNTSIKNIIEAIDA--YRPLTPEDIVVTHDSVRPFITLRMIQDNI : 126         97
S.A.   : -TDQRVKVVAGGTDRNETIMNIIDHIRN--VNGINNDDVIVTHDAVRPFLTQRIIKENI : 121         98
P.F.   : --------VTGGDARADSVRAGLTALT-CPADQ-----PVMIHDAARPLLSQTVIE>   :  69         99
A.T.   : ----DLRFAIPGKERQDSVYSGLQEID-------VNSELVCIHDSARPLVNTEDVEKVL : 193          2
H.P.   : RHYPEIKLVKGGASRQESVRNALKII----DSA-----YTLTSDVARGLANIEALKNLF : 145         77
T.P.   : RTRPVILYVPGAHTRSASVRAGLDAMAT-HAPD-----VVLVHDGARPFVSVALIHSVL : 122         78
R.C.   : -----VVLVAGGSTRSESVKNALEALEG-SDVT-----RVLIHDGARPLVPASVTAAVL : 113        100
C.C.   : --------TLGGATRALSVQAGLAALSERPGAE-----PVMIHDAARPFVSRNVILALL : 118        101
C.J.   : KFTKNYEFIEGGDTRAESLKKALELI----DSE-----FVMVSDVARVLVSKNLFDRLI : 108        102
```

FIG. 4 (CONT'D.)

Alignment of amino acid sequences orthologous to YgbP and YgbB of *E. coli*, continued

```
              240         *         260         *         280         *           (SEQ ID NO:)
E.C.    : ALSETSRTGGILAAPVRDTMKRAEPGKNAIAHTVDRNGLWHALTPQFFPRELLHDCLTR  : 180      67
H.I.    : AIED--KQGAILAIPVTDTIKRADNQ-QCIVKTEDRSQLWQAMTPQFFPVDILRDALST  : 173      68
B.S.    : AEAEQ-TGAAILAVPVKDTIKRVQ-DLQVSE-TIERSSLWAVQTPQAFRLSLLMKAHAE  : 175      69
S.S.    : EALQH-CQGLIAAMPVKDTIKIVNADGWI-TDTPDRQGLWGAQTPQGFDVALLKACHDK  : 175      70
M.T.    : EALRDGYAAVVPVLPLSDTIKAVDANGVVLG-TPERAGLRAVQTPQGFTTDLLLRSYQR  : 180      71
A.E.    : AQLGD-YHGKVVASPARDTLKEVV-EGKVI-KTLNRSLIWHAQTPQAFRRDILLECHMR  : 161      72
C.T.    : SAARKT-GAAALASPATYTIKSCAP-----VRTLDRDALAVIHTPQCLDTEVLREGLLL  : 165      73
C.P.    : ETAEKI-GATALASPIPYTIKQRNP-----VRTLDRDNLAIIHTPQCIKTEILREGLAL  : 164      74
T.M.    : RRARETGAATLALKNSDA-LVRVENDR--IEYIPRKGVYRI-LTPQAFSYEILKKAHEN  : 172      75
P.H.    : SLLDERDVITTVNPITGN-LIELDNGK--VKRIYDRSKFAIGEAPTGYRYGALKKTLEV  : 173      76
S.T.    : AISENSRVGGILASPVRDTMKRGEPGKNAIAHTVERADLWHALTPQFFPRELLHDCLTR  : 180      79
Y.P.    : SITECSQVGGILAAPVRDTMKRAEPGIQAIAHTVDRQDLWHALTPQLFPLELLKLCLSR  : 174      80
A.A.    : EIQD--DNGAILAIPATDTIKRALPS-QQIAHTEDRSQLWLAQTPQFFRADLLRDALTR  : 178      81
V.C.    : TTALAHPIGAILASPVRDTMKRGDH-LQQIVHTVDRTALWHALTPQMFRAQSLRERLFA  : 176      82
S.P.    : TSRVQFPQGAILAMPVRDTMKRANS-LGEINSTVCRDNLWHALTPQLFPTSLLRLHLQG  : 173      83
P.M.    : QVED--QNGAILAIPATDTIKRALHN-QQIHYTEDRSQLWLAQTPQFFPIATLAQALEQ  : 175      84
P.A.    : EELAEDPVGGLLAVPARDTLKRSDRD-GRVSETIDRSVVWLAYTPQMFRLGALHRALAD  : 174      85
N.G.    : EQAGNAAEGGILAVPVADTLKRAESG--QISATVDRSGLWQAQTPQLFQAGLLHRALAA  : 175      86
B.P.    : DACXXDAVGGLLALPVADTV---XAGRQRVSRTVDRDGLWLAQTPQMFRAGLLRDALAR  : 174      87
N.M.SA  : EQAGNAAEGGILAIPVADTLKCADGG--NISATVERTSLWQAQTPQLFRAGLLHRALAA  : 175      88
T.F.    : ESLANAPQGALLAVPVADTLKRGEDGCS--SGTVDREGLWRALTPQAFPLGALLAALEA  : 154      89
D.R.    : DAIAATGAATV-ALPVADTL--VRAEGQSWGQLVPREGLWAVQTPQGFRRELLLQAHAR  : 158      90
C.A.    : KYAEK-YGGAACGVQPKDTIKIKS-EDGFSEKTIDRSKLFCVQTPQCFKYDSILKAHIN  : 174      91
M.A.    : QALRDGHRAVVPALPLHDTVKAVDANGVVLG-TPERDGLRAVQTPQGFATDLLLRAYAA  : 171      92
M.B.    : EALRDGYAAVVPVLPLSDTIKAVDANGVVLG-TPERAGLRAVQTPQGFTTDLLLRSYQR  : 174      93
C.T.    : RLSAT-HGACVPATKPKDTIKYVGCNPEIFGETLDRSRLLQVQTPQGFAPAKLIEAHRL  : 187      94
P.G.    : DLAEL-KGAVAPCRPMTESLRYYATDGNY---AVDRSRYVTVQTPQTFRSEWLREAYRQ  : 168      95
E.F.    : VKCQEYGNAVTSLPYNEQIFVKETEET--TRQYINRETLRRVSTPQAYKFEKLTWAYEK  : 178      96
S.Pn.   : QLAQNHDAVDTVVEAVDTIVE--STNGQFITDIPNRAHLYQGQTPQTFRCKDFMDLYGS  : 183      97
S.A.    : EVAAKYGAVDTVIEAIDTIVM--SKDKQNIHSIPVRNEMYQGQTPQSFNIKLLQDSYRA  : 178      98
A.T.    : KDGSAV-GAAVLGVPAKATIK-----------------EVIKPELLKKGFEL         : 227       2
H.P.    : LTLQQTS----HYCIAPYL--PCYDTAIYYNEALDREAIKLIQTPQLSHTKALQSA---  : 195      77
T.P.    : EATCRYGAAVPVIEATDTP--KGVAADGSIETHLIRSRVRLAQTPQGFCYASLCAAHHR  : 179      78
R.C.    : AALETTPGAAPALAVTDAL--WRGEAGLVAGTQ-DREGLYRAQTPQGFRFPEILAAHRA  : 169     100
C.C.    : GALSDADLALPALAVADTL--KRQPTGEAAQT-VSREHLWRAQTPQAARRDTLIAAYAA  : 174     101
C.J.    : ENLDKAD------CITPAL--KVADTTLFDNEALQREKIKLIQTPQISKTKLLKKA---  : 156     102
```

*FIG. 4 (CONT'D.)*

Alignment of amino acid sequences orthologous to YgbP and YgbB of E. coli, continued

```
              300       *       320       *       340       *            (SEQ ID NO:)
E.C.    : ALNE--GATITDEASALE--YCGFHPQLVEGRADNIKVTRPEDLALAEFYLTRTIHQENT\\:  235       67
H.I.    : GIQQ--GANITDEASAIE--LAGFRPHLVAGRSDNLKVTRPEDLALAEFYLTRNKL\\    :  225       68
B.S.    : AERK--GFLGTDDASLVEQ-MEGGSVRVVEGSYTNIKLTTPDDLTSAEAIMESESGNKH\\ :  231       69
S.S.    : GKQE--GWEVTDDAALLE--KCGQPVKIVPGEDTNLKITTPVDLAIAEFILGQRSAKSA\\ :  230       70
M.T.    : GSLDLPAAEYTDDASLVE--HIGGQVQVVDGDPLAFKITTKLDLLLAQAIVRG\\       :  231       71
A.E.    : AKAE--GFVGTDDASLL-E-RYGYSVGVVEGSYWNVKITYPEDLEMVKKIMGCEED\\    :  213       72
C.T.    : ARAM--DFSLSDDTEAAE--LLGIEPTLVFSNRVQIKVTYPEDLLFAETLLSKSSTYK\\  :  219       73
C.P.    : AKEK--QLTLVDDIEAAE--IIGKPSQLVFNKHPQIKISYPEDLTIAQALL\\         :  211       74
T.M.    : G-------GEWADDTEPVQKL-GVKIALVEGDPLCFKVTFKEDLELARIIAREWERIP\\  :  222       75
P.H.    : AV-SNGTLNEIPHDIVLAMNA-GFDVYVLPCNCFNLKITFKEDIEIARTLIKMLEERE\\  :  229       76
S.T.    : ALNE--GATITDEASALE--YCGFHPALVEGRADNIKVTRPEDLALAEFYLTRTIHQE>   :  234       79
Y.P.    : ALRE--GVAVTDEASALE--HCGYHPILVTGRSDNIKVTRPEDLALAEFYLTQ>        :  223       80
A.A.    : AKQQ--QFAVTDEASAME--LAGFRPHLVAGRSDNIKVTRPEDLALAEFYLTR>        :  227       81
V.C.    : ALQQ--QVTITDEASAFE--WRGEKPALVAGRADNLKITQPEDLALAEFYLSR>        :  225       82
S.P.    : ALNA--GAVVTDEASAME--WAGISPGLVAGRADNIKVTHPDDLELAELFLMR>        :  222       83
P.M.    : ALAQ--GLQVTDEASAME--FAGFRPHLVAGRSDNIKVTRPEDFALAEFYLSRT>       :  225       84
P.A.    : ALVA--GVAITDEASAME--WAGYAPKLVEGRADNLKITTPEDL>                 :  214       85
N.G.    : ENLG--G--ITDEASAVE--KLGVRPLLIQGDARNLKLTQPQDAYIVRLLL>          :  220       86
B.P.    : ARAA--GLAVTDEASAVE--AAGHAPRLVAGALRNPKVTWPDDFELMEKWL>          :  221       87
N.M.SA  :  ENLD--G--ITDEASAVE--KLGIRPLLVQGDARNLKLTQPQDAYIVRLLL>         :  220       88
T.F.    : ARAG--NRQITDEASAME--AQGWRPRLIPGHGDNIKVTLSDDLMLA>              :  197       89
D.R.    : AEAEQYAA--TDDAGLLA--RLGVQVRLVPGDARLPKVTTPGDLALAE>             :  202       90
C.A.    : AEKE--GILATDDT-MIFE-MSGNKVYLYDGSYENLKITTPDDLYAAETLLKKNS>      :  225       91
M.A.    : GA---GTAGFTDDASLVE--HVGGQVQVVDGDPLAFKITTQLDLLLAETIVRR>        :  219       92
M.B.    : GSLDLPAAEYTDDASLVE--HIGGQVQVVDGDPLAFKITTKLDLLLAQAIV>          :  223       93
C.T.    : AGEE--QWYAXDDAALVERYFPQQAIXIYETGYHNIKITTPEDVFIGEAILAGLKARK>   :  243       94
P.G.    : PYEE--YF--TDDCSVYEHHF-GRPVALIVGNIENIKLTTPLDLSLAKLLLTS>        :  216       95
E.F.    : AFRENIGISESSYTNTMMVDL-GETLHFALGSDKNIKLTTQDDLQLFKFL>           :  227       96
S.Pn.   : LSDEEKEILTDACKIFVI---KGKDVALAKGEYSNLKITTVTDLKIAKSMIEKD>       :  234       97
S.A.    : LSSEQKEILSDACKIIIVE---SGHAVKLVRGELYNIKVTTPYDLKVANAIIQGD>      :  229       98
A.T.    : VKSE--GLEVTDDVSIVE--YLKHPVYVSQGSYTNIKVTTPDDLLLAERILSEDS>      :  278        2
H.P.    : LNQG-----DFKDESSAILQAFPDRVSYIEGSKDLHKLTTSGDLKHFTLFFNPAK----   :  245       77
T.P.    : AATD----GEQYTDDSELYARYGGTVHVCAGERSNVKITYPEDLEQRASEPALTRGISV   :  234       78
R.C.    : HPGG----A---ADDVEVARHAGLSVAIVPGHEDNLKITYAPDFARAEAILRERKGLTM   :  221      100
C.C.    : WTHG----EP--TDDAQVYEHHFGRIALTAGDPLLTKLTYPEDFAMAEHLAGVARV---   :  224      101
C.J.    : LDQN----LEFTDDSTAI-AAMGGKIWFVEGEENARKLTFKEDLKKLDL-PTPSF----   :  205      102
C.T.    :                                                     MTEIPSSF :    8      109
C.P.    :                                                      MDRDNEV :    7      110
P.F.    :      MFLKGYTSNVVLIILTFFILLTKEEKNIKNNISGYCFLNFGLKKNAIIKKREKQN :   55      132
```

FIG. 4 (CONT'D.)

Alignment of amino acid sequences orthologous to YgbP and YgbB of *E. coli*, continued

```
              360        *        380        *        400        *          (SEQ ID NO:)
H.P.   : -------DTFIGMGFDTHAFIKD-----------------KPMVLGGVVLD-CEFGL :  277       77
T.P.   : LPCTEEGALRVGLGTDMHALCAG-----------------RPLILAGIHIPSK-KGA :  273       78
R.C.   : -------DVRLGNGYDVHAFCEG-----------------DHVVLCGVKVPHV-KAL :  253      100
C.C.   : --------TRVGQGFDAHRWGPG-----------------EEVWLCGVAIKHDET-L :  255      101
C.J.   : -------EIFTGNGFDVHEFGEN-----------------RPLLLAGVQIHPT-MGL :  237      102
E.C.   :          MRIGHGFDVHAFGGE-----------------GPIIIGGVRIPY-EKGL :   31      103
H.I.   :          MIRIGHGFDVHAFGED-----------------RPLIIGGVEVPY-HTGF :   32      104
B.S.   :          MFRIGQGFDVHQLVEG-----------------RPLIIGGIEIPY-EKGL :   32      105
S.S.   :        MTALRIGNGYDIHRLVGD-----------------RPLILGGVTIAH-HLGL :   34      106
M.T.   :       MNQLPRVGLGTDVHPIEPG-----------------RPCWLVGLLFPSAD-GC :   35      107
A.E.   :         MELRIGFGFDSHEFVEG-----------------KLLILGGVEIEK-DYGL :   33      108
C.T.   : VLPDPEWIYRVGIGQDSHRFLPDEDP---------------KPCILGGIIFENTP-GF :   50      109
C.P.   : PLPKPKWIYRTGIGQDSHRFLPESST---------------KPCILGGIIFDHCP-GF :   49      110
T.M.   :        MESDPMFIGFGYDRHPLVEG-----------------RRLVLAGVEID-APLGS :   36      111
H.D.   :          MIRIGHGFDVHAFGEK-----------------RPLIIGGVTIPY-HTGF :   32      112
S.T.   :               <IGHGFDVHAFGGE-----------------GPIIIGGVRIPY-EKGL :   29      113
Y.P.   :               <IGHGFDVHKFGENGS---------------GPLIIGGVRIPY-EKGL :   31      114
A.A.   :               <IGHGFDVHAFGTN-----------------NPLIIGGVTIPF-DKGF :   29      115
V.C.   :               <IGHGFDVHRFGGE-----------------GPIIIGGVKIPY-EQGL :   29      116
S.P.   :               <IGHGFDVHKFGEP-----------------RPLILGGVEVPY-ETGL :   29      117
P.M.   :               <IGHGFDVHAFGGE-----------------GPIIIGGVAIPY-EKGL :   29      118
P.A.   :               <IGHGYDVHRFGEG-----------------DFITLGGVRIPH-KHGL :   29      119
N.G.   :               <IGQGYDVHQLTEG-----------------RKLILGGVEIPF-EKGL :   29      120
B.P.   :               <VGQGFDVHALVEG-----------------RPLIIGGVTIAH-THGL :   29      121
N.M.SA :                                               <LILGGVEIPF-EKGL :   14      122
N.M.MC :               <IGQGYDVHQLTEG-----------------RKLILGGVEIPF-EKGL :   29      123
T.F.   :               <IGHGFDVHALVPG-----------------RALILGGVSVPY-ERGL :   29      124
D.R.   :               <IGYGEDAHRLAPG-----------------LPLVLGGVAIPHAELGA :   30      125
C.A.   :               <VGIGYDVHKLVEN-----------------RKLILGGVEIQY-SKGL :   29      126
M.A.   :               <IGLGVDVHPIQPG-----------------RPCRLLGLLFDDAD-GC :   29      127
M.B.   :               <VGLGTDVHPIEPG-----------------RPCWLVGLLFPSAD-GC :   29      128
C.T.   :               <IGIGIDVHQFAEG-----------------RKLIIGGVEVPS-PIGL :   29      129
P.G.   :               <IGFGFDVHRLSEG-----------------YPLWMGGVRLEH-SKGL :   29      130
E.F.   :               <IGQGFDVHQLVPQ-----------------RPLIIGGVTLPY-EKGL :   29      131
P.F.   : LKLFCYNGIRIGQGYDIHKIKVLDEEYNTYANNDFNKNEQSFKTLTLGGVKIN--NVLV :  112      132
```

FIG. 4 (CONT'D.)

Alignment of amino acid sequences orthologous to YgbP and YgbB of E. coli, continued

```
              420         *        440         *        460        *     (SEQ ID NO:)
H.P.    : KAHSDGDALLHAVIDAILGAIKGGDIGEWFPDNDPKYKNASSKELLKIVLDFSQSIGFE  : 336    77
T.P.    : QGHSDADVLAHASIDALLGAAGLGDIGTFFPSCDGRWKDAHSCALLRHTWQLVRAACWR  : 332    78
R.C.    : LGHSDADVGMHALTDAIYGALAEGDIGRHFPPSDPQWKGAASWIFLDHAAKLAKSRGFR  : 312   100
C.C.    : VGHSDADAGLHALTDAILGAIGEGDIGDHFPPTDPKWKGAASDQFLKHAVDLVTAKGGA  : 314   101
C.J.    : KAHSDGDVLAHSLTDAILGAAGLGDIGELYPDTDMKFKNANSMELLKQAYDKVREIGFE  : 296   102
E.C.    : LAHSDGDVALHALTDALLGAAAALGDIGKLFPDTDPAFKGADSRELLREAWRRIQAKGYT : 90    103
H.I.    : IAHSDGDVALHALTDAILGAAAALGDIGKLFPDTDMQYKNADSRGLLREAFRQVQEKGYK : 91    104
B.S.    : LGHSDADVLLHTVADACLGAVGEGDIGKHFPDTDPEFKDADSFKLLQHVWGIVKQKGYV  : 91    105
S.S.    : DGHSDADVLTHALMDALLGALSLGDIGHYFPPSDARWQGADSLKLLAQVHQLILERGWR  : 93    106
M.T.    : AGHSDGDVAVHALCDAVLSAAGLGDIGEVFGVDDPRWQGVSGADMLRHVVVLITQHGYR  : 94    107
A.E.    : KGHSDGDALLHAITDAILGALGERDIGEIFKDTDPRWKNAPSRIFLEKALEVMSEKGFN  : 92    108
C.T.    : EANSDGDVVFHAICNAFSSVTHKGILGGLADELLKTKGITDSVVYLQEAVASLKPTQ-R  : 108   109
C.P.    : QANSDGDIIFHAICNAISSVTNKIILGKVADELLQTRGITDSGIYLEEALKSLKPNQ-K  : 107   110
T.M.    : LGHSDGDVLSHAIIDALLGAGCLGDIGTWFPETK-EYKDANSLDLLKETVKILEERGFS  : 94    111
H.D.    : IAHSDGDVALHALTDAILGAAAALGDIGKLFPDTDQQYKNIDSRKLLIEAYRQVQTKGYQ : 91    112
S.T.    : LAHSDGDVALHALTDALLGAAAALGDIGKLFPDTDPAFKGADSRELLREAWRRIQAKGYT : 88    113
Y.P.    : LAHSDGDVALHAATDALLGAAAALGDIGKLFPDTDPAFKGADSRGLLREAYRRILAKGYK : 90    114
A.A.    : IAHSDGDVALHALTDALLGAAAALGDIGKLFPDTDMQYKGADSRVLLREAYRQVQEKGYC : 88    115
V.C.    : IAHSDGDVALHALSDALLGAIAAGDIGRHFPDTDDKWKGADSRELLKDVYRRVKAQGYV  : 88    116
S.P.    : VAHSDGDVVLHAISDAILGAMALGDIGKHFPDTDAAYKGADSRVLLRHCYALAKAKGFE  : 88    117
P.M.    : LAHSDGDVALHALTDALLGAVALGDIGKLFPDTDMQYKGADSRGLLREAYTQVQAKGYK  : 88    118
P.A.    : VAHSDGDVLLHALSDALLGAAALGDIGKHFPDTDPRFKGADSRALLRHVVAIVAEKGWK  : 88    119
N.G.    : LGHSDADALLHAVTDALLGAAGLGDIGSHFPDTAAEFKDADSRVLLRAAYQSVQAQGWQ  : 88    120
B.P.    : LGHSDADVLLHAVTDALLGGAGLGDIGRHFPDTDPAYRGADSRVLLRAAFDKVRAAGWA  : 88    121
N.M.SA  : LGHSDADALLHAVTDALLGAAGLGDIGSHFPDTAAEFKDADSRVLLRAAYQSVQAQGWQ  : 73    122
N.M.MC  : LGHSDADALLHAVTDALLGAAGLGDIGSHFPDTAAEFKDADSRVLLRAAYQSVQAQGWQ  : 88    123
T.F.    : AGHSDADVLLHSICDALLGAAALGDIGRHFPDTDARFEGADSRLLLRHCRQLVQGKGFS  : 88    124
D.R.    : VAHSDGDAVLHAVADALLSGLALGDIGQYFPDTAAEWKGMDSRRILAKALELVEERGYR  : 89    125
C.A.    : LGHSDADVLVHAIIDSILGAAGLGDIGKLFPDSDNKYKGISSLKLLKEVNALIKDKGYK  : 88    126
M.A.    : AGHSDGDVGAHALCDAVLSAAGLGDVGAVFGVDDPRWAGVSGADMLRHVADLTARHGFR  : 88    127
M.B.    : AGHSDGDVAVHALCDAVLSAAGLGDIGEVFGVDDPRWQGVSGADMLRHVVVLITQHGYR  : 88    128
C.T.    : LGHSDADVLLHAISDALLGAAALGDIGKHFPDTSPDYKDADSMELLRHVCKLLEQEGYK  : 88    129
P.G.    : EGHSDADVLIHAICDALLGAAALRDIGYHFPPSDPQYKGIDSKILLARVMELVRSQGYE  : 88    130
E.F.    : LGHSDADVLTHAIIDAILGAAGLGDIGQLFPETDPQFKNANSVNLLKKVNEKVGRSGFT  : 88    131
P.F.    : LSHSDGDIIYHSIVDSILGALGSLDIGTLFPDKDEKNKNKNSAIFLRYARLLIYKKNYD  : 171   132
```

FIG. 4 (CONT'D.)

Alignment of amino acid sequences orthologous to YgbP and YgbB of E. coli, continued

```
              480         *         500         *         520         *          (SEQ ID NO:)
H.P.   : LFEMGATIFSEIPKITPYKPAILENLSQLLGLEKSQISLKATTMEKM----GFIGKQEG  : 391        77
T.P.   : LVNLDAVVCLEQPALHPFREAMRASLAQALDTHVTRVFVKAKTAERL----GPVGSGAA  : 387        78
R.C.   : IGNADVTLICERPKVGPHAVAMAAELARIMEIEPSRVSVKATTSERL----GFTGREEG  : 367       100
C.C.   : LVNVDVTLICERPKIKPHRQAMRERLAEILSIPVDRVSVKATTTEKM----GFTGRGEG  : 369       101
C.J.   : LINIDICVMAQSPKLKDFKQAMQSNIAHTLDLDEFRINVKATTTEKL----GFIGRKEG  : 351       102
E.C.   : LGNVDVTIIAQAPKMLPHIPQMRVFIAEDLGCHMDDVNVKATTTEKL----GFTGRGEG  : 145       103
H.I.   : IGNVDITIIAQAPKMRPHIDAMRAKIAEDLQCDIEQVNVKATTTEKL----GFTGRQEG  : 146       104
B.S.   : LGNIDCTIIAQKPKMLPYIEDMRKRIAEGLEADVSQVNVKATTTEKL----GFTGRAEG  : 146       105
S.S.   : INNLDNVIVAEQPKLKPHIQAMKENLAKVLTIDPDLIGIKATTNERL----GPTGREEG  : 148       106
M.T.   : VGNAVVQVIGNRPKIGWRRLEAQAVLSRLLN---APVSVSATTTDGL----GLTGRGEG  : 146       107
A.E.   : ISNIDCVIVADRPKIAPHKERIKESLSKLLGIPKERISLKGKRREGFCEGNGLVCMCTV  : 151       108
C.T.   : VSHLAITIEGKRPKLLPQLPSMRKRIAEVLHIPLDSINITATSGEGLTA----MGQGYG  : 163       109
C.P.   : ISHVAITIEGSRPKFLCKLSALRQNIAQVMNLTPTDIGITATSGEGLSD----FGCGDG  : 162       110
T.M.   : VVNVDATVVASIVKLSPYREKIVENLKSAL--ETSRVNVKFKSGNTL--GFEGEERG    : 147       111
H.D.   : ISNIDITIIAQAPKMRPHIDNMRQLIANDLNCDIDQINIKATTTEKL----GPTGRGEG  : 146       112
S.T.   : XGNVDVTIIAQAPKMLPHIPQMRVFIAEDLGCHMDDVNVKATTTEKL----GFTGRGEG  : 143       113
Y.P.   : LGNLDITIIAQAPKMAPHIPQMRVNLAEDLQCHMDDINVKATTTEQL----GFTGRGEG  : 145       114
A.A.   : VGNVDVTIIAQAPKMRPHIDAMRALIAQDLACDIEQVNVKATTTEKL----GFTGRGEG  : 143       115
V.C.   : LGNADVTIIAQAPKMAPYIQAMCAAIAEDLETDLGNINVKATTTEKL----GFTGRKEG  : 143       116
S.P.   : LGNLDVTIIAQAPKMAPHIEDMRQVLAADLNADVADINVKATTTEKL----GFTGRKEA  : 143       117
P.M.   : VGNVDVTIIAQAPKMRPHIDAMRAAIAEDLACDIEQVNVKATTSERL----GFTGRGEG  : 143       118
P.A.   : VGNVDATIVAQAPKMAPHIETMRGLIAEDLGVAVDQVNVKATTTERL----GFTGREEG  : 143       119
N.G.   : VVNVDTTVIAQKPKLAPHIPQMRANIAADLGIDISCVNIKGKTNEKL----GYLGRMEG  : 143       120
B.P.   : PVNVDATIHAQAPKIGPHAAAMVANIAADLALDAGAVNIKAKTNEGL----GYLGRKEG  : 143       121
N.M.SA : AVNVDTTVIAQKPTLAPHIPQMRANIAADLGIDISCVNIKGKTNEKL----GYLGRMEG  : 128       122
N.M.MC : AVNVDTTVIAQKPKLAPHIPQMRANIAADLGIDISCVNIKGKTNEKL----GYLGRMEG  : 143       123
T.F.   : VGNVDATIVCQRPKLADHIPQMRAHIAADLAVELDAVNIKATTTEQL----GYTGRGEG  : 143       124
D.R.   : PVNVALVVTLDRPKLGPLRADIAASVAELLGLPAGEVGVSFKTSE>               : 134       125
C.A.   : IGNIDSTIIAQKPKISPYIEDIKKSLCNVLDIDLGSINIKATTEEGL----GFTGRGEG  : 143       126
M.A.   : VGNAAVQVIGNRPKVGPRRAEAQRVLSELLG---APVSAATTTDGL----GLTGRGEG   : 140       127
M.B.   : VGNAVVQVIGNRPKIGWRRLEAQAVLSRLLN---APVSVSATTTDGL----GLTGRGEG  : 140       128
C.T.   : PVNVDTMLLLEKPKIAPYIDQMRRNIARCLGLEINAVSVKATTNEKL----GYVGRQEG> : 143       129
P.G.   : LGNIDATIAAEQPKLNPHIPDMQRVLAEVIQVEVSDISLKATTTEKL----GFTGREEG  : 143       130
E.F.   : IGNIDCTILAEEPKMSPYLAEMKKNLAASCHLAVTQVNIKATTMETM----GFVGKKEG  : 143       131
P.F.   : IGNVDINVIAQVPKISNIRKNIIKNISTVLNIDESQISVKGKTHEKL----GVIGEKKA  : 226       132
```

FIG. 4 (CONT'D.)

Alignment of amino acid sequences orthologous to YgbP and YgbB of E. coli, continued

```
                540                    (SEQ ID NO:)
H.P.    : LLVQAHVSMRYKQKL\\    : 406      77
T.P.    : VTAQVVVLLKKI\\       : 399      78
R.C.    : IASIATVTLIGA\\       : 379     100
C.C.    : LAASAVVAV>           : 378     101
C.J.    : MAVLSSVNLKY>         : 362     102
E.C.    : IACEAVALLIKATK\\     : 159     103
H.I.    : IACEAVALLIRQ\\       : 158     104
B.S.    : IAAQATVLIQKG\\       : 158     105
S.S.    : IAAYSVALLIKEG\\      : 161     106
M.T.    : LAAIATALVVSLR\\      : 159     107
A.E.    : LLVKM\\              : 156     108
C.T.    : VQCFCVLTIMEYCRY\\    : 178     109
C.P.    : VQCFCVLTVMEYCD\\     : 176     110
T.M.    : ISAYAVCLVEEKGCTKST\\ : 165     111
H.D.    : IACEAVALLSKKTV\\     : 160     112
S.T.    : IACEA>               : 148     113
Y.P.    : IACEAVV>             : 152     114
A.A.    : IACEA>               : 148     115
V.C.    : IACEAVVLLR>          : 153     116
S.P.    : L>                   : 144     117
P.M.    : IACEA>               : 148     118
P.A.    : IAVHA>               : 148     119
N.G.    : IEAQAAV>             : 150     120
B.P.    : I>                   : 144     121
N.M.MC  : IEAQAAVLLVR>         : 139     122
N.M.SA  : IESQAAV>             : 150     123
T.F.    : IAAHAVVLIQH>         : 154     124
C.A.    : ISSQS>               : 148     126
M.A.    : L>                   : 141     127
M.B.    : L>                   : 141     128
P.G.    : ISAYA>               : 148     130
E.F.    : I>                   : 144     131
P.F.    : IECFANILLIPKNS>      : 240     132
```

FIG. 4 (CONT'D.)

Alignment of amino acid sequences orthologous to YchB of *E. coli*

```
              *        20        *        40        *        60
E.C.   : ------------------------------------------------------------ :  -
H.I.   : ------------------------------------------------------------ :  -
B.S.   : ------------------------------------------------------------ :  -
S.S.   : ------------------------------------------------------------ :  -
M.T.   : ------------------------------------------------------------ :  -
A.E.   : ------------------------------------------------------------ :  -
C.T.   : ------------------------------------------------------------ :  -
C.P.   : ------------------------------------------------------------ :  -
T.M.   : ------------------------------------------------------------ :  -
H.P.   : ------------------------------------------------------------ :  -
T.P.   : ------------------------------------------------------------ :  -
S.TL.  : ------------------------------------------------------------ :  -
Z.M.   : ------------------------------------------------------------ :  -
S.T.   : ------------------------------------------------------------ :  -
S.P.   : ------------------------------------------------------------ :  -
Y.S.   : ------------------------------------------------------------ :  -
A.A.   : ------------------------------------------------------------ :  -
V.C.   : ------------------------------------------------------------ :  -
S.PU.  : ------------------------------------------------------------ :  -
P.M.   : ------------------------------------------------------------ :  -
P.A.   : ------------------------------------------------------------ :  -
N.G.   : ------------------------------------------------------------ :  -
B.P.   : ------------------------------------------------------------ :  -
N.M.   : ------------------------------------------------------------ :  -
K.M.   : ------------------------------------------------------------ :  -
D.R.   : ------------------------------------------------------------ :  -
B.B.   : ------------------------------------------------------------ :  -
C.D.   : ------------------------------------------------------------ :  -
C.A.   : ------------------------------------------------------------ :  -
M.A.   : ------------------------------------------------------------ :  -
M.B.   : ------------------------------------------------------------ :  -
M.L.   : ------------------------------------------------------------ :  -
C.TP.  : ------------------------------------------------------------ :  -
P.G.   : ------------------------------------------------------------ :  -
E.F.   : ------------------------------------------------------------ :  -
S.M.   : ------------------------------------------------------------ :  -
S.PG.  : ------------------------------------------------------------ :  -
S.AN.  : ------------------------------------------------------------ :  -
S.A.   : ------------------------------------------------------------ :  -
A.T.   : ------MATASPPFISTLS----FTHSSFKTSSSSSFSPKLLRPLLSFS-VKAS-----R  : 44
S.L.   : LWLPVIFFVVSNPKLILLKRVVFFQSWSNRPHGSSYFNKNIQFRRNSFVIVKASGSRTSK   : 60
S.ML.  : ------------------------------------------------------------ :  -
C.C.   : ------------------------------------------------------------ :  -
C.J.   : ------------------------------------------------------------ :  -
```

FIG. 5

Alignment of amino acid sequences orthologous to YchB of E. coli, continued

```
                *         80         *        100         *        120
E.C.   : -------------------------MRTQWPSPAKLNLFLYITGQRADGYHTLQTLFQF :  34
H.I.   : --------MKSHQFSTALCQNTTESNGQPLRFPSPAKLNLFLYINGKFPNGYHELQTLFQF :  53
B.S.   : -------------------------MRILEKAPAKINLSLDVTRKRPDGYHEVEMIMTT :  34
S.S.   : -------------------------MHSYTLHAPAKINLFLEILGDRPDGFHELVMVLQS :  35
M.T.   : -----------------------MPTGSVTVRVPGKVNLYLAVGDRREDGYHELTTVFHA :  37
A.E.   : ------------------------MIKVLSPAKINLGLWVLGRLPSGYHEILTLYQE    :  33
C.T.   : -----------------------MHFLSPAKLNLFLQILGRREDDFHEIVTRYQA      :  32
C.P.   : -----------------------MQYFSPAKLNLFLKIWGKRFDNFHELTTLYQA      :  32
T.M.   : ------------------MVENIGSGSAELVSYAKLNLYLDVLGKRSDGYHEIVGLFQT  :  41
H.P.   : ------------------------MTHVFEVYPKVNVFLKILHKEG-AYHKIISRMCL   :  33
T.P.   : -----------------------MQSLSLRAHAKVNMHLWVGARRADGLHSIESVMQR   :  35
S.TL.  : -----------------------MMTHWPSPAKLNLFLYITGQRADGYHTLQTLFQF    :  34
Z.M.   : -----------------------MPKLTEIAYAKINLALHVRGKMPNGYHALETIFAF   :  35
S.T.   : -----------------------MMTHWPSPAKLNLFLYITGQRADGYHTLQTLFQF    :  34
S.P.   : -----------------------MMTHWPSPAKLNLFLYITGQRADGYHTLQTLFQF    :  34
Y.S.   : -------------------------<KWPSPAKLNLFLYITGQRADGYHQLQTLFQF    :  31
A.A.   : -------------------------<RFPCPAKLNLFLYINGKRATGYHELQTLFQF    :  31
V.C.   : ------------------------<TVWPSPAKLNLFLYITGRRANGYHDLQTLFQF    :  32
S.PU.  : -------------------------<WPAPAKLNLFLHINGRRSDGYHELQTLFQF     :  30
P.M.   : -------------------------<RFPCPAKLNLFLYINGKRQDGYHELQTLFQF    :  31
P.A.   : ----------------------<VRLSLPAPAKLNLFLHILGRRDDGYHELQTLFQF    :  34
N.G.   : ----------------------<RQAFPAPAKLNLDLRITGRREDGYHNIESIFCL     :  33
B.P.   : -------------------------<PAPAKLNLFLHVVGRRADGYHLLQTAFRF      :  29
N.M.   : ----------------------<RQAFPAPAKLNLDLRITGRREDGYHNIESIFCL     :  33
K.M.   : ------------------------------------------------------------ :   -
D.R.   : -----------------------------<APAKINLGLSVLGVRENGYHDLHSLMVP   :  28
B.B.   : -----------------------------------<APAKINLGLSVLGVRENGYHDLHSLMVP :  -
C.D.   : -----------------------------<SRAKINLSIDVLGKRQDGYHFVEMIMQT   :  28
C.A.   : -------------------------------<AKVNISLDVIGKREDGYHLLKMIMQS   :  26
M.A.   : -----------------------------<PGKVNLYLAVGDRREDGYHELTTIFQA    :  27
M.B.   : -----------------------------<PGKVNLYLAVGDRREDGYHELTTVFHA    :  27
M.L.   : -----------------------------<PGKINLYLAVGDCCDNGYHELVTVFHA    :  27
C.TP.  : --------------------------------<AKINLGLLITSRRADGYHTLETIFAP  :  26
P.G.   : --------------------------------<AKINLGLQVVAKRADGYHNIETVFYP  :  26
E.F.   : -------------------------------<APAKINLGLDVLHKRVDGYHEVESIFAS :  28
S.M.   : -------------------------------<APAKINLGLDIAGKYQDGFHELSMIMAS :  28
S.PG.  : ---------------------------------<KIKLGLDTKNKRXDGYHDLSMVMMS  :  25
S.AN.  : -------------------------------<APAKINFTLDTLFKRNDGYHEIEMIMTT :  28
S.A.   : -------------------------------<APAKINFTLDTLFKRNDGYHEIEMIMTT :  28
A.T.   : KQVEIVFDPDERLNKIGDDVDKEAPLSRLKLFSPCKINVFLRITGKREDGFHDLASLFHV : 104
S.L.   : KQVEITYNPEEKFNKLADEVDREAGLSRLTLFSPCKINVFLRITSKRDDGYHDLASLFHV : 120
S.ML.  : ------------------------------------------------------------ :   -
C.C.   : -------------------------MRLSAFAPAKVNLFLHVGGPDGEGYHPISSLMVF  :  34
C.J.   : -------------------------<QMKAYAKANIFLKLTGFDSRKYHLLESRFIL    :  31
```

FIG. 5 (CONT'D.)

Alignment of amino acid sequences orthologous to YchB of *E. coli*, continued

```
                *         140         *         160         *         180
E.C.    : LD-YGDTISIELRD--DGDIRLLTPVEGVE-HEDNLIVRAARLLMKTAADSGRLPTGSG- :  89
H.I.    : LD-FGDWLDISIRE-QDNQIVLTPEIPNLK-TENNLIYRAAKLLQEKAN------IQLG- : 103
B.S.    : ID-LADRIELTELA-EDEVRVS-SHNRFVPDDQRNLAYQAAKLIKDRYN------VKKG- :  84
S.S.    : IA-LGDKITVRANG-TDDIRLS-CGDSPLANDATNLAYRAAQLMINNFP------QAHDN :  86
M.T.    : VS-LVDEVTVRNAD-VLSLELVGEGADQLPTDERNLAWQAAELMAEHVG------RAPD- :  88
A.E.    : IP-FYDEIYIREG-----VLRVETNIG-IP-QEENLVYKGLREFERITG------IEIN- :  78
C.T.    : IA-FGDQLSLSIS----SRDSLQVINACHLETPSNSIWKSVALFRRYTG------ITTP- :  80
C.P.    : ID-FGDTLSLKNS----MKDSLSS-NVNELLSPSNLIWKSLEIFRRETQ------IHQP- :  79
T.M.    : IS-LHDTLTVEICD----RGFYLESSVALP--SDNTIKRAWEMFRKNTG------KEFG- :  87
H.P.    : VK-NKLKDIISVKN---ALSFSLKGDFDCP-LEENSLFKALQVLKKFLVQKNFSHSVIKS :  88
T.P.    : IT-LADSLSLSRLD-IPGRCEVCSPYMALP--RENTLTRAYARFCQVTG------VHDG- :  84
S.TL.   : LD-YGDTLHIEPRH--DGEIHLLTPVNGVE-NEDNLIVRAARLLMKVASESGRLPAGSG- :  89
Z.M.    : AK-DGDILQAEANDTEDNLTITGPFSEGLEANKDNLVLRAVTALRQACPN----KIPAG- :  89
S.T.    : LD-YGDTLHIEPRH--DGEIHLLTPVTGVE-NEDNLIVRAARLLMKVASESGRLPAGSG- :  89
S.P.    : LD-YGDTLHIEPRR--DGEIHLLTPVNGVE-NEDNLIVRAAQLLMKIASESGRLPAGSG- :  89
Y.S.    : LD-YGDQLTIEPRD--DNQIRLLTPIAGVE-NEQNLIVRAAKMLQKHP---GNTPVPRG- :  83
A.A.    : VD-FGDWLHIKVRP--DGKIRLTSVIADLK-AEDNLIYRAAKLLQQYTG------CTLG- :  80
V.C.    : LD-HGDELTITANN--SGNITLSPALADVA-LEDNLIYKAAMALKNAA-----Q-SPLG- :  81
S.PU.   : VD-CCDQLDFRVTD-TPELILHSTMSAVVA-DSDNLILRAAKSLQQATG------FNGG- :  80
P.M.    : VD-FGDWLDIEVRE--DNEICLTPELPSLK-NEDNLVYRAAKLLQQKTN------CALG- :  80
P.A.    : LD-HGDELHFEARQ--DGQVRLHTEIAGVP-HDSNLIVRAARGLQEASG------SPQG- :  83
N.G.    : ID-LQDTVYLKPRD--DGKIILHNPVDGMP-QEADLSYRAASLLQKYAR------TPTG- :  82
B.P.    : ID-LADTLHFEARA--DGAIGRAYELPGVA-ESDDLVMRAARSLQRATG------TRQG- :  78
N.M.    : ID-LQDTVYLKPRD--DGKIILHNPVDGMP-QEADLSYRAASLLQKYAR------TPTG- :  82
K.M.    : ------------------------------------------------------------- :   -
D.R.    : LT-VGDELEIRPAG---ALTLRVEGADLPT-DERNLVYRAARAYLDAAG------AAGG- :  76
B.B.    : ------TIYXKARX--DGIIARAXKLPGVP-ESTNLVVRAARSLQRATG------TAKG- :  44
C.D.    : ID-LYDIVKIKELD-EDEIKVK-STSLDIPLDEDNIVYKAAKILKNKFY------IKKG- :  78
C.A.    : IN-LYDVLDIRIID-EG-IKIT-SNRRNIPTNDKNIAYRAAKLFMDTYK------IDKG- :  75
M.A.    : VS-LLDEVTVRNAD-VLSLDIVGEGADKLPTDERNLAWQAAELMAEHVG------RAPD- :  78
M.B.    : VS-LVDEVTVRNAD-VLSLELVGEGADQLPTDERNLAWQAAELMAEHVG------RAPD- :  78
M.L.    : VS-LVDQVTVRNAD-VLSLGLVGEGANHVPTDEHNIAWRAAELMAEHVG------RAPD- :  78
C.TP.   : ID-WFDTLEFTESD---AISMECSNLDLLV-DDSNLCIRAAKALQEHTG------VKRG- :  74
P.G.    : IP-LTDALEIEVRE-DTCDRLSVHGVPIDAATEDNLVMKAVMALRRKFD-------FPP- :  76
E.F.    : VD-LADHLTFENLE-EDIIRIE-TDSSFLPVDRRNHVYQAVDLLKRTYN------IHKG- :  78
S.M.    : VD-LNDYLTITEIA-EDKIVVE-SNNCKLPLNRKNDVYKAAHLLKRRYH------ISTG- :  78
S.PG.   : ID-LCDYVTVDHID-DNKIVFA-SNCPKIPINXDNDVYKIVQLMKHRFQ------VKRG- :  75
S.AN.   : VD-LNDRLTFHKRK-DRKIVVE-IEHNYVPSNHKNLAYRAAQLFIEQYQ------LKQG- :  78
S.A.    : VD-LNDRLTFHKRK-DRKIVVE-IEHNYVPSNHKNLAYRAAQLFIEQYQ------LKQG- :  78
A.T.    : IS-LGDTIKFSLSP-SKSKDRLSTNVQGVPVDGRNLIIKALNLYRKKTG------SNRF- : 155
S.L.    : IS-LGDKIKFSLSP-SKSKDRLSTNVAGVPLDERNLIIKALNLYRKKTG------TDNY- : 171
S.ML.   : ------------------------------------------------------------- :   -
C.C.    : AD-VGDRVNLQPAD-APAFETSGPIGDQIPAGGDNLVVRAGQAFHRRLG------GPVPP :  86
C.J.    : LKDVFDELELVDKE---SDSKKEFEIISNFKCENNIIQKAYLLLSRRYNN----ELKEL :  83
```

FIG. 5 (CONT'D.)

Alignment of amino acid sequences orthologous to YchB of *E. coli*, continued

```
              *         200         *         220         *         240
E.C.   : ---ANISIDKRLPMGGGLGGGSSNAATVLVALNHLWQC-GLSMDELAEMGLTLGADVPVF : 145
H.I.   : ---ANIHLDKILPMGGGVGGGSSNAATALVSLNYLWQA-NLSIDELAKLGLTLGADVPIF : 159
B.S.   : ---VSIMITKVIPVAAGLAGGSSDAAATLRGLNRLWNL-NLSAETLAELGAEIGSDVSFC : 140
S.S.   : YGGVDITLTKHIPMAAGLAGGSADAAAVLVGLDLLWNL-GLTRPELEQLAAQLGSDIPFC : 145
M.T.   : ---VSIMIDKSIPVAGGMAGGSADAAAVLVAMNSLWEL-NVPRRDLRMLAARLGSDVPFA : 144
A.E.   : ---YSIFIQKNIPPGAGLGGGSSNLAVVLKKVNELLGS-PLSEEELRELVGSISADAPFF : 134
C.T.   : ---VSWRVVKQIPVGAGLAGGSSNAATALFALNQIFKT-GLSDEEMRSLAEQLGVDTPFF : 136
C.P.   : ---VSWHLNKSIPLQSGLGGGSSNAATALYALNEHFQT-HIPITTLQLWAREIGSDVPFF : 135
T.M.   : ---LKVTLKKEIPVGSGLGGGSSNAAAVLRYLGEVFKI--P-LEDLLNIAAQVGSDVPFF : 141
H.P.   : LDTLAIEVEKNIPTQAGLGGGSADAGGLLYHLNQMFDW-RLSLKELYTMGSLVGADTNFP : 147
T.P.   : ---VRVRVVKRIPAGSGLGGGSADAAALLCGLDTLFGT-TLSARVLREVAYSVGSDVPFF : 140
S.TL.  : ---ADISIEKRLPMGGGLGGGSSNAATVLVALNHLWQC-GLSIDELATLGLTLGADVPVF : 145
Z.M.   : ---FSIILDKRLPVAAGIGGGSADAAAMLRMIGQHYQI--P-HELILSLANSLGADVPAC : 143
S.T.   : ---ADISIEKRLPMGGGLGGGSSNAATVLVALNHLWQC-GLSIDELATLGLTLGADVPVF : 145
S.P.   : ---ADISIEKRLPMGGGLGGGSSNAATVLVALNHLWQC-GLSIDELATLGLTLGADVPVF : 145
Y.S.   : ---ADISIDKCLPMGGGLGGGSSNAATVLVALNLLWQC-GLTDEQLADLGLTLGADVPVF : 139
A.A.   : ---TELTLDKILPIGGGVGGGSSNAATTLVALNHLWKT-GLSTGQLAELGLTLGADVPIF : 136
V.C.   : ---ADIQLHKVLPMGGGIGGGSSNAATTLVALNYLWQT-GLSDDQLAEIGLALGADVPVF : 137
S.PU.  : ---AEIWLDKRLPMGGGLGGGSSDAATTLVALNRLWNT-QLSHDELAAIGLKLGADIPVF : 136
P.M.   : ---ANLTLDKILPMGSGLGGGSSNAATALVALNYLWNT-QLSTKQLAKLGLMLGADVPIF : 136
P.A.   : ---VDIWLDKRLPMGGGIGGGSSDAATTLLALNHLWQL-GWDEDRIAALGLRLGADVPVF : 139
N.G.   : ---VEIWLDKKIPTGAGLGGGSSDAATVLLVLNRWWQC-GLTQRQLIDSGAALGADVPFF : 138
B.P.   : ---AQIGLHKRIPQGGGLGGGSSDAATTLIALNRLWGT-GLSRSQLMQLALPLGADVPVF : 134
N.M.   : ---VEIWLDKKIPTGAGLGGGSSDAATVLLVLNRWWQC-GLTQRQLIDSGAALGADVPFF : 138
K.M.   : ------------------------------------------------------------ :  -
D.R.   : ---ADLVLHKRLPLASGLGGGSSDAASTLLALAELYPAPDHRPVDLPALALTLGADVPFF : 133
B.B.   : ---AQIACNKRIPQAFGLASGSRNAATTLIALTRLWGT-GLSRSQLMQLALPLGADVPVF : 100
C.D.   : ---VEIFIEKNIPVAAGMAGGSSNAAAVLVGXNHLWEL-RLSEDELKEIGLNLGADVPFC : 134
C.A.   : ---ISIHINKRIPVAAGLAGGSADGAAVLKAMRDIFKK-DVSDEELINLGVKIGADIPFC : 131
M.A.   : ---VSIMIDKSIPVAGGMAGGSADAAAVLVAMNSLWEL-NVPRRDLRMLAAQLGSDVPFA : 134
M.B.   : ---VSIMIDKSIPVAGGMAGGSADAAAVLVAMNSLWEL-NVPRRDLRMLAARLGSDVPFA : 134
M.L.   : ---VSIMIDKSIPVAGGMAGGSADAAAVLVAMNSLWEL-SLPRRDLCMLAAKLGSDVPFA : 134
C.TP.  : ---ATIKLLKRVPFGAGLGGGSSDAAATLNALCKLWQI-DVPSAELHKLAVKLGADVPYF : 130
P.G.   : ---LTIELIKHIPSGAGLGGGSSNASFMLKLVRDYFSL-PIDDEELAAIALTIGADCPFF : 132
E.F.   : ---IKIYIEKRIPVAAGLAGGSSDCAAALRGLNKLWNL-GLTMDELCEIGSQIGMDVPYC : 134
S.M.   : ---LKISLQKKIPICAGLGGGSSDAAATLRALNCLWKL-NLSPKELIDVGFEIGSDVPYC : 134
S.PG.  : ---VSVYLEKRIPMCAGMGGGSSD-AVTIRALNQMWLL-TLSRKDMMDIGIPIGSDVPYC : 130
S.AN.  : ---VTISIDKEIPVSAGLAGGSADAAATLRGLNRLFDI-GASLEELALLGSKIGTDIPFC : 134
S.A.   : ---VTISIDKEIPVSAGLAGGSADAAATLRGLNRLFDI-GASLEELALLGSKIGTDIPFC : 134
A.T.   : ---FWIHLDKKVPTGAGLGGGSSNAATALWAANELNGG-LVTENELQDWSSEIGSDIPFF : 211
S.L.   : ---FWIHLDKKVPTGAGLGGGSSNAATTLWAANQFSGC-VATEKELQEWSGEIGSDIPFF : 227
S.ML.  : ------<LEKNLPIASGMGGGSADAAATLRGLXSLWGA-TVEAASLNSPALQLGADVPMC :  52
C.C.   : ---YRLILEKHLPIAAGLGGGSSDAGAALKLMRDALAP-ALSDDDLEALAASLGADGAAC : 142
C.J.   : FSKKSLKLTKNIPVCAGLGGGSSDCASFLLLINETLNL-KLNLQELINLSIQLGSDIAFF : 142
```

FIG. 5 (CONT'D.)

Alignment of amino acid sequences orthologous to YchB of *E. coli*, continued

```
                   *         260         *         280         *         300
E.C.  : VRG-HAAFAEGVGEILTPVDPPE--KWYLVAH-P-GVSIPT------------PVIFKD : 187
H.I.  : VHG-HAAFAEGVGEKITYCEPAE--KWFVILK-P-DDSIST------------AVIFQD : 201
B.S.  : VYG-GTALATGRGEKIKHISTPP-HCWVILAK-P-TIGVST------------AEVYRA : 183
S.S.  : IGG-GTAIATGRGEILDPLPDGN-CFWVVLAK-HRSIEVSTPWAYQTYRQKFGKNYLNDD : 202
M.T.  : LHG-GTALGTGRGEELATVLSRN-TFHWVLAF-ADSGLLTS---------AVYNELDRL : 191
A.E.  : LLG-KSAIGRGKGEVLEPVETEISGKITLVIP---QVSSST------------GRVYSS : 177
C.T.  : FST-GAALGVARGEKIIALEES-VSDRYVLYFSS-EGVLTS------------RAFAAV : 180
C.P.  : FSS-GTALGKGRGEHLFSIKKLNHKHKYVLYLDH-QGIPTE------------KAYQSL : 180
T.M.  : LYG-GTALVRGRGEIVEKLEDIE--GYSVDLFFP-GIHSST------------KEMYLS : 184
H.P.  : ISQYKSANATSYGEVIENFEEES-LEDRLEIYAPNHVFCST------------KAVYQA : 193
T.P.  : LAS-QAACVLGGGEQLVPLVPKT--GYLGLLVWP-GLHSGS------------AQAYED : 183
S.TL. : VRG-HAAFAEGVGEILTPVNPPE--KWYLVAH-P-GVSIPT------------PVIFKD : 187
Z.M.  : VDS-CLVRGEGVGEKLTQIGDRSLEEKPLLLVNP-RVSCST------------PMIFKN : 188
S.T.  : VRG-HAAFAEGVGEILTPVNPPE--KWYLVAH-P-GVSIPT------------PVIFKD : 187
S.P.  : VRG-HAAFAEGVGEILTPVNPPE--KWYLVAH-P-GVSIPT------------PVIFKD : 187
Y.S.  : VRG-HAAFAEGIGEKLQPAEPVE--KWYLVIH-P-GVNIPT------------PIIFSD : 181
A.A.  : VHG-KAAFAEGIGEKITYCEPPE--KWYLVLK-P-NVSIST------------AVVFSD : 178
V.C.  : TRG-FAAFAEGVGEELSAVEPEE--KWYLVXXXP-AVSIAT------------KDIFTH : 180
S.PU. : IHG-FAAFAQGVGERLQAVNPAE--LWYLVIA-P-DAHVST------------AAVFQD : 178
P.M.  : VHG-HAAFAEGVGEKITYCEPKE--KWYVVLK-P-NVSIST------------ATVFSD : 178
P.A.  : TRG-RAAFAEGVGEKLTPVDIPE--PWYLVVV-P-QVLVST------------AEIFSD : 181
N.G.  : IFG-KNAFARGIGDRLDEMDIPK--QWYVIVK-P-PVHVST------------AKIFTH : 180
B.P.  : VFG-QSAFAQGVGEDLTAVALSP--AAYLVVQ-P-DAGVPT------------AVIFSD : 176
N.M.  : IFG-KNAFARGIGDRLDEMDIPK--QWYVIVK-P-PVHVST------------AKIFTH : 180
K.M.  :          <GVGEILTPXKPEK--KWYLWPH-R-GSSIPT------------PIIFRD :  33
D.R.  : LLG-GAALAEGVGERLTPVDDLP--PVHLVLANA-GAEV>-------------------- : 168
B.B.  : VFG-QSAFAQGVGEDLTAVALPP--PAYLVVQ-P-DAGVPT------------AAIFSD : 142
C.D.  : ISG-RPALAQGIGEKLTNIKGLPCDTNILICK-P-DLFVST------------KEVYQG : 178
C.A.  : IVG-GTAFCEGIGEKITKLRSMN-GKIIVLVK-P-DFGVST------------KMVYTE : 174
M.A.  : LHG-GTALGTGRGEELATV>---------------------------------------- : 152
M.B.  : LHG-GTALGTGRGEELATV>---------------------------------------- : 152
M.L.  : LHG-GTALGTGRGEELATV>---------------------------------------- : 152
C.TP. : LEMKGLAYAAGIGEELEDLNLAL--PWHVVTVFP-EVQVPT------------AWAYKN : 174
P.G.  : VGN-RPVLATDLGQVFTPL>---------------------------------------- : 150
E.F.  : LRG-GTAFANGRGEKIEALPTMP-QCWIVLVK-P-RISVST------------STVFND : 177
S.M.  : IEA-GCALISGKGEIVEPLATTL-STWVVLVK-P-DFGIST------------KTIFKE : 177
S.PG. : LLS-GCAQVTGKGEVVCRILGLL-SSWVVLVK-P-DFGIST------------XTFFLD : 173
S.AN. : IYN-KTALCTGRGEKIEFLNKPP-SAWVILAK-P-NLGISS------------PDIFKL : 177
S.A.  : IYN-KTALCTGRGEKIEFLNKPP-SAWVILAK-P-NLGISS------------PDIFKL : 177
A.T.  : FSH-GAAYCTGRGEIVQDLPPPFPLDPMVLIKP-REACST------------AEVYKR : 256
S.L.  : FSH-GAAYCTGRGEVVQDIPSPIPFDIPMVLIKP-QQACST------------AEVYKR : 272
S.ML. : LDR-GPLVARGIGEEITPLPDLP--PXXVVLVNP-LVAVST------------PVIFRS :  95
C.C.  : LRA-RA>----------------------------------------------------- : 147
C.J.  : LSGFHSANVSSCGEIIEEFEDDIP---NLKWTFP-QISCQT------------KAVYDE : 185
```

FIG. 5 (CONT'D.)

Alignment of amino acid sequences orthologous to YchB of *E. coli*, continued

```
                    *         320         *         340         *         360
E.C.   : PELPRNTPKRSIETLLKCEF-----------------SNDCEVIARKRFREVDAVLSWL  : 229
H.I.   : PNLPRNTPKKSLAQLLSEPY-----------------KNDCEKVVINHYSNVEKALNWL  : 243
B.S.   : LKLDGIE-HPDVQGMIEAIE------EKSFQK-MCSRLGNVLESVTLDMHPEVAMIKNQM  : 235
S.S.   : QSQRARRKTIHAGPLLQGIQ------HRNPGQ-IASHIHNDLEKVVLPAHQPVAQLRQVL  : 255
M.T.   : REVGDPPRLGEPGPVLAALA------AGDPDQ-LAPLLGNEMQAAAVSLDPALARALRAG  : 244
A.E.   : LREEHFVTPEYAEEKIQRII------SG-----EVEEIENVLGDIARELYPEINEVYRFV  : 226
C.T.   : QPSDCSS--RKNLEYTQ--------------------NDLEKPVFRLRLDLKEKKHWL  : 216
C.P.   : LPQDYSTGNHNACFYGE--------------------NDLEKSVFRIRTDLKNKKHML  : 218
T.M.   : LTPEMYRKGPGRVEELHRAY------LERNYEKIKELSYNVFEKVFLEKHPEVMDGLRNF  : 238
H.P.   : YKPETCFFQAKEWLKKTSLEC--------LKTYDRNELNDLLKPALRTNPALKDIESQL  : 244
T.P.   : LDRLRACGVHAADGEQYSLRGATALSAHYAQDCARWRFFNSLDAPVQRRYPVVALARWDL  : 243
S.TL.  : PQLPRNTPKRSIDTLLKCEF-----------------SNDCEVIARKRFREVDAALSWL  : 229
Z.M.   : WDGVDRGALDSDGSILGAAR------SG----------RNDLEPPARKILPIIGEVVEWL  : 232
S.T.   : PQLPRNTPKRSIDTLLKCEF-----------------SNDCEVIARKRFREVDAALSWL  : 229
S.P.   : PQLP-NTPKRSIDTLLKCEF-----------------SNDCEVIARKRFREVDAALSWL  : 228
Y.S.   : PELKRNTPIRPLAALLSTPY-----------------ANDCEPIARKRFREVEQALSWL  : 223
A.A.   : PHLPRNTPKKSLAQLLAGKY-----------------ANDCEKVVRDHYSEVEESLNWL  : 220
V.C.   : PQLMRNTPKRDLASLLTTPY-----------------ENDCEKIVRSLYPEVDKQLSWL  : 222
S.PU.  : PLLPRNTPKLGLDTLLSQPW-----------------ANDCQELVVSKYPQVAKALGWL  : 220
P.M.   : PDLIRNTPKQSLEQLLNQKY-----------------ANDCEKVVLNHYPEVEEILHRL  : 220
P.A.   : PLLTRDSPAIKVRTVLEGDS-----------------ANDCQPVVERRYPEVRNALILL  : 223
N.G.   : EGLTRNSASSIMPTFQNLQP----------------FRNDMQAVVFKEYPEVWKAYSEL  : 223
B.P.   : PDLTRDCASVTIADFLALPT------SC--------FGRNDLEPVVLRRYPEVSGAVRWL  : 222
N.M.   : EGLTRNSASSIMPTFQNLQP----------------FRNDMQAVVFKEYPEVWKAYSEL  : 223
K.M.   : PELPRNTPRRSINTLLNCEF-----------------SNDCELIARKRFREVDAALSWL  :  75
D.R.   : ------------------------------------------------------------  :   -
B.B.   : PDLTRDCASVTIADFLALPT------FC--------FGRNDLEPVVLRRYPEVSGAVRWL  : 188
C.D.   : LDLNNIKKRPNNKYLIECLK------SEDIKA-VSESMVNILENVTIGKHKEISDIKQVM  : 231
C.A.   : YDKCLDVKHPDSEGLVKAVN------NGHFKF-VVNNMVNVLENVTAVKYKEINEIKEKA  : 227
M.A.   : ------------------------------------------------------------  :   -
M.B.   : ------------------------------------------------------------  :   -
M.L.   : ------------------------------------------------------------  :   -
C.TP.  : FHRQFERPVPDLKTLVRRLC------HERDIS-VFGVFENDPASVVFEHYPVVREVRDAL  : 227
P.G.   : ------------------------------------------------------------  :   -
E.F.   : LAVDELH-HPDIAGLRIAIE------NGDYTG-MTQTVGNALESVTIARHPIVQQIKDRM  : 229
S.M.   : IDMATIS-RVDIPALKEALL------ANYYED-ALQFMGNSLEDITIAKKPFIQKIKGRM  : 229
S.PG.  : INCKIIS-RVSTTHLVAAIE------AGNYNDGILTEMNNLLEDIFIAKRPFIQKIKEKT  : 226
S.AN.  : INLDKRY-DVHTKMCYEALE------NRDYQQ-LCQSLSNRLEPISVSKHPQIDKLKNNM  : 229
S.A.   : INLDKRY-DVHTKMCYEALE------NRDYQQ-LCQSLSNRLEPISVSKHPQIDKLKNNM  : 229
A.T.   : LRLDQTS-NINPLTLLENVT------SNGVSQ---SICVNDLEPPAFSVLPSLKRLKQRI  : 306
S.L.   : FQLDLSS-KVDPLSLLEKIS------TSGISQ---DVCVNDLEPPAFEVLPSLKRLKQRV  : 322
S.ML.  : LVRKTNPPLVLPEDARSTAE------WLT----AMAAMRNDLEPPARAHEPMIETVSNAL  : 145
C.C.   : ------------------------------------------------------------  :   -
C.J.   : ------------------------------------------------------------  :   -
```

FIG. 5 (CONT'D.)

Alignment of amino acid sequences orthologous to YchB of *E. coli*, continued

```
                *         380        *         400        *         420
E.C.   : LEYAP-----SRLTGTGACVFA------EFDTESEARQVLEQAPEWLNGFVAKGANLSP    : 277
H.I.   : LQYAP-----ARLTGTGACVFA------EFDHEAEAQAVFRQKPEAFFGFVAKGLNVSP    : 291
B.S.   : KRFGAD---AVLMSGSGPTVFG------LVQYESKVQRIYNGLRGFCDQVYAVRMIGEQ    : 285
S.S.   : QSAGGL---GTMMSGSGPSVFT------LCREQAEAEQVLAIAKEKLNDPDVDFWLTHT    : 305
M.T.   : VEAGAL---AGIVSGSGPTCAF------LCTSASSAIDVGAQLSGAGVCRTVRVATGPV    : 294
A.E.   : EYLGFK----PFVSGSGSTVYFFGG----ASEELKKAAKMRGWKVVELEL>---------   : 268
C.T.   : ENLWAELPVHIGLTGSGATLF---VRYPEILEEDLSYAAQIQRAVTLSGGLLTSPIRRDP   : 273
C.P.   : ERMWSPFESHVLMSGSGATLF---VCYLEELEQDSKVSSQIHSLIKQTQGIPVSRLYREP   : 275
T.M.   : GDGSIV----KMMTGSGSVFFA------LYPLDKGNYSFVGGV>---------------    : 271
H.P.   : SKEWF-------FSGSGSAFFR------LKNTQKGANETHCQQ>---------------    : 274
T.P.   : ARAGAC---FTAMSGSGSXVFG------LYRDEEELRRAHKLLAKRWCWCVRVRLCG>-    : 291
S.TL.  : LEYAP-----SRLTGTGACVFA------EFDTESCARQVLEQAPEWLNAFVAKGVNLSP    : 277
Z.M.   : QQQKGVS--FSRMSGSGATCFA------LFDEIEDRDTAYKKLNIDHPEWWALSSLLR>    : 282
S.T.   : LEYAP-----SRLTGTGACVFA------EFDTESCARQVLEQAPEWLNAFVAKGVNLSP    : 277
S.P.   : LEYAP-----SRLTGTGACVFA------EFDTESCARQVLEQAPEWLNAFVAKGVNLSP    : 276
Y.S.   : LEYAP-----SRLTGTGACVFA------EFDTESSARQVLSIAPEWLHGFVARGVNVSP    : 271
A.A.   : VKYAP-----ARLTGTGACVFA------EFDDKKSAQSVLQAKPKNCFGFVAKGLNHSP    : 268
V.C.   : LQYAP-----SRLTGTGSCVFA------EFSSRKDAQAVFAQLSDNVLAFVAQGRNVSP    : 270
S.PU.  : LEYAP-----SRMTGTGACVFG------EFSSQQQALAALAKLPSDMQGFVAKGMNISP    : 268
P.M.   : LQYAP-----SRLTGTGACVFA------EFNDEESAQLAFQTIPKNYFGFVAQGLNKSP    : 268
P.A.   : NKFVS-----ARLTGTGGCVFG------SFPNKAEADKVSALLPDHLQRFVAKGSNISM    : 271
N.G.   : SRYGF-----ALMTGSGACVFT------ACQDRNSAYNIYRQVSDLYEAYLAEGLSKHP    : 271
B.P.   : FEHGLR----VRMSGSGACLFA------EFPTLPEA>-------------------       : 248
N.M.   : SRYGF-----ALMTGSGACVFT------ACQDRNSAYNIYRQVSDLYEAYLAEGLSKHP    : 271
K.M.   : LEYAP-----SRLTGTGACVFA------EFNTESAARQVLDTAPAWLNGFVARGVNLSP    : 123
D.R.   : ------------------------------------------------------------  :  -
B.B.   : FEHGLR----VRMSGSGACLFA------EFPTLPEAVLAQDP>---------------     : 220
C.D.   : MKNNAL---GSMMSGSGPTVFG------LFKNKEDA>---------------------     : 258
C.A.   : LEYNSI---GTMMSGSGPTVFS------FFDNTKEAEKYFYEMKKEYNKVFITR>----    : 272
M.A.   : ------------------------------------------------------------  :  -
M.B.   : ------------------------------------------------------------  :  -
M.L.   : ------------------------------------------------------------  :  -
C.TP.  : AASGAQ---FVSLSGSGSAVYA------LYEGRADAVKAAE>---------------      : 259
P.G.   : ------------------------------------------------------------  :  -
E.F.   : LKYGAD---AALMSGSGPTVFA------LCEKKTRAQRI>------------------     : 259
S.M.   : IKCGAD---IALMTGSGPTVFA------LCRTEKRADRVV>-----------------     : 260
S.PG.  : LQAGAA---NALMTGSGPTVFA------LCQTEKQ>----------------------     : 252
S.AN.  : LKSGAD---GALMSGSGPTVYG------LARKESQAKNI>------------------     : 259
S.A.   : LKSGAD---GALMNGSGPTVYG------LARKESQAKNI>------------------     : 259
A.T.   : IASGRGEYDAVFMSGSGSTIIGIGSPDPPQFIYDDEEYKNVFLSEANFMTREANEWYKEP   : 366
S.L.   : IAAGRGQYDAVFMSGSGSTIVGVGSPDPPQFVYDDEEYKDVFLSEASFITRPANEWYVEP   : 382
S.ML.  : RDAGAA---LVRMSGSGATCFG------LFTGMKSAERAAETISAGHPRW>--------    : 186
C.C.   : ------------------------------------------------------------  :  -
C.J.   : ------------------------------------------------------------  :  -
```

FIG. 5 (CONT'D.)

Alignment of amino acid sequences orthologous to YchB of E. coli, continued

```
                    *         440            (SEQ ID NO:)
E.C.   : LHRAML>----------------- : 283       133
H.I.   : LHAMLKQLSSTHTHRQSKPEVL>- : 313       134
B.S.   : NALD>------------------- : 289       135
S.S.   : IGHGIQIMNN>------------- : 315       136
M.T.   : PGARVVSAPTEV>----------- : 306       137
A.E.   : ------------------------ :   -       138
C.T.   : TAWYSIY>---------------- : 280       139
C.P.   : -HWYSL>----------------- : 280       140
T.M.   : ------------------------ :   -       141
H.P.   : ------------------------ :   -       142
T.P.   : ------------------------ :   -       143
S.TL.  : LHRELL>----------------- : 283       144
Z.M.   : ------------------------ :   -       145
S.T.   : LHRELL>----------------- : 283       146
S.P.   : LHRELL>----------------- : 282       147
Y.S.   : LHR>-------------------- : 274       148
A.A.   : LHEML>------------------ : 273       149
V.C.   : LRKTL------------------- : 275       150
S.PU.  : L>---------------------- : 269       151
P.M.   : LHNML>------------------ : 273       152
P.A.   : LHRKL>------------------ : 276       153
N.G.   : L>---------------------- : 272       154
B.P.   : ------------------------ :   -       155
N.M.   : L>---------------------- : 272       156
K.M.   : LKQALL>----------------- : 129       157
D.R.   : ------------------------ :   -       158
B.B.   : ------------------------ :   -       159
C.D.   : ------------------------ :   -       160
C.A.   : ------------------------ :   -       161
M.A.   : ------------------------ :   -       162
M.B.   : ------------------------ :   -       163
M.L.   : ------------------------ :   -       164
C.TP.  : ------------------------ :   -       165
P.G.   : ------------------------ :   -       166
E.F.   : ------------------------ :   -       167
S.M.   : ------------------------ :   -       168
S.PG.  : ------------------------ :   -       169
S.AN.  : ------------------------ :   -       170
S.A.   : ------------------------ :   -       171
A.T.   : ASANATTSSAESRMDFQ>------ : 383       172
S.L.   : VSGSTIGDQPEFSTSFDMS>---- : 401       173
S.ML.  : ------------------------ :   -       174
C.C.   : ------------------------ :   -       175
C.J.   : ------------------------ :   -       176
```

FIG. 5 (CONT'D.)

Alignment of amino acid sequence of cloned cDNA of *ygbP* of A. *thaliana* (without leader sequence) and the amino acid sequence of the YgbP gene product found in the database

```
1  :                                                                  :   -
2  : MAMLQTNLGFITSPTFLCPKLKVKLNSYLWFSYRSQGNFSYSLYTFKPMNLWFVQKL         :  57

1  :                                        MEKSVSVILLAGGQGKRM         :  18
2  : DFSKRVNRSYKRDALLLSIKCSSSTGFDNSNAVNSNVVVKEKSVSVILLAGGQGKRM         : 114

1  : KMSMPKQYIPLLGQPIALYSFFTFSRMPEVKEIVVVCDPFFRDIFEEYEESIDVDLR         :  75
2  : KLCF------------------ WLRDVPKI-SLSLFLFCGVL-EYEESIDVDLR           : 148

1  : FAIPGKERQDSVYSGLQEIDVNSELVCIHDSARPLVNTEDVEKVLKDGSAVGAAVLG         : 132
2  : FAIPGKERQDSVYSGLQEIDVNSELVCIHDSARPLVNTEDVEKVLKDGSAVGAAVLG         : 205

1  : VPAKATIKEVNSDSLVVKTLDRKTLWEMQTPQVIKPELLKKGFELVKSEGLEVTDDV         : 189
2  : VPAKATIKE---------------------VIKPELLKKGFELVKSEGLEVTDDV          : 239

1  : SIVEYLKHPVYVSQGSYTNIKVTTPDDLLLAERILSEDS    : 228   (SEQ ID NO:1)
2  : SIVEYLKHPVYVSQGSYTNIKVTTPDDLLLAERILSEDS    : 278   (SEQ ID NO:2)
```

*FIG. 6* cDNA Sequence and corresponding protein sequence of *ygbP* gene from *A. thaliana*

```
          10        20        30        40        50        60
          |         |         |         |         |         |
GAGAAGAGTGTATCTGTGATTCTTTTAGCTGGAGGTCAAGGCAAGAGAATGAAAATGAGT

E   K   S   V   S   V   I   L   L   A   G   G   Q   G   K   R   M   K   M   S 70        80        90       100       110       120
          |         |         |         |         |         |
ATGCCAAAGCAGTACATACCACTTCTTGGTCAGCCAATTGCTTTGTATAGCTTTTTCACG

M   P   K   Q   Y   I   P   L   L   G   Q   P   I   A   L   Y   S   F   F   T 130       140       150       160       170       180
          |         |         |         |         |         |
TTTTCACGTATGCCTGAAGTGAAGGAAATTGTAGTTGTATGTGATCCTTTTTTCAGAGAC

F   S   R   M   P   E   V   K   E   I   V   V   V   C   D   P   F   F   R   D 190       200       210       220       230       240
          |         |         |         |         |         |
ATTTTTGAAGAATACGAAGAATCAATTGATGTTGATCTTAGATTCGCTATTCCTGGCAAA

I   F   E   E   Y   E   E   S   I   D   V   D   L   R   F   A   I   P   G   K 250       260       270       280       290       300
          |         |         |         |         |         |
GAAAGACAAGATTCTGTTTACAGTGGACTTCAGGAAATCGATGTGAACTCTGAGCTTGTT

E   R   Q   D   S   V   Y   S   G   L   Q   E   I   D   V   N   S   E   L   V 310       320       330       340       350       360
          |         |         |         |         |         |
TGTATCCACGACTCTGCCCGACCATTGGTGAATACTGAAGATGTCGAGAAGGTCCTTAAA

```
          370        380        390        400        410        420
           |          |          |          |          |          |
GATGGTTCCGCGGTTGGAGCAGCTGTACTTGGTGTTCCTGCTAAAGCTACAATCAAAGAG

D   G   S   A   V   G   A   A   V   L   G   V   P   A   K   A   T   I   K   E 430        440        450        460        470        480
           |          |          |          |          |          |
GTCAATTCTGATTCGCTTGTGGTGAAAACTCTCGACAGAAAACCCTATGGGAAATGCAG

V   N   S   D   S   L   V   V   K   T   L   D   R   K   T   L   W   E   M   Q 490        500        510        520        530        540
           |          |          |          |          |          |
ACACCACAGGTGATCAAACCAGAGCTATTGAAAAAGGGTTTCGAGCTTGTAAAAAGTGAA

T   P   Q   V   I   K   P   E   L   L   K   K   G   F   E   L   V   K   S   E 550        560        570        580        590        600
           |          |          |          |          |          |
GGTCTAGAGGTAACAGATGACGTTTCGATTGTTGAATACCTCAAGCATCCAGTTTATGTC

G   L   E   V   T   D   D   V   S   I   V   E   Y   L   K   H   P   V   Y   V 610        620        630        640        650        660
           |          |          |          |          |          |
TCTCAAGGATCTTATACAAACATCAAGGTTACAACACCTGATGATTTACTGCTTGCTGAG

S   Q   G   S   Y   T   N   I   K   V   T   T   P   D   D   L   L   L   A   E 670        680
           |          |
AGAATCTTGAGCGAGGACTCATGA

cDNA sequence and corresponding amino acid sequence of the *ygbP* gene of *A. thaliana*

```
          10        20        30        40        50        60        70
          |         |         |         |         |         |         |
ATGGCGATGCTTCAGACGAATCTTGGCTTCATTACTTCTCCGACATTTCTGTGTCCGAAGCTTAAAGTCAAA
 M  A  M  L  Q  T  N  L  G  F  I  T  S  P  T  F  L  C  P  K  L  K  V  K 80        90       100       110       120       130       140
          |         |         |         |         |         |         |
TTGAACTCTTATCTGTGGTTTAGCTATCGTTCTCAAGTTCAAAAACTGGATTTTTCGAAAAGGGTTAATAGA
 L  N  S  Y  L  W  F  S  Y  R  S  Q  V  Q  K  L  D  F  S  K  R  V  N  R 150       160       170       180       190       200       210
          |         |         |         |         |         |         }
AGCTACAAAAGAGATGCTTTATTATTGTCAATCAAGTGTTCTTCATCGACTGGATTTGATAATAGCAATGTT
 S  Y  K  R  D  A  L  L  L  S  I  K  C  S  S  T  G  F  D  N  S  N  V 220       230       240       250       260       270       280
          |         |         |         |         |         |         |
GTTGTGAAGGAGAAGAGTGTATCTGTGATTCTTTTAGCTGGAGGTCAAGGCAAGAGAATGAAAATGAGTATG
 V  V  K  E  K  S  V  S  V  I  L  L  A  G  G  Q  G  K  R  M  K  M  S  M 290       300       310       320       330       340       350       360
          |         |         |         |         |         |         |         |
CCAAAGCAGTACATACCACTTCTTGGTCAGCCAATTGCTTTGTATAGCTTTTTCACGTTTTCACGTATGCCT
 P  K  Q  Y  I  P  L  L  G  Q  P  I  A  L  Y  S  F  F  T  F  S  R  M  P 370       380       390       400       410       420       430
          |         |         |         |         |         |         |
GAAGTGAAGGAAATTGTAGTTGTATGTGATCCTTTTTTCAGAGACATTTTTGAAGAATACGAAGAATCAATT
 E  V  K  E  I  V  V  V  C  D  P  F  F  R  D  I  F  E  E  Y  E  E  S  I 440       450       460       470       480       490       500
          |         |         |         |         |         |         |
GATGTTGATCTTAGATTCGCTATTCCTGGCAAAGAAAGACAAGATTCTGTTTACAGTGGACTTCAGGAAATC
 D  V  D  L  R  F  A  I  P  G  K  E  R  Q  D  S  V  Y  S  G  L  Q  E  I
```

*FIG. 7B*

```
         510       520       530       540       550       560       570
          |         |         |         |         |         |         |
GATGTGAACTCTGAGCTTGTTTGTATCCACGACTCTGCCCGACCATTGGTGAATACTGAAGATGTCGAGAAG
 D  V  N  S  E  L  V  C  I  H  D  S  A  R  P  L  V  N  T  E  D  V  E  K 580       590       600       610       620       630       640
          |         |         |         |         |         |         |
GTCCTTAAAGATGGTTCCGCGGTTGGAGCAGCTGTACTTGGTGTTCCTGCTAAAGCTACAATCAAAGAGGTC
 V  L  K  D  G  S  A  V  G  A  A  V  L  G  V  P  A  K  A  T  I  K  E  V 650       660       670       680       690       700       710       720
 |         |         |         |         |         |         |         |
AATTCTGATTCGCTTGTGGTGAAAACTCTCGACAGAAAAACCCTATGGGAAATGCAGACACCACAGGTGATC
 N  S  D  S  L  V  V  K  T  L  D  R  K  T  L  W  E  M  Q  T  P  Q  V  I 730       740       750       760       770       780       790
          |         |         |         |         |         |         |
AAACCAGAGCTATTGAAAAAGGGTTTCGAGCTTGTAAAAAGTGAAGGTCTAGAGGTAACAGATGACGTTTCG
 K  P  E  L  L  K  K  G  F  E  L  V  K  S  E  G  L  E  V  T  D  D  V  S 800       810       820       830       840       850       860
               |         |         |         |         |         |         |
ATTGTTGAATACCTCAAGCATCCAGTTTATGTCTCTCAAGGATCTTATACAAACATCAAGGTTACAACACCT
 I  V  E  Y  L  K  H  P  V  Y  V  S  Q  G  S  Y  T  N  I  K  V  T  T  P 870       880       890       900
          |         |         |         |
GATGATTTACTGCTTGCTGAGAGAATCTTGAGCGAGGACTCATGA
 D  D  L  L  L  A  E  R  I  L  S  E  D  S  -
```

FIG. 7B (CONT'D.)

**cDNA sequence and corresponding protein sequence of *ychB* gene from *A. thaliana***

```
          10        20        30        40        50        60
           |         |         |         |         |         |
GCTCCTTTGTCCAGGCTTAAGCTCTTCTCACCTTGCAAGATCAATGTTTTCTTGAGGATC

A  P  L  S  R  L  K  L  F  S  P  C  K  I  N  V  F  L  R  I 70        80        90       100       110       120
           |         |         |         |         |         |
ACCGGAAAGCGAGAAGATGGGTTTCATGATTTAGCCTCTTTGTTTCATGTGATTAGCTTA

T  G  K  R  E  D  G  F  H  D  L  A  S  L  F  H  V  I  S  L 130       140       150       160       170       180
           |         |         |         |         |         |
GGAGGCACTATTAAATTCTCATTGTCACCATCAAAGTCTAAAGATCGTTTGTCTACTAAC

G  G  T  I  K  F  S  L  S  P  S  K  S  K  D  R  L  S  T  N 190       200       210       220       230       240
           |         |         |         |         |         |
GTTCAAGGAGTCCCTGTTGATGGGAGAAATCTGATTATAAAAGCACTTAACCTTTACAGG

V  Q  G  V  P  V  D  G  R  N  L  I  I  K  A  L  N  L  Y  R 250       260       270       280       290       300
           |         |         |         |         |         |
AAGAAAACTGGTAGCAACAGATTCTTCTGGATTCATTTAGATAAGAAGGTGCCTACCGGG

K  K  T  G  S  N  R  F  F  W  I  H  L  D  K  K  V  P  T  G 310       320       330       340       350       360
           |         |         |         |         |         |
GCTGGACTCGGTGGTGGAAGTAGTAATGCTGCAACTGCACTCTGGGCGGCAAATGAGCTC

```
        370       380       390       400       410       420
          |         |         |         |         |         |
AATGGAGGTCTTGTCACTGAGAACGAACTCCAGGATTGGTCAAGTGAAATTGGGTCAGAT

N  G  G  L  V  T  E  N  E  L  Q  D  W  S  S  E  I  G  S  D 430       440       450       460       470       480
          |         |         |         |         |         |
ATTCCTTTCTTCTTCTCGCATGGAGCTGCCTATTGTACCGGGAGAGGTGAGATTGTCCAA

I  P  F  F  F  S  H  G  A  A  Y  C  T  G  R  G  E  I  V  Q 490       500       510       520       530       540
          |         |         |         |         |         |
GACCTTCCTCCACCTTTTCCTCTTGATCTTCCGATGGTGCTCATAAAGCCCCGAGAAGCA

D  L  P  P  P  F  P  L  D  L  P  M  V  L  I  K  P  R  E  A 550       560       570       580       590       600
          |         |         |         |         |         |
TGTTCCACTGCTGAAGTTTACAAACGTCTTCGTTTAGATCAGACGAGCAATATTAATCCC

C  S  T  A  E  V  Y  K  R  L  R  L  D  Q  T  S  N  I  N  P 610       620       630       640       650       660
          |         |         |         |         |         |
TTGACATTACTAAAGAATGTGACCAGCAATGGTGTGTCTCAAAGCATATGCGTAAACGAT

L  T  L  L  K  N  V  T  S  N  G  V  S  Q  S  I  C  V  N  D 670       680       690       700       710       720
          |         |         |         |         |         |
TTGGAACCGCCAGCGTTTTCAGTTCTTCCATCTCTAAAACGCTTGAAGCAACGGATAATA

L  E  P  P  A  F  S  V  L  P  S  L  K  R  L  K  Q  R  I  I 730       740       750       760       770       780
          |         |         |         |         |         |
GCATCTGGACGTGGGGAATACGATGCTGTGTTTATGTCTGGGAGTGGAAGCACTATTATC

```
       790        800        810        820        830        840
        |          |          |          |          |          |
GGTATTGGTTCACCAGATCCTCCTCAATTTATATATGATGATGAAGAATACAAGGACGTG

G  I  G  S  P  D  P  P  Q  F  I  Y  D  D  E  E  Y  K  D  V 850        860        870        880        890        900
        |          |          |          |          |          |
TTCTTGTCTGAAGCAAACTTTATGACGCGTGAGGCTAATGAATGGTACAAAGAACCTGCT

F  L  S  E  A  N  F  M  T  R  E  A  N  E  W  Y  K  E  P  A 910        920        930        940        950
        |          |          |          |          |
TCTGCAAATGCTACTACCTCATCCGCCGAATCTCGCATGGATTTCCAATGA

S  A  N  A  T  T  S  S  A  E  S  R  M  D  F  Q  STOP
```

FIG. 8A (CONT'D.)

cDNA sequence and corresponding amino acid sequence of the *ychB* gene of *A. thaliana*

```
          10        20        30        40        50        60        70
           |         |         |         |         |         |         |
ATGGCAACGGCTTCTCCTCCATTTATCTCAGCTCTCAGCTTCACTCACTCTTCTTTCAAAACTTCTTCTTCT
 M  A  T  A  S  P  P  F  I  S  A  L  S  F  T  H  S  S  F  K  T  S  S  S 80        90       100       110       120       130       140
           |         |         |         |         |         |         |
TCTTCATTTTCTCCGAAGCTTCTTCGACCCCTCTTAAGCTTTTCCGTCAAAGCTTCCAGAAAGCAAGTAGAG
 S  S  F  S  P  K  L  L  R  P  L  L  S  F  S  V  K  A  S  R  K  Q  V  E 150       160       170       180       190       200       210
           |         |         |         |         |         |         }
ATAGTGTTTGATCCTGATGAGAGGCTTAATAAGATAGGTGATGATGTTGACAAAGAAGCTCCTTTGTCCAGG
 I  V  F  D  P  D  E  R  L  N  K  I  G  D  D  V  D  K  E  A  P  L  S  R 220       230       240       250       260       270       280
           |         |         |         |         |         |         |
CTTAAGCTCTTCTCACCTTGCAAGATCAATGTTTTCTTGAGGATCACCGGAAAGCGAGAAGATGGGTTTCAT
 L  K  L  F  S  P  C  K  I  N  V  F  L  R  I  T  G  K  R  E  D  G  F  H 290       300       310       320       330       340       350       360
           |         |         |         |         |         |         |         |
GATTTAGCCTCTTTGTTTCATGTGATTAGCTTAGGAGGCACTATTAAATTCTCATTGTCACCATCAAAGTCT
 D  L  A  S  L  F  H  V  I  S  L  G  G  T  I  K  F  S  L  S  P  S  K  S 370       380       390       400       410       420       430
           |         |         |         |         |         |         |
AAAGATCGTTTGTCTACTAACGTTCAAGGAGTCCCTGTTGATGGGAGAAATCTGATTATAAAAGCACTTAAC
 K  D  R  L  S  T  N  V  Q  G  V  P  V  D  G  R  N  L  I  I  K  A  L  N 440       450       460       470       480       490       500
           |         |         |         |         |         |         |
CTTTACAGGAAGAAAACTGGTAGCAACAGATTCTTCTGGATTCATTTAGATAAGAAGGTGCCTACCGGGGCT
 L  Y  R  K  K  T  G  S  N  R  F  F  W  I  H  L  D  K  K  V  P  T  G  A
```

*FIG. 8B*

```
       510        520        530        540        550        560        570
        |          |          |          |          |          |          }
GGACTCGGTGGTGGAAGTAGTAATGCTGCAACTGCACTCTGGGCGGCAAATGAGCTCAATGGAGGTCTTGTC
 G  L  G  G  G  S  S  N  A  A  T  A  L  W  A  A  N  E  L  N  G  G  L  V 580        590        600        610        620        630        640
        |          |          |          |          |          |          |
ACTGAGAACGAACTCCAGGATTGGTCAAGTGAAATTGGGTCAGATATTCCTTTCTTCTTCTCGCATGGAGCT
 T  E  N  E  L  Q  D  W  S  S  E  I  G  S  D  I  P  F  F  F  S  H  G  A 650        660        670        680        690        700        710        720
   |          |          |          |          |          |          |          |
GCCTATTGTACCGGGAGAGGTGAGATTGTCCAAGACCTTCCTCCACCTTTTCCTCTTGATCTTCCGATGGTG
 A  Y  C  T  G  R  G  E  I  V  Q  D  L  P  P  P  F  P  L  D  L  P  M  V 730        740        750        760        770        780        790
        |          |          |          |          |          |          |
CTCATAAAGCCCCGAGAAGCATGTTCCACTGCTGAAGTTTACAAACGTCTTCGTTTAGATCAGACGAGCAAT
 L  I  K  P  R  E  A  C  S  T  A  E  V  Y  K  R  L  R  L  D  Q  T  S  N 800        810        820        830        840        850        860
        |          |          |          |          |          |          }
ATTAATCCCTTGACATTACTAAAGAATGTGACCAGCAATGGTGTGTCTCAAAGCATATGCGTAAACGATTTG
 I  N  P  L  T  L  L  K  N  V  T  S  N  G  V  S  Q  S  I  C  V  N  D  L 870        880        890        900        910        920        930
        |          |          |          |          |          |          |
GAACCGCCAGCGTTTTCAGTTCTTCCATCTCTAAAACGCTTGAAGCAACGGATAATAGCATCTGGACGTGGG
 E  P  P  A  F  S  V  L  P  S  L  K  R  L  K  Q  R  I  I  A  S  G  R  G 940        950        960        970        980        990       1000
        |          |          |          |          |          |          |
GAATACGATGCTGTGTTTATGTCTGGGAGTGGAAGCACTATTATCGGTATTGGTTCACCAGATCCTCCTCAA
 E  Y  D  A  V  F  M  S  G  S  G  S  T  I  I  G  I  G  S  P  D  P  P  Q 1010       1020       1030       1040       1050       1060       1070       1080
   |          |          |          |          |          |          |          |
TTTATATATGATGATGAAGAATACAAGGACGTGTTCTTGTCTGAAGCAAACTTTATGACGCGTGAGGCTAAT
 F  I  Y  D  D  E  E  Y  K  D  V  F  L  S  E  A  N  F  M  T  R  E  A  N
```

FIG. 8B (CONT'D.)

```
          1090      1100      1110      1120      1130      1140      1150
           |         |         |         |         |         |         |
GAATGGTACAAAGAACCTGCTTCTGCAAATGCTACTACCTCATCCGCCGAATCTCGCATGGATTTCCAATGA
 E  W  Y  K  E  P  A  S  A  N  A  T  T  S  S  A  E  S  R  M  D  F  Q  -
```

FIG. 8B (CONT'D.)

ALIGNMENT OF TWO NUCLEOTIDE SEQUENCES

TM_YCHBOL.

YCHB from *L. esculentum U627773*; wild type cDNA; without putative leader sequence

TMYBOLE1.

YCHB from *L. esculentum*; Sequence adapted to *E. coli* codon usage or highly expressed genes; without putative leader sequence

```
TM_YCHBOL  - GTGGATAGAGAAGCTGGGCTTTCAAGACTCACTCTTTTTTCTCCTTGCAA  -50
TMYBOLE1   - ATGGATCGTGAAGCTGGTCTTTCACGCCTCACTCTTTTTTCTCCTTGCAA
```

──────────────────────────────── → *TM-YCHB-13*

```
TM_YCHBOL  - GATAAATGTTTTCTTGAGAATAACAAGCAAGAGGGATGACGGATATCATG  -100
TMYBOLE1   - GATTAATGTTTTCCTGCGCATCACAAGCAAACGTGATGACGGTTATCATG  -100
```

──────────→ TM-YCHB-11

```
TM_YCHBOL  - ATTTGGCGTCTCTCTTTCATGTAATTAGTCTAGGAGATAAAATAAAGTTC  -150
TMYBOLE1   - ATCTGGCGTCTCTCTTTCATGTAATTAGTCTTGGCGATAAAATTAAGTTC  -150
```

─────────→ TM-YCHB-9

```
TM_YCHBOL  - TCGCTGTCACCATCGAAGTCAAAGGATCGTTTATCTACTAATGTTGCTGG  -200
TMYBOLE1   - TCGCTGTCACCATCGAAATCAAAGGATCGTTTATCTACTAATGTTGCTGG  -200
```

─────────→ TM-YCHB-7

```
TM_YCHBOL  - AGTTCCACTCGATGAGAGAAATCTGATTATAAAGGCCCTCAATCTTTATA  -250
TMYBOLE1   - CGTTCCACTCGATGAGCGTAATCTGATTATCAAGCCCTCAATCTTTATC   -250
```

─────→ TM-YCHB-5

FIG. 8C

```
TM_YCHBOL  -  GGAAAAAGACTGGAACAGACAATTACTTTTGGATTCATCTTGATAAGAAA  -300
TMYBOLE1   -  GTAAAAAGACTGGTACAGACAATTACTTTTGGATTCATCTTGATAAGAAA  -300
                         ──────────────────────────▶  TM-YCHB-A
              ----------------------------------▶  TM-YCHB-1
              ▶  TM-YCHB-3

TM_YCHBOL  -  GTGCCTACTGGAGCTGGTCTTGGTGGTGGGAGCAGTAATGCTGCAACAAC  -350
TMYBOLE1   -  GTGCCTACTGGAGCTGGTCTTGGTGGTGGGAGCAGTAATGCTGCAACAAC  -350

TM_YCHBOL  -  TCTGTGGGCAGCAAATCAATTCAGTGGTTGTGTTGCCACTGAAAAGGAGC  -400
TMYBOLE1   -  TCTGTGGGCAGCAAATCAATTCAGTGGTTGTGTTGCCACTGAAAAGGAGC  -400

TM_YCHBOL  -  TCCAAGAGTGGTCTGGTGAGATTGGTTCTGATATTCCTTTCTTCTTCTCT  -450
TMYBOLE1   -  TCCAAGAGTGGTCTGGTGAGATTGGTTCTGATATTCCTTTCTTCTTCTCT  -450

TM_YCHBOL  -  CATGGAGCAGCCTACTGTACGGGTAGGGGTGAGGTTGTTCAGGATATCCC  -500
TMYBOLE1   -  CATGGAGCAGCCTACTGTACGGGTAGGGGTGAGGTTGTTCAGGATATCCC  -500

TM_YCHBOL  -  GTCACCCATACCATTTGACATTCCAATGGTCCTCATAAAGCCTCAACAGG  -550
TMYBOLE1   -  GTCACCCATACCATTTGACATTCCAATGGTCCTCATAAAGCCTCAACAGG  -550

TM_YCHBOL  -  CATGCTCCACTGCTGAAGTTTACAAGCGTTTTCAGTTGGATCTGTCTAGT  -600
TMYBOLE1   -  CATGCTCCACTGCTGAAGTTTACAAGCGTTTTCAGTTGGATCTGTCTAGT  -600

TM_YCHBOL  -  AAGGTTGATCCCTTGAGCTTACTGGAGAAAATCTCAACTAGTGGAATATC  -650
TMYBOLE1   -  AAGGTTGATCCCTTGAGCTTACTGGAGAAAATCTCAACTAGTGGAATATC  -650

TM_YCHBOL  -  TCAAGATGTGTGTGTCAATGATTTAGAACCTCCTGCCTTTGAAGTTCTTC  -700
TMYBOLE1   -  TCAAGATGTGTGTGTCAATGATTTAGAACCTCCTGCCTTTGAAGTTCTTC  -700
              TM-YCHB-B  ◀──────────────────
              TM-YCHB-2  ◀------------------

TM_YCHBOL  -  CATCTCTTAAAAGGTTAAAACAACGAGTAATTGCTGCTGGCCGAGGACAA  -750
TMYBOLE1   -  CATCTCTTAAACGTTTAAAACAACGTGTAATTGCTGCTGGCCGCGGTCAA  -750
              ─────────
              ----------------------------------
                    TM-YCHB-4  ◀····················

TM_YCHBOL  -  TATGATGCAGTCTTCATGTCTGGAAGTGGAAGCACAATAGTAGGGGTTGG  -800
TMYBOLE1   -  TATGATGCAGTCTTCATGTCTGGTAGTGGCAGCACAATCGTAGGTGTTGG  -800
              ------------------------------
              TM-YCHB-6  ◀──────────────────────
```

FIG. 8C (CONT'D.)

```
TM_YCHBOL  -  CTCTCCAGATCCACCACAATTTGTCTATGATGATGAAGAATACAAGGATG  -850
TMYBOLE1   -  CTCTCCAGATCCGCCACAATTTGTCTATGATGACGAAGAGTACAAAGATG  -850
```

TM-YCHB-8  ◄------------------------------------
                              TM-YCHB-10   ◄-·····

```
TM_YCHBOL  -  TCTTCTTGTCAGAAGCAAGTTTCATCACTCGACCAGCCAACGAGTGGTAT  -900
TMYBOLE1   -  TCTTCTTGTCAGAAGCAAGTTTCATCACTCGTCCAGCCAACGAGTGGTAT  -900
```
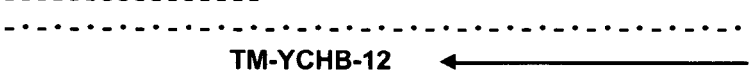
                      TM-YCHB-12   ◄————————————

```
TM_YCHBOL  -  GTTGAACCTGTTTCAGGTAGCACTATTGGTGATCAACCTGAGTTCTCTAC  -950
TMYBOLE1   -  GTTGAACCTGTTTCAGGTAGCACTATTGGTGATCAACCTGAGTTCTCTAC  -950
```

TM-YCHB-14  ◄----------------------------

```
TM_YCHBOL  -  ATCTTTTGACATGTCTTAA  -969
TMYBOLE1   -  ATCTTTTGACATGTCTTAA  -969
```

Identity: 927 (95.67%)

FIG. 8C (CONT'D.)

Nucleotide sequence of the plasmid pNCO113

```
ID  PNCO113         PRELIMINARY;    DNA;       3420 BP.
DE  EXPRESSIONPLASMID PNCOII3 (AUS PDS56-RII,NCO)
OS  ESCHERICHIA COLI
SQ  SEQUENCE   3420 BP;   888 A;   816 C;   828 G;   888 T;   0 OTHER;
    ctcgagaaat cataaaaaat ttatttgctt tgtgagcgga taacaattat aatagattca
    attgtgagcg gataacaatt tcacacagaa ttcattaaag aggagaaatt aaccatggga
    ggatccgtcg acctgcagcc aagcttaatt agctgagctt ggactcctgt tgatagatcc
    agtaatgacc tcagaactcc atctggattt gttcagaacg ctcggttgcc gccgggcgtt
    ttttattggt gagaatccaa gctagcttgg cgagattttc aggagctaag gaagctaaaa
    tggagaaaaa aatcactgga tataccaccg ttgatatatc ccaatggcat cgtaaagaac
    attttgaggc atttcagtca gttgctcaat gtacctataa ccagaccgtt cagctggata
    ttacggcctt tttaaagacc gtaaagaaaa ataagcacaa gttttatccg gcctttattc
    acattcttgc ccgcctgatg aatgctcatc cggaatttcg tatggcaatg aaagacggtg
    agctggtgat atgggatagt gttcacccct tgttacaccg tttccatgag caaactgaaa
    cgttttcatc gctctggagt gaataccacg acgatttccg gcagtttcta cacatatatt
    cgcaagatgt ggcgtgttac ggtgaaaacc tggcctattt ccctaaaggg tttattgaga
    atatgttttt cgtctcagcc aatccctggg tgagtttcac cagttttgat ttaaacgtgg
    ccaatatgga caacttcttc gcccccgttt tcaccatgca tgggcaaata ttatacgcaa
    ggcgacaagg tgctgatgcc gctggcgatt caggttcatc atgccgtctg tgatggcttc
    catgtcggca gaatgcttaa tgaattacaa cagtactgcg atgagtggca gggcggggcg
    taatttttt aaggcagtta ttggtgccct taaacgcctg gggtaatgac tctctagctt
    gaggcatcaa ataaaacgaa aggctcagtc gaaagactgg gcctttcgtt ttatctgttg
    tttgtcggtg aacgctctcc tgagtaggac aaatccgccg ctctagagct gcctcgcgcg
    tttcggtgat gacggtgaaa acctctgaca catgcagctc ccggagacgg tcacagcttg
    tctgtaagcg gatgccggga gcagacaagc ccgtcagggc gcgtcagcgg gtgttggcgg
    gtgtcggggc gcagccatga cccagtcacg tagcgatagc ggagtgtata ctggcttaac
    tatgcggcat cagagcagat tgtactgaga gtgcaccata tgcggtgtga ataccgcac
    agatgcgtaa ggagaaaata ccgcatcagg cgctcttccg cttcctcgct cactgactcg
    ctgcgctcgg tctgtcggct gcggcgagcg gtatcagctc actcaaaggc ggtaatacgg
    ttatccacag aatcagggga taacgcagga agaacatgt gagcaaaagg ccagcaaaag
    gccaggaacc gtaaaaaggc cgcgttgctg cgttttttcc ataggctccg ccccctgac
    gagcatcaca aaaatcgacg ctcaagtcag aggtggcgaa acccgacagg actataaaga
    taccaggcgt ttccccctgg aagctccctc gtgcgctctc ctgttccgac cctgccgctt
    accggatacc tgtccgcctt tctcccttcg ggaagcgtgg cgctttctca atgctcacgc
    tgtaggtatc tcagttcggt gtaggtcgtt cgctccaagc tgggctgtgt gcacgaaccc
    cccgttcagc ccgaccgctg cgccttatcc ggtaactatc gtcttgagtc aacccggta
    agacacgact tatcgccact ggcagcagcc actggtaaca ggattagcag agcgaggtat
    gtaggcggtg ctacagagtt cttgaagtgg tggcctaact acggctacac tagaaggaca
    gtatttggta tctgcgctct gctgaagcca gttaccttcg gaaaagagt tggtagctct
    tgatccggca aacaaaccac cgctggtagc ggtggttttt tgtttgcaa gcagcagatt
    acgcgcagaa aaaaggatc tcaagaagat cctttgatct tttctacggg gtctgacgct
    cagtggaacg aaaactcacg ttaagggatt ttggtcatga gattatcaaa aaggatcttc
    acctagatcc ttttaaatta aaaatgaagt tttaaatcaa tctaaagtat atatgagtaa
    acttggtctg acagttacca atgcttaatc agtgaggcac ctatctcagc gatctgtcta
```

FIG. 9A

```
tttcgttcat ccatagctgc ctgactcccc gtcgtgtaga taactacgat acgggagggc
ttaccatctg gccccagtgc tgcaatgata ccgcgagacc cacgctcacc ggctccagat
ttatcagcaa taaaccagcc agccggaagg gccgagcgca gaagtggtcc tgcaacttta
tccgcctcca tccagtctat taattgttgc cgggaagcta gagtaagtag ttcgccagtt
aatagtttgc gcaacgttgt tgccattgct acaggcatcg tggtgtcacg ctcgtcgttt
ggtatggctt cattcagctc cggttcccaa cgatcaaggc gagttacatg atcccccatg
ttgtgcaaaa aagcggttag ctccttcggt cctccgatcg ttgtcagaag taagttggcc
gcagtgttat cactcatggt tatggcagca ctgcataatt ctcttactgt catgccatcc
gtaagatgct tttctgtgac tggtgagtac tcaaccaagt cattctgaga atagtgtatg
cggcgaccga gttgctcttg cccggcgtca atacgggata ataccgcgcc acatagcaga
actttaaaag tgctcatcat tggaaaacgt tcttcggggc gaaaactctc aaggatctta
ccgctgttga gatccagttc gatgtaaccc actcgtgcac ccaactgatc ttcagcatct
tttactttca ccagcgtttc tgggtgagca aaaacaggaa ggcaaaatgc cgcaaaaaag
ggaataaggg cgacacggaa atgttgaata ctcatactct ccttttcca atattattga
agcatttatc agggttattg tctcatgagc ggatacatat ttgaatgtat ttagaaaaat
aaacaaatag gggttccgcg cacatttccc cgaaaagtgc cacctgacgt ctaagaaacc
attattatca tgacattaac ctataaaaat aggcgtatca cgaggccctt tcgtcttcac
//
```

FIG. 9A (CONT'D.)

Nucleotide sequence of the plasmid pNCO-SB-H6-ACYC184

```
ID  PNCOBH6ACYC         PRELIMINARY;   DNA;    4484 BP.
SQ  SEQUENCE   4484 BP;   1131 A;   1127 C;   1069 G;    1157 T;
    ctcgagaaat cataaaaaat ttatttgctt tgtgagcgga taacaattat aatagattca
    attgtgagcg gataacaatt tcacacagaa ttcattaaag aggagaaatt aaccatgcac
    caccaccacc accacgcgtc catggccgcg gcaaagccgt ttttccatag gctccgcccc
    cctgacaagc atcacgaaat ctgacgctca aatcagtggt ggcgaaaccc gacaggacta
    taaagatacc aggcgtttcc ccctggcggc tccctcgtgc gctctcctgt tcctgccttt
    cggtttaccg gtgtcattcc gctgttatgg ccgcgtttgt ctcattccac gcctgacact
    cagttccggg taggcagttc gctccaagct ggactgtatg cacgaacccc ccgttcagtc
    cgaccgctgc gccttatccg gtaactatcg tcttgagtcc aacccggaaa gacatgcaaa
    agcaccactg gcagcagcca ctggtaattg atttagagga gttagtcttg aagtcatgcg
    ccggttaagg ctaaactgaa aggacaagtt ttggtgactg cgctcctcca agccagttac
    ctcggttcaa agagttggta gctcagagaa ccttcgaaaa accgccctgc aaggcggttt
    tttcgttttc agagcaagag attacgcgca gaccaaaacg atctcaagaa gatcatctta
    ttaatcagat aaaatatttc tagatttcag tgcaatttat ctcttcaaat gtagcacctg
    aagtcagccc catacgatat aagttgtaat tctcatgttt gacagcttat catcgataag
    ctttaatgcg gtagtttatc acagttaaat gctaacgca gtcaggcacc gtgtatgaaa
    tctaacaatg cgctcatcgt catcctcggc accgtcaccc tggatgctgt aggcataggc
    ttggttatgc cggtactgcc gggcctcttg cgggatatcg tccattccga cagcatcgcc
    agtcactatg gcgtgctgct agcgctatat gcgttgatgc aatttctatg cgcacccgtt
    ctcggagcac tgtccgaccg ctttggccgc cgcccagtcc tgctcgcttc gctacttgga
    gccactatcg actacgcgat catggcgacc acaccgtcc tgtgggatcc gtcgacctgc
    agccaagctt aattagctga gcttggactc ctgttgatag atccagtaat gacctcagaa
    ctccatctgg atttgttcag aacgctcggt tgccgccggg cgttttttat tggtgagaat
    ccaagctagc ttggcgagat tttcaggagc taaggaagct aaaatggaga aaaaaatcac
    tggatatacc accgttgata tatcccaatg gcatcgtaaa gaacattttg aggcatttca
    gtcagttgct caatgtacct ataaccagac cgttcagctg gatattacgg cctttttaaa
    gaccgtaaag aaaaataagc acaagtttta tccggccttt attcacattc ttgcccgcct
    gatgaatgct catccggaat tcgtatggc aatgaaagac ggtgagctgg tgatatggga
    tagtgttcac ccttgttaca ccgttttcca tgagcaaact gaaacgtttt catcgctctg
    gagtgaatac cacgacgatt tccggcagtt tctacacata tattcgcaag atgtggcgtg
    ttacggtgaa aacctggcct atttccctaa agggtttatt gagaatatgt tttcgtctc
    agccaatccc tgggtgagtt tcaccagttt tgatttaaac gtggccaata tggacaactt
    cttcgccccc gttttcacca tgcatggca aatattatac gcaaggcgac aaggtgctga
    tgccgctggc gattcaggtt catcatgccg tctgtgatgg cttccatgtc ggcagaatgc
    ttaatgaatt acaacagtac tgcgatgagt ggcagggcgg ggcgtaattt ttttaaggca
    gttattggtg cccttaaacg cctggggtaa tgactctcta gcttgaggca tcaaataaaa
    cgaaaggctc agtcgaaaga ctgggccttt cgttttatct gttgtttgtc ggtgaacgct
    ctcctgagta ggacaaatcc gccgctctag agctgcctcg cgcgtttcgg tgatgacggt
    gaaaacctct gacacatgca gctcccggag acgtcacag cttgtctgta gcggatgcc
    gggagcagac aagcccgtca gggcgcgtca gcgggtgttg gcgggtgtcg gggcgcagcc
    atgacccagt cacgtagcga tagcggagtg tatactggct taactatgcg gcatcagagc
    agattgtact gagagtgcac catatgcggt gtgaaatacc gcacagatgc gtaaggagaa
    aataccgcat caggcgctct tccgcttcct cgctcactga ctcgctgcgc tcggtctgtc
```

FIG. 9B

```
ggctgcggcg agcggtatca gctcactcaa aggcggtaat acggttatcc acagaatcag
gggataacgc aggaaagaac atgtgagcaa aaggccagca aaaggccagg aaccgtaaaa
aggccgcgtt gctggcgttt ttccataggc tccgccccc tgacgagcat cacaaaaatc
gacgctcaag tcagaggtgg cgaaacccga caggactata aagataccag gcgtttcccc
ctggaagctc cctcgtgcgc tctcctgttc cgaccctgcc gcttaccgga tacctgtccg
cctttctccc ttcgggaagc gtggcgcttt ctcaatgctc acgctgtagg tatctcagtt
cggtgtaggt cgttcgctcc aagctgggct gtgtgcacga accccccgtt cagcccgacc
gctgcgcctt atccggtaac tatcgtcttg agtccaaccc ggtaagacac gacttatcgc
cactggcagc agccactggt aacaggatta gcagagcgag gtatgtaggc ggtgctacag
agttcttgaa gtggtggcct aactacggct acactagaag gacagtattt ggtatctgcg
ctctgctgaa gccagttacc ttcggaaaaa gagttggtag ctcttgatcc ggcaaacaaa
ccaccgctgg tagcggtggt ttttttgttt gcaagcagca gattacgcgc agaaaaaaag
gatctcaaga agatcctttg atcttttcta cggggtctga cgctcagtgg aacgaaaact
cacgttaagg gattttggtc atgagattat caaaaaggat cttcacctag atccttttaa
attaaaaatg aagttttaaa tcaatctaaa gtatatatga gtaaacttgg tctgacagtt
accaatgctt aatcagtgag gcacctatct cagcgatctg tctatttcgt tcatccatag
ctgcctgact ccccgtcgtg tagataacta cgatacggga gggcttacca tctggcccca
gtgctgcaat gataccgcga gacccacgct caccggctcc agatttatca gcaataaacc
agccagccgg aagggccgag cgcagaagtg gtcctgcaac tttatccgcc tccatccagt
ctattaattg ttgccgggaa gctagagtaa gtagttcgcc agttaatagt ttgcgcaacg
ttgttgccat tgctacaggc atcgtggtgt cacgctcgtc gtttggtatg gcttcattca
gctccggttc ccaacgatca aggcgagtta catgatcccc catgttgtgc aaaaaagcgg
ttagctcctt cggtcctccg atcgttgtca gaagtaagtt ggccgcagtg ttatcactca
tggttatggc agcactgcat aattctctta ctgtcatgcc atccgtaaga tgcttttctg
tgactggtga gtactcaacc aagtcattct gagaatagtg tatgcggcga ccgagttgct
cttgcccggc gtcaatacgg gataataccg cgccacatag cagaacttta aaagtgctca
tcattggaaa acgttcttcg ggcgaaaac tctcaaggat cttaccgctg ttgagatcca
gttcgatgta acccactcgt gcacccaact gatcttcagc atcttttact ttcaccagcg
tttctgggtg agcaaaaaca ggaaggcaaa atgccgcaaa aaagggaata agggcgacac
ggaaatgttg aatactcata ctcttccttt tcaatatta ttgaagcatt tatcagggtt
attgtctcat gagcggatac atatttgaat gtatttagaa aaataaacaa ataggggttc
cgcgcacatt tccccgaaaa gtgccacctg acgtctaaga aaccattatt atcatgacat
taacctataa aaataggcgt atcacgaggc cctttcgtct tcac
//
```

FIG. 9B (CONT'D.)

cDNA sequence and corresponding amino acid sequence of the *ygbB* gene of *P. falciparum*

```
          10        20        30        40        50        60        70
          |         |         |         |         |         |         |
ATGTTTTTAAAAGGATACACCTCAAATGTGGTACTAATTATATTAACATTTTTCATTCTACTAACAAAAGAA
 M  F  L  K  G  Y  T  S  N  V  V  L  I  I  L  T  F  F  I  L  L  T  K  E 80        90       100       110       120       130       140
          |         |         |         |         |         |         |
GAAAAAAATATAAAAAATAATATCTCTGGATATTGTTTTTTGAATTTTGGATTAAAAAAAAATGCAATAATA
 E  K  N  I  K  N  N  I  S  G  Y  C  F  L  N  F  G  L  K  K  N  A  I  I 150       160       170       180       190       200       210
          |         |         |         |         |         |         }
AAAAAAAGAGAAAAACAAAATTTGAAATTATTTTGTTATAATGGTATAAGAATAGGTCAAGGTTATGATATC
 K  K  R  E  K  Q  N  L  K  L  F  C  Y  N  G  I  R  I  G  Q  G  Y  D  I 220       230       240       250       260       270       280
          |         |         |         |         |         |         |
CACAAAATAAAAGTTTTAGATGAAGAATATAATACATATGCAAATAATGATTTTAATAAAAATGAACAATCT
 H  K  I  K  V  L  D  E  E  Y  N  T  Y  A  N  N  D  F  N  K  N  E  Q  S 290       300       310       320       330       340       350       360
          |         |         |         |         |         |         |         |
TTTAAAACCTTAACCTTAGGAGGAGTTAAAATAAATAATGTTTTAGTTTTATCACATAGTGATGGTGATATA
 F  K  T  L  T  L  G  G  V  K  I  N  N  V  L  V  L  S  H  S  D  G  D  I 370       380       390       400       410       420       430
          |         |         |         |         |         |         |
ATATATCATTCGATAGTTGATTCAATTTTAGGTGCCTTAGGTTCTTTAGACATAGGAACCTTATTTCCTGAT
 I  Y  H  S  I  V  D  S  I  L  G  A  L  G  S  L  D  I  G  T  L  F  P  D 440       450       460       470       480       490       500
          |         |         |         |         |         |         |
AAAGATGAAAAAAATAAAAATAAAAACTCGGCTATATTCTTAAGATATGCTAGACTTTTAATATATAAAAAA
 K  D  E  K  N  K  N  K  N  S  A  I  F  L  R  Y  A  R  L  L  I  Y  K  K
```

FIG. 10

```
       510         520         530         540         550         560         570
        |           |           |           |           |           |           |
AATTATGATATTGGGAACGTGGATATTAATGTAATAGCACAAGTTCCCAAAATAAGCAACATCAGAAAAAAT
  N  Y  D  I  G  N  V  D  I  N  V  I  A  Q  V  P  K  I  S  N  I  R  K  N 580         590         600         610         620         630         640
        |           |           |           |           |           |           |
ATTATAAAAAATATATCGACAGTGTTAAATATTGACGAGTCGCAAATATCTGTTAAAGGAAAAACTCATGAG
  I  I  K  N  I  S  T  V  L  N  I  D  E  S  Q  I  S  V  K  G  K  T  H  E 650         660         670         680         690         700         710         720
   |           |           |           |           |           |           |           |
AAATTAGGAGTAATTGGTGAGAAAAAAGCAATAGAATGCTTTGCGAATATTTTGTTAATACCTAAAAATTCA
  K  L  G  V  I  G  E  K  K  A  I  E  C  F  A  N  I  L  L  I  P  K  N  S 730         740         750
        |           |           |
TAATTTCTTTTTTTTTTTTTTTTAATGTAA
  -  F  L  F  F  F  F  L  M  -
```

ISOPRENOID BIOSYNTHESIS

RELATED APPLICATIONS

This application is a divisional application of U.S. application Ser. No. 10/048,874, having a filing date of Sep. 23, 2002, now U.S. Pat. No. 7,122,331, which is a 35 U.S.C. § 371 national phase application of International PCT Application Ser. No. PCT/EP00/07548 filed Aug. 3, 2000, which claims priority to German Patent Application No. 100 20 996.3, filed Apr. 28, 2000, German Patent Application No. 199 53 309.1, filed Nov. 5, 1999, German Patent Application No. 199 48 887.8, filed Oct. 11, 1999, German Patent Application No. 199 45 174.5, filed Sep. 21, 1999, German Patent Application No. 199 45 175.3, filed Sep. 21, 1999, and German Patent Application No. 199 36 663.2, filed Aug. 4, 1999. The contents of these applications are hereby incorporated by reference as if recited in full herein.

FIELD OF THE INVENTION

The present invention relates to isoprenoid biosynthesis and notably to genes, enzymes and intermediates involved in isoprenoid biosynthesis as well as to inhibitors, notably herbicides, for enzymes in the biosynthesis of isoprenoids. More specifically, the present invention relates to screening methods for detecting such inhibitors, and to enzymatically active proteins for performing said methods as well as purified isolated DNA coding for such proteins. Moreover, the present invention relates to novel inhibitors detectable by said screening methods as well as compositions and processes for inhibiting the synthesis of isoprenoids and for controlling the growth of organisms based on said inhibitors. The invention relates also to the development of inhibitor-resistant plant enzymes and plants, plant tissues, plant seeds and plant cells.

BACKGROUND OF THE INVENTION

By the classical research of Bloch, Cornforth, Lynen and coworkers, isopentenyl pyrophosphate (IPP) and dimethylallyl pyrophosphate (DMAPP) have become established as key intermediates in the biosynthesis of isoprenoids via mevalonic acid.

Bacteria, plants and the protist *Plasmodium falciparum* synthesize isoprenoids by an alternative pathway via 1-deoxy-D-xylulose 5-phosphate. This non-mevalonate pathway has so far only been partially explored (FIG. 1), but its absence in animals makes it an ideal target for pesticidal or medical purposes. Moreover, the idiosyncratic nature of the reactions in this pathway reduces the risk of cross-inhibitions with other, notably mammalian enzymes. For a better understanding of these aspects of the invention, the pathway shall be briefly explained. It begins with a condensation of pyruvate (1) with glycerolaldehyde 3-phosphate (2) to 1-deoxy-D-xylulose 5-phosphate (DXP) (3). Subsequently, DXP is converted to 2C-methyl-D-erythritol 4-phosphate (4) by a two-step reaction comprising a rearrangement and a reduction. The subsequent steps to isoprenoids have so far not been explored, but it may be assumed that the pathway includes intermediates of the type IPP and DMAPP. In any event, this pathway and notably these subsequent enzymatic steps are here determined to be ideal targets in screening chemical libraries for inhibitors.

The non-mevalonate pathway (alternative isoprenoid pathway), with which the present invention is concerned, generates the basic isoprenoid $C_5$-compounds (IPP and/or DMAPP or an equivalent compound) from which all higher isoprenoids derive by downstream biosynthetic pathways. Higher isoprenoids are called terpenoids. Therefore, any inhibitor of an enzyme in the non-mevalonate pathway is at the same time an inhibitor of all subsequent isoprenoid pathways, i.e. an inhibitor of the terpenoid pathways.

Wherever a phosphorylated compound or a carboxylic acid compound is mentioned it may exist as a free acid or as a salt with at least one proton replaced by ammonium or a metal ion or an organic cation. The metal ion may be an alkali metal ion or an alkaline earth metal ion. The organic cation may be derived from an amine. It may be a sulfonium ion, a guanidinium ion or a heteroaromatic ion. Such a phosphorylated compound, when in an aqueous solution, will exist in an equilibrium dissociation state.

SUMMARY OF THE INVENTION

It is a first object of the invention to provide functional enzymes which operate in the alternative isoprenoid pathway downstream from 2C-methyl-D-erythritol 4-phosphate.

It is a further object of the invention to provide purified isolated nucleic acid, notably DNA coding for an enzyme, or a vector containing such DNA.

It is another object of the invention to provide methods for screening a chemical library for inhibitors of an enzyme in the alternative isoprenoid pathway downstream from 2C-methyl-D-erythritol 4-phosphate.

It is a further object of the invention to provide intermediates in the alternative isoprenoid pathway, which are the products of the enzymes of the invention, and to provide methods of preparation of said intermediates. It is a further object of the invention to provide a use of said intermediates as substrates for screening for inhibition of the alternative isoprenoid pathway.

It is a further object of the invention to provide a method for identifying inhibitor-resistant variants of an enzyme in the alternative isoprenoid pathway as well as nucleic acids and DNA vectors encoding said variants as well as cells and seeds of plants harboring such vector, as well as a method for conferring inhibitor resistance to plants and a corresponding method of weed control.

It is a further object of the invention to provide novel inhibitors of enzymes in the alternative isoprenoid biosynthesis downstream from 2C-methyl-D-erythritol 4-phosphate, compositions of such inhibitors and methods of in vivo inhibiting the biosynthesis of isoprenoids.

It is a further object of the invention to provide an economical process for efficiently producing the intermediates from readily available starting materials.

The process can be used for producing the desired product with any desired isotopic labeling.

With the findings of the invention an overall pattern of the non-mevalonate alternative isoprenoid pathway emerges which consists of three segments. The first (previously known) segment up to 2C-methyl-D-erythritol 4-phosphate concerns the formation of the isoprenoid carbon skeleton. The present invention is concerned with the second segment in which all three steps are phosphorylation steps to establish the form of activation as 2,4-cyclopyrophosphate that is required for the subsequent segment. This establishes the functional coherence and unity of the invention. The third segment concerns unknown reductive and eliminative steps for the formation of IPP, DMAPP or equivalent compounds.

BRIEF DESCRIPTION OF THE DRAWINGS

FIG. 4 shows an alignment of YgbP and YgbB of various organisms.

FIG. 5 shows an alignment of YgbB of various organisms.

FIG. 6 shows an alignment of the amino acid sequence of the cloned cDNA of ygbP of *A. thaliana* (without leader sequence, SEQ ID NO:1) and the amino acid sequence of the YgbP gene product found in the database (SEQ ID NO:2, see Table 1).

FIG. 7A shows the cDNA sequence (SEQ ID NO:3) and the corresponding amino acid sequence (SEQ ID NO:4) of ygbP of *A. thaliana* (without leader sequence).

FIG. 7B shows the cDNA sequence (SEQ ID NO:5) and the corresponding amino acid sequence (SEQ ID NO:6) of ygbP of *A. thaliana* (with leader sequence).

FIG. 8A shows the DNA sequence (SEQ ID NO:7) and corresponding amino acid sequence (SEQ ID NO:8) of ychB of *A. thaliana* (without leader sequence).

FIG. 8B shows the cDNA sequence (SEQ ID NO:9) and corresponding amino acid sequence (SEQ ID NO:10) of ychB of *A. thaliana* (with leader sequence).

FIG. 8C shows an alignment of the wild type nucleotide sequence of ychB of *L. esculentum* (without leader sequence, SEQ ID NO:11) and of a nucleotide sequence of ychB of *L. esculentum* adapted to *E. coli* codon usage for highly expressed genes (without leader sequence, SEQ ID NO:12).

FIG. 9A shows the nucleotide sequence of the plasmid pNCO113 (SEQ ID NO:13).

FIG. 9B shows the nucleotide sequence of the plasmid pNCO-SB-H6-ACYC184 (SEQ ID NO:14).

FIG. 10 shows the cDNA sequence (SEQ ID NO:15) and corresponding amino acid sequence (SEQ ID NO:16) of ygbB of *P. falciparum*.

DETAILED DESCRIPTION OF THE INVENTION

The Bisosynthetic Pathway

Figure 1:
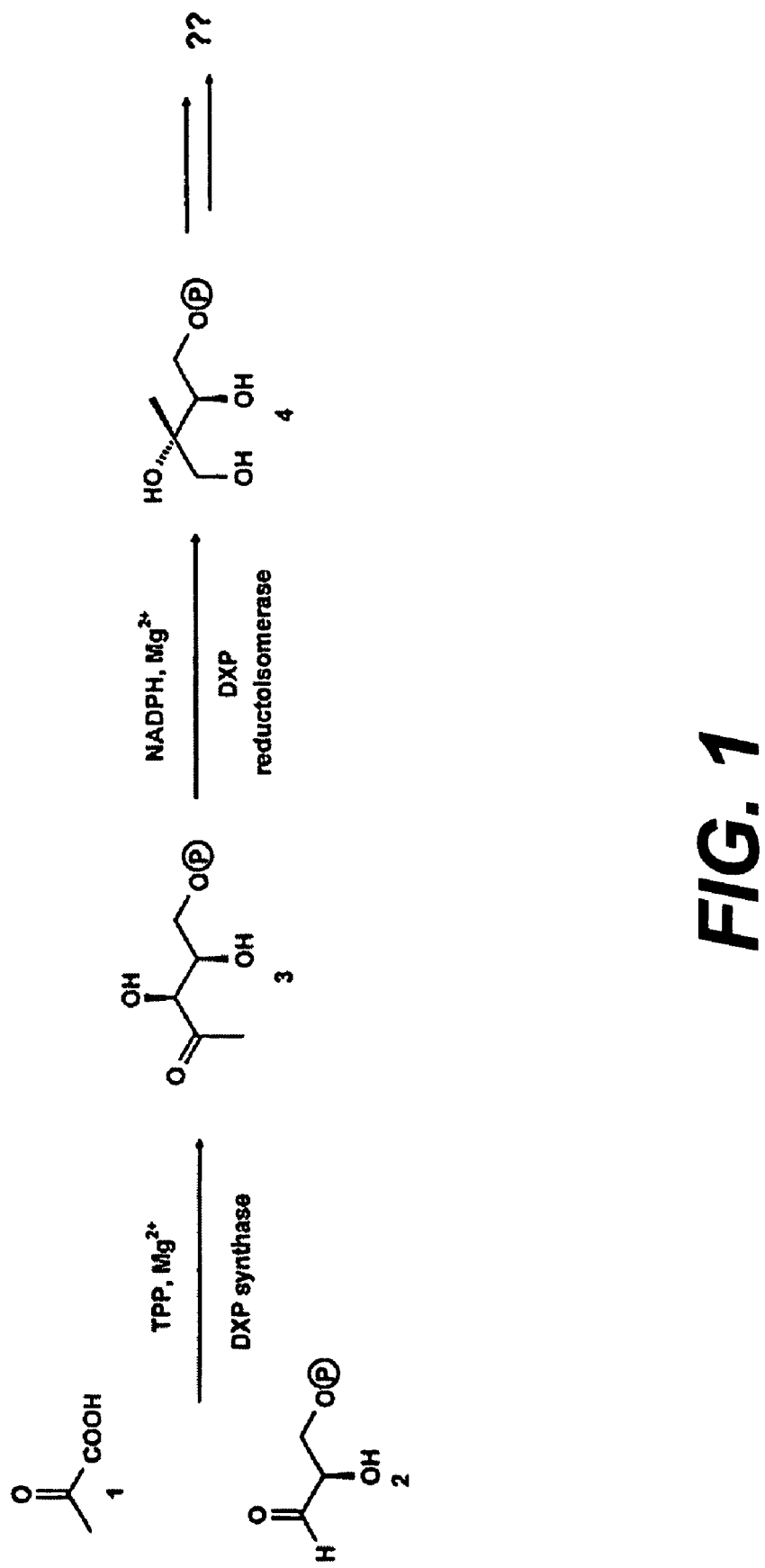
FIG. 1 shows the previously established non-mevalonate pathway.
Figure 2:
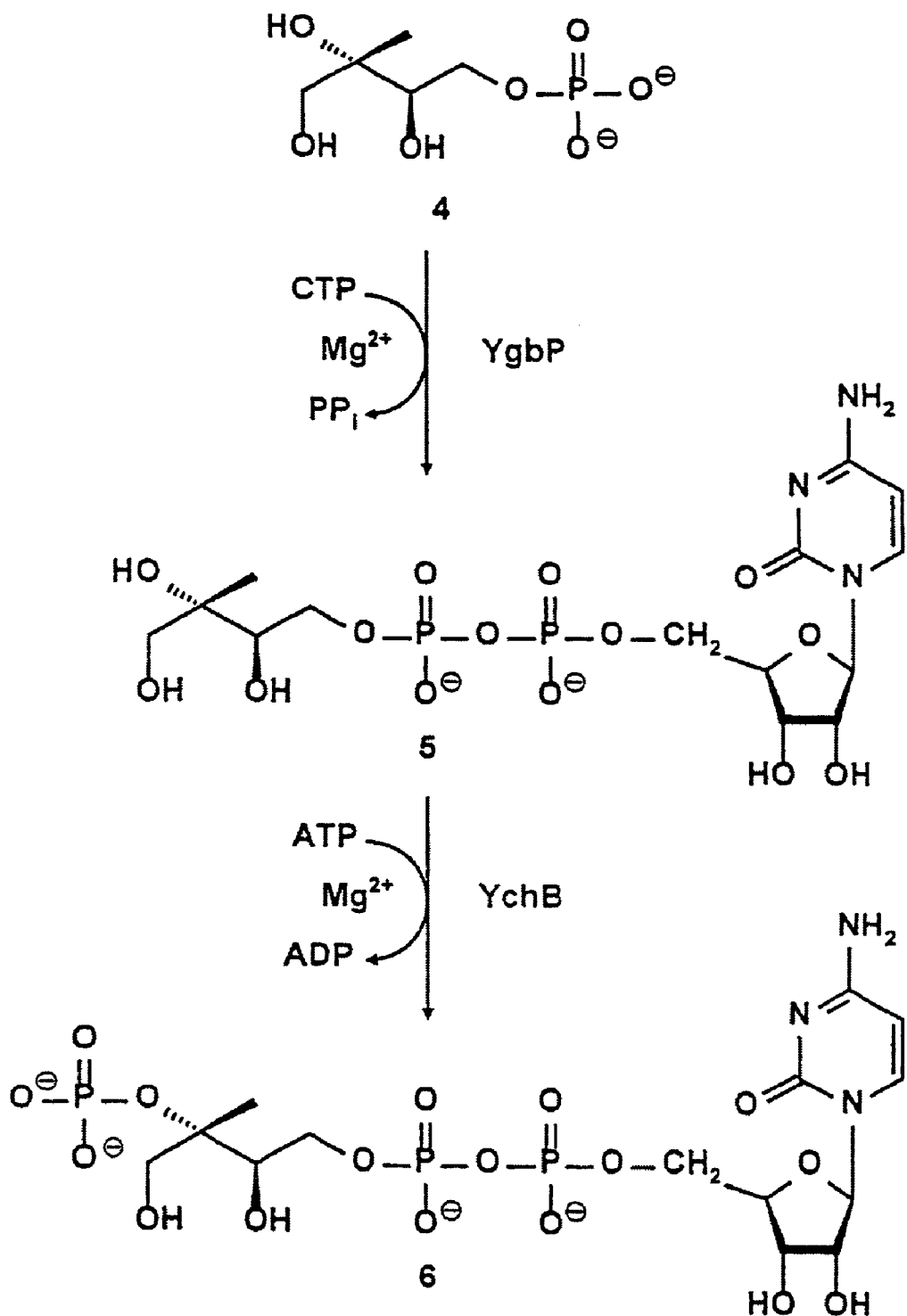
FIG. 2 shows the enzymatic steps, due to YgbP and YchB, downstream from the previously established non-mevalonate pathway of FIG. 1.

We have surprisingly discovered that the next intermediate downstream from 2C-methyl-D-erythritol 4-phosphate is 4-diphosphocytidyl-2C-methyl-D-erythritol (5) (FIG. 2). Based on this finding, we have established that this intermediate is biosynthesized from 2C-methyl-D-erythritol 4-phosphate with CTP, and we have also produced an *E. coli* protein in an enzymatically functional form for this conversion. This enzyme is called 4-diphosphocytidyl-2C-methyl-D-erythritol synthase. The amino acid sequence of this enzyme and the corresponding DNA sequence were contained as unannotated open reading frame in the genome of *E. coli* under the designation ygbP (accession number gb AE000358). The DNA corresponding to this ORF was isolated and cloned into a high copy expression vector and with this vector construct *E. coli* cells were transformed. Surprisingly in 12 tested recombinant *E. coli* clones the corresponding gene product was expressed in soluble form to a level of about 10% of the total soluble cell fraction. This was judged by SDS-PAGE. Moreover, cell extracts of 4 tested recombinant clones showed activity according to the formation of 4-diphosphocytidyl-2C-methyl-D-erythritol from CTP and 2C-methyl-D-erythritol 4-phosphate. This specific activity was at least 100 times higher than in cell extracts of *E. coli* wild type cells.

We further have established the presence of sequences highly homologous to ygbP in a number of bacteria, in *Arabidopsis thaliana* as well as in *Plasmodium falciparum* by performing a blast search in GenBank as well as in the database of completed and uncompleted genomes. We have thus opened an avenue for the expression of functional forms of the protein YgbP in any of these or other organisms. Notably, cDNA of the corresponding open reading frame (ORF) of *Arabidopsis thaliana* (see Table 1) was isolated and cloned into a high copy expression vector and the corresponding gene product was expressed heterologously in *E. coli* in enzymatically active form.

We further have established that in bacteria, ygbP is usually contained in an operon in which it is closely followed by an open reading frame (designated ygbB in *E. coli*) with a narrow gap or even an overlap. We further have established that these proteins YgbP and YgbB are fused in some bacteria to form a bifunctional enzyme. In agreement with these findings, we determined that YgbB is an enzyme active in the alternative biosynthesis of terpenoids downstream from YgbP and that it converts 4-diphosphocytidyl-2C-methyl-D-erythritol. The DNA corresponding to the ORF ygbB in the genome of *E. coli* was isolated and cloned into a high copy expression vector and the corresponding gene product was expressed in *E. coli* in enzymatically active form.

The designations of YgbP and YgbB in the *E. coli* genome are used herein also for the homologous enzymes in other organisms. A set of open reading frames homologous to ygbB and ygbP is listed in Table 1. An alignment of the amino acid sequences of the corresponding gene products is shown in FIG. 4. The alignment was constructed with the Pileup program using the default setting (Genetic Computer Group, Madison, Wis.) and it was edited with the GeneDoc program (Pittsburgh Supercomputing Center, Pittsburgh, Pa.). Organism names are abbreviated at the left side of the alignment as shown in Table 1. Amino acid residues are written in IUPAC one letter code and are numbered consecutively for reference purposes at the top of each alignment page. The YgbP functional domain extends from residue 1 to residue about 360 and the YgbB functional domain extends from residue about 360 to the end. Each accumulated total number of amino acids is given in each line in the right column of the alignment. Gaps in the alignment are symbolized by a dash (-). The symbols < and > indicate a fragment. The symbol \\ denotes a C-terminus. The symbol * denotes a stop codon due to a frame shift. In the case of a fragment, the sequences are missing at the beginning and/or end due to the fact that they are ignored by the Blast program for retrieving the sequences from the database of unfinished genomes. They are readily obtained from the corresponding nucleotide sequence, proceeding forward until the initiator codon ATG (or GTG or CTG) is encountered and backward until a stop codon is encountered.

TABLE 1

Occurence of orthologous sequences to ygbP and ygbB in various organisms

| organism | abbreviation[b] | corresponding ygbP (SEQ ID NO:) accession or Contig number[a], basepairs | corresponding ygbB (SEQ ID NO:) |
|---|---|---|---|
| Escherichia coli K-12 MG1655 | E.C. | gb AE000358, 6754-7464 (67) | gb AE000358, 6275-6754 (103) |
| Haemophilus influenzae Rd | H.I. | gb U32750, 2072-2749 (68) | gb U32750, 1599-2075 (104) |
| Bacillus subtilis 168 | B.S. | emb Z99101, 109786-110484 (69) | emb Z99101, 110477-110953 (105) |
| Synechocystis sp. PCC6803 | S.S. | dbj D990914, 29703-30395 (70) | dbj D90906, 58770-59255 (106) |
| Mycobacterium tuberculosis H37Rv | M.T. | emb Z92774, 29591-30286 (71) | emb Z92774, 29115-29594 (107) |
| Aquifex aeolicus VF5 | A.E. | gb AE000734, 10078-10719 (72) | gb AE000715, 8239-8709 (108) |
| Chlamydia trachomatis D/UW-3/CX | C.T. | gb AE001320, 3348-4007 (73) | gb AE001317, 988-1524 (109) |
| Chlamydia pneumoniae CWL029 | C.P. | gb AE001642, 7155-7790 (74) | gb AE001639, 4613-5143 (110) |
| Thermotoga maritima | T.M. | gb AE001792, 3951-4619 (75) | gb AE001738, 11427-11924 (111) |
| Pyrococcus horikoshii OT3 | P.H. | dbj AP000002, 72589-73278 (76) | —[c] |
| Helicobacter pylori strain J99 | H.P. | gb AE001474, 6197-7426[d] (77) | |
| Treponema pallidum | T.P. | gb AE001227, 7127-8326[d] (78) | |
| Haemophilus ducreyi 35000 | H.D. | n.s.[e] | gb U32175, 5939-6421 (112) |
| Salmonella typhi | S.T. | Contig404, 129036-129737 (79) | Contig404, 129746-130195 (113) |
| Yersinia pestis | Y.S. | Contig730, 87298-87966 (80) | Contig730, 88135-88605 (114) |
| Actinobacillus actinomycetemcomitans | A.A. | Contig704, 2247-2927 (81) | Contig704, 1771-2238 (115) |
| Vibrio cholerae | V.C. | asm938, 1967-2641 (82) | asm938, 2656-3129 (116) |
| Shewanella putrefaciens | S.P. | gsp_845, 694-1359 (83) | gsp_845, 183-629 (117) |
| Pasteurella multocida PM70 | P.M. | Contig556, 1199-1876 (84) | Contig556, 1891-2364 (118) |
| Pseudomonas aeruginosa | P.A. | Contig52, 647221-647862 (85) | Contig52, 652597-653061 (119) |
| Neisseria gonorrhoeae | N.G. | Contig181, 9088-9747 (86) | Contig181, 9791-10267 (120) |
| Bordetella pertussis | B.P. | Contig657, 1198-1860 (87) | Contig657, 1860-2342 (121) |
| Neisseria meningitidis MC 58 | N.M.MC | n.s. | GNMCP32F, 134-550 (122) |
| Neisseria meningitidis serogroup A | N.M.SA | Contig3, 255019-255678 (88) | Contig3, 254511-254963 (123) |
| Thiobacillus ferrooxidans | T.F. | 949, 9-599 (89) | 949, 646-1107 (124) |
| Deinococcus radiodurans | D.R. | 8896, 4825-5430 (90) | 8835, 20460-20888 (125) |
| Clostridium acetobutylicum | C.A. | AE001437, 2979884-2980552 (91) | AE001437, 160798-161262 (126) |
| Mycobacterium avium | M.A. | 5759, 2065-2721 (92) | 5759, 1598-2050 (127) |
| Mycobacterium bovis | M.B. | Contig950, 5497-6156 (93) | Contig950, 6186-6611 (128) |
| Chlorobium tepidum | C.TP. | gct_38, 2977-3687 (94) | gct_41, 1403-1873 (129) |
| Porphyromonas gingivalis W83 | P.G. | 1209, 31380-32024 (95) | 1207, 93755-94237 (130) |
| Enterococcus faecalis | E.F. | gef_6311, 4277-4960 (96) | gef_6177, 5831-6301 (131) |
| Streptococcus pneumoniae | S.PN. | sp_72, 23704-24387 (97) | n.s. |
| Staphyloccocus aureus COL | S.A. | 2204, 9831-10517 (98) | n.s. |
| Plasmodium falciparum 3D7 | P.F. | ID_M9Fe7.p1t, 22-202 (99) | gb AE001394, 2617-3495 (132) |
| Arabidopsis thaliana chromosome II BAC | A.T. | gb AC004136, 79845-81915 (2) | gb AC010852, 376-1789 |
| Rhodobacter capsulatus SB1003 | R.C. | emb X72382, 279-1418[d] (100) | |
| Caulobacter crescentus | C.C. | gcc_1641, 677-1243, gcc_574, 1870-2430[d] (101) | |
| Campylobacter jejuni NCTC 11168 | C.J. | Cj.seq, 1534779-1535867[d] (102) | |

Figure 3:
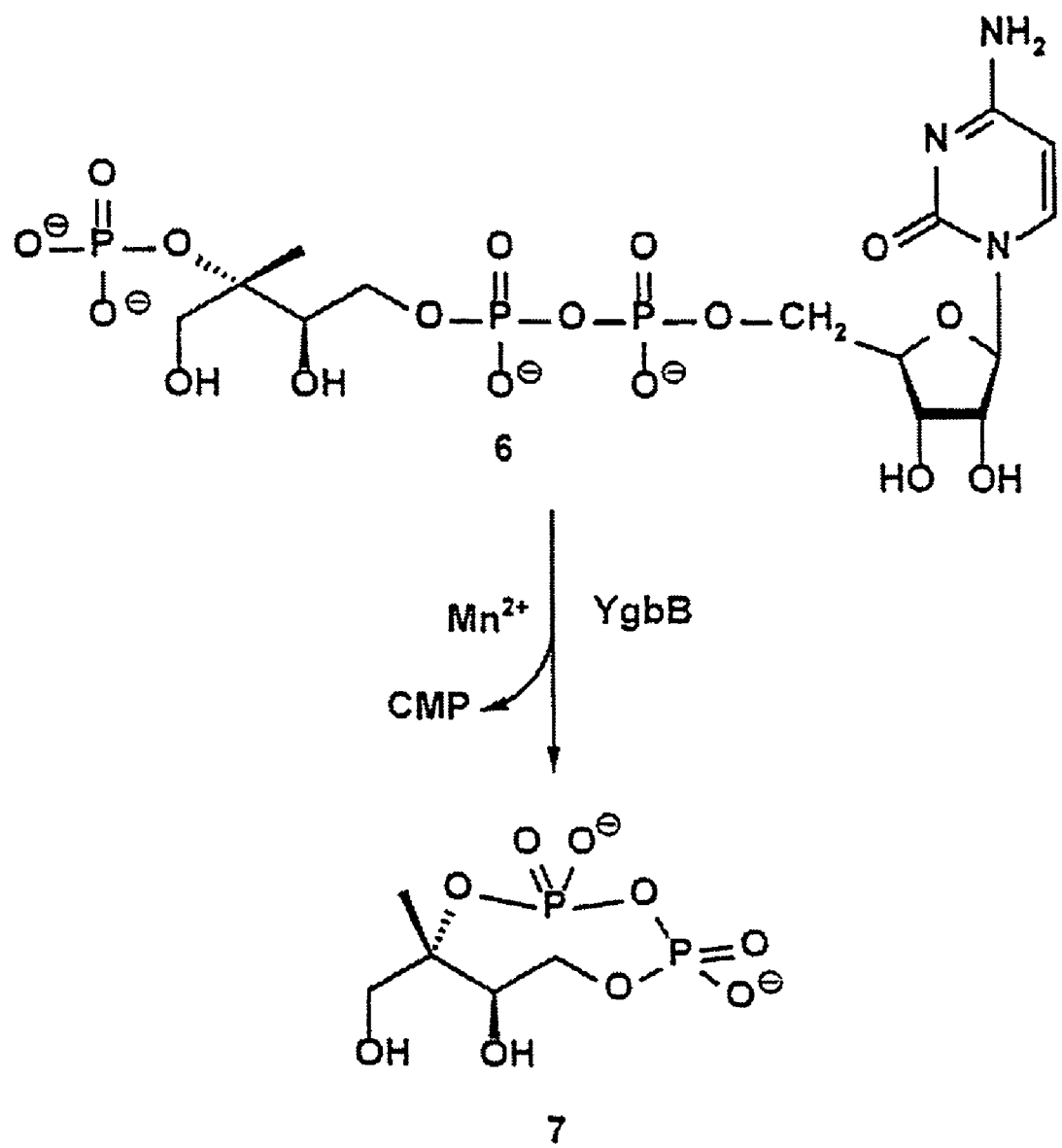
FIG. 3 shows a third enzymatic step, due to YgbB, downstream from the pathway of FIG. 2.

[a]National Center for Biotechnology Information and The Institute for Genomic Research
[b]abbreviation in alignment (FIG. 4)
[c]no homologous sequence existent in the database of complete sequenced genomes
[d]bifunctional YgbP/YgbB gene product
[e]not sequenced We have further surprisingly discovered that the next intermediates in the biosynthesis pathway downstream from 4-diphosphocytidyl-2C-methyl-D-erythritol are 4-diphosphocytidyl-2C-methyl-D-erythritol 2-phosphate (6) (FIG. 2) and 2C-methyl-D-erythritol 2,4-cyclopyrophosphate (7) (FIG. 3). Based on this finding, we have established that 4-diphosphocytidyl-2C-methyl-D-erythritol 2-phosphate is biosynthesized from 4-diphosphocytidyl-2C-methyl-D-erythritol with ATP, and we have also produced an E. coli protein (YchB) in an enzymatically functional form for this conversion. This enzyme is called 4-diphosphocytidyl-2C-methyl-D-erythritol kinase. We also found that the above-mentioned YgbB protein converts 4-diphosphocytidyl-2C-methyl-D-erythritol 2-phosphate into 2C-methyl-D-erythritol 2,4-cyclopyrophosphate (7) and CMP (FIG. 3).

The amino acid sequence of the YchB enzyme and the corresponding DNA sequence are contained as unannotated open reading frame in the genome of E. coli under the designation ychB (gb accession number AE000219). The DNA corresponding to this ORF was isolated and cloned into a high copy expression vector and with this vector construct E. coli cells were transformed. Surprisingly in 6 tested recombinant E. coli clones the corresponding gene product was ex-pressed in soluble form to a level of about 10% of the total soluble cell fraction. This was judged by SDS-PAGE. Moreover, cell extracts of 4 tested recombinant clones showed activity according to the formation of 4-diphosphocytidyl-2C-methyl-D-erythritol 2-phosphate from ATP and 4-diphosphocytidyl-2C-methyl-D-erythritol. This specific activity was at least 100 times higher than in cell extracts of E. coli wild type cells.

We further have established the presence of sequences highly homologous to ychB in a number of bacteria, in Arabidopsis thaliana as well as in Lycopersicon esculentum (tomato) by performing a blast search in GenBank as well as in the database of completed and uncompleted genomes. The orthologous cDNA pTOM41 sequence of tomato (gb accession no. U62773) was previously described erroneously as ripening associated transcription product.

We have thus opened an avenue for the expression of functional forms of the protein YchB in any of these or other organisms. Notably, the DNA corresponding to the ORF of Arabidopsis thaliana (gb accession no. AC005168) was isolated and cloned into a high copy expression vector.

The designations of YchB in the E. coli genome are used herein also for the orthologous enzymes in other organisms. The set of open reading frames homologous to ychB is listed in Table 2. An alignment of the amino acid sequences of the corresponding gene products is shown in FIG. 5. The alignment was constructed with the Pileup program using the default setting (Genetic Computer Group, Madison, Wis.) and it was edited with the GeneDoc program (Pittsburgh Supercomputing Center, Pittsburgh, Pa.). Organism names are abbreviated at the left side of the alignment as shown in Table 2. Amino acid residues are written in IUPAC one letter code and are numbered consecutively for reference purposes at the top of each alignment page. Each accumulated total number of amino acids is given in each line in the right column of the alignment. Gaps in the alignment are symbolized by a dash (-). The symbols < and > indicate a fragment. The symbol \\ denotes a C-terminus. The symbol * denotes a stop codon due to a frame shift.

In the case of a fragment, the sequences are missing at the beginning and/or end due to the fact that they are ignored by the Blast program for retrieving the sequences from the database of unfinished genomes. They are readily obtained from the corresponding nucleotide sequence, proceeding forward until the initiator codon ATG (or GTG or CTG) is encountered and backward until a stop codon is encountered.

TABLE 2

Occurrence of orthologous sequences to ychB in various organisms

| organism | abbreviation[b] | accession or Contig number[a], basepairs corresponding to ychB (SEQ ID NO:) |
|---|---|---|
| Escherichia coil K-12 MG1655 | E.C. | gb AE000219, 5720-6571 (133) |
| Haemophilus influenzae Rd KW20 | H.I. | gb U32834, 7469-8410 (134) |
| Bacillus subtilis 168 | B.S. | emb Z99104, 53514-54383 (135) |
| Synechocystis sp. PCC6803 | S.S. | dbj D90899, 101884-102831 (136) |
| Mycobacterium tuberculosis H37Rv | M.T. | emb Z94752, 23889-24809 (137) |
| Aquifex aeolicus VF5 | A.E. | gb AE000713, 10428-11234 (138) |
| Chlamydia trachomatis D/UW-3/CX | C.T. | gb AE001352, 9579-10445 (139) |
| Chlamydia pneumoniae CWL029 | C.P. | gb AE001675, 2514-3406 (140) |
| Thermotoga maritima | T.M. | gb AE001791.1, 13364-14179 (141) |
| Helicobacter pylori strain J99 | H.P. | gb AE000644, 8749-9555 (142) |
| Treponema pallidum | T.P. | gb AE001226, 5348-6223 (143) |
| Samonella typhimurium LT2 | S.TL. | gb M77236, 941-1792 (144) |
| Zymomonas mobilis | Z.M. | gb AF088896.1, 14821-15606 (145) |
| Salmonella typhi | S.T. | Contig334, 29152-30000 (146) |
| Salmonella paratyphi | S.P. | SPA.0.2446, 209-1054 (147) |
| Yersinia pestis | Y.S. | Contig648, 22578-23399 (148) |
| Actinobacillus actinomycetemcomitans | A.A. | Contig510, 1486-2304 (149) |
| Vibrio cholerae | V.C. | 666__1752, 2349936-2350756 (150) |
| Shewanella putrefaciens | S.PU. | 4279, 66514-67320 (151) |
| Pasteurella multocida PM70 | P.M. | Contig264, 2636-3454 (152) |
| Pseudomonas aeruginosa | P.A. | Contig54, 3100316-3099489 (153) |
| Neisseria gonorrhoeae | N.G. | Contig121, 24491-25306 (154) |
| Bordetella pertussis | B.P. | Contig408, 16613-17356 (155) |
| Neisseria meningitidis serogroup A | N.M. | NM.seq, 1040554-1041369 (156) |
| Klebsiella pneumoniae | K.M. | Contig31, 604-1012 (157) |
| Thiobacillus ferrooxidans | T.F. | 2031, 1218-1499 |
| Deinococcus radiodurans | D.R. | 8896, 5523-6026 (158) |
| Bordetella bronchiseptica | B.B. | Contig2244, 31-691 (159) |
| Clostridium difficile | C.D. | Contig1239, 9891-10664 (160) |
| Clostridium acetobutylicum | C.A. | AE001437, 2693910-1694725 (161) |
| Mycobacterium avium | M.A. | M. avium__24, 20876-21331 (162) |
| Mycobacterium bovis | M.B. | Contig750, 2661-3116 (163) |
| Mycobacterium leprae | M.L. | Contig1080, 6925-7380 (164) |
| Chlorobium tepidum | C.TP. | gct__5, 4007-4783 (165) |
| Porphyromonas gingivalis W83 | P.G. | 1194, 108718-109167 (166) |
| Enterococcus faecalis | E.F. | gef__6342, 2564-3340 (167) |
| Streptococcus mutans | S.M. | Contig435, 4960-5739 (168) |
| Streptococcus pyogenes | S.PG. | Contig7, 1467238-1457675 (169) |
| Staphyloccoccus aureus NCTC8325 | S.AN. | Contig856, 566-1342 (170) |
| Staphyloccoccus aureus COL | S.A. | 4357, 3-779 (171) |
| Arabidopsis thaliana chromosome II BAC F12620 | A.T. | gb AC005168, 10297-12697 (172) |
| Solanum lycopersicum | S.L. | gb U62773, 78-1283 (173) |
| Sinrhizobium meliloti | S.ML. | 423114A12.xl, 70-627, 423051H04.xl, 360-677 (174) |
| Caulobacter crescentus | C.C. | gcc__1346, 1215-1655 (175) |
| Campylobacter jejuni NCTC 11168 | C.J. | Cj.seq, 1038338-1038884 (176) |

[a]National Center for Biotechnology Information
[b]abbreviation in alignment (FIG. 4)

With these functional assignments of YgbP, YchB and YgbB and with the production of proteins having enzymatically competent folding structures, we have entered these proteins as well as the purified isolated DNA coding for these proteins as novel compounds for technical and commercial usage into the body of technical knowledge. At the same time this provides avenues for the production of the products of the enzymatic reaction of YgbP, YchB and YgbB, namely 4-diphosphocytidyl-2C-methyl-D-erythritol, 4-diphosphocytidyl-2C-methyl-D-erythritol 2-phosphate and 2C-methyl-D-erythritol 2,4-cyclopyrophosphate or salts thereof, notably salts of alkali metals, like Li, Na, K or of ammonia or amines and for their use in various in vitro or in vivo reactions of the alternative pathway to isoprenoids.

Based on this achievement, we have opened new avenues for the inhibition of the alternative isoprenoid pathway in plants as well as bacteria and also in protozoa, like *Plasmodium*.

The enzymes YgbP and YgbB as well as YchB or major core fragments thereof of various organisms have been aligned as shown in FIG. 4 and FIG. 5. Based on these alignments a broad but finite class of sequences can be defined of enzymes with the functions of YgbP, YgbB and YchB based on the amino acid variability given for each position by the alignments. For any protein in each class, a set of possible equivalent amino acids of any position can be taken immediately, unambiguously and individually from FIG. 4 and FIG. 5. This will insure sufficient functional competence with a very high likelihood.

Alternatively an orthologous sequence class is established for each gene by nucleic acid hybridization under conditions of intermediate stringency (such as an aqueous solution of 2×SSC at 65° C.) using cDNA or genome DNA or RNA.

We have found that in plants, notably *Arabidopsis thaliana* the enzymes homologous to YgbP, YchB and YgbB have a leader peptide not present in the bacterial enzymes. This leader peptide serves the purpose of transport of the enzyme into the plastids. Such specific leader sequence may be replaced by any other leader sequence from *A. thaliana* or from any other plant or it may also be eliminated.

The *A. thaliana* sequence of YgbP, identified in Table 1 and given in the alignment of FIG. 4 has been obtained by genome sequencing. We have sequenced the gene ygbP of *A. thaliana* by isolating RNA from cells of *A. thaliana*, producing cDNAs complementary to said RNA by RT-PCR, subsequently amplifying the coding region for YgbP with the appropriate gene-specific primers by PCR and finally cloning the obtained DNA. The leader sequence was first not cloned and sequenced. But later the full-length gene was cloned from RNA.

The cDNA sequence of the cloned ygbP gene from *A. thaliana* was different from the DNA sequence found in the database (gb AC004136) due to introns. The amino acid sequence corresponding to this cDNA is also different from the amino acid sequence given in the database (gb AC004136). This seems due to erroneous computational intron splicing from chromosomal DNA. This finding is shown in an alignment of the amino acid sequence of the cloned cDNA and of the amino acid sequence of the YgbP gene product found in the database (FIG. 6). The amino acid sequences are numbered at the right side of the alignment. Number 1: cloned sequence of ygbP from *A. thaliana* without leader sequence; number 2: gb AC004136. Identical residues are boxed. The cDNA sequence and the corresponding protein sequence of ygbP of *A. thaliana* are shown in FIG. 7A. The cDNA leader sequence was found to be identical to the database prediction (FIG. 7B).

The genes ygbP, ygbB and ychB of *E. coli* were obtained by PCR using primers with specific restriction sites. In this PCR reaction two recognition sites for restriction enzymes are introduced at the 5'-end and at the 3' end. The prefered recognition site is NcoI or EcoRI at the 5'-end and PstI at the 3' end. The amplified PCR fragment and an expression vector are digested with the same restriction enzymes and ligated together with T4-ligase to yield recombinant plasmid capable of autonomous replication in the host microorganism. The recombinant plasmid is used to transform the host microorganism. The preferred host is *E. coli*. The same method was used for the genes ygbP, ygbB and ychB of *Arabidopsis thaliana* and for ychB of tomato whereby the nucleotide sequence was modified for the codon usage of *E. coli* for highly expressed genes (without leader sequence).

The open reading frame of the ygbB gene from *E. coli* was cloned also into the high-copy expression vector pQE30 from Qiagen (Hilden, Germany). This vector provides the high-level expression in *E. coli* of proteins containing a tag of 6 histidine residues at the N-terminal end. The recombinant "6-His-protein" could then easily be purified in one step to homogeneity by immobilized metal chelate affinity chromatography.

The cloning of the ygbB gene of *E. coli* into the pQE30 vector led to the expression of soluble, enzymatically active YgbB gene product, which was N-terminal His-tagged. Recombinant *E. coli* cells containing the overexpressed His-tagged fusion protein showed a specific activity, notably in converting 4-diphosphocytidyl-2C-methyl-D-erythritol, which was at least 80 times higher than in *E. coli* wild-type XL1-Blue cells. This enzyme was purified according to $Ni^{2+}$ chelate affinity chromatography to homogeneity. The purity of the enzyme was judged by sodium dodecylsulfate polyacrylamide gel electropho-resis.

The same method was used for ygbB or *Plasmodium falciparum* to obtain the fusion protein 6×His-YgbB.

The corresponding protein sequence of the cloned ychB gene from *A. thaliana* was identical to the protein sequence of the computational cDNA sequence found in the database (gb AC005168). The DNA sequence and corresponding protein sequence is shown in FIG. 8A without leader sequence. The full-length YchB gene of *Arabidopsis thaliana* has been additionally cloned from RNA. The sequence is shown in FIG. 8B.

The strains harbouring the recombinant plasmids can be cultivated in conventional culture media at 15 to 40° C. The preferred temperature is 37° C. The *E. coli* strains are induced with 0.5 to 2 mM isopropyl-β-D-thiogalactoside at an opitical density at 600 nm from 0.5 to 0.8. The cells are incubated between 2 and 12 h, preferably 5 h. The cells are lysed with lysozyme and disrupted with a sonifier. The crude extract with recombinant YgbP, YgbB or YchB protein is purified by chromatography, notably anion exchange chromatography and affinity chromatography. Proteins are obtained which have the proper folding structure for exhibiting the desired enzyme activity, notably from *E. coli*, *A. thaliana*, *L. esculentum* and *P. falciparum*.

Screening

The enzymes YgbP, YgbB and YchB do not occur in animals. Therefore, inhibitors against YgbP, YgbB and YchB have great value as (a) herbicides against weed plants or algae; (b) antibiotic agents against pathogenic bacteria; (c) agents against protozoa, like *Plasmodium falciparum*, the causative pathogen of malaria.

With the finding that 4-diphosphocytidyl-2C-methyl-D-erythritol, 4-diphosphocytidyl-2C-methyl-D-erythritol 2-phosphate and 2C-methyl-D-erythritol 2,4-cyclopyrophosphate are intermediates we have also acquired essential determinants of the structures of inhibitors. Namely, the structures of a subset of inhibitors should be similar to at least a portion of the starting compounds or the products or the transition state between the starting compounds e.g. (2C-methyl-D- erythritol 4-phosphate and CTP) and the products e.g. (pyrophosphate and 4-disphosphocytidyl-2C-methyl-D-erythritol). Based on these determinants ribitol 5-phosphate and erythritol 4-phosphate have been synthesized as putative inhibitors for YgbP.

We have also provided methods of screening for inhibitors of YgbP, YgbB and YchB. In these methods one of the enzymes YgbP, YgbB or YchB of the classes of enzymes defined above can be used. A monofunctional or bifunctional enzyme may be used. The reaction should preferably be carried out at a pH of 5.5 to 9, preferably 7 to 8.5. It may be carried out in the presence of a divalent metal salt, preferably $Mg^{2+}$ in the case of YgbP or YchB and $Mn^{2+}$ or $Mg^{2+}$ in the case of YgbB. The temperature is preferably in the range of $\pm 10°$ C. from the optimum temperature. At least two consecutive enzymes of the set of enzymes YgbP, YchB and YgbB may also be used jointly in a combination screening test. Or YgbP may be combined with one or more enzymes upstream from YgbP in the pathway together with the appropriate substrates and cofactors.

The enzyme selected for the test should be preferably identical with the enzyme of the targeted organism. In case of a targeted group of plants (or bacteria), such as all mono- or dicotyledonous plants, any plant (bacterial) enzyme may be chosen or an enzyme whose sequence has the greatest commonality with all relevant plant (bacterial) sequences known and is thus representative for all relevant plant (bacterial) enzymes. In case of plant enzymes the leader sequence may be eliminated.

The start of this reaction can be timed by the addition of the last of the essential components. The reaction can be stopped by methanol, chelating agents, like EDTA or acids like trichloro acetic acid.

The activity of the enzyme can be detected (in the presence or absence of a potential inhibitor) by measuring in the case of YgbP either the formation of a product, namely pyrophosphate or 4-diphosphocytidyl-2C-methyl-D-erythritol or the consumption of starting material, namely CTP or 2C-methyl-D-erythritol 4-phosphate. In the case of YgbB the consumption of 4-diphosphocytidyl-2C-methyl-D-erythritol and/or the formation of 2C-methyl-D-erythritol 3,4-cyclophosphate may be measured; or alternatively the consumption of 4-phosphocytidyl-2C-methyl-D-erythritol 2-phosphate and/or formations of 4-diphosphocytidyl-2C-methyl-D-erythritol 2,4-cyclopyrophosphate or cytidylmonophosphate. In the case of YchB the consumption of 4-diphosphocytidyl-2C-methyl-D-erythritol and/or adenosine 5-triphosphate (ATP) may be measured or the formation of 4-diphosphocytidyl-2C-methyl-D-erythritol 2-phosphate or adenosine 5-diphosphate (ADP). The measurements may be carried out either directly with the reaction mixture or after the separation of the reaction mixture by chromatography, such as HPLC.

The rate of pyrophosphate formation can be detected by coupling with UDP-glucose pyrophosphorylase, phosphoglucomutase and glucose 6-phosphate dehydrogenase. The formation of pyrophosphate is equivalent to the formation of NADPH, which can be monitored at 340 nm in a spectrophotometer. 4-diphosphocytidyl-2C-methyl-D-erythritol can also be detected directly by using $^{14}$C-labeled substrate and detecting the product with a radiomonitor. The consumption of 2C-methyl-D-erythritol 4-phosphate (unlabeled, $^{13}$C-labeled or $^{14}$C-labeled) and the formation of 4-diphosphocytidyl-2C-methyl-D-erythritol can also be monitored during the reaction or after the reaction by $^{31}$P- or $^{13}$C-NMR spectroscopy or detection with a radiomonitor. The same method may be used for screening for an enzyme that is resistant to a specific inhibitor.

The rate of ADP formation can be detected by UV. 4-diphosphocytidyl-2C-methyl-D-erythritol 2-phosphate can also be detected directly by using $^{14}$C-labeled substrate and detecting the product with a radiomonitor. The consumption of 4-diphosphocytidyl-2C-methyl-D-erythritol (unlabeled, $^{13}$C-labeled or $^{14}$C-labeled) and the formation of 4-diphosphocytidyl-2C-methyl-D-erythritol 2-phosphate can also be monitored during the reaction or after the reaction by $^{31}$P- or $^{13}$C-NMR spectroscopy or detection with a radiomonitor.

We have determined that YgbB can convert 4-diphosphocytidyl-2C-methyl-D-erythritol 2-phosphate (6) into 2C-methyl-D-erythritol 2,4-cyclopyrophosphate (7). The structure of the product was determined. The obtained 2C-methyl-D-erythritol-2,4-cyclopyrophosphate is a valuable compound for screening processes. It can be used as a reference compound for screening procedures in which the effectiveness of prospective inhibitors against YgbB is detected by the effectiveness of YgbB to produce 2C-methyl-Drythritol-2,4-cyclopyrophosphate.

Our finding opens the way for novel screening procedures for finding inhibitors against YgbB. As an alternative to measuring the disappearance of 4-diphosphocytidyl-2C-methyl-D-erythritol 2-phosphate we can now measure the appearance of 2C-methyl-D-erythritol 2,4-cyclopyrophosphate. The measurement may be carried out either directly with the reaction mixture or after the separation of the reaction mixture by chromatography such as HPLC. The detection may be done by NMR or by a radio monitor.

The same methods may be used for screening for mutated enzymes that are resistant to a specific inhibitor.

Large Scale Preparation

The starting materials for a comprehensive large-scale preparation of an intermediate are preferably dihydroxyacetone phosphate and pyruvate, whereby these starting materials may be used as free acids or as salts with a monovalent or divalent cation, preferably sodium or potassium. They may be used in equimolar amounts or in a molar ratio of 10:1 to 1:10 of dihydroxyacetone phosphate to pyruvate.

Glyceraldehyde 3-phosphate is the substrate for 1-deoxyxylulose 5-phosphate synthase. It is equivalent to dihydroxyacetone phosphate, which serves as its source in conjunction with triosephosphate isomerase. Dihydroxyacetone phosphate is preferred in view of its stability.

Further equivalent is glucose in the presence of ATP and the glycolytic enzymes hexokinase, phosphoglucose isomerase, phosphofructokinase, aldolase and triosephosphate isomerase.

The enzymes used may all be from the same organism, e.g. *E. coli*, or from different organisms. They are used in catalytic amounts with a molar ratio of 0.00001 to 0.1, preferably 0.001 to 0.1 to dihydroxyacetone phsophate or pyruvate.

The magnesium salt may be preferably magnesium chloride or sulfate and the $Mn^{2+}$ may be a chloride or sulfate. Thiamine pyrophosphate may be used as free acid or as a salt, preferably with sodium or potassium.

Any enzymatically suitable buffer may be used. Tris hydrochloride is a preferred buffer. The pH is preferably 7 to 9 and especially 7.5 to 8.5, most notable 8.0. NADP$^+$ may be used in stoichiometric amounts. It may also be regenerated in situ. For this purpose glucose and glucose dehydrogenase may be used. The molar ratio of dihydroxyacetone phosphate to pyruvate is preferably 1 to 10 and especially 1 to 3.

The reaction temperature should be chosen in accordance with the temperature optimum of the enzymes or differing from the optimum by up to 1 0° C. or preferably up to 5° C. A preferred temperature range is 30 to 45° C. and especially 35 to 40° C.

The reaction steps defined in claim 55 may be carried out separately, each under its own optimum conditions. The intermediate reaction mixtures may be stored in a freezer preferably at −30° C. to −10° C., notably −20° C. Prior to freezing the reaction may be stopped by adding an acid, such as HCl to lower the pH to 2 to 4, notably 2.5 to 3.5, preferably 3.0. The reaction steps may also be carried out as a one pot reaction. It is preferred to remove any precipitate formed in any of the steps by centrifugation.

Labelling

The labelled substrates may be labelled by 32-phosphorus, 14-carbon, 13-carbon, deuterium or tritium. These labelling types may be used alone or in any combination such as a combination of 13-carbon and deuterium.

The labelling with 14-carbon or 13-carbon may be single whereby any one of the C-positions may be labelled. Alternatively, the substrates may be multiply labelled, such as dual, triple, quadruple or quintuple. The total C-labelling is particularly preferred in case of 13-carbon labelling.

The labelling with deuterium or tritium may be single or multiple. 1-deoxy-D-xylulose 5-phosphate may be deuterium- or tritium-labelled in positions 1, 3, 4 or 5, preferably in positions 3, 4 or 5; and 2C-methyl-D-erythritol 4-phosphate may be deuterium- or tritium-labelled in positions 1, 3, 4 or the methyl group.

Other intermediates downstream from 2C-methyl-D-erythritol 4-phosphate with corresponding labelling may be used.

The labelled substrates may be prepared enzymatically or chemically.

Enzymatically, tritiated 1-deoxy-D-xylulose 5-phosphate may be prepared from [3-3H]pyruvate for tritiation in position 1; or from [1-$^3$H]glyceraldehyde 3-phosphate or [1-$^3$H] dihydroxyacetone 3-phosphate for tritiation in position 3 or from [2-$^3$H]glyceraldehyde 3-phosphate for tritiation in position 4 or from [3-$^3$H]glyceraldehyde 3-phosphate for tritiation in position 5; and subsequently the tritiated 2C-methyl-D-erythritol 4-phosphates may be obtained enzymatically from the corresponding tritiated 1-deoxy-D-xylulose 5-phosphates.

Specifically, [1-$^3$H] glyceraldehyde 3-phosphate can be synthesized from [3-$^3$H]glucose by enzymatic action of hexokinase, phosphoglucose isomerase, phosphofructokinase, aldolase and triose phosphate isomerase. The reaction mixture containing [1-$^3$H] glyceraldehyde 3-phosphate can be directly used for synthesis of [3-$^3$H]1-deoxy-D-xylulose 5-phosphate. [3-$^3$H]1-Deoxy-D-xylulose 5-phopshate can be synthesized from [1-$^3$H] glyceraldehyde 3-phosphate and pyrurate by enzymatic action of 1-deoxy-D-xylulose 5-phosphate synthase.

[1-$^3$H]2C-methyl-D-erythritol 4-phosphate can be synthesized from [3-$^3$H]1-deoxy-D-xylulose 5-phosphate by catalytic action of 1-deoxy-D-xylulose 5-phosphate reductoisomerase.

[2-$^3$H]glyceraldehyde 3-phosphate can be synthesized from [2-$^3$H]glucose by enzymatic action of hexokinase, phosphoglucose isomerase, phosphofructokinase and aldolase. The reaction mixture containing [2-$^3$H]glyceraldehyde 3-phosphate can be directly used for synthesis of [4-$^3$H] 1-deoxy-D-xylulose 5-phosphate as described above for [3-$^3$H]1-deoxy-D-xyluose 5-phosphate. [3-$^3$H]2C-methyl-D-erythritol 4-phosphate can be synthesized from [4-$^3$H] 1-deoxy-D-xylulose 5-phosphate by catalytic action of 1-deoxy-D-xylulose 5-phosphate reductoisomerase.

Deuterium labelled, $^{13}$C-labelled or $^{14}$C-labelled substrates may be prepared analogously.

The basic enzymatic processes are known from G. A. Sprenger et al., Proc. Natl. Acad. Sci USA 94, 12857-12862 (1997); and Kuzuyama et al., Tetrahedron Lett. 39, 44509-4512 (1998).

Alternatively, the labelled 1-deoxy-D-xylulose compounds may be prepared by using the correspondingly labelled starting materials in the process described by Yokota, A and Sasajima, K. in Agric. Biol. Chem. 48, 149-158(1984) and ibid. 50, 2517-2524 (1986).

The labelled 2C-methyl-D-erythritol compounds may be obtained chemically by the following process, using correspondingly labelled starting materials:

(a) Reaction of 1,2,5,6-Di-O-ispropylidene-D-mannitol with lead tetracetate to isopropylidene glyceraldehyde; which is
(b) subsequently converted to 1,2-O-isopropylidene-(2R, 3RS)-1,2,3 butanetriol by reaction with methyl magnesium iodide;
(c) formation of 3,4-O-isopropylidene-(3R)-3,4-dihydroxy-2-butanone from the product step (b) by oxidation, preferably with sodium periodate in the presence of ruthenium dioxide;
(d) formation of 1,2-O-isopropylidene-3-O-trimethylsilyl-(2R,3RS)-1,2,3 trihydroxy-3-cyano-butane by reacting the product of step (c) with trimethylsilyl cyanide;
(e) conversion of the product of step (d) to a mixture of 2C-methyl-D-erythrono-1,4-lactone and 2C-methyl-D-threono-1,4-lactone by hydrolysis with an acid;
(f) production of 2,3-O-isopropylidene-2C-methyl-D-erythrono-1,4-lactone by reaction of the products of step (e) with acetone in the presence of anhydrous zink chloride;
(g) conversion of the product of step (f) to 2,3-O-ispropylidene-2C-methyl D-erythrofuranose by reaction with a hydride donor, preferably diisobutylaluminum hydride;
(h) conversion of the product of step (g) to 2,3-O-isopropylidene-2C-methyl D-erythrose-(O-benzyl)oxime by reaction with O-benzylhydroxylamine;
(i) reaction of the product of step (h) with tribenzylphosphite and iodine to obtain 2,3-O-isopropylidene-2C-methyl-D-erythrose-(O-benzyl)oxime 4 dibenzylphosphate;
(j) conversion of the product of step (i) to 2,3-O-isopropylidene-2C-methyl D-erythrose 4-dibenzylphosphate by ozonization;
(k) conversion of the product of step 0) to 2,3-O-isopropylidene-2C-methyl D-erythritol 4-dibenzylphosphate by reaction with sodium borohydride;
(l) converting the product of step (k) into 2C-methyl-D-rythritol 4-phosphate.

Tritiation in position 1 is possible by carrying out step (k) with tritiated sodium borohydride under otherwise identical conditions for the subsequent step (l). Tritiation in position 2' is possible by carrying out step (b) with tritiated methyl magnesium iodide prepared from tritiated methyl iodide and magnesium. The subsequent steps (c) to (l) remain unchanged. The combination of the tritiation steps is possible affording 2C-methyl-D-erythritol 4-phosphate acid tritiated in positions 1 and/or 2.

Deuterium labelled, $^{13}$C-labelled or $^{14}$C-labelled substrates may be prepared analogously.

Total C-labelling can be carried out advantageously starting from [U-$^{13}$C$_6$] glucose and [U-$^{13}$C$_3$] sodium pyruvate or [2,3-$^{13}$C$_2$]pyruvate. In the presence of thiamine pyrophosphate, ATP and MgCl$_2$ the following enzymes are used for preparing [U-$^{13}$C$_5$] 1-deoxy-D-xylulose 5-phosphate: triose phosphate isomerase, hexokinase, phosphoglucose isomerase, phosphofructokinase, aldolase and 1-deoxy-D-xylulose 5-phosphate synthase. Subsequently, the product can be converted to [U-$^{13}$C$_5$]2C-methyl-D-erythritol 4-phosphate with 1-deoxy-D-xylulose 5-phosphate reductoisomerase, glucose dehydrogenase and glucose, NADP$^+$ and MgCl$_2$.

Further [U-$^{13}$C$_5$]2C-methyl-D-erythritol 4-phosphate can be converted into [U-$^{13}$C$_5$]4-diphosphocydidyl-2C-methyl-D-erythritol, [U-$^{13}$C$_5$]4-diphosphocytidyl-2C-methyl-D-erythritol 2-phosphate and [U-$^{13}$C$_5$]2C-methyl-D-erythritol 2,4-cyclopyrophosphate using the enzymes YgbP, YchB and YgbB in the presence of CTP, ATP, MgCl$_2$ and MnCl$_2$. For regeneration of ATP it is possible to use also pyruvate kinase in the presence of phosphoenol pyruvate.

Nucleic Acids, Vectors, Expression Systems and Polypeptides

In practicing the present invention, many techniques in molecular biology, microbiology, recombinant DNA, and protein biochemistry such as these explained fully in, for example, Sambrook et al., 1989, *Molecular Cloning*, A Laboratory Manual, Second Edition, Cold Spring Harbor Laboratory Press, Cold Spring Harbor, N.Y.; *DNA Cloning: A practical Approach*, Volumes I and II, 1985 (D. N. (Glover ed.); Oligonucleotide Synthesis, 1984, (M. L. Gait ed.); Transcription and Translation, 1984 (Hames and Higgins eds.); *A Practical Guide to Molecular Cloning*; the series, *Methods in Enzymology* (Academic Press, Inc.); and *Protein Purification: Principles and Practice*, Second Edition (Springer-Verlag, NY.) are used.

The present invention encompasses nucleic acid sequences encoding (notably plant) enzyme, enzymatically active fragments derived therefrom, and related derived sequences from other (notably plant) species. As used herein, a nucleic acid that is "derived from" a sequence refers to a nucleic acid sequence that corresponds to a region of the sequence, sequences that are homologous or complementary to the sequence, and "sequence-conservative variants" and "function-conservative variants". Sequence-conservative variants are those in which a change of one or more nucleotides in a given codon position results in no alteration in the amino acid encoded at that position. Function-conservative variants are those in which a given amino acid residue has been changed without altering the overall conformation and function of the polypeptide, including, but not limited to, replacement of an amino acid with one having similar physico-chemical properties (such as, for example, acidic, basic, hydrophobic, and the like). Enzymes fragments that retrain enzymatic activity can be identified according to the methods described herein, e.g., expression in *E. coli* followed by enzymatic assay of the cell extract.

Sequences derived from plants other than *Arabidopsis thaliana* can be isolated by routine experimentation using the methods and compositions provided herein. For example, hybridization of a nucleic acid comprising all or part of *Arabidopsis* sequence under conditions of intermediate stringency (such as, for example, an aqueous solution of 2×SSC at 65° C.) to cDNA or genomic DNA derived from, other plant species can be used to identify homologues. cDNA libraries derived from different plant species are commercially available (Clontech, Palo Alto, Calif.; Stratagene, La Jolla, Calif.). Alternatively, PCR-based methods can be used to amplify related sequences from cDNA or genomic DNA derived from other plants. Expression of the identified sequence in, e.g., *E. coli*, using methods described in more detail herein, is then performed to confirm the enzymatic activity of the polypeptide encoded by the sequence. Accordingly, sequences derived from dicotyledonous and monocotyledenous plants are within the scope of the invention.

The nucleic acids of the present invention include purine- and pyrimidine-containing polymers of any length, either polyribonucleotides or polydeoxyribonucleotides or mixed polyribo-polydeoxyribo-nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. The nucleic acids may be isolated directly from cells. Alternatively, PCR can be used to produce the nucleic acids of the invention, using either chemically synthesized strands or genomic material as templates. Primers used for PCR can be sythesized using the sequence information provided herein and can further be designed to introduce appropriate new restriction sites, if desirable, to introduce appropriate new restriction sites, if desirable, to facilitate incorporation into a given vector for recombinant expression.

The nucleic acids of the present invention may be flanked by natural *Arabidopsis* regulatory sequences, or may be associated with heterologous sequences, including promoters, enhancers, response elements, signal sequences, polyadenylation sequences, introns, 5'- and 3'-noncoding regions and the like. The nucleic acids may also be modified by many means known in the art. Non-limiting examples of such modification include methylation, "caps", substitution of one or more of the naturally occuring nucleotides with an analog, and internucleotide modification such as, for example, those with uncharged linkages (e.g., methyl phosphonates, phosphotriesters, phosphoromidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-Lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed sequences or derivatives or fragments thereof. A large number of vectors, including plasmid and fungal vectors, have been described for replication and/or expression in an variety of eukaryotic and prokaryotic hosts. Non-limiting examples include pKK plasmids (Clontech), pUC plasmids, pET plasmids (Novagen, Inc., Madison, Wis.), or PRSET or pREP (Invitrogen, San Diego, Calif.), and many appropriate host cells, using methods disclosed or cited herein or otberwise known to those skilled in the relevant art. Recombinant cloning vectors will often include one or more replication sytems for cloning or expression, one or more markers for selection in the host, e.g. antibiotic resistance, and one or mose expression cassettes. Suitable host cells may be transformed/transfected/infected as appropriate by any suitable method including electroporation, CaCl$_2$ mediated DNA uptake, tungae infection, microinjection, miroprojectile, or other established methods.

Appropriate host cells include bacteria, archaebacteria, fungi, especially yeast, plant and animal cells, especially mammalian cells. Of particular interest are *E. coli, B. Subtilis,*

*Saccharomyces cerevisiae, Saccharomyces carlsbergensis, Schizosacchromyces pombi*, SF9 cells, C129 cells, 293 cells, *Neurospora*, and CHO cells, COS cells, HeLa cells, and immortalized mammalian myeloid and lyphoid cell lines. Preferred replication systems include M13, ColE1, SV40, baculovirus, lambda, adenovirus, and the like. A large number of transcription initation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced enzyme-derived peptides and polypeptides.

Advantageously, vectors may also include a transcription regulatory element (i.e., a promoter) operably linked to the enzyme portion. The promoter may optionally contain operator portions and/or ribosome binding sites. Non-limiting examples of bacterial promoters compatible with *E. coli* include: trc promoter, β-lactamase (penicillinase) promoter; lactose promoter; tryptophan (trp) promoter; arabinose BAD operon promoter, lambda-derived PI promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

Nucleic acids encoding wild-type or variant enzyme polypeptides may also be introduced into cells by recombination events. For example, such a sequence can be introduced into a cell, and thereby effect homologous recombination at the site of endogenous gene or a sequence with substantial identity to the gene. Other recombination-based methods, such as non-homologous recombinations or deletion of endogenous genes by homologous recombination, may also be used.

Enzyme-derived polypeptides according to the present invention, including function-conservative enzyme variants may be isolated from wild-type or mutant *Arabidopsis* cells, or from heterologous organisms or cells (including, but not limited to, bacteria, fungi, insect, plant, and mammalia cells) into which an enzyme-derived protein-coding sequence has been introduced and expressed. Furthermore, the polypeptides may be part of recombinant fusion proteins. Alternatively, polypeptides may be chemically synthesized by commercially available automated procedures, including, without limitation, exclusive solid phase synthesis, partial solid phase methods, fragment condensation or classical solution synthesis.

"Purification" of an enzyme polypeptide refers to the isolation of the enzyme polypeptide in a form that allows its enzymatic activity to be measured without interference by other components of the cell in which the polypeptide is expressed. Methods for polypeptide purification are well-known in the art, including, without limitation, preparative disc-gel electrophoresis, isoelectric focusing, reversed-phase HPLC gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibobdies produced against the enzyme or against peptides derived therefrom can be used as purification reagents. Other purification methods are possible.

The present invention also encompasses derivatives and homologues of the enzyme polypeptides. For some purposes, nucleic acid sequences encoding the peptides may be altered by substitutions, additions, or deletions that provide for functionally equivalent molecules, i.e., function conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Genes corresponding to YgbP (or YgbB) or YchB from any plant may be readily isolated by well known techniques, for example by Southern hybridization or by PCR using degenerated primers. Notably, cDNA library of this plant in question is screened using the nucleic acid direct labelling and detection system kit supplied from Amersham-Pharmacia-Biotech (Heidelberg, Germany). Hybridization conditions are for example 7% sodium dodecyl sulfate (SDS), 0.5. Positively hybrizing plaques are detected by luminescence detection (or in other systems by autoradiography). After purification to single plaques, cDNA inserts are isolated, and their sequences determined by the chain termination method using dideoxy terminators labeled with fluorescent dyes (Applied Biosystems, Inc., Foster City, Calif.). This experimental protocol can be used by one of ordinary skill in the art to obtain genes substantially similar to the *Arabidopsis* gene from any other plant species.

Screening Methods to Identifiy Enzyme Inhibitors/Herbicides

The methods and compositions of the present invention can be used to identify compounds that inhibit the function of the enzymes and thus are for example useful as herbicides or as lead compounds for the development of useful herbicides. This may be achieved by providing a cell that expresses the enzyme and thereby produces cell cultures expressing the enzyme are incubated in the presence of test compounds to form test cultures, and in the absence of lest compounds to form control cultures. Incubation is allowed to proceed for a sufficient time and under appropriate conditions to allow for interference with enzyme function. At a predetermined time after the start of incubation with a test compound, an assay is performed to monitor enzymatic activity. In one embodiment, enzyme activity is monitored in whole cells. Alternatively, enzymatic activity may be monitored in cell extracts or media containing the isolated enzyme using assays such as that described below. Additional controls, with respect to both cultur samples and assay samples, are also included, such as, for example, a host cell not expressing the enzyme (e.g., a host cell transformed with an expression plasmid containing the enzyme gene in a reverse orientation or with no insert). Enzyme inhibitory compounds are identified as those that reduce enzyme activity in the test cultures relative to the control cultures.

Host cells that may be used in practicing the present invention include without limitation bacterial, fungal, insect, mammalian, and plant cells. Preferably, bacterial cells are used. Most preferably, the bacterial cell is a variant (such as, e.g. the imp mutant of *E. coli*) that exhibits increased membrane permeability for test compounds relative to a wild-type host cell.

Preferably, the methods of the present invention are adapted to a high-throughput screen, allowing a multiplicity of compounds to be tested in a single assay. Such inhibitory compounds may be found in, for example, natural product libraries, fermentation libraries (encompassing plants and microorganisms), combinatorial libraries, compount files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondell et al., TibTech 14:60, 1996). Inhibitor assays according to the present invention are advantageous in accommodating many different types of solvents and thus allowing the testing of compounds from many sources.

Once a compound has been identified by the methods of the present invention as inhibitor, in vivo and in vitro tests may be performed to further characterize the nature and mechanism of the inhibitory activity. The effect of an identified compound on in vitro enzymatic activity of purified or partially purified may be determined and enzyme kinetic plots may be used to distinguish, e.g., competitive and non-competitive inhibitors.

Compounds identified as inhibitors using the methods of the present invention may be modified to enhance potency, efficacy, uptake, stability, and suitability for use in commercial herbicide applications, etc. These modifications are achieved and tested using methods well-known in the art.

Isolation of Herbicide-Resistant Enzyme Variants

The present invention encompasses the isolation of enzyme variants that are resistant to the action of enzyme inhibitors/herbicides. The enzyme variants may be naturally occurring or may be obtained by random or site-directed mutagenesis.

In one embodiment, a population of cells or organisms expressing the enzyme of interest is mutagenized using procedures well-known in the art, after which the cells or organisms are subjected to a screening or selection procedure to identify those that are resistant to the toxic effects of an inhibitor. The variant enzyme gene is then isolated from the resistant cell or organism using, e.g., PCR techniques.

In another embodiment, an isolated enzyme gene is subjected to random or site-directed mutagenesis in vitro, after which mutagenized versions of the gene are reintroduced into an appropriat cell such as, e.g., *E. coli*, and the cells are subjected to a selection or screening procedure as above.

The variant enzyme genes are expressed in an appropriate host cell, and the enzymatic properties of variant enzyme polypeptides are compared to the wild-type enzyme. Preferably, a given mutation results in an enzyme variant polypeptide that retains in vitro enzymatic activity, while exhibiting catalytic activity that is relatively more resistant to the selected herbicide(s) than is wild-type enzyme. Preferably, when expressed in a cell that requires enzyme activity for viability, the variant exhibits (i) catalytic activity alone sufficient to maintain the viability of a cell in which it is expressed; or catalytic activity in combination with any herbicide resistant enzyme variant protein also expressed in the cell, which may be the same as or different than the first enzyme protein, sufficient to maintain the viability of a cell in which it is expressed; and (ii) catalytic activity that is more resisant to the herbicide than is wild type enzyme.

Therefore, any one specific enzyme variant protein need not have the total catalytic activity necessary to maintain the viability of the cell, but must have some catalytic activity in an amount, alone or in combination with the catalytic activity of additional copies of the same enzyme variant and/or the catalytic activity of other enzyme variant protein(s), sufficient to maintain the viability of a cell that requires enzyme activity for viability. For example, catalytic activity may be increased to minimum acceptable levels by introducing multiple copies of a variant encoding gene into the cell or by introducing the gene which further includes a relatively strong promoter to enhance the production of the variant.

More resistant means that the catalytic activity of the variant is diminished by the herbicide(s), if at all, to a lesser degree than wild-type enzyme catalytic activity is diminished by the herbicide(s). Preferred more resistant variant enzyme retains sufficient catalytic activity to maintain the viability of a cell, plant, or organism wherein at the same concentration of the same herbicide(s), wild-type enzyme would not retain sufficient catalytic activity to maintain the viability of the cell, plant or organism.

Preferably, the catalytic activity in the absence of herbicide(s) is at least about 5% and, most preferably, is more than about 20% of the catalytic activity of the wild-type enzyme in the absence of herbicide(s).

Herbicide-resistant enzyme variants can be used as genetic markers in any cell that is normally sensitive to the inhibitory effects of the herbicide formation. In one embodiment, DNA encoding an herbicide-resistant enzyme variant is incorporated into a plasmid under the control of a suitable promoter. Any desired gene can then be incorporated into the plasmid, and the final recombinant plasmid introduced into an herbicide-sensitive cell. Cells that have been transformed with the plasmid are then selected or screened by incubation in the presence of a concentration of herbicide sufficient to inhibit growth and/or pigment formation.

Chemical-Resistant Plants and Plants Containing Variant Enzyme Genes

The present invention encompasses transgenic cells, including, but not limited to seeds, organisms, and plants into which genes encoding herbicide-resistant enzyme variants have been introduced. Non-limiting examples of suitable recipient plants are listed in Table 3 below:

TABLE 3

RECIPIENT PLANTS

| COMMON NAME | FAMILY | LATIN NAME |
|---|---|---|
| Maize | Gramineae | *Zea mays* |
| Maize; Dent | Gramineae | *Zea mays dentiformis* |
| Maize, Flint | Gramineae | *Zea mays vulgaris* |
| Maize, Pop | Gramineae | *Zea mays microsperma* |
| Maize, Soft | Gramineae | *Zea mays amylacea* |
| Maize, Sweet | Gramineae | *Zea mays amyleasaccharata* |
| Maize, Sweet | Gramineae | *Zea mays saccharate* |
| Maize, Waxy | Gramineae | *Zea mays ceratina* |
| Wheat, Dinkel | Pooideae | *Triticum spelta* |
| Wheat, *Durum* | Pooideae | *Triticum durum* |
| Wheat, English | Pooideae | *Triticum turgidum* |
| Wheat, Large Spelt | Pooideae | *Triticum spelta* |
| Wheat, Polish | Pooideae | *Triticum polonium* |
| Wheat, Poulard | Pooideae | *Triticum turgidum* |
| Wheat, singlegrained | Pooideae | *Triticum monococcum* |
| Wheat, Small Spelt | Pooideae | *Triticum monococcum* |
| Wheat, Soft | Pooideae | *Triticum aestivum* |
| Rice | Gramineae | *Oryza sativa* |
| Rice, American Wild | Gramineae | *Zizania aquatica* |
| Rice, Australian | Gramineae | *Oryza australiensis* |
| Rice, Indian | Gramineae | *Zizania aquatica* |
| Rice, Red | Gramineae | *Oryza glaberrima* |
| Rice, Tuscarora | Gramineae | *Zizana aquatica* |
| Rice, West African | Gramineae | *Oryza glaberrima* |
| Barley | Pooideae | *Hordeum vulgare* |
| Barley, Abyssinianintermediate, also Irregular | Pooideae | *Hordeum irregulare* |
| Barley, Ancestral Tworow | Pooideae | *Hordeum spontaneum* |
| Barley, Beardless | Pooideae | *Hordeum trifurcatum* |
| Barley, Egyptian | Pooideae | *Hordeum trifurcatum* |
| Barley, fourrowed | Pooideae | *Hordeum vulgare polystichon* |
| Barley, sixrowed | Pooideae | *Hordeum vulgare hexastichon* |
| Barley, Tworrowed | Pooideae | *Hordeum distichon* |
| Cotton, Abroma | Dicotyledoneae | *Abroma augusta* |
| Cotton, American Upland | Malvaceae | *Gossypium hirsutum* |
| Cotton, Asiatic Tree also Indian Tree | Malvaceae | *Gossypium arboreum* |
| Cotton, Brazilian, also, Kidney, and, Pernambuco | Malvaceae | *Gossypium barbadense brasiliense* |
| Cotton, Levant | Malvaceae | *Gossypium herbaceum* |
| Cotton Long Silk, also Long Staple, Sea Island | Malvaceae | *Gossypium barbadense* |
| Cotton Mexican, alsoShort Staple | Malvaveae | *Gossypium hirsutum* |
| Soybean, Soya | Leguminosae | *Glycine max* |
| Sugar beet | Chenopodiaceae | *Beta vulgaris altissima* |
| Sugar cane | Woody-plant | *Arenga pinnata* |
| Tomato | Solanaceae | *Lycopersicon esculentum* |
| Tomato, Cherry | Solanaceae | *Lycopersicon esculentum cerasiforme* |
| Tomato, Common | Solanaceae | *Lycopersicon esculentum commune* |
| Tomato, Currant | Solanaceae | *Lycopersicon pimpinellifolium* |
| Tomato, Husk | Solanaceae | *Physalis ixocarpa* |
| Tomato, Hyenas | Solanaceae | *Solanum incanum* |
| Tomato, Pear | Solanaceae | *Lycopersicon esculentum pyriforme* |
| Tomato, Tree | Solanaceae | *Cyphomandra betacea* |
| Potato | Solanaceae | *Solanum tuberosum* |
| Potato, Spanish, Sweet potato | Convolvulaceae | *Ipormoca batatas* |
| Rye, Common | Pooideae | *Secale cereale* |
| Rye, Mountain | Pooideae | *Secale montanum* |
| Pepper, Bell | Solanaceae | *Capsicum annuum grossum* |
| Pepper, Bird, also Cayenne, Guinea | Solanaceae | *Capsicum annuum minimum* |
| Pepper, Bonnet | Solanaceae | *Capsicum sinense* |
| Pepper, Bullnose, also Sweet | Solanaceae | *Capsicum annuum grossum* |
| Pepper, Cherry | Solanaceae | *Capiscum annuum cerasiforme* |
| Pepper, Cluster, also Red Cluster | Solanaceae | *Capsicum annuum fasciculatum* |
| Pepper, Cone | Solanaceae | *Capsicum annuum conoides* |
| Pepper, Goat, also Spur | Solanaceae | *Capsicum frutescens* |
| Pepper, Long | Solanaceae | *Capsicum frutescens longum* |

TABLE 3-continued

RECIPIENT PLANTS

| COMMON NAME | FAMILY | LATIN NAME |
|---|---|---|
| Pepper, Ornamental Red, also Wrinkled | Solanaceae | *Capsicum annuum abbreviatum* |
| Pepper, Tabasco Red | Solanaceae | *Capsicum annuum conoides* |
| Lettuce, Garden | Compositae | *Lactuca sativa* |
| Lettuce, Asparagus, also Celery | Compositae | *Lactuca sativa asparagina* |
| Lettuce, Blue | Compositae | *Lactuca perennis* |
| Lettuce, Blue, also Chicory | Compositae | *Lactuca pulchella* |
| Lettuce, Cabbage, also Head | Compositae | Lactuca satica capitata |
| Lettuce, Cos, also Longleaf, Romain | Compositae | *Lactuca sativa longifolia* |
| Lettuce, Crinkle, also Curled, Cutting, Leaf | Compositae | *Lactuca sativa crispa* |
| Celery | Umbelliferae | *Apium graveolens dulce* |
| Celery, Blanching, also Garden | Umbelliferae | *Apium graveolens dulce* |
| Celery, Root, also Turniproote | Umbelliferae | *Apium graveolens rapaceum* |
| Eggplant, Garden | Solanaceae | *Solanum melongena* |
| Sorghum | Sorghum | All crop specie |
| Alfalfa | Leguminosae | *Medicago sativum* |
| Carrot | Umbelliferae | *Daucus carota sativa* |
| Bean, Climbing | Leguminosae | *Phaseolus vulgaris vulgaris* |
| Bean, Sprouts | Leguminosae | *Phaseolus aureus* |
| Bean, Brazilian Broad | Leguminosae | *Canavalia ensiformis* |
| Bean, Broad | Leguminosae | *Vicia faba* |
| Bean, Common, also French, White, Kidney | Leguminosae | *Phaseolus vulgaris* |
| Bean, Egyptian | Leguminosae | *Dolichos lablab* |
| Bean, Long, also Yardlong | Leguminosae | *Vigna sesquipedalis* |
| Bean, Winged | Leguminosae | *Psophocarpus teragonolobus* |
| Oat, also Common, Side, Tree | Avena | *Sativa* |
| Oat, Black, also Bristle, Lopsided | Avena | *Strigosa* |
| Oat, Bristle | Avena | |
| Pea, also Garden, Green, Shelling | Leguminosae | *Pisum, sativum sativum* |
| Pea, Blackeyed | Leguminosae | *Vigna sinensis* |
| Pea, Edible Podded | Leguminosae | *Pisum sativum axipluum* |
| Pea, Grey | Leguminosae | *Pisum sativum speciosum* |
| Pea, Winged | Leguminosae | *Tetragonolobus purpureus* |
| Pea, Wrinkled | Leguminosae | *Pisum sativum meduilare* |
| Sunflower | Compositae | *Helianthus annuus* |
| Squash, Autumn, Winter | Dicotyledoneae | *Cucurbita maxima* |
| Squash, Bush, also Summer | Dicotyledoneae | *Cucurbita pepo melopepo* |
| Squash, Turban | Dicotyledoneae | *Cucurbita maxima turbaniformis* |
| Cucumber | Dicotyledoneae | *Cucumis sativus* |
| Cucumber, African, also Bitter | | *Momordica charantia* |
| Cucumber, Squirting, also Wild | | *Ecbalium elaterium* |
| Cucumber, Wild | | *Cucumis anguria* |
| Poplar, California | Woody-Plant | *Populus trichocarpa* |
| Poplar, European Black | | *Populus nigra* |
| Poplar, Gray | | *Populus canescens* |
| Poplar, Lombardy | | *Populus italica* |
| Poplar, Silverleaf, also White | | *Populus alba* |
| Poplar, Wester Balsam | | *Populus trichocarpa* |
| Tobacco | Solanaceae | *Nicotiana* |
| Arabidopsis Thaliana | Cruciferae | *Arabidopsis thaliana* |
| Turfgrass | Lolium | |
| Turfgrass | Agrostis | |
| | Other families of turfgrass | |
| Clover | Leguminosae | |

Expression of the variant polypeptides in transgenic plants confers a high level of resistance to herbicides allowing the use of these herbicides during cultivation of the transgenic plants.

Methods for the introduction of foreign genes into plants are known in the art. Non-limiting examples of such methods include *Agrobacterium* infection, particle bombardment, polyethylene glycol (PEG) treatment of protoplasts, electroporation of protoplasts, microinjection, macroinjection, tiller injection, pollen tube pathway, dry seed inhibition, laser perforation, and electrophoresis. These methods are described in, for example, B. Jenes et al., and S. W, Ritchie et al. In Transgenic Plants, Vol. 1, Engineering and Utilization, ed. S.-D. Kung, R. Wu, Academic Press, Inc., Harcourt Brace Jovanovich 1993; and L. Mannonen et al., Critical Reviews in Biotechnology, 14:287-310, 1994.

In a preferred embodiment, the DNA encoding a variant enzyme is cloned into a DNA vector containing an antibiotic resistance marker gene, and the recombinant enzyme DNA-containing plasmid is introduced into *Agrobacterium tumefaciens* containing a Ti plasmid. This "binary vector system" is described in, for example, U.S. Pat. No. 4,490,838, and in An et al. Plant Mol. Biol. Manual A3:1-19 (1988). The transformed *Agrobacterium* is then co-cultivated with leaf disks from the recipient plant to allow infection and transformation of plant cells. Transformed plant cells are then cultivated in regeneration medium, which promotes the formation of shoots, first in the presence of the appropriate antibiotic to select for transformed cells, then in the presence of herbicide. In plant cells successfully transformed with DNA encoding herbicide-resistant enzyme, shoot formation occurs even in the presence of levels of herbicide that inhibit shoot formation from non-transformed cells. After confirming the presence of variant enzyme DNA using, for example, polymerase chain reaction (PCR) analysis, transformed plants are tested for their ability to withstand herbicide spraying and for their capabilities for seed germination and root initiation and proliferation in the presence of herbicide.

The methods and compositions of the present invention can be used for the production of herbicide-resistant enzyme variants, which can be incorporated into plants to confer selective herbicide resistance on the plants. Intermediate variants of enzyme (for example, variants that exhibit sub-optimal specific activity but high herbicide resistance, or the converse) are useful as templates for the design of second-generation enzyme variants that retain adequate specific activity and high resistance.

Herbicide resistant enzyme genes can be tansformed into crop species in single or multiple copies to confer herbicide resistance. Genetic engineering of crop species with reduced sensitivity to herbicides can:

(1) Increase the spectrum and flexibility of application of specific effective and enviromentally benign herbicides;
(2) Enhance the commercial value of these herbicides;
(3) Reduce weed pressure in crop fields by effective use of herbicides on herbicide resistant crop species and a corresponding increase in harvest yields;
(4) Increase sales of seed for herbicid resistant plants;
(5) Increase resistance to crop damage from carry-over of herbicides applied in previous planting;
(6) Decrease susceptiblity to changes in herbicide characteristics due to adverse climate conditions; and
(7) Increase tolerance to unevenly or mis-applied herbicides.

For example, transgenic enzyme variant protein containing plants can be cultivated. The crop can be treated with a weed controlling effective amount of the herbicide to which the enzyme variant transgenic plant is resistant, resulting in weed control in the crop without detrimentally affecting the cultivated crop.

The compounds detected as inhibitors by the above screening methods may be used as pure compound or in combination together with appropriate additives for inhibiting the enzymes in plant, bacterial or protozoa organisms. Conventional additives in the field of herbicides, antibacterial agents or antiprotozoal agents may be used.

The invention shall now be described with reference to specific examples.

EXAMPLE 1

Construction of Expression Vectors (a) pNCO113

2.0 µg of the vector pQE30 (Qiagen, Hilden, Germany) is digested with 30 U of NcoI (New England Biolabs, Schwalbach, Germany (NEB)) in a total volume of 60 µl containing 6 µl of NEB4 buffer. The reaction mix is incubated for 3 h at 37° C. After adding 33 µM of each dNTP (NEB) and 5 U Klenow fragment of polymerase I from *E. coli* (NEB) the reaction mix is incubated for additional 30 min at 25° C. The vector DNA is purified using the PCR purification kit from Qiagen. 500 µl of buffer PB (Qiagen) are added to 98 µl of PCR reaction mixture and applied to a Quiaquick column and centrifuged for 1 min at 114,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of $H_2O$ (redistilled, sterile) are added to the column and it is centrifuged for 1 min at 14,000 rpm. The flow through contained 1.5 µg of purified vector DNA.

20 ng of vector DNA is religated with 1 U of T4-Ligase from Gibco-BRL (Eggenstein, Germany), 2 µl of T4-Ligase buffer (Gibco-BRL) in a total volume of 10 µl yielding the plasmid pQE_noNco. The ligation mixture is incubated over night at 4° C. With 2 µl of the ligation mixture electrocompetent *E. coli* XL1-Blue (Bullock, W. O., Fernandez, J. M., and Short, J. M. (1987). XL1-Blue: a high efficiency plasmid transforming recA *Escherichia coli* with β-galactosidase selection. *BioTechniques* 5, 376-379; commercial source: Stratagene, LaJolla, Calif., USA) cells are transformed.

Preparation of electrocompetent cells: 1 liter of LB medium is inoculated 1:100 with fresh overnight culture. The cells are grown at 37° C. with shaking at 220 rpm to an optical density of 0.5 at 600 nm. The cells are chilled on ice for 20 min and centrifuged for 15 min at 4,000 rpm at 4° C. The supernatant is removed and the pellet is resuspended in 1 liter of ice-cold sterile 10% (v/v) glycerol. The cells are centrifuged two times as described before resuspending the cells in 0.5 liter and in 20 ml of ice-cold sterile 10% (v/v) glycerol, respectively. The cells are centrifuged an additional time and the pellet is resuspended in a volume of 2 ml of ice-cold 10% (v/v) glycerol. This suspension is frozen in aliquots of 80 µl and stored in liquid nitrogen.

Electro-transformation using the Gene Pulser apparatus from Biorad (Munich, Germany): The electrocompetent cells are thawed on ice. 40 µl of the cell suspension are mixed with 2 µl of ligation mixture and transferred into a prechilled, sterile 0.2 cm cuvette (Biorad). The suspension is shaked to the bottom and the cuvette is placed into the prechilled chamber slide. The chamber slide is pushed into the chamber and the cells are pulsed at 2.50 kV, 25 µF and Pulse Controller setting 200Ω. The cuvette is removed from the chamber and the cells are suspended in 1 ml of SOC medium (2% (w/v) casein hydrolysate, 0.5% (w/v) yeast extract, 10 mM NaCl, 2.5 mM KCl, 10 mM $MgCl_2$, 10 mM $MgSO_4$ and 20 mM glucose. The suspension is shaked for 1 h at 37° C. and 100 µl of the suspension is plated on LB plates containing 150 mg/l ampicillin for maintenance of the plasmid pQE_noNco.

Cells of *Escherichia coli* XL1-Blue harboring the vector pQE_noNco, are grown overnight in Luria Bertani (LB) medium containing 180 mg/l of ampicillin for maintenance of the plasmid in the host cells. 7 ml of the culture are centrifuged for 20 min at 5,000 rpm. The cell pellet is used for isolation of the plasmid pQE_noNco with the mini plasmid isolation kit from Qiagen (Hilden, Germany). The pellet is resuspended in 0.3 ml of 10 mM EDTA in 50 mM Tris hydrochloride, pH 8.0. 30 µg RNase A are added. 0.3 ml of 1% (w/v) SDS in 200 mM sodium hydroxide are added and incubated for 5 min at room temperature. 0.3 ml of chilled 3.0

M sodium acetate, pH 5.5 are added and incubated for 10 min on ice. The mixture is centrifuged for 15 min at 14,000 rpm in a minifuge. The supernatant is applied onto a Quiagen-tip 20, which is previously equilibrated with 1 ml of 750 mM NaCl, 15% (v/v) ethanol and 0.15% (v/v) Triton X-100 in 50 mM MOPS, pH 7.0. The Quiagen-tip is washed four times with 1 ml of of 1000 mM NaCl and 15% (v/v) ethanol in 50 mM MOPS, pH 7.0. The DNA is eluted with 0.8 ml of 1250 mM NaCl and 15% (v/v) ethanol in 50 mM Tris hydrochloride, pH 8.5. The DNA is precipitated with 0.56 ml of isopropanol, centrifuged 30 min at 14,000 rpm and washed with 1 ml of ice-cold 70% (v/v) ethanol. After drying in a speedvac for 5 min, the DNA is dissolved in 50 µl of redistilled $H_2O$. The solution contained 8.3 µg of the vector DNA pQE_noNco.

The DNA sequence of the vector pQE_noNco is sequenced by the automated dideoxynucleotide method (Sanger, F., S. Nicklen, und A. R. Coulson. (1977). DNA sequence analysis with chain terminating inhibitors. *Proc. Acad. Natl. Sci. USA* 74, 5463-5468) using an ABI Prism 377™ DNA sequencer from Perkin Elmer (Norwalk, USA) with the ABI Prism™ Sequencing Analysis Software from Applied Biosystems Divisions (Foster City, USA).

The DNA sequence is found to be as expected.

2.0 µg of the vector pQE_noNco is digested with 30 U of EcoRI and 30 U of SalI (NEB) in a total volume of 60 µl containing 6 µl of EcoRI buffer (NEB). The reaction mix is incubated for 3 h at 37° C. The vector DNA is purified using the PCR purification kit from Qiagen.

25 pmol of the oligonucleotides 5'-CACACAGAATTCAT-TAAAGAGGAGAAATTAACCATGGGAG-GATCCGTCGACCTGCA GCC-3' (SEQ ID NO:17) and 5'-GGCTGCAGGTCGACGGATCCTCCCATG-GTTAATTTCTCCTCTTTAATGAATTCTGT GTG-3' (SEQ ID NO:18) are dissolved in 6 µl EcoRI buffer (NEB and 54 µl $H_2O$. The solution is heated at 96° C. for 2 min and cooled down to 10° C. within 12 h in order to hybridisize the DNA linker. The reaction mix is supplied with 30 U of EcoRI and 30 U of SalI (NEB) and incubated for 3 h at 37° C. The reaction mix is heated to 65° C. for 30 min in order to inactivate the enzymes and cooled down to 10° C. within 12 h for hybridisation. The reaction mix contains approximately 730 ng of the DNA linker.

20 ng of the digested pQE_noNco vector DNA (see above) and 300 pg of the DNA linker, 2 µl of T4-Ligase buffer (Gibco-BRL) are ligated together with 1 U of T4-Ligase from Gibco-BRL (Eggenstein, Germany)), 2 µl of T4-Ligase buffer (Gibco-BRL) in a total volume of 10 µl yielding the plasmid pNCO113. The ligation mixture is incubated over night at 4° C. With 2 µl of the ligation mixture electrocompetent *E. coli* XL1-Blue cells are transformed.

5 µg of the plasmid pNCO113 are isolated and the DNA sequence of the vector pNCO113 is sequenced as described above. The DNA sequence is shown in FIG. 9A. The culture is on deposit with ATCC as a patent deposit with the title *Escherichia coli* strain XL1-Blue habouring plasmid pNCO113, assigned PTA-852, date of deposit: Oct. 14, 1999.

(b) pNCO-SB-$H_6$-ACYC184 (Expression of $His_6$-X Fusion Proteins)

5.0 µg of the vector pACYC184 (New England Biolabs, Schwalbach, Germany (NEB)) is digested with 30 U of NcoI (NEB) and 40 U of BamHI (NEB) in a total volume of 70 µl containing 7 µl of NEB4 buffer. The reaction mixture is incubated for 3 h at 37° C. and size-separated on a 0.8% agarose gel electrophoresis. A 2.2 kB NcoI/BamHI DNA fragment is excised from the gel and purified with the QIAquick gel extraction kit from Qiagen (Hilden, Germany). To 500 mg of gel slice 1500 µl of QG buffer are added and the mixture is incubated at 50° C. for 10 min. 500 µl of isopropanol are added and the mixture is applied to a Quiaquick spin column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of $H_2O$ (redistilled, sterile) are added to the column and it is centrifuged for 1 min at 14,000 rpm. The flow through contains 1.5 µg of purified DNA fragment NB-ACYC184.

3 µg of the vector pNCO113 is digested with 30 U of NcoI (NEB) and 40 U of BamHI (NEB) in a total volume of 70 µl containing 7 µl of NEB4 buffer. The reaction mixture is incubated for 3 h at 37° C. The NcoI/BamHI digested pNCO113 vector is purified with the PCR purification kit from Qiagen. 210 µl of PB buffer are added to the 70 µl of the restriction mixture and the total mixture is applied to a Quiaquick spin column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of $H_2O$ (redistilled, sterile) are added to the column and it is centrifuged for 1 min at 14,000 rpm. The flow through contains 1.4 µg of the purified NcoI/BamHI restricted vector pNCO113.

20 ng of vector DNA and 10 ng of the DNA fragment NB-ACYC184 are ligated with 1 U of T4-Ligase from Gibco-BRL (Eggenstein, Germany), 2 µl of T4-Ligase buffer (Gibco-BRL) in a total volume of 10 µl yielding the plasmid pNCO-NB-ACYC184.

The ligation mixture is incubated over night at 4° C. With 2 µl of the ligation mixture electrocompetent *E. coli* XL1-Blue (Bullock, W. O., Fernandez, J. M., and Short, J. M. (1987). XL1-Blue: a high efficiency plasmid transforming recA *Escherichia coli* with β-galactosidase selection. Bio-Techniques 5, 376-379; commercial source: Stratagene, LaJolla, Calif., USA) cells are transformed.

Preparation of electrocompetent cells: 1 liter of LB medium is inoculated 1:100 with fresh overnight culture. The cells are grown at 37° C. with shaking at 220 rpm to an optical density of 0.5 at 600 nm. The cells are chilled on ice for 20 min and centrifuged for 15 min at 4,000 rpm at 4° C. The supernatant is removed and the pellet is resuspended in 1 liter of ice-cold sterile 10% (v/v) glycerol. The cells are centrifuged two times as described before resuspending the cells in 0.5 liter and in 20 ml of ice-cold sterile 10% (v/v) glycerol, respectively. The cells are centrifuged an additional time and the pellet is resuspended in a volume of 2 ml of ice-cold 10% (v/v) glycerol. This suspension is frozen in aliquots of 80 µl and stored in liquid nitrogen.

Electro-transformation using the Gene Pulser apparatus from Biorad (Munich, Germany): The electrocompetent cells are thawed on ice. 40 µl of the cell suspension are mixed with 2 µl of ligation mixture and transferred into a prechilled, sterile 0.2 cm cuvette (Biorad). The suspension is shaked to the bottom and the cuvette is placed into the prechilled chamber slide. The chamber slide is pushed into the chamber and the cells are pulsed at 2.50 kV, 25 pF and Pulse Controller setting 200Ω. The cuvette is removed from the chamber and the cells are suspended in 1 ml of SOC medium (2% (w/v) casein hydrolysate, 0.5% (w/v) yeast extract, 10 mM NaCl, 2.5 mM KCl, 10 mM $MgCl_2$, 10 mM $MgSO_4$ and 20 mM glucose. The suspension is shaked for 1 h at 37° C. and 100 µl of the suspension is plated on LB plates containing 150 mg/l ampicillin for maintenance of the plasmid pNCO-NB-ACYC184.

Cells of *Escherichia coli* XL1-Blue harboring the vector pNCO-NB-ACYC184, are grown overnight in Luria Bertani (LB) medium containing 180 mg/l of ampicillin for maintenance of the plasmid in the host cells. 7 ml of the culture are centrifuged for 20 min at 5,000 rpm. The cell pellet is used for isolation of the plasmid pNCO-NB-ACYC184 with the mini plasmid isolation kit from Qiagen. The pellet is resuspended in 0.3 ml of 10 mM EDTA in 50 mM Tris hydrochloride, pH 8.0. 30 µg RNase A are added. 0.3 ml of 1% (w/v) SDS in 200 mM sodium hydroxide are added and incubated for 5 min at room temperature. 0.3 ml of chilled 3.0 M sodium acetate, pH 5.5 are added and incubated for 10 min on ice. The mixture is centrifuged for 15 min at 14,000 rpm in a minifuge. The supernatant is applied onto a Quiagen-tip 20, which is previously equilibrated with 1 ml of 750 mM NaCl, 15% (v/v) ethanol and 0.15% (v/v) Triton X-100 in 50 mM MOPS, pH 7.0. The Quiagen-tip is washed four times with 1 ml of of 1000 mM NaCl and 15% (v/v) ethanol in 50 mM MOPS, pH 7.0. The DNA is eluted with 0.8 ml of 1250 mM NaCl and 15% (v/v) ethanol in 50 mM Tris hydrochloride, pH 8.5. The DNA is precipitated with 0.56 ml of isopropanol, centrifuged 30 min at 14,000 rpm and washed with 1 ml of ice-cold 70% (v/v) ethanol. After drying in a speedvac for 5 min, the DNA is dissolved in 50 µl of redistilled $H_2O$. The solution contains 7.5 µg of the vector DNA pNCO-NB-ACYC184.

The DNA sequence of the vector pNCO-NB-ACYC184 is sequenced by the automated dideoxynucleotide method (Sanger, F., S. Nicklen, und A. R. Coulson. (1977). DNA sequence analysis with chain terminating inhibitors. Proc. Acad. Nat. Sci. USA 74, 5463-5468) using an ABI Prism 377™ DNA sequencer from Perkin Elmer (Norwalk, USA) with the ABI Prism™ Sequencing Analysis Software from Applied Biosystems Divisions (Foster city, USA).

The DNA sequence is found to be as expected.

4.0 µg of the vector pNCO-NB-ACYC184 is digested with 30 U of NcoI and 30 U of SacII (NEB) in a total volume of 60 µl containing 6 µl of NEB4 buffer (NEB). The reaction mix is incubated for 3 h at 37° C. The reaction mixture si size-seperated by agarose gel electrophoresis and the vector DNA is purified using the Gel extraction kit kit from Qiagen as described above. 2.1 µg DNA are obtained.

Each 1 nmol of the oligonucleotides 5'-CATGCACCAC-CACCACCACCACGCGTCCATGGCCGC-3' (SEQ ID NO:19) and 5'-GGCCATGGACGCGTGGTGGTGGTG-GTGGTG-3' (SEQ ID NO:20) are dissolved in 15 µl of 66 mM $MgCl_2$, 0.5 mM NaCl, 10 mM DTT and 66 mM Tris hydrochloride, pH 7.6. Water is added to a final volume of 100 µl and the reaction mixture is heated at 94° C. for 15 min. After heating at 60° C. for further 15 min the reaction mixture is cooled down to room temperature within 1 h in order to hybridisize the His-tag DNA linker.

20 ng of the digested vector DNA (see above) and 300 pg of the DNA linker, 2 µl of T4-Ligase buffer (Gibco-BRL, Eggenstein, Germany) are ligated together with 1 U of T4-Ligase from Gibco-BRL, 2 µl of T4-Ligase buffer (Gibco-BRL) in a total volume of 10 µl yielding the plasmid pNCO-SB-$H_6$-ACYC184. The ligation mixture is incubated over night at 4° C. With 2 µl of the ligation mixture electrocompetent *E. coli* XL1-Blue cells are transformed.

4.5 µg of the plasmid pNCO-SB-$H_6$-ACYC184 are isolated and the DNA sequence of the vector pNCO-SB-$H_6$-ACYC184 is sequenced as described above. The DNA sequence is shown in FIG. 9B.

EXAMPLE 2

Production of an Expression Clone and Construction of an Expression Vector for ygbP of *E. coli*

Cells of *Escherichia coli* XL1-Blue harboring the expression vector pNCO113, are grown overnight in Luria Bertani (LB) medium containing 180 mg/l of ampicillin for maintenance of the plasmid in the host cells. 7 ml of the culture are centrifuged for 20 min at 5,000 rpm. The cell pellet is used for isolation of the plasmid pNCO113 with the mini plasmid isolation kit from Qiagen (Hilden, Germany). The pellet is resuspended in 0.3 ml of 10 mM EDTA in 50 mM Tris hydrochloride, pH 8.0. 30 µg RNase are added. 0.3 ml of 1% (w/v) SDS in 200 mM sodium hydroxide are added and incubated for 5 min at room temperature. 0.3 ml of chilled 3.0 M sodium acetate, pH 5.5 are added and incubated for 10 min on ice. The mixture is centrifuged for 15 min at 14,000 rpm in a minifuge. The supernatant is applied onto a Quiagen-tip 20, which is previously equilibrated with 1 ml of 750 mM NaCl, 15% (v/v) ethanol and 0.15% (v/v) Triton X-100 in 50 mM MOPS, pH 7.0. The Quiagen-tip is washed four times with 1 ml of of 1000 mM NaCl and 15% (v/v) ethanol in 50 mM MOPS, pH 7.0. The DNA is eluted with 0.8 ml of 1250 mM NaCl and 15% (v/v) ethanol in 50 mM Tris hydrochloride, pH 8.5. The DNA is precipitated with 0.56 ml of isopropanol, centrifuged 30 min at 14,000 rpm and washed with 1 ml of ice-cold 70% (v/v) ethanol. After drying in a speedvac for 5 min, the DNA is dissolved in 50 µl of redistilled $H_2O$. The solution contained 8.3 µg of DNA.

Chromosomal DNA from *Escherichia coli* strain XL1-Blue is isolated according to a method described by Meade et al. (Meade, H. M., Long, S. R., Ruvkun, C. B., Brown, S. E., and Auswald, F. M. (1982). Physical and genetic characterization of symbiotic and auxotrophic mutants of *Rhizobium meliloti* induced by transposon Tn5 mutagenis. *J. Bacteriol.* 149, 114-122). The *E. coli* ORF ygbP (accession no. gb AE000358) from basepair (bp) position 6754 to 7464 is amplified by PCR using chromosomal *E. coli* DNA as template. The reaction mixture contained 25 pmol of primer AAATTAACCATGGCMCCACTCATTTGG (SEQ ID NO:21), 25 pmol of primer TTGGGCCTGCAGCGC-CAAAGG (SEQ ID NO:22), 20 ng of chromosomal DNA, 2U of Taq DNA polymerase (Eurogentec, Seraing, Belgium) and 20 nmol of dNTPs in 1.5 mM $MgCl_2$, 50 mM KCl, 10 mM Tris-hydrochloride, pH 8.8 and 0.1% (w/w) Triton X-100 in a total volume of 100 µl.

The mixture is denaturated for 3 min at 95° C. Then 25 PCR cycles for 30 sec at 94° C., 30 sec at 50° C. and 45 sec at 72° C. follow. After further incubation for 7 min at 72° C., the mixture is cooled to 4° C. An aliquot of 2 µl is subjected to agarose gel electrophoresis. The PCR amplificate is purified with PCR purification kit from Qiagen. 500 µl of buffer PB (Qiagen) are added to 98 µl of PCR reaction mixture and applied to a Quiaquick column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of $H_2O$ (redistilled, sterile) are added to the column and it is centrifuged for 1 min at 14,000 rpm. The flow through contained 1.5 µg of purified PCR product.

2.0 µg of the vector pNCO113 and 1.5 µg of the purified PCR product are digested in order to produce DNA fragments with overlapping ends. Each restriction mixture contained 7 µl of NEB3 buffer (NEB), 7 µg of BSA, 40 U of NcoI (NEB), 30 U of PstI (NEB) in a total volume of 70 µl and is incubated for 3 h at 37° C. Digested vector DNA and PCR product are purified using the PCR purification kit from Qiagen.

20 ng of vector DNA and 16 ng of PCR product are ligated together with 1 U of T4-Ligase from Gibco-BRL (Eggenstein, Germany), 2 µl of T4-Ligase buffer (Gibco) in a total volume of 10 µl yielding the plasmid pNCOygbP. The ligation mixture is incubated over night at 4° C. With 2 µl of the ligation mixture electrocompetent *E. coli* XL1-Blue cells are transformed.

The plasmid pNCOygbP is isolated as described in example 1.

The DNA insert of the plasmid pNCOygbP is sequenced as described in example 1.

EXAMPLE 3a

Construction of an Expression Vector for ygbP of *A. thaliana* without Leader Sequence 1 g of 2 weeks old *Arabidopsis thaliana* var. *Columbia* plants (stems and leafs) are frozen and homogenisated in liquid nitrogen. 8 ml of a sterile solution of 600 g/l guanidine thiocyanate, 5 g/l sodium-N-lauroylsarcosine, 50 mM trisodium citrate and 5 ml/l 2-mercaptoethanol are added. This mixture is added carefully to 3 ml of a solution (autoclaved) of 959 g/l CsCl and 37.2 g/l EDTA and centrifugated at 33000 rpm at 18° C. for 24 h. The supernatant is dicarded and the pellet is airdried for 10 min. The dried pellet is dissolved in 360 ml $H_2O$ (double distillied, sterile). The solution is centrifugated at 14000 rpm for 10 min. The supernatant is mixed with 40 ml 3 M sodium acetate and 1 ml ethanol. The RNA is precipitated over night at −20° C., centrifugated at 14000 rpm at 4° C. for 15 min. and washed twice with 500 ml 75% ethanol. The pellet is airdried and dissolved in 200 ml $H_2O$ (bidestillated, sterile). 500 µg RNA are obtained.

A mixture containing 2.75 mg RNA, 50 nmol dNTP's, 1 mg random hexameric primer, 1 mg $T_{15}$-primer and 20% first strand 5× buffer (Promega, Madison, USA) in a total volume of 50 ml is incubated for 5 min. at 95° C., cooled on ice and 500 U M-MLV reverse transkriptase (Promega) are added. The mixture is incubated for 1 h at 42° C. After incubation at 92° C. for 5 min., RNase A (20 U) and RNase H (2 U) are added and the mixture is incubated for 30 min. at 37° C.

The resulting cDNA (1 ml of this mixture) is used for the amplification of the ygbP gene by PCR.

The expression vector pNCO113 is isolated as described in example 1. The *A. thaliana* ORF ygbP (accession no. gbAL004136) without the coding region for the putative leader sequence from basepair (bp) position 79845 to 81915 is amplified by PCR using cDNA from *A. thaliana* as template. The reaction mixture contained 25 pmol of primer TTGTTGTGMGGAGAAGAGTG (SEQ ID NO:23), 25 pmol of primer CATGCATACCCTTGACACGTC (SEQ ID NO:24), 1 µg of cDNA, 2U of Taq DNA polymerase (Eurogentec, Seraing, Belgium) and 20 nmol of dNTPs in 1.5 mM $MgCl_2$, 50 mM KCl, 10 mM Tris-hydrochloride, pH 8.8 and 0.1% (w/w) Triton X-100 in a total volume of 100 µl.

The mixture is denaturated for 3 min at 95° C. Then 40 PCR cycles for 45 sec at 94° C., 45 sec at 50° C. and 60 sec at 72° C. followed. After further incubation for 20 min at 72° C., the mixture is cooled to 4° C. An aliquot of 2 µl is subjected to agarose gel electrophoresis. The PCR amplificate is purified with the PCR purification kit from Qiagen as described in Example 1. 1.5 µg of purified PCR product are obtained.

The PCR amplificate is used as template for a second PCR reaction. The reaction mixture contained 25 pmol of primer CAATGTTGTTGCCAT GGAGAAG (SEQ ID NO:25), 25 pmol of primer ACACGTCTTCTGCAGAAGTAAATG (SEQ ID NO:26), 2 µl of the first PCR amplification, 2U of Taq DNA polymerase (Eurogentec, Seraing, Belgium) and 20 nmol of dNTPs in a total volume of 100 µl of 1.5 mM $MgCl_2$, 50 mM KCl, 10 mM Tris-hydrochloride, pH 8.8 and 0.1% (w/w) Triton X-100.

The mixture is denaturated for 3 min at 95° C. Then 40 PCR cycles for 45 sec at 94° C., 45 sec at 50° C. and 60 sec at 72° C. follow. After further incubation for 20 min at 72° C., the mixture is cooled to 4° C. An aliquot of 2 µl is subjected to agarose gel electrophoresis. An aliquot of 2 µl is subjected to agarose gel electrophoresis.

The PCR amplificate is purified with PCR purification kit from Qiagen as described in Example 1. 1.2 µg of purified PCR product are obtained. 2.0 µg of the vector pNCO113 (isolated as described in example 2) and 1.5 µg of the purified PCR product are digested in order to produce DNA fragments with overlapping ends. Each restriction mixture contained 7 µl of NEB3 buffer, 40 U of NcoI (NEB), 30 U of PstI (NEB) in a total volume of 70 µl and is incubated for 3 h at 37° C. Digested vector DNA and PCR product are purified using the PCR purifiaction kit from Qiagen.

20 ng of vector DNA and 8 ng of PCR product are ligated together with 1 U of T4-Ligase (Gibco), 2 µl of T4-Ligase buffer (Gibco) in a total volume of 10 µl, yielding the plasmid PNCOygbPara. The ligation mixture is incubated over night at 4° C. 2 µl of the ligation mixture is transformed into electrocompetent *E. coli* XL1-Blue cells as described in example 1. The electrocompetent cells are prepared as described in example 1.

The DNA insert of the plasmid pNCOygbPara is sequenced as described in Example 1. The results are shown in FIG. 7A.

EXAMPLE 3b

Production of an Expression Clone and Construction of an Expression Vector for the Full-Length ygbP of *Arabidopsis thaliana*

1 g of 2 weeks old *Arabidopsis thaliana* var. *Columbia* plants (stems and leafs) are frozen and homogenisated in liquid nitrogen. 8 ml of a sterile solution of 600 g/l guanidine thiocyanate, 5 g/l sodium-N-lauroylsarcosine, 50 mM trisodiumcitrate and 5 ml/l 2-mercaptoethanol are added. This mixture is added carefully to 3 ml of a solution (autoclaved) of 959 g/l CsCl and 37.2 g/l EDTA and centrifugated at 33,000 rpm at 18° C. for 24 h. The supernatant is dicarded and the pellet is airdried for 10 min. The dried pellet is dissolved in 360 µl $H_2O$ (double distillied, sterile). The solution is centrifugated at 14,000 rpm for 10 min. The supernatant is mixed with 40 µl 3 M sodium acetate and 1 ml ethanol. The RNA is precipitated over night at −20° C., centrifugated at 14,000 rpm at 4° C. for 15 min. and washed twice with 500 µl 75% ethanol. The pellet is airdried and dissolved in 200 µl $H_2O$ (double distilled, sterile). 500 µg RNA are obtained.

A mixture containing 2.75 µg RNA, 50 nmol dNTP's, 1 µg random hexameric primer, 1 µg $T_{15}$-primer and 20% first strand 5× buffer (Promega) in a total volume of 50 µl is incubated for 5 min. at 95° C., cooled on ice and 500 U M-MLV reverse transkriptase (Promega) are added. The mixture is incubated for 1 h at 42° C. After incubation at 92° C. for 5 min., RNase A (20 U) and RNase H (2 U) are added and the mixture is incubated for 30 min. at 37° C.

The resulting cDNA (1 µl of this mixture) is used for the amplification of ygbP by PCR.

The expression vector pQE30 (Qiagen) is isolated as described in example 1. The full-length *A. thaliana* ORF ygbP (accession no. gb AC004136) is amplified from base pair (bp) position 19412 to 21482 by PCR using cDNA from *A. thaliana* as template (see above). The reaction mixture contains 25 pmol of the primer 5'-CTTCTCTCAGGC-GAGATAAAACATGG-3' (SEQ ID NO:27), 25 pmol of the primer 5'-CATGCATACCCTTGACACGTC-3' (SEQ ID NO:24), 1 µg of cDNA, 2 U of Taq-DNA polymerase (Eurogentec, Seraing, Belgium) and 20 nmol of dNTPs in a total volume of 100 µl of 1.5 mM $MgCl_2$, 50 mM KCl, 10 mM Tris-hydrochloride, pH 8.8 and 0.1% (w/w) Triton X-100.

The mixture is denatured for 3 min at 95° C. Then 40 PCR cycles for 45 sec at 94° C., 45 sec at 50° C. and 60 sec at 72° C. followed. After further incubation for 20 min at 72° C., the mixture is cooled to 4° C. An aliquot of 2 µl is subjected to agarose gel electrophoresis. The PCR amplificate is purified with the PCR purification kit from Qiagen as described in Example 1. 1.7 µg of purified PCR product are obtained.

The PCR amplificate is used as template for a second PCR reaction. The reaction mixture contains 25 pmol of the primer 5'-GGCGAGAGGATCCATGGCGATGTCTCAGACG-3' (SEQ ID NO:28), 25 pmol of the primer 5'-ACACGTCT-TCTGCAGMGTAAATG-3' (SEQ ID NO:26), 2 µl of the first PCR amplification, 2 U of Taq DNA polymerase (Eurogentec, Seraing, Belgium) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denatured for 3 min at 95° C. Then 40 PCR cycles for 45 sec at 94° C., 45 sec at 50° C. and 60 sec at 72° C. follow. After further incubation for 20 min at 72° C., the mixture is cooled to 4° C. An aliquot of 2 µl is subjected to agarose gel electrophoresis. An aliquot of 2 µl is subjected to agarose gel electrophoresis.

The PCR amplificate is purified with PCR purification kit from Qiagen as described in Example 1. 1.2 µg of purified PCR product are obtained. 2.0 µg of the vector pQE30 and 1.5 µg of the purified PCR product are digested in order to produce DNA fragments with overlapping ends. Each restriction mixture contains 7 µl of NEB3 buffer from New England Biolabs (NEB), 40 U of BamH/(NEB), 30 U of PstI (NEB) in a total volume of 70 µl and is incubated for 3 h at 37° C. Digested vector DNA and PCR product are purified using the PCR purification kit from Qiagen.

20 ng of vector DNA and 8 ng of PCR product are ligated together with 1 U of T4-Ligase (Gibco), 2 µl of T4-Ligase buffer (Gibco) in a total volume of 10 µl, yielding the plasmid pQEygbParakom. The ligation mixture is incubated over night at 4° C. 2 µl of the ligation mixture is transformed into electrocompetent *E. coli* XL1-Blue cells as described in example 1. The electrocompetent cells are prepared as described in example 1.

The DNA insert of the plasmid pQEygbParakom is sequenced as described in example 1 and is not identical to the caclulated cDNA sequence of the database entry (gb AC004136). The DNA and the corresponding amino acid sequence of the full-length ygbP gene of *A. thaliana* is shown in FIG. 7B.

EXAMPLE 4

Preparation and Purification of Recombinant YgbP Protein of *E. coli*

0.5 liter of Luria Bertani (LB) medium containing 90 mg of ampicillin are inoculated with 10 ml of an overnight culture of *E. coli* strain XL1-Blue harboring plasmid pNCOygbP. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 50 mM Tris hydrochloride pH 8.0, centrifuged as above and frozen at –20° C. for storage.

The cells are thawed in 10 ml of 20 mM tris hydrochloride pH 8.0 containing 1 mM dithioerythritol, 0.02% sodium azide (buffer A) in the presence of 4 mg/ml lysozyme and 10 µg/ml DNaseI. The mixture is incubated at 37° C. for 1 h, cooled on ice and sonified 6×10 sec with a Branson Sonifier 250 (Branson SONIC Power Company, Danbury, USA) set to 70% duty cycle output, control value of 4 output. The suspension is centrifuged at 15,000 rpm at 4° C. for 30 min. The supernatant is applied on a column of Sepharose Q FF (size 4.6×24 cm, Amersham Pharmacia Biotech, Freiburg, Germany) previously equilibrated with 200 ml buffer A. The column is washed with buffer A monitoring at 280 nm. 4-diphosphocytidyl-2C-methyl-D-erythritol synthase is eluted from the column with a gradient from 0-0.5 M sodium chloride in 300 ml of buffer A. The enzyme is identified by SDS-PAGE showing a band at 26 kDa. Fractions showing this protein band are collected and dialysed against buffer A overnight. The enzyme is further purified on a column of Red Sepharose CL-6B (size 2.6×10 cm, Amersham Pharmacia Biotech) equilibrated with buffer A. The enzyme is passed throughout the column which is loaded on Source 15Q (column volume 20 ml, Amersham Pharmacia Biotech). The enzyme is eluted by gradient of 0-0.5 M sodium chloride in 250 ml buffer A. The homogeneity of 4-diphosphocytidyl-2C-methyl-D-erythritol synthase is judged by SDS-PAGE.

EXAMPLE 5

Preparation and Purification of Recombinant YgbP Protein of *A. thaliana* without Leader Sequence Cells of *E. coli* strain XL1-Blue harboring the plasmid pNCOygbPara were grown, induced and harvested as described in example 3. The cells (2 g) are suspended in 30 ml of buffer A (50 mM Tris HCl pH 8.0, 1 mM DTE, 0.02% sodium azide) in the presence of 12 mg of lysozyme, 1.2 mg of DNaseI. The suspension is incubated at 37° C. for 30 min. The extraction is performed by ultrasonification as described in example 4. Cell debris is got rid by centrifugation at 15,000 rpm for 30 min. The cell free extract is loaded on Sepharose Q FF (size 2.6×10 cm) equilibrated with buffer A at flow rate 3 ml/min. The column is washed with buffer A monitoring at OD 280 nm. 4-diphosphocytidyl-2C-methyl-D-erythritol synthase from *A. thaliana* is eluted by linear gradient of 0-0.5 M NaCl in buffer A. The fractions containing enzyme activity are pooled. The volume of pooled fraction is reduced to ca. 2 ml by ultrafiltration (MWCO 10 kDa, Amicon, USA). The concentrated 4-diphosphocytidyl-2C-methyl-D-erythritol synthase from *A. thaliana* loaded on Superdex 75 HR 26/60 at flow rate 2 ml/min using buffer A containing 100 mM NaCl as a running buffer. The active fractions are pooled. The elution volume of 4-diphosphocytidyl-2C-methyl-D-erythritol synthase from *A. thaliana* is 140 ml. The homogeinity of 4-diphosphocytidyl-2C-methyl-D-erythritol synthase from *A. thaliana* is judged by SDS-PAGE.

EXAMPLE 6

Preparation of D-erythritol 4-phosphate

The sodium salt of D-erythrose 4-phosphate (14.6 mg, 65.7 pmol) is dissolved in methanol (600 μl, 40% (v/v)). Sodium borohydride is added. The reaction is monitored by detection of the aldehyde according to the method of Stahl (Bollinger, H. R., Brenner, M., Gänshirt, H., Mangold, H. K., Seiler, H., Stahl, E. ad Waldi, D. (1964) IN: Dünnschicht-Chromatographie; Ein Laboratoriumshandbuch (ed. Stahl, E.) Springer Verlag, Berlin, Göttingen; Heidelberg). After consumption of the aldehyde the pH of the solution is adjusted with acetic acid to 4-5. The reaction mixture is lyophillized yielding D-erythritol 4-phosphate as a dry compound.

$^1$H-NMR (500 MHz, D$_2$O, pH 7) d (ppm) 1.81 (s, acetate), 3.20-3.55 (m, 1H), 3.60-3.67 (m, 2H), 3.68-3.71 (m, 1H), 3.80-3.87 (m, 1H), 3.88-3.92 (m, 1H).

EXAMPLE 7

Preparation of D-ribitol 5-phosphate

The sodium salt of D-ribose 5-phosphate (18.5 mg, 67.5 μmol) is dissolved in methanol (600 μl, 40% (v/v)). Sodium borohydride is added. The reaction is monitored by detection of the aldehyde according to the method of Stahl (Bollinger, H. R., Brenner, M., Gänshirt, H., Mangold, H. K., Seiler, H., Stahl, E. ad Waldi, D. (1964) IN: Dünnschicht-Chromatographie; Ein Laboratoriumshandbuch (ed. Stahl, E.) Springer Verlag, Berlin, Göttingen; Heidelberg). After consumption of the aldehyde the pH of the solution is adjusted with acetic acid to 4-5. The reaction mixture is lyophillized yielding D-ribitol 5-phosphate as a dry compound.

$^1$H-NMR (500 MHz, D$_2$O, pH 7) d (ppm) 1.81 (s, acetate), 3.54 (dd, J=11.9 Hz, J=7.1 Hz, 1H), 3.63 (t, J=3.3 Hz, 1H), 3.69 (dd, J=11.9 Hz, J=3.0 Hz, 1H), 3.73-3.76 (m, 1H), 3.80-3.87 (m, 2H), 3.93 (ddd, J=2.9 Hz, J=5.8 Hz, J=8.6 Hz, 1H).

EXAMPLE 8

Screening of 4-diphosphocytidyl-2C-methyl-D-erythritol synthase 8.1 By Spectrophotometric Method Recombinant 4-diphosphocytidyl-2C-methyl-D-erythritol synthase is tested by a spectrophotometric assay at 340 nm, in which the inorganic pyrophosphate formed from 2-C-methyl-D-erythritol 4-phosphate and CTP is used in a cascade of downstream reactions leading to the reduction of NADP$^+$. Reactions mixtures contained 50 mM Tris hydrochloride pH 8.0, 200 μM 2C-methyl-D-erythritol 4-phosphate, 200 μM CTP, 5 mM MgCl$_2$, 1 mM DTT, 1 μM glucose 1,6-biphosphate, 500 μM UDP-Glucose, 174 μM NADP$^+$, 0.125 U of UDP-glucose pyrophosphorylase, 0.16 U of phosphoglucomutase, and 1 U of glucose 6-phosphate deydrogenase, various concentrations of D-erythritol 4-phosphate respectively D-ribitol 5-phosphate as shown in Table 4 and 10 μl of enzyme in a total volume of 1 ml. One unit of enzyme activity is defined as the amount of enzyme catalyzing the conversion of 1 μmol of substrate per min at 37° C. The results are shown in Table 4.

TABLE 4

Inhibition of YgbP by D-erythritol 4-phosphate and D-ribitol 5-phospate

| test compound concentration (mM) | D-erythritol 4-phosphate specific activity (μmol min$^{-1}$ mg$^{-1}$) | D-ribitol 5-phosphate specific activity (μmol min$^{-1}$ mg$^{-1}$) |
| --- | --- | --- |
| 0 | 17.2 (100%) | 16.1 (100%) |
| 0.2 | 15.9 (92%) | 16.5 (102%) |
| 0.4 | 15.9 (92%) | n.d.$^a$ |
| 0.8 | 12.9 (75%) | n.d. |
| 1.6 | 5.9 (34%) | 16.9 (105) |
| 3.2 | 0 (0%) | n.d. |

$^a$not determined 8.2 By Phosphor Imager Screening Method

Assay mixtures containing 100 mM Tris hydrochloride pH 8.0, 20 mM sodium fluoride, 10 mM MgCl$_2$, 100 μM CTP, 10 nCi of [2-$^{14}$C]2C-methyl-D-erythritol-4-phosphate, various concentrations of D-erythritol 4-phosphate respectively D-ribitol 5-phosphate as shown in Table 4 and YgbP protein are incubated at 37° C. for 20 min. The reaction is terminated by addition of 20 μl of methanol. After centrifugation, aliquots are spotted on Polygram® SIL N-HR thin layer plates (Macherey-Nagel, Düren, Germany) which are developed with a mixture of n-propanol/ethyl acetate/H$_2$O (6:1:3, v/v). The radiochromatogram is monitored and evaluated by a Phosphor Imager (Storm 860, Molecular Dynamics, USA). The Rf value of the product is 0.36. Similar results are obtained as in example 8.1

8.3 By Nuclear Magnetic Resonance (NMR) Method

A solution containing 100 mM Tris HCl pH 8.0, 10 mM MgCl$_2$, 5 mM CTP, 5 mM of 2C-methyl-D-erythritol 4-phosphate, various concentrations of D-erythritol 4-phosphate resp. D-ribitol 5-phosphate as shown in Table 4 and 0.1 mg of YgbP protein from recombinant *E. coli* is incubated at 37° C. for 1 h. The reaction is monitored by $^{31}$P-NMR.

$^{31}$P-NMR spectra are recorded using a AC 250 spectrometer from Bruker at a transmitter frequency of 101.3 MHz. The chemical shifts are referenced to external 85% H$_3$PO$_4$. The product displayed two $^{31}$P NMR doublets at −7.2 ppm and −7.8 ppm. Similar results are obtained as in example 8.1

EXAMPLE 9

Enzymatic Production of 4-diphosphocytidyl-2C-methyl-D-erythritol

A solution containing 100 mM Tris HCl pH 8.0, 10 mM MgCl$_2$, 10 mM CTP, 0.12 μCi of [2-$^{14}$C]2C-methyl-D-erythritol 4-phosphate, 46 mM of 2C-methylerythritol 4-phosphate and 225 μg of YgbP protein from recombinant *E. coli* is incubated at 37° C. for 1 h. The reaction is monitored by $^{31}$P-NMR. The product displaying two $^{31}$P NMR doublets at −7.2 ppm and −7.8 ppm is purified by HPLC on a column of the anionic exchanger Nucleosil 10SB (4.6×250 mm) using 0.1 M ammonium formate in 40% (v/v) methanol as eluent at a flow rate of 1 ml/min. The eluent is monitored by a UV-diode array detector (J&M TIDAS) and a radiomonitor from Berthold. 4-diphosphocytidyl-2C-methyl-D-erythritol is eluted at 30 ml. The fraction containing 4-diphosphocytidyl- 2C-methyl-D-erythritol is collected and lyophyllized. The residue is dissolved in 0.5 ml of deuterated water and subjected to NMR analysis.

EXAMPLE 10

Identification of 4-d iphosphocytidyl-2C-methyl-D-erythritol

'H NMR and 'H decoupled $^{13}$C NMR spectra are recorded using a AVANCE DRX 500 spectrometer from Bruker, Karlsruhe, Germany. The frequencies are 500.1 MHz and 125.6 MHz for $^1$H and $^{13}$C, respectively. The chemical shifts are referenced to external trimethylsilylpropane sulfonate. Two-dimensional correlation experiments (gradient enhanced double quantum filtered COSY, HMQC) are performed using XWINNMR software from Bruker. $^{31}$P NMR spectra are recorded using a AC 250 spectrometer from Bruker at a transmitter frequency of 101.3 MHz. The chemical shifts are referenced to external 85% H$_3$PO$_4$.

The structure of the product is evaluated by a multinuclear multidimensional NMR approach (Table 5). Specifically, the compound is characterized by two $^{31}$P NMR signals at −7.2 ppm and −7.8 ppm (doublets with $^{31}$P-$^{31}$P coupling constants of 20 Hz, each). A $^{31}$P NMR signal for the substrate 2-C-methylerythritol 4-phosphate (singlet at 4.9 ppm) is absent. The detected $^{31}$P NMR chemical shift range, as well as the $^{31}$P-$^{31}$P couplings implied that the unknown compound is a pyrophosphate. For comparison, the $^{31}$P NMR signals of cytidine diphosphate (CDP) are found as doublets at −5.1 ppm and −7.6 ppm with coupling constants of 21.5 Hz, each (2J$_{PP}$).

The presence of phosphorous atoms in the unknown compound is further reflected in the $^{13}$C NMR spectrum where four of 14 signals showed coupling with $^{31}$P ($^{31}$P-$^{13}$C coupling constants in the range of 9 Hz to 5 Hz).

The $^1$H NMR and $^{13}$C NMR signals are further analyzed by two-dimensional COSY and HMQC experiments. Whereas the detected chemical shifts are different from CDP and 2C-methylerythritol 4-phosphate, the observed correlation patterns in the homonuclear $^1$H-$^1$H COSY and in the heteronuclear $^1$H-$^{13}$C HMQC experiment matched perfectly the correlation signatures of CDP (comprising the spin systems of the ribosyl moiety and the cytosine moiety) and of 2C-methyl-D-erythritol 4-phosphate. This result established the structure of the product as the 4-diphosphocytidyl adduct of 2-C-methyl-D-erythritol.

TABLE 5

NMR-data of 4-diphosphocytidyl-2C-methyl-D-erythritol

| | Chemical shifts, ppm | | | Coupling constants, Hz | | | |
|---|---|---|---|---|---|---|---|
| Position | $^1$H | $^{13}$C | $^{31}$P | J$_{HH}$ | J$_{PH}$ | J$_{PC}$ | J$_{PP}$ |
| 1 | 3.36 (d, 1H)$^a$ | 66.24 (s)$^b$ | | 11.7 (1*)$^c$ | | | |
| 1* | 3.48 (d, 1H) | | | 11.7 (1) | | | |
| 2 | | 73.76 (s) | | | | | |
| 2-Me | 1.02 (s) | 18.13 (s) | | | | | |
| 3 | 3.72 (dd, 1H) | 73.27 (d) | | 8.3 (4), 2.7 (4*) | | 7.5 | |
| 4 | 3.85 (ddd, 1H) | 66.87 (d) | | 11.0 (4*), 8.3 (3) | 6.8 | 5.7 | |
| 4* | 4.10 (ddd, 1H) | | | 11.0 (4), 2.7 (3) | 6.1 | | |
| 1' | 5.68 (d, 1H) | 89.25 (s) | | 4.1 (2') | | | |
| 2' | 4.24 (m, 1H) | 74.21 (s) | | | | | |
| 3' | 4.21 (m, 1H) | 69.09 (s) | | | | | |
| 4' | 4.17 (m, 1H) | 82.83 (d) | | | | 9.1 | |
| 5' | 4.10 (m, 1H) | 64.41 (d) | | | | 5.5 | |
| 5'* | 4.17 (m, 1H) | | | | | | |
| Cyt-2 | | 163.87 (s) | | | | | |
| Cyt-4 | | 170.51 (s) | | | | | |
| Cyt-5 | 6.09 (d, 1H) | 95.99 (s) | | 7.8 (Cyt-6) | | | |
| Cyt-6 | 7.96 (d, 1H) | 142.46 (s) | | 7.8 (Cyt-5) | | | |
| P | | | −7.2 (d)$^d$ | | | | 19.6 |
| P* | | | −7.8 (d) | | | | 20.4 |

$^a$Referenced to external trimethylsilylpropane sulfonate. The multiplicities and the relative integral values of signals in the $^1$H NMR spectrum are given in parentheses.
$^b$Referenced to external trimethylsilylpropane sulfonate. The multiplicities of the $^1$H decoupled $^{13}$C NMR signals are given in parentheses.
$^c$Coupling partners as analysed from two-dimensional COSY experiments are given in parentheses.
$^d$Referenced to external 85% ortho-phosphoric acid. The multiplicities of the $^1$H decoupled $^{31}$P NMR signals are given in parentheses.

EXAMPLE 11

Production of an Expression Clone and Construction of an Expression Vector for ychB of *E. coli*

Chromosomal DNA from *Escherichia coli* strain XL1-Blue is isolated according to a method described by Meade et al. (Meade, H. M., Long, S. R., Ruvkun, C. B., Brown, S. E., and Auswald, F. M. (1982). Physical and genetic characterization of symbiotic and auxotrophic mutants of *Rhizobium meliloti* induced by transposon Tn5 mutagens. *J. Bacteriol.* 149, 114-122).

The *E. coli* ORF ychB (accession no. gb AE000219) from basepair (bp) position 5720 to 6571 is amplified by PCR using chromosomal *E. coli* DNA as template. The reaction mixture contained 25 pmol of primer 5'-GAGGAGAAATTMCCAT-GCGGACACAGTGGCC-3' (SEQ ID NO:29), 25 pmol of primer 5'-GTCACCGMCTGCAGCTTGCCCG-3' (SEQ ID NO:30), 20 ng of chromosomal DNA, 2U of Taq DNA polymerase (Eurogentec, Seraing, Belgium) and 20 nmol of dNTPs in of 1.5 mM MgCl$_2$, 50 mM KCl, 10 mM Tris-hydrochloride, pH 8.8 and 0.1% (w/w) Triton X-100 in a total volume of 100 μl.

The mixture is denaturated for 3 min at 95° C. Then 25 PCR cycles for 30 sec at 94° C., 30 sec at 50° C. and 45 sec at 72° C. follow. After further incubation for 7 min at 72° C., the mixture is cooled to 4° C. An aliquot of 2 μl is subjected to agarose gel electrophoresis. The PCR amplificate is purified with PCR purification kit from Qiagen. 1.5 μg of purified PCR product are obtained.

The PCR amplificate is used as template for a second PCR reaction. The reaction mixture contained 25 pmol of primer 5'-ACACAGMTTCATTAAAGAGGAGAAATTMCCATG-3' (SEQ ID NO:31), 25 pmol of primer GTCACCGAACTG-CAGCTTGCCCG-3 (SEQ ID NO:30), 2 μl of the first PCR amplification, 2U of Taq DNA polymerase (Eurogentec, Seraing, Belgium) and 20 nmol of dNTPs in a total volume of 100 μl of 1.5 mM MgCl$_2$, 50 mM KCl, 10 mM Tris-hydrochloride, pH 8.8 and 0.1% (w/w) Triton X-100.

The mixture is denaturated for 3 min at 95° C. Then 40 PCR cycles for 45 sec at 94° C., 45 sec at 50° C. and 60 sec at 72° C. follow. After further incubation for 20 min at 72° C., the mixture is cooled to 4° C. An aliquot of 2 μl is subjected to agarose gel electrophoresis.

The PCR amplificate is purified with the PCR purification kit from Qiagen as described in example 1.

2.0 μg of the vector pNCO113 and 1.5 μg of the purified PCR product are digested in order to produce DNA fragments with overlapping ends. Each restriction mixture contained 6 μl of NEB3 buffer, 6 μg of BSA, 30 U of EcoRI (NEB), 30 U of PstI (NEB) in a total volume of 60 μl and is incubated for 3 h at 37° C. Digested vector DNA and PCR product are purified using the PCR purification kit from Qiagen.

20 ng of vector DNA and 18 ng of PCR product are ligated together with I U of T4-Ligase from Gibco-BRL (Eggenstein, Germany), 2 μl of T4-Ligase buffer (Gibco-BRL) in a total volume of 10 μl yielding the plasmid pNCOychB. The ligation mixture is incubated over night at 4° C. With 2 μl of the ligation mixture electrocompetent E. coli XL1-Blue cells are transformed and 100 μl of the cell/DNA suspension is plated on LB plates containing 150 mg/l ampicillin for maintenance of the plasmid pNCOychB. The plasmid pNCOychB is isolated as described before. 9 μg of plasmid DNA are obtained.

The DNA insert of the plasmid pNCOychB is sequenced as described in example 1. The DNA sequence is found to be identical with the sequence in the data base (accession no. gb AE000219).

EXAMPLE 12a

Cloning of the ychB Gene from *A. thaliana* without Leader Sequence

Arbabidopsis cDNA is prepared as described in example 3.

The resulting cDNA (1 ml of this mixture) is used for the amplification of ychB by PCR.

The expression vector pNCO113 is isolated as described in example 1. The *A. thaliana* ORF ychB without the coding region for the putative leader sequence is amplified by PCR using cDNA from *A. thaliana* as template. The reaction mixture contained 25 pmol of primer 5'-CTGATGAGAGGCT-TAATMGATAGG-3' (SEQ ID NO:32), 25 pmol of primer 5'-TTACATGTTTGTAACATCTCATTGG-3' (SEQ ID NO:33), 1 μg of cDNA, 2 U of Taq DNA polymerase (Eurogentec, Seraing, Belgium) and 20 nmol of dNTPs 1.5 mM MgCl$_2$, 50 mM KCl, 10 mM Tris-hydrochloride, pH 8.8 and 0.1% (w/w) Triton X-100 in a total of 100 μl.

The mixture is denaturated for 3 min at 95° C. Then 40 PCR cycles for 45 sec at 94° C., 45 sec at 50° C. and 60 sec at 72° C. followed. After further incubation for 20 min at 72° C., the mixture is cooled to 4° C. An aliquot of 2 μl is subjected to agarose gel electrophoresis. The PCR amplificate is purified with the PCR purification kit from Qiagen as described in Example 2. 2.1 μg of purified PCR product are obtained.

The PCR amplificate is used as template for a second PCR reaction. The reaction mixture contained 25 pmol of primer 5'-GTTGACACCATGGCTCCTTTGTCC-3' (SEQ ID NO:34), 25 pmol of primer 5'-TGTTTGTCTGCAGCTCAT-TGGAAATCC-3' (SEQ ID NO:35), 2 μl of the first PCR amplification, 2U of Taq DNA polymerase (Eurogentec, Seraing, Belgium) and 20 nmol of dNTPs in a total volume of 100 μl of 1.5 mM MgCl$_2$, 50 mM KCl, 10 mM Tris-hydrochloride, pH 8.8 and 0.1% (w/w) Triton X-100.

The mixture is denaturated for 3 min at 95° C. Then 40 PCR cycles for 45 sec at 94° C., 45 sec at 50° C. and 60 sec at 72° C. follow. After further incubation for 20 min at 72° C., the mixture is cooled to 4° C. An aliquot of 2 μl is subjected to agarose gel electrophoresis.

The PCR amplificate is purified with PCR purification kit from Qiagen as described in Example 2. 2.4 μg of purified PCR product are obtained. 2 μg of the vector pNCO113 (isolated as described in example 1) and 2.5 μg of the purified PCR product are digested in order to produce DNA fragments with overlapping ends. Each restriction mixture contained 6 μl of NEB3 buffer from New England Biolabs (NEB), 30 U of NcoI (NEB), 30 U of PstI (NEB) in a total volume of 60 p, and is incubated for 3 h at 37° C. Digested vector DNA and PCR product are purified using the PCR purifiaction kit from Qiagen.

20 ng of vector DNA and 23 ng of PCR product are ligated together with I U of T4-Ligase (Gibco-BRL), 2 μl of T4-Ligase buffer (Gibco-BRL) in a total volume of 10 μl, yielding the plasmid pNCOychBara. The ligation mixture is incubated over night at 4° C.

2 μl of the ligation mixture is transformed into electrocompetent E. coli XL1-Blue cells as described in example 1. The electrocompetent cells are prepared as described in example 1. The plasmid pNCOychBara is isolated as described before. 6 μg of plasmid DNA are obtained.

The DNA insert of the plasmid pNCOychBara is sequenced as described in example 1. The corresponding protein sequence is identical to the calculated protein sequence of the calculated cDNA squence in the database (gb accession no. AC005168) as shown in FIG. 8A.

EXAMPLE 12b

Construction of an Expression Vector and Production of an Expression Clone for the Full-Length ychB Gene of *A. thaliana*

The cDNA of *A. thaliana* is prepared as described in example 2.

The expression vector pQE30 is isolated as described in example 1. The full-length *A. thaliana* ORF ychB (accession no. gb AC005168) from basepair (bp) position 82996 to 85396 is amplified by PCR using cDNA from *A. thaliana* as template. The reaction mixture contains. 25 pmol of the primer 5'-GGTGACATATCAGATCAAAGAG-3' (SEQ ID NO:36), 25 pmol of primer 5'-TTACATGTTTGTAACATCT-CATTGG-3' (SEQ ID NO:33), 1 μg of cDNA, 2 U of Taq-DNA polymerase (Eurogentec, Seraing, Belgium) and 20 nmol of dNTPs in a total volume of 100 μl of 1.5 mM MgCl$_2$, 50 mM KCl, 10 mM Tris hydrochloride, pH 8.8 and 0.1% (w/w) Triton X-100.

The mixture is denaturated for 3 min at 95° C. Then 40 PCR cycles for 60 sec at 94° C., 60 sec at 50° C. and 90 sec at 72°

C. follow. After further incubation for 20 min at 72° C., the mixture is cooled to 4° C. An aliquot of 2 µl is subjected to agarose gel electrophoresis. The PCR amplificate is purified with the PCR purification kit from Qiagen as described in Example 1. 1.9 µg of purified PCR product are obtained.

The PCR amplificate is used as template for a second PCR reaction. The reaction mixture contains 25 pmol of primer 5'-AGAAACAGGATCCATGGCAACGGCT-TCTCCTCCTCC-3' (SEQ ID NO:37), 25 pmol of primer ACACGTCTTCTGCAGAAGTAAATG (SEQ ID NO:26), 2 µl of the first PCR amplification, 2 U of Taq-DNA polymerase (Eurogentec, Seraing, Belgium) and 20 nmol of dNTPs in a total volume of 100 µl containing 1.5 mM $MgCl_2$, 50 mM KCl, 10 mM Tris-hydrochloride, pH 8.8 and 0.1% (w/w) Triton X-100.

The mixture is denaturated for 3 min at 95° C. Then 40 PCR cycles for 60 sec at 94° C., 60 sec at 50° C. and 90 sec at 72° C. follow. After further incubation for 20 min at 72° C., the mixture is cooled to 4° C. An aliquot of 2 µl is subjected to agarose gel electrophoresis. An aliquot of 2 µl is subjected to agarose gel electrophoresis.

The PCR amplificate is purified with PCR purification kit from Qiagen as described in Example 1. 1.4 µg of purified PCR product are obtained. 2.0 µg of the vector pQE30 and 1.5 µg of the purified PCR product are digested in order to produce DNA fragments with overlapping ends. Each restriction mixture contains 7 µl of NEB3 buffer from New England Biolabs (NEB), 40 U of BamHI (NEB), 30 U of PstI (NEB) in a total volume of 70 µl and is incubated for 3 h at 37° C. Digested vector DNA and PCR product are purified using the PCR purifiaction kit from Qiagen.

20 ng of vector DNA and 12 ng of PCR product are ligated together with 1 U of T4-Ligase (Gibco), 2 µl of T4-Ligase buffer (Gibco) in a total volume of 10 µl, yielding the plasmid pQEychBarakom. The ligation mixture is incubated over night at 4° C. 2 µl of the ligation mixture is transformed into electrocompetent *E. coli* XL1-Blue cells as described in example 1. The electrocompetent cells are prepared as described in example 1.

The DNA insert of the plasmid pQEychBarakom is sequenced as described in example 1. The DNA and the corresponding amino acid sequence of the full-length ychB gene of *A. thaliana* is shown in FIG. 8B.

EXAMPLE 12c

Construction of a Synthetic Gene and an Expression for ychB of *Lycopersicon esculentum* (Tomato) without Leader Sequence A cDNA library of tomato leafs is prepared as described by Schmid J. et al., 1992 (Schmid J., Schaller A., Leibinger U., Boll W. and Amrhein, N. (1992). The in-vitro synthesized tomato shikimate kinase precursor is enzymatically active and is imported and processed to the mature enzyme by chloroplasts. *The Plant Journal* 2(3), 375-383).

In order to adapt the codon usage for high level expression in *E. coli* a synthetic gene coding for the putative tomato YchB protein (accession no. gb U62773, bp position 78 to 1283) was constructed by 8 consecutive PCR reactions using the cDNA library of tomato as template. The oligonucleotides used and the resulting DNA sequence of this gene are shown in FIG. 8C.

Step 1

A part of the *L. esculentum* ORF ychB is amplified by PCR using cDNA from *L. esculentum* (from leaf) as template. The reaction mixture contains 25 pmol of primer TM-YCHB-A 5'-GGTACAGACMTTACTTTTGGATTCATC-3' (SEQ ID NO:38), 25 pmol of primer TM-YCHB-B 5'-AAGAGATG-GMGAACTTCAAAGGCAGGAGG-3' (SEQ ID NO:39), 1 µl of cDNA library, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denaturated for 5 min at 95° C. Then 20 PCR cycles for 30 sec at 95° C., 30 sec at 48° C. and 45 sec at 72° C. follow. After further incubation for 3 min at 72° C., the mixture is cooled to 4° C. The total mixture is subjected to a 2% agarose gel electrophoresis. The PCR product with 447 bp is excised from the gel and is purified using the PCR purification kit from Quiagen as described in example 1.

Step 2

20 ng of the PCR product from step 1 is used as template for a second PCR. The reaction mixture contains 25 pmol of primer TM-YCHB-1 5'-CTGATTATCAAAGCCCT-CAATCTTTATCGTAAAAAGACCGGTACA-GACAATTACTTT TGGATTCATC-3' (SEQ ID NO:40), 25 pmol of primer TM-YCHB-2 5'-GACCGCGGCCAGCAGC-MTTACACGTTGTTTTAAACGTTTM-GAGATGGAAGAACT TCAAAGCAGGAGG-3' (SEQ ID NO:41), 20 ng of the purified product of the first PCR, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denaturated for 5 min at 95° C. Then 20 PCR cycles for 30 sec at 95° C., 30 sec at 48° C. and 45 sec at 72° C. follow. After further incubation for 3 min at 72° C., the mixture is cooled to 4° C. The total mixture is subjected to a 2% agarose gel electrophoresis. The PCR product with 525 bp is excised from the gel and is purified using the PCR purification kit from Quiagen as described above.

Step 3

20 ng of the PCR product from step 2 is used as template for a 3. PCR. The reaction mixture contains 25 pmol of primer TM-YCHB-3 5'-ACTMTGTTGCTGGCGTTCCACTC-GATGAGCGTMTCTGATTATCAAAGCCCTCM TCTT-TATCG-3' (SEQ ID NO:42), 25 pmol of primer TM-YCHB-4 5'-TGTGCTGCCACTACCAGACATGMGACTG-CATCATATTGACCGCGGCCAGCAGCA ATTACACG-3' (SEQ ID NO:43), 20 ng of the purified product of the first PCR, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denaturated for 5 min at 95° C. Then 20 PCR cycles for 30 sec at 95° C., 30 sec at 48° C. and 45 sec at 72° C. follow. After further incubation for 3 min at 72° C., the mixture is cooled to 4° C. The total mixture is subjected to a 2% agarose gel electrophoresis. The PCR product with 599 bp is excised from the gel and is purified using the PCR purification kit from Quiagen as described above.

Step 4

20 ng of the PCR product from step 3 is used as template for a 4. PCR. The reaction mixture contains 25 pmol of primer TM-YCHB-5 5'-AAAATTAAGTTCTCGCTGTCAC-CATCGAAATCAAAGGATCGTTTATCTACTAATGTT GCTGGCGTTCCACTC-3' (SEQ ID NO:44), 25 pmol of primer TM-YCHB-6 5'-CATAGACAAATTGTGGC- GATCTGGAGAGCCAACACCTACGATTGT-
GCTGCCACTAC CAGACATGMG-3' (SEQ ID NO:45), 20 ng of the purified product of the first PCR, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denatured for 5 min at 95° C. Then 20 PCR cycles for 30 sec at 95° C., 30 sec at 48° C. and 45 sec at 72° C. follow. After further incubation for 3 min at 72° C., the mixture is cooled to 4° C. The total mixture is subjected to a 2% agarose gel electrophoresis. The PCR product with 690 bp is excised from the gel and is purified using the PCR purification kit from Quiagen as described above.

Step 5

20 ng of the PCR product from 4 is used as template for a 5. PCR. The reaction mixture contains 25 pmol of primer TM-YCHB-7 5'-GACGGTTATCATGATCTG-GCGTCTCTCTTTCATGTAATTAGTCTTG-GCGATAAAATT AAGTTCTCGCTGTCACC-3' (SEQ ID NO:46), 25 pmol of primer TM-YCHB-8 5'-TGCTTCTGA-CAAGMGACATCTTTGTACTCTTCGTCAT-CATAGACAAATTGTGGCGG ATCTGG-3' (SEQ ID NO:47), 20 ng of the purified product of the first PCR, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denatured for 5 min at 95° C. Then 20 PCR cycles for 30 sec at 95° C., 30 sec at 48° C. and 60 sec at 72° C. follow. After further incubation for 3 min at 72° C., the mixture is cooled to 4° C. The total mixture is subjected to a 2% agarose gel electrophoresis. The PCR product with 779 bp is excised from the gel and is purified using the PCR purification kit from Quiagen as described above.

Step 6

20 ng of the PCR product from step 5 is used as template for a 6. PCR. The reaction mixture contains 25 pmol of primer TM-YCHB-9 5'-TTTTCTCCTTGCAAGATTAAT-GTTTTCCTGCGCATCACAAGCAAACGT-GATGACGGT TATCATGATCTGGCGTCTC-3' (SEQ ID NO:48), 25 pmol of primer TM-YCHB-10 5'-CMCATAC-CACTCGTTGGCTGGACGAGTGAT-GAAACTTGCTTCTGACMGMGACA TCTTTG-3' (SEQ ID NO:49), 20 ng of the purified product of the first PCR, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denatured for 5 min at 95° C. Then 20 PCR cycles for 30 sec at 95° C., 30 sec at 48° C. and 60 sec at 72° C. follow. After further incubation for 3 min at 72° C., the mixture is cooled to 4° C. The total mixture is subjected to a 2% agarose gel electrophoresis. The PCR product with 867 bp is excised from the gel and is purified using the PCR purification kit from Quiagen as described above.

Step 7

20 ng of the PCR product from step 6 is used as template for a 7. PCR. The reaction mixture contains 25 pmol of primer TM-YCHB-11 5'-CGTGMGCTGGTCTTTCACGCCT-CACTCTTTTTTCTCCTTGCAAGATTAATGTTTTC CTG-3' (SEQ ID NO:50), 25 pmol of primer TM-YCHB-12 5'-CAGGTTGATCACCMTAGTGCTACCT-GAAACAGGTTCAACATACCACTCGTTGGCT GGACG-3' (SEQ ID NO:51), 20 ng of the purified product of the first PCR, 1 U of Vent DNA polymerase (New England Biolabs, Schwalbach, Germany), 20 nmol of dNTPs in a total volume of 100 µl containing 10 mM KCl, 10 mM $(NH_4)_2SO_4$, 2 mM $MgSO_4$, 0.1% Triton X-100, 20 mM Tris hydrochloride, pH 8.8.

The mixture is denatured for 5 min at 95° C. Then 20 PCR cycles for 30 sec at 95° C., 30 sec at 48° C. and 60 sec at 72° C. followed. After further incubation for 3 min at 72° C., the mixture is cooled to 4° C. The total mixture is subjected to a 2% agarose gel electrophoresis. The PCR product with 933 bp is cleaved out of the gel and is purified using the PCR purification kit from Quiagen as described above.

Step 8

20 ng of the PCR product from step 7 is used as template for a 8. PCR. The reaction mixture contains 25 pmol of primer TM-YCHB-13 5'-ATMTAGAATTCATTAAAGAG-GAGAAATTAACCATGGATCGTGAAGCTG-GTCTTTCA CGCCTC-3' (SEQ ID NO:52), 25 pmol of primer TM-YCHB-14 5'-TATTATTATAAG CTTMGACAT-GTCAAAAGATGTAGAGMCTCAG GTTGATCACCAA TAGTGCTACC-3' (SEQ ID NO:53), 20 ng of the purified product of the first PCR, 0.5 U of Goldstar-Taq-DNA polymerase (Eurogentec, Seraing, Belgium), 20 nmol of dNTPs in a total volume of 100 µl containing 1.5 mM $MgCl_2$, 75 mM Tris hydrochloride, pH 9.0; 20 mM $(NH_4)_2SO_4$ and 0.01% (w/v) Tween 20.

The mixture is denatured for 5 min at 95° C. Then 20 PCR cycles for 30 sec at 95° C., 30 sec at 48° C. and 60 sec at 72° C. followed. After further incubation for 7 min at 72° C., the mixture is cooled to 4° C. An aliquot of 2 µl is subjected to a 2% agarose gel electrophoresis. The PCR product with 1015 bp is purified using the PCR purification kit from Quiagen as described above.

2 µg of the vector pNCO-SB-H6-ACYC184 (isolated as described in example 1) and 2 µg of the purified PCR product from step 8 are digested in order to produce DNA fragments with overlapping ends. Each restriction mixture contains 10 µl of OPA buffer (10×; 500 mM Potassium acetate; 100 mM Magnesium acetate; 100 mM Tris acetate, pH 7.5) from Amersham Pharmacia Biotech (Freiburg, Germany) and 50 U of HindIII (Amersham Pharmacia Biotech, Freiburg, Germany) in a total volume of 100 µl and is incubated for 3 h at 37° C. After incubation 18 µl OPA buffer and 50 U of NcoI (Amersham Pharmacia Biotech, Freiburg, Germany) are added to a total volume of 140 µl. The resulting mixture is incubated for additional 3 h. Digested vector DNA and PCR product are purified using the PCR purification kit from Quiagen as described above.

20 ng of prepared vector DNA and 25 ng of PCR product are ligated together with 1 U of T4-Ligase (Gibco-BRL, Eggenstein, Germany), 4 µl of T4-Ligase buffer (5×; 250 mM Tris/HCl, pH 7.6; 50 mM $MgCl_2$; 5 mM ATP; 5 mM DTT; 25% (w/v) Polyethyleneglycol-8000) in a total volume of 20 µl, yielding the plasmid pNCO-HIS6-TM-YCHB. The incubation mixture is incubated over night at 4° C. Competent *E. coli* XL1-Blue cells (Stratagene, LaJolla, Calif., USA) are transformed with the ligation mixture. Cells are selected on LB-plates containing 170 mg/l ampicillin. Competent cells are prepared using the method from Hanahan D. (Hanahan, D. Studies on transformation of *Escherichia coli* with plasmids. *J Mol. Biol.* 1983, 166(4), 557-80).

The plasmid is isolated as described above. 5 µg DNA are obtained.

The DNA insert of the plasmid pNCO-HIS6-TM-YCHB is sequenced as described in example 1 using the following oligonucleotides as primers: TM-YCHB-A 5'-GGTACA-GACMTTACTTTTGGATTCATC-3' (SEQ ID NO:38), TM-YCHB-B 5'-AAGAGATGGAAGMCTTCAAAGGCAG-GAGG-3' (SEQ ID NO:39), PNC0-T5 5'-GAGCGGATAACAATTATAATAGATTC-3' (SEQ ID NO:54) and mRNA5 5'-CTCCATTTTAGCTTCCT-TAGCTCCTG-3' (SEQ ID NO:55). The corresponding protein sequence is identical to the calculated protein sequence of the calculated cDNA sequence in the database (GenBank accession no. U62773).

EXAMPLE 13a

Preparation and Purification of Recombinant YchB Protein of *E. coli*

0.5 liter of Luria Bertani (LB) medium containing 90 mg of ampicillin are inoculated with 10 ml of an overnight culture of *E. coli* strain XL1-Blue harboring plasmid pNCOychB. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 50 mM Tris hydrochloride pH 8.0, centrifuged as above and frozen at −20° C. for storage.

The cells are thawed in 10 ml of 20 mM tris hydrochloride pH 8.0 containing 1 mM dithioerythritol, 0.02% sodium azide (buffer A) in the presence of 4 mg/ml lysozyme and 10 μg/ml DNaseI. The mixture is incubated at 37° C. for 1 h, cooled on ice and sonified 6×10 sec with a Branson Sonifier 250 (Branson SONIC Power Company, Danbury, USA) set to 70% duty cycle output, control value of 4 output. The suspension is centrifuged at 15,000 rpm at 4° C. for 30 min. The supernatant is applied on a column of Sepharose QFF (column volume 30 ml, Amersham Pharmacia Biotech, Freiburg, Germany) previously equilibrated with 150 ml buffer A. The column is washed with buffer A monitoring at 280 nm. YchB protein is eluted from the column with a gradient from 0-0.5 M sodium chloride in 150 ml of buffer A. The enzyme is identified by SDS-PAGE showing a band at 30 kDa. Fractions showing this protein band are collected and added ammonium sulfate to 0.5 M final concentration. The enzyme is further purified on a column of Phenyl Sepharose 6FF (column volume 16 ml, Amersham Pharmacia Biotech) equilibrated with buffer A containing 0.5 M ammonium sulftate. Then the YchB protein is eluted by linear gradient from 0.5-0 M ammonium sulfate in 100 ml of buffer A. Fractions containing protein are pooled and concentrated to 3 ml by ultrafiltration (MWCO 10 kDa, Amicon, USA). Then the enzyme is further purified on Superdex 75 HR 26/60 equilibrated with buffer A in the presence of 100 mM sodium chloride. The YchB protein is eluted at 165 ml. The homogeneity of the YchB protein is judged by SDS-PAGE.

EXAMPLE 13b

Preparation and Purification of the Recombinant 6×His-YchB Fusion Protein of Tomato 0.5 liter of Luria Bertani (LB) medium containing 90 mg of ampicillin are inoculated with 10 ml of an overnight culture of *E. coli* strain XL1-Blue harboring plasmid pNCO-HIS6-TM-YCHB. The culture is grown in a shaking culture at 37° C. At an optical density (600 nm) of 0.7, the culture is induced with 2 mM IPTG. The culture is grown for further 5 h. The cells are harvested by centrifugation for 20 min at 5,000 rpm and 4° C. The cells are washed with 50 mM Tris hydrochloride pH 8.0, centrifuged as above and frozen at −20° C. for storage.

The cells are thawed in 20 ml of 20 mM imidazole in 100 mM tris hydrochloride pH 8.0 and 0.5 M sodium chloride (standard buffer) in the presence of 1 mg/ml lysozyme and 100 μg/ml DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant YchB protein of tomato is applied on a column of $Ni^{2+}$-Chelating sepharose FF (size 2.6×6 cm, Amersham Pharmacia Biotech) previously equilibrated with 20 mM imidazole in standard buffer. The column is washed with 100 ml of starting buffer. YchB protein is eluted with a linear gradient of 20-500 mM imidazole in 100 ml of standard buffer. YchB protein containing fractions are combined according to SDS-PAGE and dialysed overnight against 100 mM Tris hydrochloride pH 8.0, 5 mM dithioerythritol, 0.02% sodium azide. The dialysed YchB protein is loaded on a Mono Q HR 5/5 column (Amersham Pharmacia Biotech). The column is developed with a linear gradient of 0-0.5 M sodium chloride in 60 ml standard buffer. The homogeneity YchB protein is judged by SDS-PAGE. The objected band at 43 kDa is in agreement with the calculated molecular mass. 3 mg of pure enzyme were obtained.

EXAMPLE 14

Screening of YchB Enzyme Activity 14.1 By a Radiochemical Method Using $[2-^{14}C]$4-diphosphocytidyl-2C-methyl-D-erythritol as substrate Assay mixtures, containing 100 mM Tris hydrochloride, pH 8.0, 100 μM ATP, 10 mM $MgCl_2$, 1 mM DTT, 20 mM sodium fluoride, 10 nCi of $[2-^{14}C]$4-diphosphocytidyl-2C-methyl-D-erythritol and YchB protein and are incubated at 37° C. for 30 min. After centrifugation, aliquots are spotted on SIL-NHR thin layer plates which are developed with a mixture of n-propanol/ethyl acetate/$H_2O$ (6:1:3, v/v). The radiochromatogram is monitored and evaluated using a Phosphor Imager (Storm 860, Molecular Dynamics, USA). The Rf value of the YchB product is 0.25. This screening method can be carried out in the presence or absence of prospective inhibitors.

14.2 By a Nuclear Magnetic Resonance (NMR) Method using 4-diphosphocytidyl-2C-methyl-D-erythritol as sSbstrate A solution containing 100 mM Tris hydrochloride, pH 8.0, 10 mM $MgCl_2$, 5 mM ATP, 1 mM DTT, 5 mM of $[2,2-Me-^{13}C_2]$4-diphosphocytidyl-2C-methyl-D-erythritol and 0.1 mg of YchB protein from recombinant *E. coli* is incubated at 37° C. for 1 h. The reaction is monitored by $^{13}C$-NMR. $^{13}C$ NMR spectra are recorded using a DRX 500 spectrometer from Bruker at a transmitter frequency of 125.6 MHz. The product displayes two intense double doublets at 81.91 and 16.86 ppm (referenced to external trimethyl silyipropane sulfonate) with coupling constants of 38.9 and 7.4 Hz, and 38.9 and 1.9 Hz, respectively.

EXAMPLE 15

Enzymatic Preparation of 4-diphosphocytidyl-2C-methyl-D-erythritol 2-phosphate A solution, containing 5 mM [2-$^{14}$C]4-diphosphocytidyl-2C-methyl-D-erythritol (0.04 μCi/mmol), 5 mM ATP, 5 mM MgCl$_2$, 5 mM DTT, 100 μg of purified YchB protein and 100 mM Tris-hydrochloride, pH 8.0 in a total volume of 4 ml is incubated for 2 h at 37° C. The reaction is monitored by $^{31}$P-NMR spectroscopy. Then the sample is centrifuged through a Nanosep 10K membrane (PALLGelmann, Roβdorf, Germany). The product displaying $^{31}$P signals at 0.49, −7.28, and −8.00 ppm (referenced to external 85% phosphoric acid) is purified by HPLC on a column of the anionic exchanger Nucleosil 10SB (4.6×250 mm, Macherey-Nagel, Düren, Germany), equilibrated with 0.1 M ammonium formate in 40% (v/v) methanol at a flow rate of 1 ml/min. The HPLC system is equipped with a Wellchrom HPLC pump K-1001, a Wellchrom Spectro-Photometer K-2600 (Knauer, Berlin, Germany) and a radiomonitor (Berthold, Wildbad, Germany). After injection of the sample, the column is washed with 30 ml of 0.1 M ammonium formate in 40% (v/v) methanol. 4-diphosphocytidyl-2C-methyl-D-erythritol 2-phosphate is eluted at 14 ml by a linear gradient from 0.1 M ammonium formate in 40% (v/v) methanol to 1 M ammonium formate in 0% (v/v) methanol in 30 ml. Fractions containing 4-diphosphocytidyl-2C-methyl-D-erythritol 2-phosphate are collected and lyophylized. The residue is dissolved in 0.5 ml of deuterated water and subjected to NMR analysis. The concentration of 4-diphosphocytidyl-2C-methyl-D-erythritol 2-phosphate is 21 mM.

EXAMPLE 16

Identification of 4-diphosphocytidyl-2C-methyl-D-erythritol 2-phosphate

The elucidation of the structure is performed with [2,2-Me-$^{13}$C$_2$]—, [1,3,4-$^{13}$C$_1$]- and [1,2,2-Me,3,4-$^{13}$C$_5$]4-diphosphocytidyl-2C-methyl-D-erythritol 2-phosphate (Table 6).

The $^1$H-decoupled $^{31}$P NMR spectrum of the enzyme product obtained from [2,2-Me-$^{13}$C$_2$]4-diphosphocytidyl-2C-methyl-D-erythritol displays two doublets at −7.28 ppm resp. −8.00 ppm ($^{31}$P-$^{31}$P coupling constant, 20.8 Hz) and a double-doublet at 0.49 ppm ($^{31}$P-$^{13}$C coupling constants, 7.6 Hz and 1.7 Hz). Without $^1$H-decoupling the $^{31}$P NMR signals at −7.28 and −8.00 ppm are broadened whereas the signal at 0.49 ppm is not affected by $^1$H coupling. The chemical shifts as well as the observed coupling pattern suggest the presence of a pyrophosphate moiety and a monophosphate moiety located at position 2 of the 2C-methyl-erythritol moiety. More specifically, scalar coupling between $^{31}$P and $^1$H is expected in the case of a phosphate residue at position 1 or 3. On the other hand, no $^{31}$P coupling is expected in the case of a phosphate moiety at position 2. Moreover the observed scalar coupling between the $^{13}$C-2-Methyl and the $^{31}$P atom of the phosphate group is only compatible with location 2.

The $^{31}$P-$^{13}$C coupling pattern is further analyzed using a sample obtained from [1,3,4-13C$_1$]4-diphosphocytidyl-2C-methyl-Drythritol (Table 6). The $^{13}$C and $^1$H NMR signals are assigned by HMQC, HNQC-TOCSY, and INADEQUATE experiments using the sample obtained from [1,2,2-Me,3,4-$^{13}$C$_5$]4-diphosphocytidyl-2C-methyl-D-erythritol. With these assignments the structure of 4-diphosphocytidyl-2C-methyl-D-erythritol 2-phosphate is established.

TABLE 6

NMR-data of 4-diphosphocytidyl-2C-methyl-D-erythritol 2-phosphate

| Position | Chemical shifts, ppm | | | Coupling constants, Hz | | | | | |
|---|---|---|---|---|---|---|---|---|---|
| | $^1$H | $^{13}$C | $^{31}$P | $J_{HH}$ | $J_{PH}$ | $J_{PC}$ | $J_{PP}$ | $J_{CH}$ | $J_{CC}$ |
| 1 | 3.58 (m, 1) | 65.78$^e$ (d) | | | | 3.8$^e$ (P-2) | | 1.7$^d$ | 39.8$^f$ (2) |
| 1* | 3.64 (m, 1) | | | | | | | | |
| 2 | | 81.91$^d$ (dd) | | | | 7.4$^d$ (P-2) | | | 38.9$^d$ (2-Me) |
| 2-Methyl | 1.26 (s, 3) | 17.92$^d$ (dd) | | | | 1.9$^d$ (P-2) | | 127.9$^d$, 3.9$^d$ | 38.9$^d$ (2) |
| 3 | 3.81 (m, 1) | 73.96$^e$ (t) | | | | 7.3$^e$ (P-2, P-4) | | | |
| 4 | 3.89 (m, 1) | 67.16$^e$ (d) | | | | 5.7$^e$ (P-4) | | | 42.9$^f$ (3) |
| 4* | 4.19 (m, 1) | | | | | | | | |
| 1' | 5.87 (d, 1) | | | 4.4 | | | | | |
| 2' | 4.21 (t, 1) | | | 4.9 | | | | | |
| 3' | 4.25 (t, 1) | | | 4.9 | | | | | |
| 4' | 4.17 (m, 1) | | | | | | | | |
| 5' | 4.09 (ddd, 1) | | | 12.2, 5.4 | 3.2 | | | | |
| 6' | 4.17 (m, 1) | | | | | | | | |
| Cyt-2 | | | | | | | | | |
| Cyt-4 | | | | | | | | | |
| Cyt-5 | 6.07 (d, 1) | | | 7.6 | | | | | |
| Cyt-6 | 7.92 (d, 1) | | | 7.6 | | | | | |
| P (2) | | | 0.49$^d$ (dd) | | | 1.7$^d$ (2-Me), 7.6$^d$ (2) | | | |
| P (4) | | | −7.28$^d$ (d) | | | | 20.8 | | |
| P (5') | | | −8.00$^d$ (d) | | | | 20.8 | | |

$^a$Referenced to external trimethylsilylpropane sulfonate. The multiplicities and the relative integral values of signals in the $^1$H NMR spectrum are given in parentheses.
$^b$Referenced to external trimethylsilylpropane sulfonate. The multiplicities of the $^1$H decoupled $^{13}$C NMR signals are given in parentheses.
$^c$Referenced to external 85% ortho-phosphoric acid. The multiplicities of the $^1$H decoupled $^{31}$P NMR signals are given in parentheses.
$^d$observed with [2,2-Me-$^{13}$C$_2$]4-diphophocytidyl-2C-methyl-D-erythritol 2-phosphate
$^e$observed with [1,3,4-$^{13}$C$_1$]4-diphophocytidyl-2C-methyl-D-erythritol 2-phosphate
$^f$from the spectrum of [1,2,2-Me,3,4-$^{13}$C$_5$]4-diphophocytidyl-2C-methyl-D-erythritol 2-phosphate

EXAMPLE 17

Construction of an Expression Clone for ygbB from E. coli

The E. coli ORF ygbB (accession no. gb AE000358) from bp position 6231 to 6754 is amplified by PCR using chromosomal E. coli DNA as template. Chromosomal DNA from Escherichia coli strain XL1-Blue is isolated according to a method described by Meade et al., (Meade, H. M., Long, S. R., Ruvkun, C. B., Brown, S. E., and Auswald, F. M. (1982). Physical and genetic characterization of symbiotic and auxotrophic mutants of Rhizobium meliloti induced by transposon Tn5 mutagens. J. Bacteriol. 149, 114-122).

The reaction mixture contained 10 pmol of primer GAGGAGAAATTMCCATGCGAATTGGACACGGTTTTG (SEQ ID NO:56), 10 pmol of primer TATTATCTGCAGCCTTGCGGTTTACCGTGGAGG (SEQ ID NO:57), 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM Tris-hydrochloride, pH 8.8 and 0.1% (w/w) Triton X-100.

The mixture is denaturated for 5 min at 94° C. Then 30 PCR cycles for 30 sec at 94° C., 45 sec at 50° C. and 45 sec at 72° C. followed. After further incubation for 7 min at 72° C., the mixture is cooled to 4° C. An aliquot of 2 µl is subjected to agarose gel electrophoresis. The PCR amplificate is used as template for a second PCR reaction. The reaction mixture contained 50 pmol of primer ACACAGAATTCATTAAAGAGGAGAAATTMCCATG (SEQ ID NO:58), 50 pmol of primer TATTATCTGCAGCCTTGCGGTTTACCGTGGAGG (SEQ ID NO:57), 2.5 µl of the first PCR amplification, 10 U of Taq DNA polymerase (Eurogentec, Seraing, Belgium) and 100 nmol of dNTPs in a total volume of 500 µl of 1.5 mM $MgCl_2$, 50 mM KCl, 10 mM Tris-hydrochloride, pH 8.8 and 0.1% (w/w) Triton X-100. The mixture is apportioned in 5 PCR-tubes.

The mixtures are denaturated for 5 min at 94° C. Then 25 PCR cycles for 30 sec at 94° C., 45 sec at 50° C. and 45 sec at 72° C. followed. After further incubation for 7 min at 72° C., the mixture is cooled to 4° C. An aliquot of 2 µl is subjected to a agarose gel electrophoresis.

The PCR amplificates are purified with a PCR purification kit from Qiagen as described in example 1.

4.5 µg of the vector pNCO113 (isolated as described in example 1) and 3.4 µg of the purified PCR product are digested in order to produce DNA fragments with overlapping ends. Each restriction mixture contains 20 µl of NEB3 buffer, 100 U of EcoRI (NEB), 100 U of PstI (NEB) in a total volume of 200 µl and is incubated for 3 h at 37° C. Digested vector DNA and PCR product are purified using the PCR purification kit from Qiagen as described in Example 1.

100 ng of vector DNA and 35 ng of PCR product are ligated together with 1 U of T4-Ligase (Gibco), 2 µl of T4-Ligase buffer (Gibco) in a total volume of 10 µl, yielding the plasmid pNCOygbB. The ligation mixture is incubated for 2 h at 25° C. 1 µl of the ligation mixture is transformed into electrocompetent E. coli XL1-Blue cells as described in Example 1. The electrocompetent cells are prepared as described in Example 1.

EXAMPLE 18

Preparation and Purification of Recombinant YgbB Protein of E. coli

The cell free extract of YgbB protein from E. coli is prepared identical to the preparation in example 4. The supernatant is applied on a column of Sepharose Q FF (column volume 30 ml, Amersham Pharmacia Biotech, Freiburg, Germany) previously equilibrated with 120 ml of buffer A. The column is washed with 90 ml of buffer A. Then the YgbB protein is eluted with a linear gradient of 0-0.5 M NaCl in 150 ml buffer A. The homogeneity of YgbB protein is judged by SDS-PAGE.

EXAMPLE 19

Screening of YgbB Enzyme Activity

The YgbB enzyme activity is screened by radiochemical method. Assay mixtures contained 100 mM tris hydrochloride pH 8.0, 10 mM $MnCl_2$, 14 nCi of [$2-^{14}C$]4-diphosphocytidyl-2C-methyl-D-erythritol and 2 µg of YgbB protein from recombinant E. coli. They are incubated at 37° C. for 30 min. After centrifugation, aliquots are spotted on SiI-NHR thin layer plates which are developed with a mixture of n-propanol/ethyl acetate/$H_2O$ (6:1:3, v/v). The radiochromatogram is monitored and evaluated by Phosphor Imager (Storm 860, Molecular Dynamics, USA). The Rf value of the YgbB product is 0.5. This screening method can be carried out in the presence or absence of prospective inhibitors.

EXAMPLE 20a

Production of an Expression Clone and Construction of an Expression Vector for a 6×His-ygbB Fusion Protein of E. coli The E. coli ORF ygbB (accession no. gb AE000358) from bp position 6231 to 6754 is amplified by PCR using chromosomal E. coli DNA as template. Chromosomal DNA from Escherichia coli strain XL1-Blue is isolated according to a method described in example 2.

The reaction mixture contained 10 pmol of primer GAGAAGGATCCATGCGAATTGGACACGGTTTTGACG (SEQ ID NO:59), 10 pmol of primer TATTATCTGCAGCCTTGCGGTTTACCGTGGAGG (SEQ ID NO:57), 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM Tris-hydrochloride, pH 8.8 and 0.1% (w/w) Triton X-100.

The mixture is denaturated for 5 min at 94° C. Then 30 PCR cycles for 30 sec at 94° C., 45 sec at 50° C. and 45 sec at 72° C. followed. After further incubation for 7 min at 72° C., the mixture is cooled to 4° C. An aliquot of 2 µl is subjected to agarose gel electrophoresis.

The PCR amplificate is purified with a PCR purification kit from Qiagen as described in example 1.

1.0 µg of the vector pQE30, isolated as described in example 1 (Quiagen) and 0.5 µg of the purified PCR product are digested in order to produce DNA fragments with overlapping ends. Each restriction mixture contains 10 µl of NEB3 buffer from New England Biolabs (NEB), 100 U of BamHI (NEB), 100 U of PstI (NEB) in a total volume of 100 µl and is incubated for 3 h at 37° C. Digested vector DNA and PCR product are purified using the PCR purification kit from Qiagen as described in example 1.

5 fmol of vector DNA and 14 fmol of PCR product are ligated together with 1 U of T4-Ligase (Gibco), 2 µl of T4-Ligase buffer (Gibco) in a total volume of 10 µl, yielding the plasmid pQEygbB. The ligation mixture is incubated for 2 h at 25° C. 1 µl of the ligation mixture is transformed into electrocompetent E. coli XL1-Blue cells as described in example 2. The electrocompetent cells are prepared as described in example 1. The plasmid pQEygbB is isolated as described in example 1. 12 µg of plasmid DNA are obtained.

The DNA insert of the plasmid pQEygbB is sequenced as described in example 2 and is identical to the sequence in the database (accession no. gb AE000358). The 5'-end of the DNA insert carries the coding region for 6 histidine residues.

EXAMPLE 20b

Construction of Expression Vectors and Production of Expression Clones for ygbB of *Plasmodium falciparum*

The expression vector pQE30 is isolated as described in example 1.

A cDNA library from *P. falciparum* (strain HB3) is prepared using the SuperSrip Plasmid System for cDNA Synthesis and plasmid cloning from Gibco.

The full-length *P. falciparum* ORF ygbB (accession no. gb AE001394) from bp position 2617 to 3495 is amplified by PCR using cDNA from *P. falciparum* as template. The reaction mixture contains 25 pmol of primer 5'-TCCATATG-GATCCATGITTTIAAAAGGATACACC-3' (SEQ ID NO:60), 25 pmol of primer 5'-GACCTGCCTGCAGTTAT-GAATTTTTAGGTATTMC-3' (SEQ ID NO:61), 1 µg of cDNA, 2 U of Taq DNA polymerase (Eurogentec, Seraing, Belgium) and 20 nmol of dNTPs in a total volume of 100 µl 1.5 mM MgCl$_2$, 50 mM KCl, 10 mM Trishydrochloride, pH 8.8 and 0.1% (w/w) Triton X-100.

The mixture is denatured for 3 min at 95° C. Then 30 PCR cycles for 45 sec at 94° C., 45 sec at 50° C. and 60 sec at 72° C. followed. After further incubation for 20 min at 72° C., the mixture is cooled to 4° C. An aliquot of 2 µl is subjected to agarose gel electrophoresis. The PCR amplificate is purified with the PCR purification kit from Qiagen as described in Example 1. 2.2 µg of purified PCR product are obtained.

2.0 µg of the vector pQE30 and 1.5 µg of the purified PCR product are digested in order to produce DNA fragments with overlapping ends. Each restriction mixture contains 7 µl of NEB3 buffer from New England Biolabs (NEB), 40 U of BamHI (NEB), 30 U of PstI (NEB) in a total volume of 70 µl and is incubated for 3 h at 37° C. Digested vector DNA and PCR product are purified using the PCR purifiaction kit from Qiagen.

20 ng of vector DNA and 8 ng of PCR product are ligated together with 1 U of T4-Ligase (Gibco), 2 µl of T4-Ligase buffer (Gibco) in a total volume of 10 µl yielding the plasmid pQEygbBPlaskom The ligation mixture is incubated over night at 4° C. 2 µl of the ligation mixture is transformed into electrocompetent E. coli XL1-Blue cells as described in example 1. The electrocompetent cells are prepared as described in example 1.

The DNA insert of the plasmid pQEygbBPlaskom is sequenced as described in example 1 and is identical to the calculated cDNA sequence of the database entry (gb AE001394). The cDNA sequence and corresponding amino acid sequence of the ygbB gene of *P. falciparum* is shown in FIG. 10.

A N-terminal truncated ygbB expression clone of *P. falciparum* ORF ygbB was constructed lacking the coding region for the putative leader sequence. The PCR reaction mixture contains 25 pmol of primer 5'-TTATTTGGATCCATGGG-TATAAGAATAGGTCAAGG-3' (SEQ ID NO:62), 25 pmol of primer 5'-GACCTGCCTGCAGTTATGAATTTTTAGG-TATTAAC-3' (SEQ ID NO:61), 1 µg of cDNA, 2 U of Taq DNA polymerase (Eurogentec, Seraing, Belgium) and 20 nmol of dNTPs in a total volume of 100 µl 1.5 mM MgCl$_2$, 50 mM KCl, 10 mM Tris hydrochloride, pH 8.8 and 0.1% (w/w) Triton X-100.

The mixture is denatured for 3 min at 95° C. Then 30 PCR cycles for 45 sec at 94° C., 45 sec at 50° C. and 45 sec at 72° C. followed. After further incubation for 20 min at 72° C., the mixture is cooled to 4° C. An aliquot of 2 µl is subjected to agarose gel electrophoresis. The PCR amplificate is purified with the PCR purification kit from Qiagen as described in Example 1. 3.0 µg of purified PCR product are obtained.

2.0 µg of the vector pQE30 and 1.5 µg of the purified PCR product are digested in order to produce DNA fragments with overlapping ends. Each restriction mixture contains 7 µl of NEB3 buffer from New England Biolabs (NEB), 40 U of BamHI (NEB), 30 U of PstI (NEB) in a total volume of 70 µl and is incubated for 3 h at 37° C. Digested vector DNA and PCR product are purified using the PCR purifiaction kit from Qiagen.

20 ng of vector DNA and 6 ng of PCR product are ligated together with 1 U of T4-Ligase (Gibco), 2 µl of T4-Ligase buffer (Gibco) in a total volume of 10 µl, yielding the plasmid pQEygbBPlas The ligation mixture is incubated over night at 4° C. 2 µl of the ligation mixture is transformed into electrocompetent E. coli XL1-Blue cells as described in example 1. The electrocompetent cells are prepared as described in example 1.

The DNA insert of the plasmid pQEygbBPlas is sequenced as described in example 1.

EXAMPLE 21a

Preparation and Purification of Recombinant 6×His-YgbB Fusion Protein of *E. coli*

Recombinant XL1-Blue cells of *E. coli* containing overexpressed YgbB (N-terminal His-tagged) of *E. coli* are prepared as in example 12. The cells are thawed in 20 ml of 20 mM imidazole in 100 mM tris hydrochloride pH 8.0 and 0.5 M sodium chloride (standard buffer) in the presence of 1 mg/ml lysozyme and 100 µg/ml DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant YgbB protein of *E. coli* is applied on a column of Ni$^{2+}$-Chelating sepharose FF (column volume 25 ml, Amersham Pharmacia Biotech) previously equilibrated with 20 mM imidazole in standard buffer. The column is washed with 100 ml of starting buffer. YgbB protein is eluted with a linear gradient of 20-500 mM imidazole in standard buffer. YgbB protein containing fractions are combined according to SDS-PAGE and dialysed overnight against 100 mM tris hydrochloride pH 8.0. The dialysed YgbB protein is concentrated by ultrafiltration (MWCO 10 kDa, Amicon, USA.) and applied on Superdex 75 HR 26/60 (Amersham Pharmacia Biotech). The homogeneity YgbB protein is judged by SDS-PAGE. The objected band at 17 kDa is in agreement with the calculated molecular mass. 27 mg of pure enzyme were obtained.

EXAMPLE 21b

Preparation and Purification of the Recombinant 6×His-YgbB Fusion Protein of P. falciparum Recombinant cells of strain XL1-pQEygbBPlas containing overexpressed YgbB protein of P. falciparum are prepared as described in example 6.

The cells are thawed in 20 ml of 20 mM imidazole in 100 mM tris hydrochloride pH 8.0 and 0.5 M sodium chloride (standard buffer) in the presence of 1 mg/ml lysozyme and 100 µg/ml DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant YgbB protein of tomato is applied on a column of $Ni^{2+}$-Chelating sepharose FF (column volume 25 ml, Amersham Pharmacia Biotech) previously equilibrated with 20 mM imidazole in standard buffer. The column is washed with 100 ml of starting buffer. YgbB protein is eluted with a linear gradient of 20-500 mM imidazole in standard buffer. YgbB protein containing fractions are combined according to SDS-PAGE and dialysed overnight against 100 mM Tris hydrochloride pH 8.0. The dialysed YgbB protein is concentrated by ultrafiltration (MWCO 10 kDa, Amicon, USA.) and applied on Superdex 75 HR 26/60 (Amersham Pharmacia Biotech). The homogeneity YgbB protein is judged by SDS-PAGE. The objected band at 22 kDa is in agreement with the calculated molecular mass. 22 mg of pure enzyme are obtained.

EXAMPLE 22

Enzymatic Production of 2C-methyl-D-erythritol 3,4-cyclophosphate

A solution of 500 µl containing 100 mM Tris HCl, pH 8.0, 10 mM $MnCl_2$, 0.12 µCi of [2-$^{14}$C]diphosphocytidyl-2C-methyl-D-erythritol, 46 mM of diphosphocytidyl-2C-methyl-D-erythritol and 225 µg of YgbB protein from recombinant E. coli is incubated at 37° C. for 1 h. The reaction is monitored by $^{31}$P-NMR. The product displaying one $^{31}$P NMR singlet at +21.7 ppm is purified by HPLC on a column of the anionic exchanger Nucleosil 10SB (4.6×250 mm) using 50 mM ammonium formate in 40% (v/v) methanol as eluent at a flow rate of 1 ml/min. The eluent is monitored by a radiomonitor from Berthold. 2C-methyl-D-eryrithritol 3,4-cyclophosphate is eluted at 10 ml. The fraction containing 2C-methyl-D-eryrithritol 3,4-cyclophosphate is collected and lyophilized (2.6 mg). The residue is dissolved in 0.5 ml of deuterated water and subjected to NMR analysis.

EXAMPLE 23

Identification of 2C-methyl-D-erythritol 3,4-cyclophosphate $^1$H NMR and $^1$H decoupled $^{13}$C NMR spectra are recorded using a AVANCE DRX 500 spectrometer from Bruker, Karlsruhe, Germany. The frequencies are 500.1 MHz and 125.6 MHz for $^1$H and $^{13}$C, respectively. The chemical shifts are referenced to external trimethylsilylpropane sulfonate. Two-dimensional correlation experiments (gradient enhanced double quantum filtered COSY, HMQC) are performed using XWINNMR software from Bruker. $^{31}$P NMR spectra are recorded using a AC 250 spectrometer from Bruker at a transmitter frequency of 101.3 MHz. The chemical shifts are referenced to external 85% $H_3PO_4$.

The structure of the product is evaluated by a multinuclear multidimensional NMR approach (Table 7). Specifically, the compound is characterized by a single $^{31}$P NMR signal at +21.7 ppm. The detected $^{31}$P NMR chemical shift range implied that the unknown compound is a pentacyclic monophosphate.

The presence of a phosphorous atom in the unknown compound is further reflected in the $^{13}$C NMR spectrum where three of five signals showed coupling with $^{31}$P ($^{31}$P-$^{13}$C coupling constants in the range of 6 Hz to 1 Hz).

More specifically, the $^{13}$C NMR signal of C2 is a doublet with a $^{31}$P-$^{13}$C coupling constant of 6.5 Hz being typical for a $^3J_{PC}$ coupling constant. The $^{31}$P-$^{13}$C couplings for C3 and C4 are smaller (1.7 resp. 1.1 Hz) reflecting $^2J_{PC}$ coupling constants. Thus the detected $^{31}$P-$^{13}$C coupling signature implied a 3,4-cyclophosphate structure.

TABLE 7

NMR-data of 2C-methyl-D-erythritol 3,4-cyclomonophosphate

| | Chemical shifts, ppm | | | Coupling constants, Hz | | |
|---|---|---|---|---|---|---|
| Position | $^1$H | $^{13}$C | $^{31}$P | $J_{HH}$ | $J_{PH}$ | $J_{PC}$ |
| 1 | 3.38 (d, 1H)$^a$ | 65.84 (s)$^b$ | | 12.0 (1*)$^c$ | | |
| 1* | 3.47 (d, 1H) | | | 12.0 (1) | | |
| 2 | | 73.02 (d) | | | | 6.5 |
| 2-Me | 1.09 (s) | 17.73 (s) | | | | |
| 3 | 4.15 (m, 1H) | 77.61 (d) | | | | 1.7 |
| 4 | 4.18 (m, 1H) | 64.96 (d) | | | | 1.1 |
| 4* | 4.34 (ddd, 1H) | | | 11.2 (4), 3.8 (3) | 7.2 | |
| P | | | +21.67 (s)$^d$ | | | |

$^a$Referenced to external trimethylsilylpropane sulfonate. The multiplicities and the relative integral values of signals in the $^1$H NMR spectrum are given in parentheses.
$^b$Referenced to external trimethylsilylpropane sulfonate. The multiplicities of the $^1$H decoupled $^{13}$C NMR signals are given in parentheses.
$^c$Coupling partners as analysed from two-dimensional COSY experiments are given in parentheses.
$^d$Referenced to external 85% ortho-phosphoric acid. The multiplicities of the $^1$H decoupled $^{31}$P NMR signals are given in parentheses.

EXAMPLE 24

Screening of YgbB Enzyme Activity by NMR

A solution containing 100 mM Tris HCl pH 8.0, 10 mM $MnCl_2$, 5 mM of 4-diphosphocytidyl-2C-methyl-D-erythritol and 0.1 mg of YgbB protein from recombinant E. coli is incubated at 37° C. for 1 h. The reaction is monitored by $^{31}$P-NMR. $^{31}$P NMR spectra are recorded using an AC 250 spectrometer from Bruker at a transmitter frequency of 101.3 MHz. The chemical shifts are referenced to external 85% $H_3PO_4$. The screening method is carried out in the presence or absence of prospective inhibitors by measuring the residual starting material and comparing the results.

The product displayed one $^{31}$P singlet at +21.7. The enzyme activity can therefore also be determined by measuring this signal for determining the amount of product.

EXAMPLE 25

Enzymatic Preparation of 2C-methyl-D-erythritol 2,4-cylopyrophosphate

A solution containing 5 mg [2-$^{14}$C]4-diphosphocytidyl-2C-methyl-D-erythritol (0.02 µCi/mmol), 5 mM MgCl$_2$, 5 mM ATP, 5 mM DDT, 100 µg purified YchB protein, 200 µg purified YgbB protein and 100 mM Tris hydrochloride pH 8.0 in a total volume of 4 ml is incubated for 2 h at 37° C. The reaction is monitored by $^{13}$C NMR and $^{31}$P spectroscopy. The solution is passed through a Nanosep 10K membrane (PALLGemann, Roβdorf, Germany). The product displaying two $^{31}$P NMR signals at −7.65 ppm and −11.66 ppm (doublets, $^{31}$P-$^{31}$P coupling constant, 23.6 Hz) and displaying two intense $^{13}$C NMR signals at 83.87 ppm is purified by HPLC on a column of the anionic exchanger Nucleosil 10SB (4.6× 250 mm, Macherey-Nagel, Duren, Germany) using 40% (v/v) methanol containing 0.1 M ammonium formate as eluent at a flow rate of 1 ml/min. 2C-methyl-D-erythritol 2,4-cyclopyrophosphate is eluted at 34 ml. Fractions containing 2C-methyl-D-erythritol 2,4-cyclopyrophosphate are collected and lyophylized. The residue is dissolved in 0.5 ml of deuterated water and subjected to NMR analysis. The concentration of 2C-methyl-D-erythritol 2,4-cyclopyrophosphate is 18 mM.

EXAMPLE 26

Identification of 2C-methyl-D-erythritol 2,4-cyclopyrophosphate

The elucidation of the structure is performed with [2,2'-Me-$^{13}$C$_2$]2C-methyl-D-erythritol 2,4-cyclopyrophosphate (Table 8).

$^1$HNMR and $^1$H decoupled $^{13}$C NMR spectra are recorded using a AVANCE DRX 500 spectrometer from Bruker (Karlsruhe, Germany). The frequencies are 500.1 MHZ and 125.6 Mhz for $^1$H and $^{13}$C, respectively. The chemical shifts are referenced to external trimethylsilylpropane sulfonate. $^{31}$P NMR spectra are recorded using a AC 250 spectrometer from Bruker at a frequency of 101.3 MHz. The chemical shifts are referenced to external 85% H$_3$PO$_4$.

The structure of the product is evaluated by a multinuclear multidimensional NMR approach (Table 8). Specifically, the compound is characterized by two $^1$H decoupled $^{31}$P NMR signals at −7.65 ppm (doublet with 31P-$^{31}$P coupling constant of 23.6 Hz) and −11.66 ppm (double-double doublet with $^{31}$P-$^{31}$P coupling constant of 23.6 Hz and 31P-$^{13}$C coupling constants of 8.5 Hz, respectively). The $^{31}$P NMR signal at 7.65 ppm is broadened without $^1$H decoupling. The detected $^{31}$P NMR chemical shift range, as well as the $^{31}$P-$^{31}$P couplings implied that the unknown compound is a pyrophosphate. Moreover, the detected $^{31}$P-$^{13}$C couplings for the $^{31}$P NMR signal at −11.66 ppm in conjunction with the missing. $^{31}$P-$^1$H coupling for the signal indicates that one phosphate unit of the pyrophosphate moiety is connected to C-2 of 2C-methyl-D-erythritol. In line with this conclusion. $^{13}$C-$^{31}$P couplings are observed for the $^{13}$C NMR signals reflecting C-2 and C-2-methyl.

In conjunction with the observed $^{13}$C-$^{13}$C couplings (Table 8), these data are the basis of the $^1$H and $^{13}$C NMR signal assignments. The $^{13}$C signal at 65.72 ppm (reflecting C4) showed $^{13}$C-$^{31}$P coupling suggesting that the pyrophosphate motif is also connected to C-4. The $^{13}$C NMR assignments are further confirmed by two-dimensional INADEQUATE experiments establishing the $^{13}$C-$^{13}$C connectivities.

In summary, the $^1$H, $^{13}$C and $^{31}$P NMR data clearly established the product as 2C-methyl-D-erythritol 2,4-cylopyrophosphate. The NMR data were in close correspondence to reported data for this compound (Ostrovsky, D., Kharatian, E.; Dubrovsky, T., Ogrel, O., Shipanova, I., and Sibeldina, L. (1992). The ability of bacteria to synthesize a new cyclopyrophosphate correlates with their tolerance to redox-cycling drugs: on a crossroad of chemotherapy, environmental toxicology and immunobiochemical problems. Biofactors 4 (1), 63-68; 1992; Truner, D. L., Santos, H., Fareleira, P., Pacheco, I., LeGall, J., and Xavier, A. V. (1992). Structure determination of a novel cyclic phosphocompound isolated from *Desulfovibrio desulfuricans*. Biochem. J. 285, 387-390.)

TABLE 8

NMR data of [2,2-Me-$^{13}$C$_2$]2C-methyl-D-erythritol 2,4-cyclopyrophosphate

| | Chemical shifts, ppm | | | Coupling constants, Hz | | | | | |
|---|---|---|---|---|---|---|---|---|---|
| Position | $^1$H | $^{13}$C | $^{31}$P | $J_{PH}$ | $J_{PC}$ | $J_{PP}$ | $J_{CH}$ | $J_{CC}$ | $J_{HH}$ |
| 1 | 3.51 (dt, 1H)[a] | 66.95 (d)[b] | | | | | 1.7 | 41.8 (2) | 12.4 (1) |
| 1* | 3.66 (dd, 1H) | | | | | | 1.8 | | 12.4 (1) |
| 2 | | 83.87 (dd) | | | 8.4 | | | 39.8 (2-Me) | |
| 2-Methyl | 1.31 (dd, 3H) | 16.30 (dd) | | | 5.3 | | 128.4, 4.0 | 39.8 (2) | |
| 3 | 3.98 | 68.42 (dm) | | | n.d. | | | 46.0 (2) | n.d |
| 4 | | 65.72 (d) | | | 6.6 | | | | n.d. |
| 4* | 4.13 (m, 3H) | | | | | | | | n.d. |
| P (4) | | | −7.65 (d)[c] | n.d. | | 23.6 | | | |
| P (2) | | | −11.66 (ddd) | | 8.5, 5.3 | 23.6 | | | |

[a]Referenced to external trimethylsilylpropane sulfonate. The multiplicities and the relative integral values of signals in the $^1$H NMR spectrum are given in parentheses.
[b]Referenced to external trimethylsilylpropane sulfonate. The multiplicities of the $^1$H decoupled $^{13}$C NMR signals are given in parentheses.
[c]Referenced to external 85% ortho-phosphoric acid. The multiplicities of the $^1$H decoupled $^{31}$P NMR signals are given in parentheses.

EXAMPLE 27

Production of an expression clone and construction of an expression vector for 1-deoxy-D-xylulose 5-phosphate synthase of Bacillus subtilis The expression vector pNCO113 is isolated as described in example 1. Chromosomal DNA from Bacillus subtilis strain BR151 (Williams, D. M., Duvall E. J., and Lovett, P. S. (1981). Cloning restriction fragments that promote expression of a gene in Bacillus subtilis. J. Bacteriol. 146(3), 1162-1165.1981) is isolated according to a method described in example 2.

The putative ORF yqiE coding for 1-deoxy-D-xylulose 5-phosphate synthase of B. subtilis (accession no. dbj D84432) from basepair (bp) position 193991 to 195892 is amplified by PCR using chromosomal B. subtilis DNA as template. The reaction mixture contained 25 pmol of primer TGATCCGCCATGGATCTTTTATCMTACAGG (SEQ ID NO:63), 25 pmol of primer TTGAATAGAGGATCCCCGCC (SEQ ID NO:64), 20 ng of chromosomal DNA, 2U of Taq DNA polymerase (Eurogentec, Seraing, Belgium) and 20 nmol of dNTPs in a total volume of 1.5 mM $MgCl_2$, 50 mM KCl, 10 mM Tris-hydrochloride, pH 8.8 and 0.1% (w/w) Triton X-100 in a total volume of 100 µl.

The mixture is denaturated for 3 min at 95° C. Then 30 PCR cycles for 60 sec at 94° C., 60 sec at 50° C. and 120 sec at 72° C. follow. After further incubation for 20 min at 72° C., the mixture is cooled to 4° C. An aliquot of 2 µl is subjected to agarose gel electrophoresis. The PCR amplificate is purified with PCR purification kit from Qiagen. 500 µl of buffer PB (Qiagen) are added to 98 µl of PCR reaction mixture and applied to a Quiaquick column and centrifuged for 1 min at 14,000 rpm. The flow through is discarded. 0.75 ml of buffer PE (Qiagen) are loaded on the column and centrifuged as before. The flow through is discarded and the column is centrifuged for an additional 1 min at 14,000 rpm. The column is placed in a clean 1.5 ml eppendorf tube. 50 µl of $H_2O$ (redistilled, sterile) are added to the column and it is centrifuged for 1 min at 14,000 rpm. The flow through contained 1.8 µg of purified PCR product.

2.0 µg of the vector pNCO113 and 1.8 µg of the purified PCR product are digested in order to produce DNA fragments with overlapping ends. Each restriction mixture contained 7 µl of SalI buffer from (NEB), 7 µg of BSA (NEB), 40 U of NcoI (NEB), 30 U of SalI (NEB) in a total volume of 70 µl and is incubated for 3 h at 37° C. Digested vector DNA and PCR product are purified using the PCR purification kit from Qiagen.

20 ng of vector DNA and 34 ng of PCR product are ligated together with 1 U of T4-Ligase from Gibco-BRL (Eggenstein, Germany), 2 µl of T4-Ligase buffer (Gibco-BRL) in a total volume of 10 µl yielding the plasmid pNCODXS-BACSU. The ligation mixture is incubated over night at 4° C. With 2 µl of the ligation mixture electrocompetent E. coli XL1-Blue cells are transformed as described in example 2. 6 µg of plasmid DNA pNCODXSBACSU were isolated.

The DNA insert of the plasmid pNCODXSBACSU is sequenced as described in example 1. The sequence is identical with the sequence found in the database (accession no. dbj D84432).

EXAMPLE 28

Production of an expression clone and construction of an expression vector for 1-deoxy-D-xylulose 5-phosphate reductoisomerase of E. coli The E. coli ORF yaeM (accession no. gb AE000126) from bp position 9887 to 11083 is amplified by PCR using chromosomal E. coli DNA as template. Chromosomal DNA from Escherichia coli strain XL1-Blue is isolated according to a method described in example 2.

The reaction mixture contained 25 pmol of primer GGAGGATCCATGAAGCAACTCACC (SEQ ID NO:65), 25 pmol of primer GCGCGACTCTCTGCAGCCGG (SEQ ID NO:66), 20 ng of chromosomal DNA, 2 U of Taq DNA polymerase (Eurogentec, Seraing, Belgium) and 20 nmol of dNTPs in a total volume of 100 µl of 1.5 mM $MgCl_2$, 50 mM KCl, 10 mM Tris-hydrochloride, pH 8.8 and 0.1% (w/w) Triton X-100.

The mixture is denaturated for 3 min at 94° C. Then 30 PCR cycles for 45 sec at 94° C., 45 sec at 50° C. and 75 sec at 72° C. followed. After further incubation for 7 min at 72° C., the mixture is cooled to 4° C. An aliquot of 2 µl is subjected to agarose gel electrophoresis.

The PCR amplificates are purified with a PCR purification kit from Qiagen as described in example 1.

2.5 µg of the vector pQE30 (Quiagen), isolated as described in example 2, and 2.0 µg of the purified PCR product are digested in order to produce DNA fragments with overlapping ends. Each restriction mixture contains 7 µl of NEB3 buffer, 50 U of BamHI (NEB), 40 U of PstI (NEB) in a total volume of 70 µl and is incubated for 3 h at 37° C. Digested vector DNA and PCR product are purified using the PCR purification kit from Qiagen as described in example 1.

20 ng of vector DNA and 22 ng of PCR product are ligated together with 1 U of T4-Ligase (Gibco), 2 µl of T4-Ligase buffer (Gibco) in a total volume of 10 µl, yielding the plasmid pQEyaeM. The ligation mixture is incubated overnight at 4° C. Each 2 µl of the ligation mixture is used for transforming electrocompetent E. coli XL1-Blue and M15[pREP4] (Zamenhof et al., 1972) cells as described in example 1. The electrocompetent cells are prepared as described in example 1.

12 µg DNA of plasmid pQEyaeM are obtained.

The DNA insert of the plasmid pQEyaeM is sequenced as described in example 2 and is identical with the sequence in the database (accession no. gb AE000126).

EXAMPLE 29

Preparation and purification of recombinant 1-deoxy-D-xylulose 5-phosphate synthase of B. subtilis E. coli XL1-Blue cells harboring the plasmid pNCODXS-BACSU are grown, induced, harvested and stored as described in example 1.

2 g of the cells are thawed in 10 ml of 25 mM tris-HCl pH 8.0 containing 1 mM dithioerythritol, 10 mM EDTA and 6 mM phenylmethylsulfonyl fluoride in the presence of 1 mg lysozyme. The mixture is incubated at 37° C. for 0.5 h, cooled on ice and sonified 6×10 sec with a Branson Sonifier 250

(Branson SONIC Power Company, Danbury, USA), control value of 4 output. The suspension is centrifuged at 15,000 rpm at 4° C. for 30 min. The supernatant is applied on a column of Sepharose QFF (26 cm$^3$, Amersham Pharmacia Biotech, Freiburg, Germany) previously equilibrated with 200 ml 25 mM tris-HCl pH 8.0 containing 0.5 mM MgCl$_2$ and 0.03% sodium azid (buffer A). The column is washed with 60 ml buffer A monitoring the extinction at 280 nm. 1-deoxy-D-xylulose-5-phosphate synthase is eluted from the column with a gradient from 0-1 M sodium chloride in 300 ml of buffer A. The enzyme is identified by SDS-PAGE showing a band at 68 kDa. Fractions showing this protein band are collected and dialysed against buffer A overnight.

The enzyme is further purified on a column of hydroxyl apatite (Macro pep 40 µm (size 2.5 6 cm, Biorad, Munich, Germany) equilibrated with buffer A. The enzyme is eluted by gradient of 0 1 M potassium phosphate, pH 6.5. The homogeneity of 1-deoxy-D-xylulose-5-phosphate synthase is judged by SDS-PAGE. A prominent band at 67 kDa is visible, which is in agreement to the calaculated molecular mass. The yield of pure 1-deoxy-D-xylulose-5-phosphate synthase is 44 mg.

EXAMPLE 30

Preparation and purification of recombinant 1-deoxy-D-xylulose 5-phosphate reductoisomerase of *E. coli*

Recombinant M15[pREP4] cells of *E. coli* containing overexpressed 1-deoxy-D-xylulose 5-phosphate reductoisomerase of *E. coli* are prepared identical to the preparation of example 1. The cells are thawed in 20 ml of 20 mM imidazole in 100 mM tris hydrochloride pH 8.0 and 0.5 M sodium chloride (standard buffer) in the presence of 1 mg/ml lysozyme and 100 µg/ml DNaseI. The mixture is incubated at 37° C. for 30 min, cooled on ice and sonified 6×10 sec with a Branson Sonifier 250 (Branson SONIC Power Company) set to 70% duty cycle output, control value of 4 output. The suspension is centrifuged at 15,000 rpm at 4° C. for 30 min. The cell free extract of recombinant 1-deoxy-D-xylulose 5-phosphate reductoisomerase of *E. coli* is applied on a colunm of Ni$^{2+}$-Chelating sepharose FF (column volume 25 ml, Amersham Pharmacia Biotech) previously equilibrated with 20 mM imidazole in standard buffer. The column is washed with 100 ml of starting buffer. 1-Deoxy-D-xylulose-5-phosphate reductoisomerase is eluted with a linear gradient of 20-500 mM imidazole in standard buffer. 1-Deoxy-D-xylulose 5-phosphate reductoisomerase containing fractions are combined according to SDS-PAGE and dialysed overnight against 100 mM tris hydrochloride pH 8.0. The dialysed 1-deoxy-D-xylulose 5-phosphate reductoisomerase is concentrated by ultrafiltration (MWCO 10 kDa, Amicon, USA.) and applied on a Superdex 75 HR 26/60 column (Amersham Pharmacia Biotech). The homogeneity of 1-deoxy-D-xylulose 5-phosphate reductoisomerase is judged by SDS-PAGE. One band at 43 kDa is visible, which is in line with the calculated molecular mass. The yield of pure 1-deoxy-D-xylulose 5-phosphate is 60 mg.

EXAMPLE 31

Determination of 1-deoxy-D-xylulose-5-phosphate synthase activity 31.1. By Nuclear Magnetic Resonance (NMR)

The assay mixture contains 400 mM tris hydrochloride pH 8.0, 25 mM [2-$^{13}$C]-sodium pyruvate, 50 mM D,L-glyceraldehyde-3 phosphate, 10 mM MgCl$_2$, 2 mM thiamine pyrophosphate, 1 mM dithiothreitol, 0.5 mM EDTA, 10% D$_2$O and 0.8 mg enzyme sample in a total volume of 0.5 ml. The mixture is incubated 3 h at 37° C. Protein is precipitated by the addition of 0.1 ml 50% trichloroacetic acid (TCA). After centrifugation a $^{13}$C-NMR-spectrum (62.9 Mhz, Bruker, Karlsruhe, Germany) is recorded. The turnover is calculated by integration of the 2C-signals of pyruvate and 1-deoxy-D-xylulose 5-phosphate. Pyruvate displays a 2C-signal at 196.5 ppm and a signal at 92.7 ppm which is assigned to the corresponding hydrate. 1-Deoxy-D-xylulose 5-phosphate displays a signal at 212.5 ppm.

31.2. By Photometric Detection (Variant A)

The assay mixture contains 200 mM tris hydrochloride pH 8.0, 25 mM sodium pyruvate, 50 mM D,L-glyceraldehyde 3-phosphate (previously neutralized with NaOH), 10 mM MgCl$_2$, 4 mM thiamine pyrophosphate, 8 mM dithiothreitol and 0.02 mg enzyme sample in a total volume of 25 ml. The mixture is incubated 20 min at 37° C. 25 ml of 30% TCA are added. The supernatant is added to a buffer containing 200 mM tris hydrochloride pH 8.0, 1 mM MnSO$_4$, 0.5 mM NADPH in a total volume of 0.95 ml. The extinction at 340 nm is determined. A solution (50 ml, 0.1 U) of 1-deoxy-D-xylulose 5-phosphate reductoisomerase is added and the mixture is incubated 30 min at 37° C. The extinction at 340 nm is determined again. The extinction difference is equivalent to the amount of consumed NADPH ($e_{340}$=6300 M$^{-1}$cm$^{-1}$) which is equivalent to the amount of produced 1-deoxy-D-xylulose-5-phosphate.

31.3. By Photometric Detection (Variant B)

The assay mixture contains 200 mM tris hydrochloride pH 8.0, 5 mM sodium pyruvate, 10 mM D,L-glyceraldehyde-3-phosphate, 1 mM MnSO$_4$, 1 mM thiamine pyrophosphate, 1 mM dithiothreitol, 0.5 mM NADPH and 1 U of 1-deoxy-D-xylulose-5-phosphate reductoisomerase in a total volume of 1 ml. The mixture is incubated at 37° C. in a thermostated cuvette and the extinction at 340 nm is monitored. The assay is started by the addition of 5 ml enzyme sample. The negative slope of the extinction is equivalent to the rate of the 1-deoxy-D-xylulose-5-phosphate synthase reaction.

EXAMPLE 32

Determination of 1-deoxy-D-xylulose-5-phosphate reductoisomerase activity

Assay mixtures contain 100 mM tris hydrochloride pH 8.0, 1 mM MnCl$_2$, 0.5 mM NADPH and 5 µg enzyme sample in a total volume of 1 ml. The mixture is incubated at 37° C. in a thermostated cuvette and the reaction is monitored spectrophotometically at 340 nm.

The assay is started by the addition of 10 ml of 50 mM 1-deoxy-D-xylulose-5 phosphate. The negative slope of the extinction is equivalent to the rate of the 1-deoxy-D-xylulose-5-phosphate reductoisomerase reaction.

EXAMPLE 33

Comprehensive Enzymatic Synthesis of [2,2'-Me-$^{13}$C$_2$]4-diphosphocytidyl-2C-methyl-D-erythritol Step a) Enzymatic synthesis of [1,2-$^{13}$C$_2$]1-deoxy-D-xylulose 5-phosphate Crude dihydroxyacetone phosphate is prepared as described by Effenberger, F., and Straub, A. (1987). A novel convinient preparation of dihydroxy aceton phosphate and its use in enzymatic aldol reactions. Tetrahedron Lett. 28, 1641-1644. 1 g of dihydroxyacetone phosphate is dissolved in 70 ml of a solution of 57 mM [2,3-$^{13}C_2$]sodium pyruvate, 10 mM $MgSO_4$ and 2.5 mM thiaminepyrophosphate in 150 mM Tris hydrochloride, pH 8.0. 17000 units of triose phosphate isomerase (rabbit muscle) are added and the solution is incubated 105 min at 37° C. 0.774 ml (7.4 units) of recombinant 1-deoxyxylulose 5-phosphate synthase from *B. subtilis* are added. The reaction is monitored as described in example 17. After 8 h the reaction is stopped by adjusting the pH to a value of 3 by addition of 1 M HCl (11.2 ml). The reaction mixture is stored at −20° C.

Step b) Enzymatic synthesis of [2,2'-Me-$^{13}C_2$]-2C-methyl-D-erythritol-4 phosphate To the reaction mixture obtained in step a, containing [1,2-$^{13}C_2$]1-deoxy-D-xylulose 5-phosphate, 19 ml of 1 M Tris-buffer, pH 8.0, 1.1 ml of 1M $MgCl_2$ solution, 3 g glucose (72 mmol) and 6 ml of solution of 0.1 M $MnCl_2$ are added and the pH is adjusted to 8.0 with (7 ml 1 M NaOH). Precipitate is separated by centrifugation. To a final volume of 200 ml, water, 250 units of glucose dehydrogenase from *B. megaterium* and 56.6 mg NADP$^+$ (80 μmol) are added. After 5 min of preincubation at 37° C., 2 ml (11.2 units) of recombinant 1-deoxy-D-xylulose-5 phosphate reductoisomerase from *E. coli* are added. After ca. 30 h the reaction is stopped by the addition of 8 ml of 2 N HCl. The reaction mixture is stored at −20° C.

Step c) Enzymatic synthesis of [2,2-Me-$^{13}C_2$]-4-diphosphocytidyl-2C-methyl-D-erythritol The pH of the reaction mixture obtained in step b, containing [2,2-Me-$^{13}C_2$]1-methyl-D-erythritol 4-phosphate, is adjusted to 7.0 by addition of 4 ml 2 M NaOH. 1.4 g of CTP 2.5 mmol) are added and the pH is adjusted to 8.0 with 6 ml 2 N NaOH. After 5 min of preincubation at 37° C., 1.5 ml (51.8 units) of YgbP protein from *E. coli* solution are added. The reaction is monitored as described in, example 7. After ca. 5 h the reaction mixture is purified and lyophilized as described in example 8. 550 mg of pure 4-diphosphocytidyl-[2,2'-$_{13}C_2$]-methyl-D-erythritol are obtained.

EXAMPLE 34

Enzymatic synthesis of 4-diphosphocytidyl-[2,2'-Me-$^{13}C_2$]2C-methyl-D-erythritol in a one vial reaction A reaction mixture containing 3 g glucose, 1 g of dihydroxyacetone phosphate (5,7 mmol), 1.4 g of CTP (2,5 mmol), 0.45 g of 2,3-$^{13}C_2$-sodiumpyruvate (4 mmol), 56,6 mg NADP$^+$ (80 μmol), in 150 mM Tris hydrochloride, pH 8.0 is prepared. 17000 units of triose phosphate isomerase, 250 units of glucose dehydrogenase, 7 units of 1-deoxyxylulose 5-phosphate synthase, 13 units of 1-deoxy-D-xylulose-5 phosphate reductoisomerase and 55 units of YgbP protein are added. To a final volume of 200 ml, 10 mM $MgCl_2$, 10 mM $MnSO_4$, 2.5 mM thiamine pyrophosphate in 150 mM Tris hydrochloride, pH 8.0 are added. The pH is adjusted to 8.0 with 5 ml 1 M NaOH. The reaction mixture is incubated at 37° C. The reaction is monitored as described in example 7. After 30 h the reaction mixture is purified and lyophilized as described in example 8. 490 mg of pure 4-diphosphocytidyl-[2,2-Me-$^{13}C_2$]-methyl-D-erythritol are obtained.

EXAMPLE 35

Preparation synthesis of 2C-methyl-D-erythritol 4-phosphate (large scale up)

This preparation can be performed with any $^{13}$C-labeled sample of glucose or pyruvate as starting materials. In this example it is described for [U-$^{13}C_6$]glucose and [2,3-$^{13}C_2$] pyruvate.

Step A) preparative synthesis of [U-$^{13}C_5$]1-deoxy-D-xylulose 5-phosphate

A reaction mixture containing 166 mg [U-$^{13}C_6$]glucose (0.89 mmol), 44 mg thiamine pyrophosphate, 1.02 g of ATP (1.79 mmol), 200 mg of [2,3-$^{13}C_2$]pyruvate (1.79 mmol), 6 mM $MgCl_2$ in 150 mM Tris hydrochloride, pH 8.0 is prepared. 410 units of triose phosphate isomerase (from rabbit muscle, Type III-S, E. C. 5.3.1.1, Sigma), 360 U hexokinase (from Bakers Yeast, Type VI, E. C. 2.7.1.1, Sigma), 50 U phosphoglucose isomerase (from Bakers Yeast, Type III, E. C. 5.3.1.9, Sigma), 20 U phosphofructokinase (from *Bacillus stearothermophilus*, Type VII, E. C. 2.7.1.11, Sigma), 35 U aldolase (from rabbit muscle, E C. 4.1.2.13, Sigma) and 2 U recombinant DXP synthase from *B. subtilis* are added to a final volume of 58 ml. The reaction mixture is incubated at 37° C. overnight. During the reaction the pH is hold at a constant value of 8.0 by the addition of 1 M NaOH (2 ml). The reaction is stopped by adding of 3 ml of 2 N hydrochloric acid. $^{13}$C-NMR-spectra are recorded for monitoring the conversion (Table 9).

TABLE 9

NMR data of [U-$^{13}C_5$]1-deoxy-D-xylulose 5-phosphate

| Position | Chemical shifts, ppm$^a$ $^{13}$C | Coupling constants, Hz $J_{PC}$ | $J_{CC}$ |
|---|---|---|---|
| 1 | 25.9 | | 41.1 (2), 12.8 (3) |
| 2 | 213.1 | | 41.3 (1), 41.3 (3), 3.1 (5) |
| 3 | 77.0 | | 41.5 (2), 40.2 (4), 12.8 (1) |
| 4 | 70.7 | 6.9 | 43.2 (5), 39.6 (3) |
| 5 | 64.3 | 4.6 | 43.4 (4), 3.1 (2) |

$^a$Referenced to external trimethylsilylpropane sulfonate.

Step B) Preparative synthesis of [U-$^{13}C_5$]2C-methyl-D-erythritol 4-phosphate To the solution of step A 10 U DXP reductoisomerase, 120 U glucose dehydrogenase (from *Bacillus megaterium*, E. C. 1.1.1.47, Sigma), 0.97 g glucose, 200 mM $MgCl_2$ and 0.3 mM NADP$^+$ are added. The pH is adjusted to 8.0 with 1.5 ml of 4 N sodium hydroxide. After centrifugation the volume is 72 ml. The reaction mixture is incubated at 37° C. overnight. The conversion is monitored by recording $^{13}$C-NMR-spectra of the accumulating product. (Table 10). The reaction product is purified by HPLC on a column of the anionic exchanger Nucleosil 10 SB (16×250 mm) using 0.5 M formic acid as eluent at a flow rate of 13 ml/min. The eluent is monitored by a refractometer (GAT-LCD210 from Gamma Analyse Technik, Bremerhafen, Germany). The product is eluted at 14.5 min. The fraction containing [U-$^{13}C_5$]2C-methyl-D-erythritol 4-phosphate is collected and lyophylized. The amount is 86 mg.

TABLE 10

NMR data of [U-$^{13}C_5$]2C-methyl-D-erythritol

| Position | Chemical shifts, ppm[a] |
|---|---|
| 1 | 66.5 |
| 2 | 74.1 |
| 2-Methyl | 18.5 |
| 3 | 74.1 |
| 4 | 64.6 |

[a]Referenced to external trimethylsilylpropane sulfonate.

EXAMPLE 36

Enzymatic synthesis of 4-diphosphocytidyl-2C-methyl-D-erythritol 2-phosphate

This preparation can be performed with any $^{13}$C-labeled sample of 2C-methyl-D-erythritol-4-phosphate as starting material. In this example it is described for [1,3,4-13C]2C-methyl-D-erythritol 4-phosphate.

To a reaction mixture, containing 15 mg of purified [1,3,4-$^{13}$C]2C-methyl-D-erythritol 4-phosphate (69 µmol), 34 mg CTP (69 µmol), 16 mg sodium phosphoenol pyruvate (69 µmol), 1,9 mg ATP (3.5 µmol), 10 mg MgCl$_2$, 5 mM DTT, 10 mM KCl and 150 mM Tris hydrochloride, pH 8.0, 60 µl of YgbP protein (2.1 mg/ml), 200 µl of YchB protein (0.3 mg/ml) and 100 U of pyruvate kinase (from rabbit muscle, Type VII, E. C. 2.7.1.40, Sigma) are added. The final volume is 5 ml. The reaction mixture is incubated at 37° C. for 4 h. The reaction is monitored as described in example 15.

4-diphosphocytidyl-methyl-D-erythritol 2-phosphate is purified by HPLC on a column of the anionic exchanger Nucleosil 5 SB (7.5×150 mm) using a gradient of 1 M Amoniumformiat (B) and 100 mM Ammoniumformiat (A) as eluent at a flow rate of 3.1 ml/min.

| t(min) | A(%) | B(%) |
|---|---|---|
| 0 | 100 | 0 |
| 5 | 100 | 0 |
| 35 | 30 | 70 |
| 40 | 30 | 70 |

The eluent is monitored by a UV-detector (Knauer) at 275 nm. 4-diphosphocytidyl-methyl-D-erythritol 2-phosphate is eluted at 26-27 min.

PREPARATION EXAMPLES FOR LABELLED SUBSTRATES

Preparation Example 1

(a) 1,2-O-Isopropylidene-(2R,3RS)-1,2,3-butanetriol (7)

1,2,5,6-Di-O-isopropylidene-D-mannitol (5) (14 g, 53.4 mmol) was dissolved in 200 ml of dry chloroform. Anhydrous potassium carbonate (50.5 g, 366 mmol) was added, and the suspension was cooled to 0° C. Lead tetraacetate (27.1 g, 61.1 mmol) was added in small portions under vigorous stirring. The orange coloured suspension was allowed to stand at room temperature over night. Potassium carbonate was filtered off by suction, and the filter cake was washed repeatedly with ether. The combined filtrate and washings were dried with magnesium sulphate and the solvent was removed under reduced pressure. The oil containing the isopropylidene glyceraldehyde was distilled quickly (60° C. at 30-40 mbar) affording 10.5 g (80,7 mmol, 76%) of pure isopropylidene glyceraldehyde (6). The product was immediately dissolved in 35 ml of dry ether to avoid polymerisation. The solution of isopropylidene glyceraldehyde was added to a cooled solution of methyl magnesium iodide prepared from 5.1 g (207 mmol) of magnesium and 13.0 ml (209 mmol) of methyl iodide in 140 ml ether. After the aldehyde was added completely, the solution was stirred at room temperature over night. The solution was then slowly poured on crushed ice, and precipitated magnesium hydroxide was dissolved by the addition of saturated ammonium chloride (50 ml). The organic layer was removed, and the water phase was saturated with sodium chloride and extracted with chloroform (3×50 ml). The combined organic layers were dried with magnesium sulphate, and the solvent was removed under reduced pressure affording 9.9 g (67.8 mmol, 84%) of 1,2-O-Isopropylidene-(2R,3RS)-1,2,3-butanetriol (8).

$^1$H NMR (360 MHZ, CDCl$_3$): δ (ppm) 0.96 (d, $^3$J=6.5 Hz), 1.07 (d, $^3$J=6.5 Hz), 1.24 (s), 1.25 (2), 1.29 (s), 1.33 (s), 3.41-3.47 (m), 3.67-3.78 (m), 3.82-3.97 (m), 4.67 (d, $^3$J=4.6 Hz), 4.75 (d, $^3$J=5.2 Hz) (underlined signals belong to the diastereomer which is formed predominantly); $^{13}$C NMR (90 MHz, CDCl$_3$): δ (ppm) 18.0, 19.8, 24.8, 26.1, 64.3, 65.9, 66.1, 66.9, 79.1, 79.3, 107.7, 107.7 (underlined signals belong to the diastereomer which is formed predominantly; anal. calcd. for C$_7$H$_{14}$O$_3$: C, 57.5, H, 9.9, O, 32.6 found: C, 57.2, H, 9.9, O, 32.8.

(b) 3,4-O-Isopropylidene-(3R)-3,4-dihydroxy-2-butanone (8)

1:2-O-Isopropylidene-(2R,3RS)-1,2,3-butanetriol (7) (9.9 g, 67.8 mmol) was dissolved in 100 ml of chloroform. Water (100 ml), 30 g of potassium carbonate (217 mmol) and 50 mg of ruthenium dioxide hydrate were added. The suspension was stirred vigorously at room temperature, and 29 g (136 mmol) of sodium periodate were added in small portions. When the pH dropped below 7 it was adjusted to pH 8-8.5 with potassium carbonate. After the addition of periodate was complete the suspension was stirred for two days at room temperature. Before work up an aliquot of the reaction mixture was controlled by $^1$H NMR spectroscopy. If starting material was still present, an additional amount of periodate was added. When the oxidation was complete the suspension was filtered by suction, and the filtrate was extracted with chloroform (4×50 ml). The combined organic layers were dried with magnesium sulphate, and the solvent was removed under reduced pressure affording 7.2 g (50 mmol, 74%) of 3,4-O-Isopropylidene-(3R)-3,4-dihydroxy-2-butanone (8).

$^1$H NMR (250 MHz, CDCl$_3$): δ (ppm) 1.4 (s, 3H), 1.5 (s, 3H), 2.27 (s, 3H), 4.0 (dd, $^2$J=8.54 Hz, $^3$J=5.50 Hz, 1H), 4.2(dd, $^2$J=8.54 Hz, $^3$J=7.95 Hz, 1H), 4.41 (dd, $^3$J=7.94 Hz, $^3$J=5.5 Hz, 1H); $^{13}$C NMR (62 MHz, CDCl$_3$): δ (ppm) 25.3 (CH$_3$), 25.6 (CH$_3$), 26.3 (CH$_3$), 66.4 (CH$_2$), 80.4 (CH), 110.9 (C$_q$).

(c) 1,2-O-Isopropylidene-3-O-trimethylsilyl-(2R,3RS)-1,2,3-trihydroxy-3-cyano-butane (9)

3,4-O-Isopropylidene-(3R-3,4-dihydroxy-2-butanone (8) (7.2 g, 50 mmol) was dissolved in 50 ml of dry dichloromethane. Catalytic amounts of potassium cyanide (20 mg) and 18-crown-6 (20 mg) were added. Under cooling with ice, 9.4 ml (70 mmol) of trimethylsilyl cyanide were added within 20 minutes. The solvent and excess trimethylsilyl cyanide were removed under reduced pressure. The orange coloured oily residue (12.0 g, 49.3 mmol, 99%) was a mixture of the erythro and threo form of 1,2-O-isopropylidene-3-O-trimethylsilyl-(2R,3RS)-1,2,3-trihydroxy-3-cyano-butane (9) in a ratio of 3:1 which did not contain significant amounts of other products.

$^1$H NMR (360 MHz, CDCl$_3$): δ (ppm) 0.17 and 0.18 (2s, 9H), 1.12 (s), 1.29 (s), 1.40 (s), 1.43 (s), 1.46 (s), 1.57 (s) (9H) 3.85-3.90 (m, 1H), 3.97-4.10, (m, 2H); $^{13}$C NMR (90 MHz, CDCl$_3$): erythro δ (ppm) 1.2 (TMS), 24.0 (CH$_3$), 25.0 and 26.0 ((CH$_3$)$_2$), 65.0 (CH$_2$), 80.4 (CH), 110.9 (CN); threo δ (ppm) −3.1 (TMS), 25.2 (CH$_3$), 26.2 and 26.4 ((CH$_3$)$_2$), 66.4 (CH$_2$), 80.8 (CH), 120.7 (CN).

(d) 2C-Methyl-D-erythrono-1,4-lactone (11) and 2C-Methyl-D-threono-1,4-lactone (12)

1,2-O-Isopropylidene-3-O-trimethylsilyl-(2R,3RS)-1,2,3-trihydroxy-3-cyano-butane (9) (12.0 g, 49.3 mmol) was suspended in 30 ml of 25% hydrochloric acid. Ethanol (10 ml) was added to improve the solubility of the lipophilic cyanohydrin. The reaction mixture was stirred at 45° C. for 30 minutes and subsequently under reflux for three hours. The mixture became brown, and a precipitate of ammonium chloride was formed. The acid was neutralized with concentrated ammonia. The mixture was evaporated to dryness. The product mass was triturated with 50 ml of methanol. Insoluble ammonium chloride was filtered off. Methanol was removed under reduced pressure. The residual oil contained the lactones 11 and 12, and the open chain carboxylic acids (10). Lactonisation was brought to completion by boiling the residue with 50% formic acid (30 ml) for 2 hours. When no more open chain carboxylic acids were present the reaction mixture was concentrated under reduced pressure. The residual oil was dissolved in a mixture of ethyl acetate, 2-propanol and water (5 ml, 65:23.5:11.5, v/v). The solution was placed on a column of silica gel (acidic form) and was developed with the ethyl acetate/2-propanol water mixture. Fractions were combined, and concentrated under reduced pressure. The residue was lyophilised. The residual colourless oil (5.9 g, 44.7 mmol, 91%) contained 2C-methyl-D-erythrono-1,4-lactone and 2C-Methyl-D-threono-1,4-lactone in a ratio of about 3:1 as determined by NMR spectroscopy.

2-Methyl-D-threono-1,4-lactone $^1$H NMR (250 MHz, CD$_3$OD): δ (ppm) 1.30 (s, 3H), 3.92 (dd, $^2$J=4.27 Hz, $^3$J=9.16 Hz, 1H), 4.13 (dd, $^2$J=4.27 Hz, $^3$J=5.50 Hz, 1H), 4.44 (dd, $^2$J=5.50 Hz, $^3$J=9.15 Hz 1H); $^{13}$C NMR (63 MHz, CD$_3$OD): δ (ppm) 17.9 (CH$_3$), 73.1 (CH$_2$), 78.8 (CH), 85.8 (C$_q$), 161.8 (C$_q$); IR (film): 1770 cm$^{-1}$; anal. calcd. for C$_5$H$_8$O$_4$: C, 45.4, H, 6.0, 48.3 found: C, 46.2, H, 6.5, O, 47.3.

2C-methyl-D-erythrono-1,4-lactone $^1$H NMR (250 MHz, CD$_3$OD): δ (ppm) 1.33 (s, 3H), 4.00 (dd, $^2$J=1.83 Hz, $^3$J=4.27 Hz, 1H), 4.09 (dd, $^2$J=1.83 Hz, $^3$J=9.77 Hz, 1H), 4.38 (dd, $^2$J=4.27 Hz, $^3$J=10.38 Hz, 1H); $^{13}$C NMR (63 MHz, CD$_3$OD): δ (ppm) 21.9 (CH$_3$), 73.6 (CH$_2$), 75.0 (CH), 75.8 (C$_q$), 164.9 (C$_q$); IR (film): 1770 cm$^{-1}$.

open chain carboxylic acids (isomeric mixture 1:1) $^1$H NMR (250 MHz, D$_2$O): δ (ppm) 1.14 (s, 3H), 1.17 (s, 3H), 3.45-3,85 (m, 6H), $^{13}$C NMR (63 MHz, D$_2$O): δ (ppm) 19.8 (CH$_3$), 20.7 (CH$_3$), 64.9 (CH$_2$), 65.2 (CH$_2$), 70.1 (CH), 70.3 (CH), 77.8 (C$_q$), 77.9 (C$_q$), 182.5 (C$_q$), 182.8 (C$_q$).

(e) 2,3-O-Isopropylidene-2C-methyl-D-erythrono-1,4-lactone (13)

Anhydrous zinc chloride (14.1 g, 103 mmol) was dissolved in 100 ml of acetone. The solution was cooled with ice, and 5.9 g of a mixture of 2C-methyl-D-erythrono-1,4-lactone (11) (33.5 mmol) and 2C-methyl-D-threono-1,4-lactone (12) (11.2 mmol) dissolved in 13 ml acetone was added. After 18 hours the solution was diluted with 150 ml of chloroform. Zinc chloride and unreacted 2C-methyl-D-threono-1,4-lactone were removed by washing with water (3×100 ml). The organic layer was dried with magnesium sulphate, and the solvent was removed under reduced pressure affording pure 2:3-O-isopropylidene-2C-methyl-D-erythrono-1,4-lactone (13) (4.4 g, 25.6 mmol, 76% from 2C-methyl-D-erythrono-1,4-lactone) as a colorless oil which crystallized at −20° C.

$^1$H NMR (360 MHz, CDCl$_3$): δ (ppm) 1.33 (s, 3H), 1.37 (s, 3H), 1.48 (s, 3H), 4.24 (dd, $^3$J=3.54 Hz, $^2$J=11.06 Hz, 1H), 4.34 (dd, $^2$J=11.06 Hz, $^3$J=0 Hz, 1H), 4.41 (dd, $^2$J=3.50 Hz, $^3$J=0 Hz, 1H); $^{13}$C NMR (90 MHz, CDCl$_3$): δ (ppm) 18.4 (CH$_3$), 26.5 (CH$_3$), 26.9 (CH$_3$), 68.9 (CH$_2$), 80.3 (CH), 81.4 (C$_q$), 113.0 (C$_q$), 176.7 (C$_q$).

(f) 2,3-O-Isopropylidene-2C-methyl-D-erythrofuranose (14)

2:3-O-Isopropylidene-2Cmethyl-D-erythrono-1,4-lactone (13) (2.2 g, 12.9 mmol) was dissolved in 60 ml of dry tetrahydrofurane. The mixture was cooled to −78° C. under an atmosphere of nitrogen. A solution of di-isobutylaluminum hydride (1 M in hexane, 17 ml, 17 mmol) was added slowly. The solution was allowed to stand in the cooling bath over night. Wet ether (180 ml) and wet silica gel (30 g) were added. The mixture was stirred for one hour and was allowed to warm to room temperature. The mixture was then filtered. The solution was dried with magnesium sulphate, and the solvent was removed under reduced pressure. The residual oil was purified by chromatography on silica gel with a mixture of hexane/ethyl acetate (1:2, v/v) affording 2.0 g (11.5 mmol, 89%) of 2:3-O-isopropylidene-2C-methyl-D-erythrofuranose (14) as an anomeric mixture (α:β=1:1).

$^1$H NMR (360 MHz, CDCl$_3$): δ (ppm) 1.29 (s), 1.30 (s), 1.34 (s), 135 (s), 1.37 (s) (18H), 3.46 (dd, $^3$J=3.54 Hz, $^2$J=11.06 Hz, 1H), 3.55 (m, 1H), 3.78 (d, $^2$J=11.50 Hz, 2H), 3.84 (d, $^2$J=11.06 Hz, 1H), 3.97 (dd, $^3$J=3.80 Hz, $^2$J=10.40 Hz, 1H), 4.29 (dd, $^3$J=3.10 Hz, $^3$J=8.85 Hz, 2H), 4.52 (d, $^2$J=11.06 Hz, 1H), 5.13 (d, $^3$J=2.65 Hz, 1H); $^{13}$C NMR (90 MHz, CDCl$_3$): δ (ppm) 19.4 (CH$_3$), 21.4 (CH$_3$), 26.3 (CH$_3$), 26.9 (CH$_3$), 27.2 (CH$_3$), 28.0 (CH$_3$), 67.1 (CH$_2$), 715 (CH$_2$), 84.9 (CH), 86.0 (C$_q$), 86.1 (CH), 91.4 (C$_q$), 101.4 (C$_q$), 103.3 (C$_q$), 112.4 (CH), 112.9 (CH).

(g) 2:3-O-Isopropylidene-2C-methyl-D-erythrose-(O-benzyl)oxime (15)

2:3-O-Isopropylidene-2C-methyl-D-erythrofuranose (14) (0.5 g, 2.87 mmol) was dissolved in 12 ml of dry dichloromethane. Dry pyridine (1 ml) and 0.88 g (5.5 mmol) of O-benzylhydroxylamine hydrochloride were added in one portion. The hydroxylamine dissolved within 20 minutes, and the reaction mixture became turbid after 40 minutes. The mixture was stirred for 15 hours at room temperature and was evaporated to dryness under reduced pressure. The residue was suspended in a mixture of chloroform/ethyl acetate (1:4, v:v, 1 ml). The solution was placed on a silica gel column (1 cm×30 cm). The product was eluted with the solvent mixture.

Fractions containing 2,3-O-isopropylidene-2C-methyl-D-erythrose-(O-benzyl)oxime were combined and the solvent was removed under reduced pressure affording 0.53 g (1.9 mmol, 66%) of 2:3-O-isopropylidene-2C-methyl-D-erythrose(O-benzyl)oxime as colourless oil.

$^1$H NMR (250 MHz, CDCl$_3$): δ (ppm) 1.26 (s, 3H), 1.31 (s, 3H), 1.33 (s, 3H), 3.42-3.56 (m, 2H), 3.86 (dd, $^3$J=4.89 Hz, $^3$J=6.72 Hz, 1H), 4.92 (s, 2H), 7.15-7.25 (m, 5H), 7.32 (s, 1H); $^{13}$C NMR (63 MHz, CDC): δ (ppm) 22.8 (CH$_3$), 26.6 (CH$_3$), 27.9 (CH$_3$), 60.7 (CH$_2$), 76.0 (CH$_2$), 80.5 (CH), 84.3 (C$_q$), 109.4 (C$_q$), 127.9 (CH), 128.2 (CH), 128.3 (CH), 137.2 (C$_q$), 152.0 (CH).

(h) 2,3-O-Isopropylidene-2C-methyl-D-erythrose-(O-benzyl)oxime 4-dibenzylphosphate (16)

Tribenzylphosphite (1.3 g, 3.7 mmol) was dissolved in 20 ml of dry dichloromethane. The solution was cooled to −20° C. Iodine (0.96 g, 3.8 mmol) was added in one portion. The mixture was protected from light and was allowed to come to room temperature when the violet color had disappeared. 2:3-O-Isopropylidene-2C-methyl-D-erythrose-(O-benzyl)oxime (15) (0.53 g, 1.9 mmol) was dissolved in 20 ml of dichloromethane, and 2.5 ml pyridine (31.6 mmol) was added. The solution was cooled to −20° C. and the solution of dibenzyl iodophosphate was added slowly. The reaction mixture was stirred for 2 hours at room temperature and was washed subsequently with sodium hydrogen sulphate (30%, w/v, 2×10 ml), a solution of sodium hydrogen carbonate (5%, w/v, 10 ml), and water (10 ml). The organic phase was dried with magnesium sulphate. The solution was evaporated to dryness. The residue was suspended in a mixture of hexane/ethyl acetate (3:1, v:v, 2 ml). The mixture was placed on a silica gel column (1 cm×20 cm) which was developed with hexane/ethyl acetate (3:1, v/v) until benzyl iodide was completely washed out. The product was then eluted with a mixture of chloroform/ethyl acetate (1:4, v/v). Fractions were combined. The solvent was removed under reduced pressure affording 0.73 g (1.35 mmol, 71%) of 2,3-O-isopropylidene-2C-methyl-D-erythrose-(O-benzyl)oxime 4-dibenzylphosphate.

$^1$H NMR (250 MHz, CDCl$_3$): δ (ppm) 1.31 (s, 3H), 1.37 (s, 3H), 1.39 (s, 3H), 3.90-3.99 (m, 3H), 4.94 (s, 1H), 4.97-5.02 (m, 6H), 7.24-7.33 (m, 15H); $^{13}$C NMR (63 MHz, CDCl$_3$): δ (ppm) 22.0 (CH$_3$), 26.6 (CH$_3$), 28.0 (CH$_3$), 65.3 (d, $^2$J$_{CP}$=5.5 Hz, CH$_2$), 69.1-69.5 (m, CH$_2$), 76.2 (CH$_2$), 80.2 (C$_q$), 82.5 (d, $^3$J$_{CP}$=7.9 Hz, CH), 109.7 (C$_q$), 127.9-128.5 (CH), 135.6 (d, $^3$J$_{CP}$=6.8 Hz, C$_q$), 137.9 (C$_q$), 150.3 (CH); $^{31}$P NMR (101 MHz, CDCl$_3$): δ (ppm) −0.8 (s).

(i) 2,3-O-Isopropylidene-2C-methyl-D-erythrose 4-dibenzylphosphate (17)

2:3-O-Isopropylidene-2C-methyl-D-erythrose-(O-benzyl)oxime 4-dibenzylphosphate (16) (0.26 g, 0.43 mmol) was dissolved in 15 ml of dichloromethane containing 2 ml of pyridine. The solution was cooled to −78° C. and was ozonized for 7 minutes with an ozone flow of about 3 g/min (0.44 mmol). Nitrogen was then bubbled through the dark blue reaction mixture. When the blue color had vanished, 2 ml of dimethylsulfide were added. The mixture was allowed to stand at −78° C. for 1 hour and was then brought to room temperature. Solvent and pyridine was removed under reduced pressure, and the crude oil was purified by column chromatography (silica gel; chloroform/ethyl acetate 1/4, v/v) affording 0.17 g (0.39 mol, 81%) of pure aldehyde.

$^1$H NMR (360 MHz, CDCl$_3$): δ (ppm) 1.24 (s, 3H), 1.36 (s, 3H), 1.46 (s, 3H), 3.93-4.02 (m, 2H), 4.05-4.13 (m, 1H), 4.92-5.00 (m, 4H), 7.23-7.30 (m, 10H), 9.51 (s, 1H); $^{13}$C NMR (90 MHz, CDCl$_3$): δ (ppm) 19.7 (CH$_3$), 26.5 (CH$_3$), 27.8 (CH$_3$), 64.3 (d, $^2$J$_{CP}$=6.0 Hz, CH$_2$), 69.5 (m, CH$_2$), 82.7 (d, $^3$J$_{CP}$=8.7 Hz, CH), 85.1 (C$_q$), 110.9 (C$_q$), 126.8 (d, $^4$J$_{CP}$=14.5 Hz, CH), 127.9 (CH), 128.6 (CH), 135.6 (d, $^3$J$_{CP}$=7.3 Hz, C$_q$), 202.0 (CH); $^{31}$P NMR (101 MHz, CDCl$_3$): δ (ppm) −1.0 (s).

(j) 2,3-O-Isopropylidene-2C-methyl-D-erythritol 4-dibenzylphosphate (18)

2,3-O-Isopropylidene-2C-methyl-D-erythrose 4-dibenzylphosphate (17) (85 mg, 0.2 mmol) was dissolved in 3 ml of dry methanol, and the solution was cooled to 0° C. Sodium borohydride, 20 mg, (0.5 mmol) was added in one portion. Water (5 ml) was added to destroy the excess of borohydride, and the mixture was adjusted to pH 5 with concentrated acetic acid. The suspension was extracted 4 times with 10 ml of chloroform, and the organic solution was washed with 20 ml of 5% sodium hydrogen carbonate. The organic phase was dried with magnesium sulphate, and the solvent was removed under reduced pressure affording 85.5 mg (0.2 mmol, 100%) pure 18.

$^1$H NMR (250 MHz, CDCl$_3$): δ (ppm) 1.20 (s, 3H), 1.30 (s, 3H), 1.36 (s, 3H), 1.89 (s, broad, 2H), 3.34 m, 2H), 3.95 (dd, J=4.70 Hz, J=7.10 Hz, 1H), 4.08-4.20 (m, 2H), 5.00 (dd, J=1.83 Hz, J=8.55 Hz, 4H), 7.29 (m, 10H); $^{13}$C NMR (63 MHz, CDCl$_3$): δ (ppm) 22.1 (CH$_3$), 26.4 (CH$_3$), 28.1 (CH$_3$), 65.0 (CH$_2$), 65.2 (d, $^2$J$_{CP}$=5.45 Hz, CH$_2$), 69.4 (dd, $^2$J$_{CP}$=2.72 Hz $^2$J$_{CP}$=5.45 Hz, CH$_2$), 81.1 (d, $^3$J$_{CP}$=8.18 Hz, CH), 81.7 (C$_q$), 108.5 (C$_q$), 126.9 (CH), 128.6 (CH), 135.6 (d, $^3$J$_{CP}$=6.80 Hz, C$_q$); $^{31}$P NMR (101 MHz, CDCl$_3$):δ (ppm) 0.5 (s).

(k) 2C-Methyl-D-erythritol 4-phosphoric acid (4)

2:3-O-Isopropylidene-2C-methyl-D-erythritol 4-dibenzylphosphate (18) (85.5 mg, 196 μmol) was suspended in 8 ml of a mixture containing 4 ml of methanol and 4 ml of water. A catalytic amount of palladium on charcoal was added, and the suspension was hydrogenated for 20 hours at atmospheric pressure. The catalyst was removed by filtrating through a 0.2 μm membrane filter. The acidic solution (pH 2) was heated to 70° C. for 60 minutes. Methanol was removed under reduced pressure at 40° C., and the residue was lyophilized affording 35.3 mg (163 μmol, 83%) of the crude phosphoric acid. The phosphoric acid was dissolved in 1 ml of water. The solution was placed on a Nucleosil SB$_{10}$ HPLC column and was eluted with 0.5 M formic acid at a flow rate of 1 ml/min. The effluent was monitored refractometrically. Fractions containing the product (retention volume 15 ml) were pooled and freeze-dried affording 18.0 mg of pure 4.

$^1$H NMR (500 MHz, D$_2$O): δ (ppm) 1.04 (s, 3H), 3.37 (d, $^2$J=11.77 Hz, 1H), 3.50 (d, $^2$J=11.78 Hz, 1H), 3.64 (dd, $^3$J=2.60 Hz, $^3$J=8.10 Hz, 1H), 3.77 (ddd, $^3$J$_{HP}$=6.20 Hz, $^3$J=8.10 Hz, $^3$J=10.80 Hz, 1H), 4.01 (ddd, $^3$J=2.50 Hz, $^3$J$_{HP}$=6.00 Hz, $^3$J=10.80 Hz, 1H), $^{13}$C NMR (125 MHz, D$_2$O): δ (ppm) 18.2 (C$_3$), 65.9 (d $^2$J$_{PC}$=5.14 Hz, CH$_2$), 66.2 (CH$_2$), 73.1 (d, $^3$J$_{CP}$=7.58 Hz, CH), 73.8 (C$_q$); $^{31}$P NMR (101 MHz, D$_2$O): δ (ppm) 3.7 (s).

Preparation Example 2

[1-$^2$H$_1$]-2C-Methyl-D-erythritol 4-phosphoric acid
(4)

2,3-O-Isopropylidene-2C-methyl-D-erythrose 4-dibenzylphosphate (17), 85 mg, (0.2 mmol) was dissolved in 3 ml of dry methanol, and the solution was cooled to 0° C. [$^2$H]-NaBH$_4$ (20 mg, 0.5 mmol) was added in one portion. Water (5 ml) was added to destroy the excess of borohydride, and the mixture was adjusted to pH 5 with concentrated acetic acid. The suspension was extracted 4 times with 10 ml of chloroform, and the organic solution was washed with 20 ml of 5% sodium hydrogen carbonate. The organic phase was dried with magnesium sulphate, and the solvent was removed under reduced pressure affording 85.5 mg (0.2 mmol, 100%) pure [1-$^2$H$_1$]-2,3-O-Isopropylidene-2C-methyl-D-erythritol-4-dibenzylphosphate (21).

[1-$^2$H]-2,3-O-Isopropylidene-2C-methyl-D-erythritol 4-dibenzylphosphate (85.5 mg, 196 μmol) was then suspended in 8 ml of a mixture containing 4 ml of methanol and 4 ml of water. A catalytic amount of palladium on charcoal was added, and the suspension was hydrogenated for 20 hours at atmospheric pressure. The catalyst was removed by filtrating through a 0.2 pm membrane filter. The acidic solution (pH 2) was heated to 70° C. for 60 minutes. Methanol was removed under reduced pressure at 40° C., and the residue was lyophilized affording 35.3 mg (163 μmol, 83%) of the crude phosphoric acid. The phosphoric acid was dissolved in 1 ml of water. The solution was placed on a Nucleosil SB$_{10}$ HPLC column and was eluted with 0.5 M formic acid at a flow rate of 1 ml/min. The effluent was monitored refractometrically. Fractions containing the product (retention volume 15 ml) were pooled and freeze-dried affording pure [1-2H$_1$]-4.

Preparation Example 3

[1-$^3$H$_1$]-2C-Methyl-D-erythritol 4-phosphoric acid
(4)

[$^3$H]-NaBH$_4$ (8.5 μmol, 100 mCi, 11.8 Ci/mmol) was suspended in 500 μl of dry methanol. 170 μl of a solution containing 33.3 μmol of 2,3-O-Isopropylidene-2C-methyl-D-erythrose 4-dibenzylphosphate (17) in dry methanol was added in one portion to the borohydride suspension at room temperature. After 1 hour at room temperature 1 ml of water was added to destroy unreacted borohydride. The resulting suspension was extracted with chloroform (3×170 μl), the organic phases were combined and the solvent was removed under reduced pressure without drying.

The residue was dissolved in 50% methanol (1 ml), a catalytic amount of Pd on charcoal was added and the mixture was hydrogenated for 12 hours (room temperature, 1 atm). The catalyst was removed by filtration. Acetic acid (100%, 1 ml) was added and the mixture was heated to 60° C. for 30 minutes.

Preparation Example 4

The repetition of preparation example 1 with [$^{13}$C]methyl iodide in step (a) affords the $^{13}$C-labelled product (4).

Preparation Example 5

The repetition of preparation example 1 with [$^2$H$_3$]methyl iodide affords the deuterium labelled product (4).

Preparation Example 6

The repition of preparation Example 1 with [$^3$H] methyl iodide affords the tritium labelled product (4).

Preparation Example 7

The repetition of preparation example 1 with potassium $^{14}$C-cyanide in step (c) affords $^4$C-labelled product (4).

Preparation Example 8

[1,2-$^{14}$C$_2$] 1-Deoxy-D-xylulose 5-phosphate (specific activity: 62.5 m Ci/mmol) was prepared biosynthetically by the method described in Sprenger et al Proc. Natl. Acad. Sci. USA 94 (1997) 12857-12862, using [U-$^{14}$C]pyruvate (specific activity: 150 m Ci/mmol) and D,L-glyceraldehyde 3-phosphate.

Preparation Example 9

[1-$^3$H] 1-Deoxy-D-xylulose 5-phosphate (specific activity: 5 mCi/mmol) was synthesized in accordance with Preparation Example 7 by using [3-$^3$H]pyruvate (specific activity: 72.3 Ci/mmol).

Preparation Example 10

[1,2-$^{14}$C$_2$] 1-Deoxy-D-xylulose (specific activity: 62.5 mCi/mmol) was prepared from [U-$^{14}$C] pyruvate with a specific radioactivity of 150 mCi/mmol and D-glyceraldehyde by using as catalyst the pyruvate dehydrogenase complex of E-coli DH5α. The yield was 80%. The method of Yokota, A. and Sasajima, K. Agric. Biol. Chem. 48 149-158 (1984) and ibid 50, 2517-2524 (1986) was used.

---

The invention claimed is:

1. A method for screening a chemical library for an inhibitor of the biosynthesis of isoprenoids by blocking the conversion of 4-diphosphocytidyl-2C-methyl-D-erythritol, comprising:

(a) reacting an aqueous mixture comprising:
  i) a protein that is enzymatically functional for the conversion of 4-diphosphocytidyl-2C-methyl-D-erythritol,
  ii) 4-diphosphocytidyl-2C-methyl-D-erythritol or a source thereof selected from the group consisting of glyceraldehyde-3-phosphate, pyruvate, 1-deoxy-D-xylulose 5-phosphate, and 2C-methyl-D-erythritol-4-phosphate, and
  iii) a divalent metal salt;
for a predetermined period of time at a predetermined temperature;

(b) detecting the level of conversion of 4-diphosphocytidyl-2C-methyl-D-erythritol in step (a);

(c) repeating steps (a) and (b) in the presence of a test sample of the chemical library;

(d) detecting the level of conversion of 4-diphosphocytidyl-2C-methyl-D-erythritol in step (c); and (e) comparing the level of conversion in step (b) with the level of conversion in step (d), whereby a decrease in the level of conversion in step (d) identifies the test sample as an inhibitor of the biosynthesis of isoprenoids by blocking the conversion of 4-diphosphocytidyl-2C-methyl-D-erythritol.

2. The method according to claim 1, wherein steps (b) and (d) are carried out by measuring the level of formation of 2C-methyl-D-erythritol 3,4-cyclomonophosphate, or CMP or by measuring the consumption of 4-diphosphocytidyl-2C-methyl-D-erythritol.

3. The method according to claim 1, wherein the divalent metal salt is a salt of divalent manganese.

4. A method for screening a chemical library for an inhibitor of the biosynthesis of isoprenoids by blocking the synthesis of 4-diphosphocytidyl-2C-methyl-D-erythritol 2-phosphate from 4-diphosphocytdiyl-2C-methyl-D-erythritol and adenosine triphosphate in accordance with the following steps:

(a) preparing an aqueous mixture comprising
  (i) a protein that is enzymatically functional for the conversion of 4-diphosphocytidyl-2C-methyl-D-erythritol and adenosine triphosphate into 4-diphosphocytidyl-2C-methyl-D-erythritol 2-phosphate,
  (ii) 4-diphosphocytidyl-2C-methyl-D-erythritol or a source thereof selected from the group consisting of glyceraldehyde-3-phosphate, pyruvate, 1-deoxy-D-xylulose 5-phosphate and 2C-methyl-D-erythritol-4-phosphate,
  (iii) adenosine triphosphate, and
  (iv) a divalent metal salt; and
reacting said mixture for a predetermined period of time at a predetermined temperature;
(b) detecting the level of conversion of 4-diphosphocytidyl-2C-methyl-D-erythritol in step (a);
(c) repeating steps (a) and (b) in the presence of a test sample of the chemical library;
(d) detecting the level of conversion of 4-diphosphocytidyl-2C-methyl-D-erythritol in step (c);
(e) comparing the level of conversion in step (b) with the level of conversion in step (d), whereby a decrease in the level of conversion in step (d) identifies the test sample as an inhibitor of the biosynthesis of isoprenoids by blocking the synthesis of 4-diphosphocytidyl-2C-methyl-D-erythritol 2-phosphate from 4-diphosphocytdiyl-2C-methyl-D-erythritol and adenosine triphosphate.

5. The method according to claim 4, wherein steps (b) and (d) are carried out by measuring the level of formation of 4-diphosphocytidyl-2C-methyl-D-erythritol 2-phosphate or adenosine diphosphate, or by measuring the consumption of 4-diphosphocytidyl-2C-methyl-D-erythritol or of adenosine triphosphate.

6. The method according to claim 4, wherein the divalent metal salt is a magnesium salt.

* * * * *

UNITED STATES PATENT AND TRADEMARK OFFICE
CERTIFICATE OF CORRECTION

PATENT NO. : 7,534,742 B2
APPLICATION NO. : 11/526318
DATED : May 19, 2009
INVENTOR(S) : Eisenreich et al.

Page 1 of 1

It is certified that error appears in the above-identified patent and that said Letters Patent is hereby corrected as shown below:

On Title Page:
Item 76, Inventors: Please correct "Silvia Sagner"
 to read -- Silvia Sagner-Grehn --

Item 76, Inventors: Please correct Adelbert Bacher's address "Köigsberger Str." to read -- Königsberger Str. --

Column 37, Line 63: Please correct "$(2J_{PP})$" to read -- $(^{2}J_{PP})$ --

Signed and Sealed this

Twenty-eighth Day of July, 2009

JOHN DOLL
*Acting Director of the United States Patent and Trademark Office*

SEQUENCE LISTING

```
<160> NUMBER OF SEQ ID NOS: 176

<210> SEQ ID NO 1
<211> LENGTH: 228
<212> TYPE: PRT
<213> ORGANISM: Arabidopsis thaliana

<400> SEQUENCE: 1

Met Glu Lys Ser Val Ser Val Ile Leu Leu Ala Gly Gly Gln Gly Lys
1               5                   10                  15
```

Arg Met Lys Met Ser Met Pro Lys Gln Tyr Ile Pro Leu Leu Gly Gln
            20                  25                  30

Pro Ile Ala Leu Tyr Ser Phe Phe Thr Phe Ser Arg Met Pro Glu Val
        35                  40                  45

Lys Glu Ile Val Val Cys Asp Pro Phe Phe Arg Asp Ile Phe Glu
50                  55                  60

Glu Tyr Glu Glu Ser Ile Asp Val Asp Leu Arg Phe Ala Ile Pro Gly
65                  70                  75                  80

Lys Glu Arg Gln Asp Ser Val Tyr Ser Gly Leu Gln Glu Ile Asp Val
                85                  90                  95

Asn Ser Glu Leu Val Cys Ile His Asp Ser Ala Arg Pro Leu Val Asn
            100                 105                 110

Thr Glu Asp Val Glu Lys Val Leu Lys Asp Gly Ser Ala Val Gly Ala
            115                 120                 125

Ala Val Leu Gly Val Pro Ala Lys Ala Thr Ile Lys Glu Val Asn Ser
130                 135                 140

Asp Ser Leu Val Val Lys Thr Leu Asp Arg Lys Thr Leu Trp Glu Met
145                 150                 155                 160

Gln Thr Pro Gln Val Ile Lys Pro Glu Leu Leu Lys Lys Gly Phe Glu
                165                 170                 175

Leu Val Lys Ser Glu Gly Leu Glu Val Thr Asp Asp Val Ser Ile Val
            180                 185                 190

Glu Tyr Leu Lys His Pro Val Tyr Val Ser Gln Gly Ser Tyr Thr Asn
            195                 200                 205

Ile Lys Val Thr Thr Pro Asp Asp Leu Leu Leu Ala Glu Arg Ile Leu
210                 215                 220

Ser Glu Asp Ser
225

<210> SEQ ID NO 2
<211> LENGTH: 278
<212> TYPE: PRT
<213> ORGANISM: Arabidopsis thaliana

<400> SEQUENCE: 2

Met Ala Met Leu Gln Thr Asn Leu Gly Phe Ile Thr Ser Pro Thr Phe
1               5                   10                  15

Leu Cys Pro Lys Leu Lys Val Lys Leu Asn Ser Tyr Leu Trp Phe Ser
            20                  25                  30

Tyr Arg Ser Gln Gly Asn Phe Ser Tyr Ser Leu Tyr Thr Phe Lys Pro
        35                  40                  45

Met Asn Leu Trp Phe Val Gln Lys Leu Asp Phe Ser Lys Arg Val Asn
50                  55                  60

Arg Ser Tyr Lys Arg Asp Ala Leu Leu Leu Ser Ile Lys Cys Ser Ser
65                  70                  75                  80

Ser Thr Gly Phe Asp Asn Ser Asn Ala Val Asn Ser Asn Val Val Val
                85                  90                  95

Lys Glu Lys Ser Val Ser Val Ile Leu Leu Ala Gly Gly Gln Gly Lys
            100                 105                 110

Arg Met Lys Leu Cys Phe Trp Leu Arg Asp Val Pro Lys Ile Ser Leu
            115                 120                 125

Ser Leu Phe Leu Phe Cys Gly Val Leu Glu Tyr Glu Glu Ser Ile Asp
130                 135                 140

Val Asp Leu Arg Phe Ala Ile Pro Gly Lys Glu Arg Gln Asp Ser Val
145                 150                 155                 160

```
Tyr Ser Gly Leu Gln Glu Ile Asp Val Asn Ser Glu Leu Val Cys Ile
            165                 170                 175

His Asp Ser Ala Arg Pro Leu Val Asn Thr Glu Asp Val Glu Lys Val
        180                 185                 190

Leu Lys Asp Gly Ser Ala Val Gly Ala Ala Val Leu Gly Val Pro Ala
    195                 200                 205

Lys Ala Thr Ile Lys Glu Val Ile Lys Pro Glu Leu Leu Lys Lys Gly
210                 215                 220

Phe Glu Leu Val Lys Ser Glu Gly Leu Glu Val Thr Asp Asp Val Ser
225                 230                 235                 240

Ile Val Glu Tyr Leu Lys His Pro Val Tyr Val Ser Gln Gly Ser Tyr
                245                 250                 255

Thr Asn Ile Lys Val Thr Thr Pro Asp Asp Leu Leu Leu Ala Glu Arg
            260                 265                 270

Ile Leu Ser Glu Asp Ser
            275
```

<210> SEQ ID NO 3
<211> LENGTH: 684
<212> TYPE: DNA
<213> ORGANISM: Arabidopsis thaliana
<220> FEATURE:
<221> NAME/KEY: CDS
<222> LOCATION: (1)..(681)

<400> SEQUENCE: 3

```
gag aag agt gta tct gtg att ctt tta gct gga ggt caa ggc aag aga        48
Glu Lys Ser Val Ser Val Ile Leu Leu Ala Gly Gly Gln Gly Lys Arg
1               5                   10                  15 atg aaa atg agt atg cca aag cag tac ata cca ctt ctt ggt cag cca        96
Met Lys Met Ser Met Pro Lys Gln Tyr Ile Pro Leu Leu Gly Gln Pro
            20                  25                  30 att gct ttg tat agc ttt ttc acg ttt tca cgt atg cct gaa gtg aag       144
Ile Ala Leu Tyr Ser Phe Phe Thr Phe Ser Arg Met Pro Glu Val Lys
        35                  40                  45 gaa att gta gtt gta tgt gat cct ttt ttc aga gac att ttt gaa gaa       192
Glu Ile Val Val Val Cys Asp Pro Phe Phe Arg Asp Ile Phe Glu Glu
    50                  55                  60 tac gaa gaa tca att gat gtt gat ctt aga ttc gct att cct ggc aaa       240
Tyr Glu Glu Ser Ile Asp Val Asp Leu Arg Phe Ala Ile Pro Gly Lys
65                  70                  75                  80 gaa aga caa gat tct gtt tac agt gga ctt cag gaa atc gat gtg aac       288
Glu Arg Gln Asp Ser Val Tyr Ser Gly Leu Gln Glu Ile Asp Val Asn
                85                  90                  95 tct gag ctt gtt tgt atc cac gac tct gcc cga cca ttg gtg aat act       336
Ser Glu Leu Val Cys Ile His Asp Ser Ala Arg Pro Leu Val Asn Thr
            100                 105                 110 gaa gat gtc gag aag gtc ctt aaa gat ggt tcc gcg gtt gga gca gct       384
Glu Asp Val Glu Lys Val Leu Lys Asp Gly Ser Ala Val Gly Ala Ala
        115                 120                 125 gta ctt ggt gtt cct gct aaa gct aca atc aaa gag gtc aat tct gat       432
Val Leu Gly Val Pro Ala Lys Ala Thr Ile Lys Glu Val Asn Ser Asp
    130                 135                 140 tcg ctt gtg gtg aaa act ctc gac aga aaa acc cta tgg gaa atg cag       480
Ser Leu Val Val Lys Thr Leu Asp Arg Lys Thr Leu Trp Glu Met Gln
145                 150                 155                 160 aca cca cag gtg atc aaa cca gag cta ttg aaa aag ggt ttc gag ctt       528
Thr Pro Gln Val Ile Lys Pro Glu Leu Leu Lys Lys Gly Phe Glu Leu
                165                 170                 175
```

```
gta aaa agt gaa ggt cta gag gta aca gat gac gtt tcg att gtt gaa    576
Val Lys Ser Glu Gly Leu Glu Val Thr Asp Asp Val Ser Ile Val Glu
        180                 185                 190 tac ctc aag cat cca gtt tat gtc tct caa gga tct tat aca aac atc    624
Tyr Leu Lys His Pro Val Tyr Val Ser Gln Gly Ser Tyr Thr Asn Ile
        195                 200                 205 aag gtt aca aca cct gat gat tta ctg ctt gct gag aga atc ttg agc    672
Lys Val Thr Thr Pro Asp Asp Leu Leu Leu Ala Glu Arg Ile Leu Ser
210                 215                 220 gag gac tca tga                                                    684
Glu Asp Ser
225

<210> SEQ ID NO 4
<211> LENGTH: 227
<212> TYPE: PRT
<213> ORGANISM: Arabidopsis thaliana

<400> SEQUENCE: 4

Glu Lys Ser Val Ser Val Ile Leu Leu Ala Gly Gly Gln Gly Lys Arg
1               5                   10                  15

Met Lys Met Ser Met Pro Lys Gln Tyr Ile Pro Leu Leu Gly Gln Pro
            20                  25                  30

Ile Ala Leu Tyr Ser Phe Phe Thr Phe Ser Arg Met Pro Glu Val Lys
        35                  40                  45

Glu Ile Val Val Cys Asp Pro Phe Phe Arg Asp Ile Phe Glu Glu
    50                  55                  60

Tyr Glu Glu Ser Ile Asp Val Asp Leu Arg Phe Ala Ile Pro Gly Lys
65                  70                  75                  80

Glu Arg Gln Asp Ser Val Tyr Ser Gly Leu Gln Glu Ile Asp Val Asn
                85                  90                  95

Ser Glu Leu Val Cys Ile His Asp Ser Ala Arg Pro Leu Val Asn Thr
            100                 105                 110

Glu Asp Val Glu Lys Val Leu Lys Asp Gly Ser Ala Val Gly Ala Ala
        115                 120                 125

Val Leu Gly Val Pro Ala Lys Ala Thr Ile Lys Glu Val Asn Ser Asp
    130                 135                 140

Ser Leu Val Val Lys Thr Leu Asp Arg Lys Thr Leu Trp Glu Met Gln
145                 150                 155                 160

Thr Pro Gln Val Ile Lys Pro Glu Leu Leu Lys Lys Gly Phe Glu Leu
                165                 170                 175

Val Lys Ser Glu Gly Leu Glu Val Thr Asp Asp Val Ser Ile Val Glu
            180                 185                 190

Tyr Leu Lys His Pro Val Tyr Val Ser Gln Gly Ser Tyr Thr Asn Ile
        195                 200                 205

Lys Val Thr Thr Pro Asp Asp Leu Leu Leu Ala Glu Arg Ile Leu Ser
    210                 215                 220

Glu Asp Ser
225

<210> SEQ ID NO 5
<211> LENGTH: 909
<212> TYPE: DNA
<213> ORGANISM: Arabidopsis thaliana
<220> FEATURE:
<221> NAME/KEY: CDS
<222> LOCATION: (1)..(906)
```

<400> SEQUENCE: 5

```
atg gcg atg ctt cag acg aat ctt ggc ttc att act tct ccg aca ttt      48
Met Ala Met Leu Gln Thr Asn Leu Gly Phe Ile Thr Ser Pro Thr Phe
1               5                   10                  15 ctg tgt ccg aag ctt aaa gtc aaa ttg aac tct tat ctg tgg ttt agc      96
Leu Cys Pro Lys Leu Lys Val Lys Leu Asn Ser Tyr Leu Trp Phe Ser
            20                  25                  30 tat cgt tct caa gtt caa aaa ctg gat ttt tcg aaa agg gtt aat aga     144
Tyr Arg Ser Gln Val Gln Lys Leu Asp Phe Ser Lys Arg Val Asn Arg
        35                  40                  45 agc tac aaa aga gat gct tta tta ttg tca atc aag tgt tct tca tcg     192
Ser Tyr Lys Arg Asp Ala Leu Leu Leu Ser Ile Lys Cys Ser Ser Ser
    50                  55                  60 act gga ttt gat aat agc aat gtt gtt gtg aag gag aag agt gta tct     240
Thr Gly Phe Asp Asn Ser Asn Val Val Val Lys Glu Lys Ser Val Ser
65                  70                  75                  80 gtg att ctt tta gct gga ggt caa ggc aag aga atg aaa atg agt atg     288
Val Ile Leu Leu Ala Gly Gly Gln Gly Lys Arg Met Lys Met Ser Met
                85                  90                  95 cca aag cag tac ata cca ctt ctt ggt cag cca att gct ttg tat agc     336
Pro Lys Gln Tyr Ile Pro Leu Leu Gly Gln Pro Ile Ala Leu Tyr Ser
            100                 105                 110 ttt ttc acg ttt tca cgt atg cct gaa gtg aag gaa att gta gtt gta     384
Phe Phe Thr Phe Ser Arg Met Pro Glu Val Lys Glu Ile Val Val Val
        115                 120                 125 tgt gat cct ttt ttc aga gac att ttt gaa gaa tac gaa gaa tca att     432
Cys Asp Pro Phe Phe Arg Asp Ile Phe Glu Glu Tyr Glu Glu Ser Ile
    130                 135                 140 gat gtt gat ctt aga ttc gct att cct ggc aaa gaa aga caa gat tct     480
Asp Val Asp Leu Arg Phe Ala Ile Pro Gly Lys Glu Arg Gln Asp Ser
145                 150                 155                 160 gtt tac agt gga ctt cag gaa atc gat gtg aac tct gag ctt gtt tgt     528
Val Tyr Ser Gly Leu Gln Glu Ile Asp Val Asn Ser Glu Leu Val Cys
                165                 170                 175 atc cac gac tct gcc cga cca ttg gtg aat act gaa gat gtc gag aag     576
Ile His Asp Ser Ala Arg Pro Leu Val Asn Thr Glu Asp Val Glu Lys
            180                 185                 190 gtc ctt aaa gat ggt tcc gcg gtt gga gca gct gta ctt ggt gtt cct     624
Val Leu Lys Asp Gly Ser Ala Val Gly Ala Ala Val Leu Gly Val Pro
        195                 200                 205 gct aaa gct aca atc aaa gag gtc aat tct gat tcg ctt gtg gtg aaa     672
Ala Lys Ala Thr Ile Lys Glu Val Asn Ser Asp Ser Leu Val Val Lys
    210                 215                 220 act ctc gac aga aaa acc cta tgg gaa atg cag aca cca cag gtg atc     720
Thr Leu Asp Arg Lys Thr Leu Trp Glu Met Gln Thr Pro Gln Val Ile
225                 230                 235                 240 aaa cca gag cta ttg aaa aag ggt ttc gag ctt gta aaa agt gaa ggt     768
Lys Pro Glu Leu Leu Lys Lys Gly Phe Glu Leu Val Lys Ser Glu Gly
                245                 250                 255 cta gag gta aca gat gac gtt tcg att gtt gaa tac ctc aag cat cca     816
Leu Glu Val Thr Asp Asp Val Ser Ile Val Glu Tyr Leu Lys His Pro
            260                 265                 270 gtt tat gtc tct caa gga tct tat aca aac atc aag gtt aca aca cct     864
Val Tyr Val Ser Gln Gly Ser Tyr Thr Asn Ile Lys Val Thr Thr Pro
        275                 280                 285 gat gat tta ctg ctt gct gag aga atc ttg agc gag gac tca tga         909
Asp Asp Leu Leu Leu Ala Glu Arg Ile Leu Ser Glu Asp Ser
    290                 295                 300
```

<210> SEQ ID NO 6
<211> LENGTH: 302
<212> TYPE: PRT
<213> ORGANISM: Arabidopsis thaliana

<400> SEQUENCE: 6

```
Met Ala Met Leu Gln Thr Asn Leu Gly Phe Ile Thr Ser Pro Thr Phe
1               5                   10                  15

Leu Cys Pro Lys Leu Lys Val Lys Leu Asn Ser Tyr Leu Trp Phe Ser
            20                  25                  30

Tyr Arg Ser Gln Val Gln Lys Leu Asp Phe Ser Lys Arg Val Asn Arg
        35                  40                  45

Ser Tyr Lys Arg Asp Ala Leu Leu Ser Ile Lys Cys Ser Ser Ser
    50                  55                  60

Thr Gly Phe Asp Asn Ser Asn Val Val Val Lys Glu Lys Ser Val Ser
65                  70                  75                  80

Val Ile Leu Leu Ala Gly Gly Gln Gly Lys Arg Met Lys Met Ser Met
                85                  90                  95

Pro Lys Gln Tyr Ile Pro Leu Leu Gly Gln Pro Ile Ala Leu Tyr Ser
            100                 105                 110

Phe Phe Thr Phe Ser Arg Met Pro Glu Val Lys Glu Ile Val Val Val
        115                 120                 125

Cys Asp Pro Phe Arg Asp Ile Phe Glu Glu Tyr Glu Glu Ser Ile
    130                 135                 140

Asp Val Asp Leu Arg Phe Ala Ile Pro Gly Lys Glu Arg Gln Asp Ser
145                 150                 155                 160

Val Tyr Ser Gly Leu Gln Glu Ile Asp Val Asn Ser Glu Leu Val Cys
                165                 170                 175

Ile His Asp Ser Ala Arg Pro Leu Val Asn Thr Glu Asp Val Glu Lys
            180                 185                 190

Val Leu Lys Asp Gly Ser Ala Val Gly Ala Ala Val Leu Gly Val Pro
        195                 200                 205

Ala Lys Ala Thr Ile Lys Glu Val Asn Ser Asp Ser Leu Val Val Lys
    210                 215                 220

Thr Leu Asp Arg Lys Thr Leu Trp Glu Met Gln Thr Pro Gln Val Ile
225                 230                 235                 240

Lys Pro Glu Leu Leu Lys Gly Phe Glu Leu Val Lys Ser Glu Gly
                245                 250                 255

Leu Glu Val Thr Asp Asp Val Ser Ile Val Glu Tyr Leu Lys His Pro
            260                 265                 270

Val Tyr Val Ser Gln Gly Ser Tyr Thr Asn Ile Lys Val Thr Thr Pro
        275                 280                 285

Asp Asp Leu Leu Leu Ala Glu Arg Ile Leu Ser Glu Asp Ser
    290                 295                 300
```

<210> SEQ ID NO 7
<211> LENGTH: 951
<212> TYPE: DNA
<213> ORGANISM: Arabidopsis thaliana
<220> FEATURE:
<221> NAME/KEY: CDS
<222> LOCATION: (1)..(948)

<400> SEQUENCE: 7

```
gct cct ttg tcc agg ctt aag ctc ttc tca cct tgc aag atc aat gtt      48
Ala Pro Leu Ser Arg Leu Lys Leu Phe Ser Pro Cys Lys Ile Asn Val
1               5                   10                  15
```

```
ttc ttg agg atc acc gga aag cga gaa gat ggg ttt cat gat tta gcc      96
Phe Leu Arg Ile Thr Gly Lys Arg Glu Asp Gly Phe His Asp Leu Ala
         20                  25                  30 tct ttg ttt cat gtg att agc tta gga ggc act att aaa ttc tca ttg     144
Ser Leu Phe His Val Ile Ser Leu Gly Gly Thr Ile Lys Phe Ser Leu
     35                  40                  45 tca cca tca aag tct aaa gat cgt ttg tct act aac gtt caa gga gtc     192
Ser Pro Ser Lys Ser Lys Asp Arg Leu Ser Thr Asn Val Gln Gly Val
 50                  55                  60 cct gtt gat ggg aga aat ctg att ata aaa gca ctt aac ctt tac agg     240
Pro Val Asp Gly Arg Asn Leu Ile Ile Lys Ala Leu Asn Leu Tyr Arg
 65                  70                  75                  80 aag aaa act ggt agc aac aga ttc ttc tgg att cat tta gat aag aag     288
Lys Lys Thr Gly Ser Asn Arg Phe Phe Trp Ile His Leu Asp Lys Lys
                 85                  90                  95 gtg cct acc ggg gct gga ctc ggt ggt gga agt agt aat gct gca act     336
Val Pro Thr Gly Ala Gly Leu Gly Gly Gly Ser Ser Asn Ala Ala Thr
            100                 105                 110 gca ctc tgg gcg gca aat gag ctc aat gga ggt ctt gtc act gag aac     384
Ala Leu Trp Ala Ala Asn Glu Leu Asn Gly Gly Leu Val Thr Glu Asn
        115                 120                 125 gaa ctc cag gat tgg tca agt gaa att ggg tca gat att cct ttc ttc     432
Glu Leu Gln Asp Trp Ser Ser Glu Ile Gly Ser Asp Ile Pro Phe Phe
    130                 135                 140 ttc tcg cat gga gct gcc tat tgt acc ggg aga ggt gag att gtc caa     480
Phe Ser His Gly Ala Ala Tyr Cys Thr Gly Arg Gly Glu Ile Val Gln
145                 150                 155                 160 gac ctt cct cca cct ttt cct ctt gat ctt ccg atg gtg ctc ata aag     528
Asp Leu Pro Pro Pro Phe Pro Leu Asp Leu Pro Met Val Leu Ile Lys
                165                 170                 175 ccc cga gaa gca tgt tcc act gct gaa gtt tac aaa cgt ctt cgt tta     576
Pro Arg Glu Ala Cys Ser Thr Ala Glu Val Tyr Lys Arg Leu Arg Leu
            180                 185                 190 gat cag acg agc aat att aat ccc ttg aca tta cta aag aat gtg acc     624
Asp Gln Thr Ser Asn Ile Asn Pro Leu Thr Leu Leu Lys Asn Val Thr
        195                 200                 205 agc aat ggt gtg tct caa agc ata tgc gta aac gat ttg gaa ccg cca     672
Ser Asn Gly Val Ser Gln Ser Ile Cys Val Asn Asp Leu Glu Pro Pro
    210                 215                 220 gcg ttt tca gtt ctt cca tct cta aaa cgc ttg aag caa cgg ata ata     720
Ala Phe Ser Val Leu Pro Ser Leu Lys Arg Leu Lys Gln Arg Ile Ile
225                 230                 235                 240 gca tct gga cgt ggg gaa tac gat gct gtg ttt atg tct ggg agt gga     768
Ala Ser Gly Arg Gly Glu Tyr Asp Ala Val Phe Met Ser Gly Ser Gly
                245                 250                 255 agc act att atc ggt att ggt tca cca gat cct cct caa ttt ata tat     816
Ser Thr Ile Ile Gly Ile Gly Ser Pro Asp Pro Pro Gln Phe Ile Tyr
            260                 265                 270 gat gat gaa gaa tac aag gac gtg ttc ttg tct gaa gca aac ttt atg     864
Asp Asp Glu Glu Tyr Lys Asp Val Phe Leu Ser Glu Ala Asn Phe Met
        275                 280                 285 acg cgt gag gct aat gaa tgg tac aaa gaa cct gct tct gca aat gct     912
Thr Arg Glu Ala Asn Glu Trp Tyr Lys Glu Pro Ala Ser Ala Asn Ala
    290                 295                 300 act acc tca tcc gcc gaa tct cgc atg gat ttc caa tga                 951
Thr Thr Ser Ser Ala Glu Ser Arg Met Asp Phe Gln
305                 310                 315

<210> SEQ ID NO 8
<211> LENGTH: 316
```

```
<212> TYPE: PRT
<213> ORGANISM: Arabidopsis thaliana

<400> SEQUENCE: 8

Ala Pro Leu Ser Arg Leu Lys Leu Phe Ser Pro Cys Lys Ile Asn Val
 1               5                  10                  15

Phe Leu Arg Ile Thr Gly Lys Arg Glu Asp Gly Phe His Asp Leu Ala
             20                  25                  30

Ser Leu Phe His Val Ile Ser Leu Gly Gly Thr Ile Lys Phe Ser Leu
         35                  40                  45

Ser Pro Ser Lys Ser Lys Asp Arg Leu Ser Thr Asn Val Gln Gly Val
 50                  55                  60

Pro Val Asp Gly Arg Asn Leu Ile Ile Lys Ala Leu Asn Leu Tyr Arg
 65                  70                  75                  80

Lys Lys Thr Gly Ser Asn Arg Phe Phe Trp Ile His Leu Asp Lys Lys
             85                  90                  95

Val Pro Thr Gly Ala Gly Leu Gly Gly Gly Ser Ser Asn Ala Ala Thr
            100                 105                 110

Ala Leu Trp Ala Ala Asn Glu Leu Asn Gly Gly Leu Val Thr Glu Asn
        115                 120                 125

Glu Leu Gln Asp Trp Ser Ser Glu Ile Gly Ser Asp Ile Pro Phe Phe
130                 135                 140

Phe Ser His Gly Ala Ala Tyr Cys Thr Gly Arg Gly Glu Ile Val Gln
145                 150                 155                 160

Asp Leu Pro Pro Pro Phe Pro Leu Asp Leu Pro Met Val Leu Ile Lys
                165                 170                 175

Pro Arg Glu Ala Cys Ser Thr Ala Glu Val Tyr Lys Arg Leu Arg Leu
            180                 185                 190

Asp Gln Thr Ser Asn Ile Asn Pro Leu Thr Leu Leu Lys Asn Val Thr
        195                 200                 205

Ser Asn Gly Val Ser Gln Ser Ile Cys Val Asn Asp Leu Glu Pro Pro
210                 215                 220

Ala Phe Ser Val Leu Pro Ser Leu Lys Arg Leu Lys Gln Arg Ile Ile
225                 230                 235                 240

Ala Ser Gly Arg Gly Glu Tyr Asp Ala Val Phe Met Ser Gly Ser Gly
                245                 250                 255

Ser Thr Ile Ile Gly Ile Gly Ser Pro Asp Pro Gln Phe Ile Tyr
            260                 265                 270

Asp Asp Glu Glu Tyr Lys Asp Val Phe Leu Ser Glu Ala Asn Phe Met
        275                 280                 285

Thr Arg Glu Ala Asn Glu Trp Tyr Lys Glu Pro Ala Ser Ala Asn Ala
290                 295                 300

Thr Thr Ser Ser Ala Glu Ser Arg Met Asp Phe Gln
305                 310                 315

<210> SEQ ID NO 9
<211> LENGTH: 1152
<212> TYPE: DNA
<213> ORGANISM: Arabidopsis thaliana
<220> FEATURE:
<221> NAME/KEY: CDS
<222> LOCATION: (1)..(1149)

<400> SEQUENCE: 9 atg gca acg gct tct cct cca ttt atc tca gct ctc agc ttc act cac      48
Met Ala Thr Ala Ser Pro Pro Phe Ile Ser Ala Leu Ser Phe Thr His
 1               5                  10                  15
```

```
tct tct ttc aaa act tct tct tct tct tca ttt tct ccg aag ctt ctt        96
Ser Ser Phe Lys Thr Ser Ser Ser Ser Ser Phe Ser Pro Lys Leu Leu
            20                  25                  30 cga ccc ctc tta agc ttt tcc gtc aaa gct tcc aga aag caa gta gag       144
Arg Pro Leu Leu Ser Phe Ser Val Lys Ala Ser Arg Lys Gln Val Glu
        35                  40                  45 ata gtg ttt gat cct gat gag agg ctt aat aag ata ggt gat gat gtt      192
Ile Val Phe Asp Pro Asp Glu Arg Leu Asn Lys Ile Gly Asp Asp Val
    50                  55                  60 gac aaa gaa gct cct ttg tcc agg ctt aag ctc ttc tca cct tgc aag      240
Asp Lys Glu Ala Pro Leu Ser Arg Leu Lys Leu Phe Ser Pro Cys Lys
65                  70                  75                  80 atc aat gtt ttc ttg agg atc acc gga aag cga gaa gat ggg ttt cat      288
Ile Asn Val Phe Leu Arg Ile Thr Gly Lys Arg Glu Asp Gly Phe His
                85                  90                  95 gat tta gcc tct ttg ttt cat gtg att agc tta gga ggc act att aaa      336
Asp Leu Ala Ser Leu Phe His Val Ile Ser Leu Gly Gly Thr Ile Lys
            100                 105                 110 ttc tca ttg tca cca tca aag tct aaa gat cgt ttg tct act aac gtt      384
Phe Ser Leu Ser Pro Ser Lys Ser Lys Asp Arg Leu Ser Thr Asn Val
        115                 120                 125 caa gga gtc cct gtt gat ggg aga aat ctg att ata aaa gca ctt aac      432
Gln Gly Val Pro Val Asp Gly Arg Asn Leu Ile Ile Lys Ala Leu Asn
    130                 135                 140 ctt tac agg aag aaa act ggt agc aac aga ttc ttc tgg att cat tta      480
Leu Tyr Arg Lys Lys Thr Gly Ser Asn Arg Phe Phe Trp Ile His Leu
145                 150                 155                 160 gat aag aag gtg cct acc ggg gct gga ctc ggt ggt gga agt agt aat      528
Asp Lys Lys Val Pro Thr Gly Ala Gly Leu Gly Gly Gly Ser Ser Asn
                165                 170                 175 gct gca act gca ctc tgg gcg gca aat gag ctc aat gga ggt ctt gtc      576
Ala Ala Thr Ala Leu Trp Ala Ala Asn Glu Leu Asn Gly Gly Leu Val
            180                 185                 190 act gag aac gaa ctc cag gat tgg tca agt gaa att ggg tca gat att      624
Thr Glu Asn Glu Leu Gln Asp Trp Ser Ser Glu Ile Gly Ser Asp Ile
        195                 200                 205 cct ttc ttc ttc tcg cat gga gct gcc tat tgt acc ggg aga ggt gag      672
Pro Phe Phe Phe Ser His Gly Ala Ala Tyr Cys Thr Gly Arg Gly Glu
    210                 215                 220 att gtc caa gac ctt cct cca cct ttt cct ctt gat ctt ccg atg gtg      720
Ile Val Gln Asp Leu Pro Pro Pro Phe Pro Leu Asp Leu Pro Met Val
225                 230                 235                 240 ctc ata aag ccc cga gaa gca tgt tcc act gct gaa gtt tac aaa cgt      768
Leu Ile Lys Pro Arg Glu Ala Cys Ser Thr Ala Glu Val Tyr Lys Arg
                245                 250                 255 ctt cgt tta gat cag acg agc aat att aat ccc ttg aca tta cta aag      816
Leu Arg Leu Asp Gln Thr Ser Asn Ile Asn Pro Leu Thr Leu Leu Lys
            260                 265                 270 aat gtg acc agc aat ggt gtg tct caa agc ata tgc gta aac gat ttg      864
Asn Val Thr Ser Asn Gly Val Ser Gln Ser Ile Cys Val Asn Asp Leu
        275                 280                 285 gaa ccg cca gcg ttt tca gtt ctt cca tct cta aaa cgc ttg aag caa      912
Glu Pro Pro Ala Phe Ser Val Leu Pro Ser Leu Lys Arg Leu Lys Gln
    290                 295                 300 cgg ata ata gca tct gga cgt ggg gaa tac gat gct gtg ttt atg tct      960
Arg Ile Ile Ala Ser Gly Arg Gly Glu Tyr Asp Ala Val Phe Met Ser
305                 310                 315                 320 ggg agt gga agc act att atc ggt att ggt tca cca gat cct cct caa     1008
Gly Ser Gly Ser Thr Ile Ile Gly Ile Gly Ser Pro Asp Pro Pro Gln
```

```
                     325                 330                 335
ttt ata tat gat gat gaa gaa tac aag gac gtg ttc ttg tct gaa gca    1056
Phe Ile Tyr Asp Asp Glu Glu Tyr Lys Asp Val Phe Leu Ser Glu Ala
        340                 345                 350 aac ttt atg acg cgt gag gct aat gaa tgg tac aaa gaa cct gct tct    1104
Asn Phe Met Thr Arg Glu Ala Asn Glu Trp Tyr Lys Glu Pro Ala Ser
    355                 360                 365 gca aat gct act acc tca tcc gcc gaa tct cgc atg gat ttc caa tga    1152
Ala Asn Ala Thr Thr Ser Ser Ala Glu Ser Arg Met Asp Phe Gln
    370                 375                 380
```

<210> SEQ ID NO 10
<211> LENGTH: 383
<212> TYPE: PRT
<213> ORGANISM: Arabidopsis thaliana

<400> SEQUENCE: 10

```
Met Ala Thr Ala Ser Pro Pro Phe Ile Ser Ala Leu Ser Phe Thr His
1               5                   10                  15

Ser Ser Phe Lys Thr Ser Ser Ser Ser Phe Ser Pro Lys Leu Leu
            20                  25                  30

Arg Pro Leu Leu Ser Phe Ser Val Lys Ala Ser Arg Lys Gln Val Glu
        35                  40                  45

Ile Val Phe Asp Pro Asp Glu Arg Leu Asn Lys Ile Gly Asp Asp Val
    50                  55                  60

Asp Lys Glu Ala Pro Leu Ser Arg Leu Lys Leu Phe Ser Pro Cys Lys
65                  70                  75                  80

Ile Asn Val Phe Leu Arg Ile Thr Gly Lys Arg Glu Asp Gly Phe His
                85                  90                  95

Asp Leu Ala Ser Leu Phe His Val Ile Ser Leu Gly Gly Thr Ile Lys
            100                 105                 110

Phe Ser Leu Ser Pro Ser Lys Ser Lys Asp Arg Leu Ser Thr Asn Val
        115                 120                 125

Gln Gly Val Pro Val Asp Gly Arg Asn Leu Ile Ile Lys Ala Leu Asn
    130                 135                 140

Leu Tyr Arg Lys Lys Thr Gly Ser Asn Arg Phe Phe Trp Ile His Leu
145                 150                 155                 160

Asp Lys Lys Val Pro Thr Gly Ala Gly Leu Gly Gly Gly Ser Ser Asn
                165                 170                 175

Ala Ala Thr Ala Leu Trp Ala Ala Asn Glu Leu Asn Gly Gly Leu Val
            180                 185                 190

Thr Glu Asn Glu Leu Gln Asp Trp Ser Ser Glu Ile Gly Ser Asp Ile
        195                 200                 205

Pro Phe Phe Phe Ser His Gly Ala Ala Tyr Cys Thr Gly Arg Gly Glu
    210                 215                 220

Ile Val Gln Asp Leu Pro Pro Phe Pro Leu Asp Leu Pro Met Val
225                 230                 235                 240

Leu Ile Lys Pro Arg Glu Ala Cys Ser Thr Ala Glu Val Tyr Lys Arg
                245                 250                 255

Leu Arg Leu Asp Gln Thr Ser Asn Ile Asn Pro Leu Thr Leu Leu Lys
            260                 265                 270

Asn Val Thr Ser Asn Gly Val Ser Gln Ser Ile Cys Val Asn Asp Leu
        275                 280                 285

Glu Pro Pro Ala Phe Ser Val Leu Pro Ser Leu Lys Arg Leu Lys Gln
    290                 295                 300
```

| | | | | | | | | | | | |
|---|---|---|---|---|---|---|---|---|---|---|---|
| Arg | Ile | Ile | Ala | Ser | Gly | Arg | Gly | Glu | Tyr | Asp | Ala | Val | Phe | Met | Ser |
| 305 | | | | 310 | | | | 315 | | | | 320 | | | |

Gly Ser Gly Ser Thr Ile Ile Gly Ile Gly Ser Pro Asp Pro Pro Gln
              325                  330                  335

Phe Ile Tyr Asp Asp Glu Glu Tyr Lys Asp Val Phe Leu Ser Glu Ala
            340                  345                  350

Asn Phe Met Thr Arg Glu Ala Asn Glu Trp Tyr Lys Glu Pro Ala Ser
        355                  360                  365

Ala Asn Ala Thr Thr Ser Ser Ala Glu Ser Arg Met Asp Phe Gln
        370              375              380

<210> SEQ ID NO 11
<211> LENGTH: 969
<212> TYPE: DNA
<213> ORGANISM: Lycopersicon esculentum

<400> SEQUENCE: 11

```
gtggatagag aagctgggct ttcaagactc actcttttt ctccttgcaa gataaatgtt      60
ttcttgagaa taacaagcaa gagggatgac ggatatcatg atttggcgtc tctctttcat    120
gtaattagtc taggagataa aataaagttc tcgctgtcac catcgaagtc aaaggatcgt    180
ttatctacta atgttgctgg agttccactc gatgagagaa atctgattat aaaggccctc    240
aatctttata ggaaaaagac tggaacagac aattactttt ggattcatct tgataagaaa    300
gtgcctactg gagctggtct tggtggtggg agcagtaatg ctgcaacaac tctgtgggca    360
gcaaatcaat tcagtggttg tgttgccact gaaaaggagc tccaagagtg gtctggtgag    420
attggttctg atattccttt cttcttctct catggagcag cctactgtac gggtaggggt    480
gaggttgttc aggatatccc gtcacccata ccatttgaca ttccaatggt cctcataaag    540
cctcaacagg catgctccac tgctgaagtt tacaagcgtt ttcagttgga tctgtctagt    600
aaggttgatc ccttgagctt actggagaaa atctcaacta gtggaatatc tcaagatgtg    660
tgtgtcaatg atttagaacc tcctgccttt gaagttcttc catctcttaa aaggttaaaa    720
caacgagtaa ttgctgctgg ccgaggacaa tatgatgcag tcttcatgtc tggaagtgga    780
agcacaatag taggggttgg ctctccagat ccaccacaat tgtctatga tgatgaagaa    840
tacaaggatg tcttccttgt cagaagcaagt ttcatcactc gaccagccaa cgagtggtat    900
gttgaacctg tttcaggtag cactattggt gatcaacctg agttctctac atcttttgac    960
atgtcttaa                                                              969
```

<210> SEQ ID NO 12
<211> LENGTH: 969
<212> TYPE: DNA
<213> ORGANISM: Lycopersicon esculentum

<400> SEQUENCE: 12

```
atggatcgtg aagctggtct ttcacgcctc actcttttt ctccttgcaa gattaatgtt      60
ttcctgcgca tcacaagcaa acgtgatgac ggttatcatg atctggcgtc tctctttcat    120
gtaattagtc ttggcgataa aattaagttc tcgctgtcac catcgaaatc aaaggatcgt    180
ttatctacta atgttgctgg cgttccactc gatgagcgta atctgattat caaagccctc    240
aatctttatc gtaaaaagac tggtacagac aattactttt ggattcatct tgataagaaa    300
gtgcctactg gagctggtct tggtggtggg agcagtaatg ctgcaacaac tctgtgggca    360
gcaaatcaat tcagtggttg tgttgccact gaaaaggagc tccaagagtg gtctggtgag    420
```

```
attggttctg atattccttt cttcttctct catggagcag cctactgtac gggtaggggt      480
gaggttgttc aggatatccc gtcacccata ccatttgaca ttccaatggt cctcataaag      540
cctcaacagg catgctccac tgctgaagtt tacaagcgtt ttcagttgga tctgtctagt      600
aaggttgatc ccttgagctt actggagaaa atctcaacta gtggaatatc tcaagatgtg      660
tgtgtcaatg atttagaacc tcctgccttt gaagttcttc catctcttaa acgtttaaaa      720
caacgtgtaa ttgctgctgg ccgcggtcaa tatgatgcag tcttcatgtc tggtagtggc      780
agcacaatcg taggtgttgg ctctccagat ccgccacaat ttgtctatga tgacgaagag      840
tacaaagatg tcttccttgtc agaagcaagt ttcatcactc gtccagccaa cgagtggtat      900
gttgaacctg tttcaggtag cactattggt gatcaacctg agttctctac atcttttgac      960
atgtcttaa                                                              969
```

<210> SEQ ID NO 13
<211> LENGTH: 3420
<212> TYPE: DNA
<213> ORGANISM: Escherichia coli

<400> SEQUENCE: 13

```
ctcgagaaat cataaaaaat ttatttgctt tgtgagcgga taacaattat aatagattca       60
attgtgagcg ataacaatt tcacacagaa ttcattaaag aggagaaatt aaccatggga      120
ggatccgtcg acctgcagcc aagcttaatt agctgagctt ggactcctgt tgatagatcc      180
agtaatgacc tcagaactcc atctggattt gttcagaacg ctcggttgcc gccgggcgtt      240
ttttattggt gagaatccaa gctagcttgg cgagattttc aggagctaag gaagctaaaa      300
tggagaaaaa aatcactgga tataccaccg ttgatatatc ccaatggcat cgtaaagaac      360
attttgaggc atttcagtca gttgctcaat gtacctataa ccagaccgtt cagctggata      420
ttacggcctt tttaaagacc gtaaagaaaa ataagcacaa gttttatccg gcctttattc      480
acattcttgc ccgcctgatg aatgctcatc cggaatttcg tatggcaatg aaagacggtg      540
agctggtgat atgggatagt gttcacccctt gttacaccgt tttccatgag caaactgaaa      600
cgttttcatc gctctggagt gaataccacg acgatttccg gcagtttcta cacatatatt      660
cgcaagatgt ggcgtgttac ggtgaaaacc tggcctattt ccctaaaggg tttattgaga      720
atatgttttt cgtctcagcc aatccctggg tgagtttcac cagttttgat ttaaacgtgg      780
ccaatatgga caacttcttc gcccccgttt tcaccatgca tgggcaaata ttatacgcaa      840
ggcgacaagg tgctgatgcc gctggcgatt caggttcatc atgccgtctg tgatggcttc      900
catgtcggca gaatgcttaa tgaattacaa cagtactgcg atgagtggca gggcggggcg      960 taatttttt aaggcagtta ttggtgccct taaacgcctg ggtaatgac tctctagctt     1020 gaggcatcaa ataaaacgaa aggctcagtc gaaagactgg gcctttcgtt ttatctgttg     1080
tttgtcggtg aacgctctcc tgagtaggac aaatccgccg ctctagagct gcctcgcgcg     1140
tttcggtgat gacggtgaaa acctctgaca catgcagctc ccggagacgg tcacagcttg     1200
tctgtaagcg gatgccggga gcagacaagc ccgtcagggc gcgtcagcgg gtgttggcgg     1260
gtgtcggggc gcagccatga cccagtcacg tagcgatagc ggagtgtata ctggcttaac     1320
tatgcggcat cagagcagat tgtactgaga gtgcaccata tgcggtgtga ataccgcac     1380 agatgcgtaa ggagaaaata ccgcatcagg cgctcttccg cttcctcgct cactgactcg     1440
ctgcgctcgg tcgtcggct gcggcgagcg gtatcagctc actcaaaggc ggtaatacgg     1500
ttatccacag aatcagggga taacgcagga aagaacatgt gagcaaaagg ccagcaaaag     1560
```

-continued

```
gccaggaacc gtaaaaaggc cgcgttgctg gcgttttcc ataggctccg cccccctgac    1620
gagcatcaca aaaatcgacg ctcaagtcag aggtggcgaa acccgacagg actataaaga   1680
taccaggcgt ttccccctgg aagctccctc gtgcgctctc ctgttccgac cctgccgctt   1740
accggatacc tgtccgcctt tctcccttcg ggaagcgtgg cgctttctca atgctcacgc   1800
tgtaggtatc tcagttcggt gtaggtcgtt cgctccaagc tgggctgtgt gcacgaaccc   1860
cccgttcagc ccgaccgctg cgccttatcc ggtaactatc gtcttgagtc caacccggta   1920
agacacgact tatcgccact ggcagcagcc actggtaaca ggattagcag agcgaggtat   1980
gtaggcggtg ctacagagtt cttgaagtgg tggcctaact acggctacac tagaaggaca   2040
gtatttggta tctgcgctct gctgaagcca gttaccttcg gaaaaagagt tggtagctct   2100
tgatccggca aacaaaccac cgctggtagc ggtggttttt ttgtttgcaa gcagcagatt   2160
acgcgcagaa aaaaggatc tcaagaagat cctttgatct tttctacggg gtctgacgct   2220
cagtggaacg aaaactcacg ttaagggatt ttggtcatga gattatcaaa aaggatcttc   2280
acctagatcc ttttaaatta aaaatgaagt tttaaatcaa tctaaagtat atatgagtaa   2340
acttggtctg acagttacca atgcttaatc agtgaggcac ctatctcagc gatctgtcta   2400
tttcgttcat ccatagctgc ctgactcccc gtcgtgtaga taactacgat acgggagggc   2460
ttaccatctg gccccagtgc tgcaatgata ccgcgagacc cacgctcacc ggctccagat   2520
ttatcagcaa taaaccagcc agccggaagg gccgagcgca gaagtggtcc tgcaacttta   2580
tccgcctcca tccagtctat taattgttgc cgggaagcta gagtaagtag ttcgccagtt   2640
aatagtttgc gcaacgttgt tgccattgct acaggcatcg tggtgtcacg ctcgtcgttt   2700
ggtatggctt cattcagctc cggttcccaa cgatcaaggc gagttacatg atcccccatg   2760
ttgtgcaaaa aagcggttag ctccttcggt cctccgatcg ttgtcagaag taagttggcc   2820
gcagtgttat cactcatggt tatggcagca ctgcataatt ctcttactgt catgccatcc   2880
gtaagatgct tttctgtgac tggtgagtac tcaaccaagt cattctgaga atagtgtatg   2940
cggcgaccga gttgctcttg cccggcgtca atacgggata ataccgcgcc acatagcaga   3000
actttaaaag tgctcatcat tggaaaacgt tcttcgggc gaaaactctc aaggatctta   3060
ccgctgttga tccagttc gatgtaaccc actcgtgcac ccaactgatc ttcagcatct   3120
tttactttca ccagcgtttc tgggtgagca aaaacaggaa ggcaaaatgc cgcaaaaaag   3180
ggaataaggg cgacacggaa atgttgaata ctcatactct tcctttttca atattattga   3240
agcatttatc agggttattg tctcatgagc ggatacatat ttgaatgtat ttagaaaaat   3300
aaacaaatag gggttccgcg cacatttccc cgaaaagtgc cacctgacgt ctaagaaacc   3360
attattatca tgacattaac ctataaaaat aggcgtatca cgaggccctt tcgtcttcac   3420
```

<210> SEQ ID NO 14
<211> LENGTH: 4484
<212> TYPE: DNA
<213> ORGANISM: Escherichia coli

<400> SEQUENCE: 14

```
ctcgagaaat cataaaaaat ttatttgctt tgtgagcgga taacaattat aatagattca     60
attgtgagcg gataacaatt tcacacagaa ttcattaaag aggagaaatt aaccatgcac    120
caccaccacc accacgcgtc catggccgcg gcaaagccgt ttttccatag gctccgcccc    180
cctgacaagc atcacgaaat ctgacgctca aatcagtggt ggcgaaaccc gacaggacta    240
```

```
taaagatacc aggcgtttcc ccctggcggc tccctcgtgc gctctcctgt tcctgccttt    300
cggtttaccg gtgtcattcc gctgttatgg ccgcgtttgt ctcattccac gcctgacact    360
cagttccggg taggcagttc gctccaagct ggactgtatg cacgaacccc ccgttcagtc    420
cgaccgctgc gccttatccg gtaactatcg tcttgagtcc aacccggaaa gacatgcaaa    480
agcaccactg gcagcagcca ctggtaattg atttagagga gttagtcttg aagtcatgcg    540
ccggttaagg ctaaactgaa aggacaagtt ttggtgactg cgctcctcca agccagttac    600
ctcggttcaa agagttggta gctcagagaa ccttcgaaaa accgccctgc aaggcggttt    660
tttcgttttc agagcaagag attacgcgca gaccaaaacg atctcaagaa gatcatctta    720
ttaatcagat aaaatatttc tagatttcag tgcaatttat ctcttcaaat gtagcacctg    780
aagtcagccc catacgatat aagttgtaat tctcatgttt gacagcttat catcgataag    840
ctttaatgcg gtagtttatc acagttaaat tgctaacgca gtcaggcacc gtgtatgaaa    900
tctaacaatg cgctcatcgt catcctcggc accgtcaccc tggatgctgt aggcataggc    960
ttggttatgc cggtactgcc gggcctcttg cgggatatcg tccattccga cagcatcgcc   1020
agtcactatg gcgtgctgct agcgctatat gcgttgatgc aatttctatg cgcacccgtt   1080
ctcggagcac tgtccgaccg ctttggccgc cgcccagtcc tgctcgcttc gctacttgga   1140
gccactatcg actacgcgat catggcgacc acacccgtcc tgtgggatcc gtcgacctgc   1200
agccaagctt aattagctga gcttggactc ctgttgatag atccagtaat gacctcagaa   1260
ctccatctgg atttgttcag aacgctcggt tgccgccggg cgttttttat tggtgagaat   1320
ccaagctagc ttggcgagat tttcaggagc taaggaagct aaaatggaga aaaaaatcac   1380
tggatatacc accgttgata tatcccaatg gcatcgtaaa gaacattttg aggcatttca   1440
gtcagttgct caatgtacct ataaccagac cgttcagctg gatattacgg ccttttttaaa   1500
gaccgtaaag aaaaataagc acaagtttta tccggccttt attcacattc ttgcccgcct   1560
gatgaatgct catccggaat tccgtatggc aatgaaagac ggtgagctgg tgatatggga   1620
tagtgttcac ccttgttaca ccgttttcca tgagcaaact gaaacgtttt catcgctctg   1680
gagtgaatac cacgacgatt tccggcagtt tctacacata tattcgcaag atgtggcgtg   1740
ttacggtgaa aacctggcct atttccctaa agggtttatt gagaatatgt ttttcgtctc   1800
agccaatccc tgggtgagtt tcaccagttt tgatttaaac gtggccaata tggacaactt   1860
cttcgccccc gttttcacca tgcatggca aatattatac gcaaggcgac aaggtgctga   1920
tgccgctggc gattcaggtt catcatgccg tctgtgatgg cttccatgtc ggcagaatgc   1980
ttaatgaatt acaacagtac tgcgatgagt ggcagggcgg ggcgtaattt ttttaaggca   2040
gttattggtg cccttaaacg cctggggtaa tgactctcta gcttgaggca tcaaataaaa   2100
cgaaaggctc agtcgaaaga ctgggccttt cgttttatct gttgtttgtc ggtgaacgct   2160
ctcctgagta ggacaaatcc gccgctctag agctgcctcg cgcgtttcgg tgatgacggt   2220
gaaaacctct gacacatgca gctcccggag acggtcacag cttgtctgta agcggatgcc   2280
gggagcagac aagcccgtca gggcgcgtca gcgggtgttg gcgggtgtcg ggcgcagcc    2340
atgacccagt cacgtagcga tagcggagtg tatactggct taactatgcg gcatcagagc   2400
agattgtact gagagtgcac catatgcggt gtgaaatacc gcacagatgc gtaaggagaa   2460
aataccgcat caggcgctct tccgcttcct cgctcactga ctcgctgcgc tcggtctgtc   2520
ggctgcggcg agcggtatca gctcactcaa aggcggtaat acggttatcc acagaatcag   2580
gggataacgc aggaaagaac atgtgagcaa aaggccagca aaaggccagg aaccgtaaaa   2640
```

-continued

```
aggccgcgtt gctggcgttt ttccataggc tccgccccccc tgacgagcat cacaaaaatc    2700
gacgctcaag tcagaggtgg cgaaacccga caggactata agataccag gcgtttcccc     2760 ctggaagctc cctcgtgcgc tctcctgttc cgaccctgcc gcttaccgga tacctgtccg    2820
cctttctccc ttcgggaagc gtggcgcttt ctcaatgctc acgctgtagg tatctcagtt    2880
cggtgtaggt cgttcgctcc aagctgggct gtgtgcacga accccccgtt cagcccgacc    2940
gctgcgcctt atccggtaac tatcgtcttg agtccaaccc ggtaagacac gacttatcgc    3000
cactggcagc agccactggt aacaggatta gcagagcgag gtatgtaggc ggtgctacag    3060
agttcttgaa gtggtggcct aactacggct acactagaag gacagtattt ggtatctgcg    3120
ctctgctgaa gccagttacc ttcggaaaaa gagttggtag ctcttgatcc ggcaaacaaa    3180
ccaccgctgg tagcggtggt ttttttgttt gcaagcagca gattacgcgc agaaaaaaag    3240
gatctcaaga agatcctttg atcttttcta cggggtctga cgctcagtgg aacgaaaact    3300
cacgttaagg gattttggtc atgagattat caaaaaggat cttcacctag atccttttaa    3360
attaaaaatg aagttttaaa tcaatctaaa gtatatatga gtaaacttgg tctgacagtt    3420
accaatgctt aatcagtgag gcacctatct cagcgatctg tctatttcgt tcatccatag    3480
ctgcctgact ccccgtcgtg tagataacta cgatacggga gggcttacca tctggcccca    3540
gtgctgcaat gataccgcga gacccacgct caccggctcc agatttatca gcaataaacc    3600
agccagccgg aagggccgag cgcagaagtg gtcctgcaac tttatccgcc tccatccagt    3660
ctattaattg ttgccgggaa gctagagtaa gtagttcgcc agttaatagt ttgcgcaacg    3720
ttgttgccat tgctacaggc atcgtggtgt cacgctcgtc gtttggtatg gcttcattca    3780
gctccggttc ccaacgatca aggcgagtta catgatcccc catgttgtgc aaaaaagcgg    3840
ttagctcctt cggtcctccg atcgttgtca gaagtaagtt ggccgcagtg ttatcactca    3900
tggttatggc agcactgcat aattctctta ctgtcatgcc atccgtaaga tgcttttctg    3960
tgactggtga gtactcaacc aagtcattct gagaatagtg tatgcggcga ccgagttgct    4020
cttgcccggc gtcaatacgg gataataccg cgccacatag cagaacttta aaagtgctca    4080
tcattggaaa acgttcttcg gggcgaaaac tctcaaggat cttaccgctg ttgagatcca    4140
gttcgatgta acccactcgt gcacccaact gatcttcagc atcttttact ttcaccagcg    4200
tttctgggtg agcaaaaaca ggaaggcaaa atgccgcaaa aaagggaata agggcgacac    4260
ggaaatgttg aatactcata ctcttccttt ttcaatatta ttgaagcatt tatcagggtt    4320
attgtctcat gagcggatac atatttgaat gtatttagaa aaataaacaa ataggggttc    4380
cgcgcacatt tccccgaaaa gtgccacctg acgtctaaga aaccattatt atcatgacat    4440
taacctataa aaataggcgt atcacgaggc cctttcgtct tcac                     4484
```

<210> SEQ ID NO 15
<211> LENGTH: 750
<212> TYPE: DNA
<213> ORGANISM: Plasmodium falciparum
<220> FEATURE:
<221> NAME/KEY: CDS
<222> LOCATION: (1)..(720)

<400> SEQUENCE: 15

```
atg ttt tta aaa gga tac acc tca aat gtg gta cta att ata tta aca    48
Met Phe Leu Lys Gly Tyr Thr Ser Asn Val Val Leu Ile Ile Leu Thr
1               5                   10                  15 ttt ttc att cta cta aca aaa gaa gaa aaa aat ata aaa aat aat atc    96
```

```
Phe Phe Ile Leu Leu Thr Lys Glu Glu Lys Asn Ile Lys Asn Asn Ile
            20                  25                  30 tct gga tat tgt ttt ttg aat ttt gga tta aaa aaa aat gca ata ata      144
Ser Gly Tyr Cys Phe Leu Asn Phe Gly Leu Lys Lys Asn Ala Ile Ile
        35                  40                  45 aaa aaa aga gaa aaa caa aat ttg aaa tta ttt tgt tat aat ggt ata      192
Lys Lys Arg Glu Lys Gln Asn Leu Lys Leu Phe Cys Tyr Asn Gly Ile
 50                  55                  60 aga ata ggt caa ggt tat gat atc cac aaa ata aaa gtt tta gat gaa      240
Arg Ile Gly Gln Gly Tyr Asp Ile His Lys Ile Lys Val Leu Asp Glu
 65                  70                  75                  80 gaa tat aat aca tat gca aat aat gat ttt aat aaa aat gaa caa tct      288
Glu Tyr Asn Thr Tyr Ala Asn Asn Asp Phe Asn Lys Asn Glu Gln Ser
                 85                  90                  95 ttt aaa acc tta acc tta gga gga gtt aaa ata aat aat gtt tta gtt      336
Phe Lys Thr Leu Thr Leu Gly Gly Val Lys Ile Asn Asn Val Leu Val
            100                 105                 110 tta tca cat agt gat ggt gat ata ata tat cat tcg ata gtt gat tca      384
Leu Ser His Ser Asp Gly Asp Ile Ile Tyr His Ser Ile Val Asp Ser
        115                 120                 125 att tta ggt gcc tta ggt tct tta gac ata gga acc tta ttt cct gat      432
Ile Leu Gly Ala Leu Gly Ser Leu Asp Ile Gly Thr Leu Phe Pro Asp
130                 135                 140 aaa gat gaa aaa aat aaa aat aaa aac tcg gct ata ttc tta aga tat      480
Lys Asp Glu Lys Asn Lys Asn Lys Asn Ser Ala Ile Phe Leu Arg Tyr
145                 150                 155                 160 gct aga ctt tta ata tat aaa aaa aat tat gat att ggg aac gtg gat      528
Ala Arg Leu Leu Ile Tyr Lys Lys Asn Tyr Asp Ile Gly Asn Val Asp
            165                 170                 175 att aat gta ata gca caa gtt ccc aaa ata agc aac atc aga aaa aat      576
Ile Asn Val Ile Ala Gln Val Pro Lys Ile Ser Asn Ile Arg Lys Asn
        180                 185                 190 att ata aaa aat ata tcg aca gtg tta aat att gac gag tcg caa ata      624
Ile Ile Lys Asn Ile Ser Thr Val Leu Asn Ile Asp Glu Ser Gln Ile
             195                 200                 205 tct gtt aaa gga aaa act cat gag aaa tta gga gta att ggt gag aaa      672
Ser Val Lys Gly Lys Thr His Glu Lys Leu Gly Val Ile Gly Glu Lys
        210                 215                 220 aaa gca ata gaa tgc ttt gcg aat att ttg tta ata cct aaa aat tca      720
Lys Ala Ile Glu Cys Phe Ala Asn Ile Leu Leu Ile Pro Lys Asn Ser
225                 230                 235                 240 taatttcttt ttttttttt tttaatgtaa                                      750

<210> SEQ ID NO 16
<211> LENGTH: 240
<212> TYPE: PRT
<213> ORGANISM: Plasmodium falciparum

<400> SEQUENCE: 16

Met Phe Leu Lys Gly Tyr Thr Ser Asn Val Val Leu Ile Ile Leu Thr
1               5                   10                  15

Phe Phe Ile Leu Leu Thr Lys Glu Glu Lys Asn Ile Lys Asn Asn Ile
            20                  25                  30

Ser Gly Tyr Cys Phe Leu Asn Phe Gly Leu Lys Lys Asn Ala Ile Ile
        35                  40                  45

Lys Lys Arg Glu Lys Gln Asn Leu Lys Leu Phe Cys Tyr Asn Gly Ile
 50                  55                  60

Arg Ile Gly Gln Gly Tyr Asp Ile His Lys Ile Lys Val Leu Asp Glu
 65                  70                  75                  80
```

```
Glu Tyr Asn Thr Tyr Ala Asn Asn Asp Phe Asn Lys Asn Glu Gln Ser
                85                  90                  95

Phe Lys Thr Leu Thr Leu Gly Gly Val Lys Ile Asn Asn Val Leu Val
            100                 105                 110

Leu Ser His Ser Asp Gly Asp Ile Ile Tyr His Ser Ile Val Asp Ser
        115                 120                 125

Ile Leu Gly Ala Leu Gly Ser Leu Asp Ile Gly Thr Leu Phe Pro Asp
    130                 135                 140

Lys Asp Glu Lys Asn Lys Asn Lys Asn Ser Ala Ile Phe Leu Arg Tyr
145                 150                 155                 160

Ala Arg Leu Leu Ile Tyr Lys Lys Asn Tyr Asp Ile Gly Asn Val Asp
                165                 170                 175

Ile Asn Val Ile Ala Gln Val Pro Lys Ile Ser Asn Ile Arg Lys Asn
            180                 185                 190

Ile Ile Lys Asn Ile Ser Thr Val Leu Asn Ile Asp Glu Ser Gln Ile
        195                 200                 205

Ser Val Lys Gly Lys Thr His Glu Lys Leu Gly Val Ile Gly Glu Lys
    210                 215                 220

Lys Ala Ile Glu Cys Phe Ala Asn Ile Leu Leu Ile Pro Lys Asn Ser
225                 230                 235                 240
```

<210> SEQ ID NO 17
<211> LENGTH: 59
<212> TYPE: DNA
<213> ORGANISM: Artificial sequence
<220> FEATURE:
<223> OTHER INFORMATION: DNA linker

<400> SEQUENCE: 17
cacacagaat tcattaaaga ggagaaatta accatgggag gatccgtcga cctgcagcc    59

<210> SEQ ID NO 18
<211> LENGTH: 59
<212> TYPE: DNA
<213> ORGANISM: Artificial sequence
<220> FEATURE:
<223> OTHER INFORMATION: DNA linker

<400> SEQUENCE: 18
ggctgcaggt cgacggatcc tcccatggtt aatttctcct ctttaatgaa ttctgtgtg    59

<210> SEQ ID NO 19
<211> LENGTH: 36
<212> TYPE: DNA
<213> ORGANISM: Artificial sequence
<220> FEATURE:
<223> OTHER INFORMATION: DNA linker

<400> SEQUENCE: 19
catgcaccac caccaccacc acgcgtccat ggccgc                              36

<210> SEQ ID NO 20
<211> LENGTH: 30
<212> TYPE: DNA
<213> ORGANISM: Artificial sequence
<220> FEATURE:
<223> OTHER INFORMATION: DNA linker

<400> SEQUENCE: 20
ggccatggac gcgtggtggt ggtggtggtg                                     30

<210> SEQ ID NO 21
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 21
aaattaacca tggcaaccac tcatttgg                                    28

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 22
ttgggcctgc agcgccaaag g                                           21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 23
ttgttgtgaa ggagaagagt g                                           21

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 24
catgcatacc cttgacacgt c                                           21

<210> SEQ ID NO 25
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 25
caatgttgtt gccatggaga ag                                          22

<210> SEQ ID NO 26
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 26
acacgtcttc tgcagaagta aatg                                        24

<210> SEQ ID NO 27
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 27
cttctctcag gcgagataaa acatgg                                      26

<210> SEQ ID NO 28
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 28
ggcgagagga tccatggcga tgtctcagac g                                31

<210> SEQ ID NO 29
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 29
gaggagaaat taaccatgcg gacacagtgg cc                               32

<210> SEQ ID NO 30
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 30
gtcaccgaac tgcagcttgc ccg                                         23

<210> SEQ ID NO 31
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 31
acacagaatt cattaaagag gagaaattaa ccatg                            35

<210> SEQ ID NO 32
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 32
ctgatgagag gcttaataag atagg                                       25

<210> SEQ ID NO 33
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 33
ttacatgttt gtaacatctc attgg                                       25

<210> SEQ ID NO 34

```
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 34
gttgacacca tggctccttt gtcc                                          24

<210> SEQ ID NO 35
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 35
tgtttgtctg cagctcattg gaaatcc                                       27

<210> SEQ ID NO 36
<211> LENGTH: 22
<212> TYPE: DNA
<213> ORGANISM: Artificial sequence
<220> FEATURE:
<223> OTHER INFORMATION: Synthetic oligonucleotide primer

<400> SEQUENCE: 36
ggtgacatat cagatcaaag ag                                            22

<210> SEQ ID NO 37
<211> LENGTH: 36
<212> TYPE: DNA
<213> ORGANISM: Artificial sequence
<220> FEATURE:
<223> OTHER INFORMATION: Synthetic oligonucleotide primer

<400> SEQUENCE: 37
agaaacagga tccatggcaa cggcttctcc tcctcc                             36

<210> SEQ ID NO 38
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 38
ggtacagaca attactttg gattcatc                                       28

<210> SEQ ID NO 39
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 39
aagagatgga agaacttcaa aggcaggagg                                    30

<210> SEQ ID NO 40
<211> LENGTH: 67
<212> TYPE: DNA
<213> ORGANISM: Artificial sequence
<220> FEATURE:
<223> OTHER INFORMATION: Synthetic oligonucleotide primer

<400> SEQUENCE: 40
```

```
ctgattatca aagccctcaa tctttatcgt aaaaagaccg gtacagacaa ttacttttgg    60
attcatc                                                              67

<210> SEQ ID NO 41
<211> LENGTH: 69
<212> TYPE: DNA
<213> ORGANISM: Artificial sequence
<220> FEATURE:
<223> OTHER INFORMATION: Synthetic oligonucleotide primer

<400> SEQUENCE: 41
gaccgcggcc agcagcaatt acacgttgtt ttaaacgttt aagagatgga agaacttcaa    60
agcaggagg                                                            69

<210> SEQ ID NO 42
<211> LENGTH: 65
<212> TYPE: DNA
<213> ORGANISM: Artificial sequence
<220> FEATURE:
<223> OTHER INFORMATION: Synthetic oligonucleotide primer

<400> SEQUENCE: 42
actaatgttg ctggcgttcc actcgatgag cgtaatctga ttatcaaagc cctcaatctt    60
tatcg                                                                65

<210> SEQ ID NO 43
<211> LENGTH: 63
<212> TYPE: DNA
<213> ORGANISM: Artificial sequence
<220> FEATURE:
<223> OTHER INFORMATION: Synthetic oligonucleotide primer

<400> SEQUENCE: 43
tgtgctgcca ctaccagaca tgaagactgc atcatattga ccgcggccag cagcaattac    60
acg                                                                  63

<210> SEQ ID NO 44
<211> LENGTH: 72
<212> TYPE: DNA
<213> ORGANISM: Artificial sequence
<220> FEATURE:
<223> OTHER INFORMATION: Synthetic oligonucleotide primer

<400> SEQUENCE: 44
aaaattaagt tctcgctgtc accatcgaaa tcaaggatc gtttatctac taatgttgct     60
ggcgttccac tc                                                        72

<210> SEQ ID NO 45
<211> LENGTH: 67
<212> TYPE: DNA
<213> ORGANISM: Artificial sequence
<220> FEATURE:
<223> OTHER INFORMATION: Synthetic oligonucleotide primer

<400> SEQUENCE: 45
catagacaaa ttgtggcgat ctggagagcc aacacctacg attgtgctgc cactaccaga    60
catgaag                                                              67

<210> SEQ ID NO 46
<211> LENGTH: 74
<212> TYPE: DNA
```

```
<213> ORGANISM: Artificial sequence
<220> FEATURE:
<223> OTHER INFORMATION: Synthetic oligonucleotide primer

<400> SEQUENCE: 46
gacggttatc atgatctggc gtctctcttt catgtaatta gtcttggcga taaaattaag    60
ttctcgctgt cacc                                                      74

<210> SEQ ID NO 47
<211> LENGTH: 63
<212> TYPE: DNA
<213> ORGANISM: Artificial sequence
<220> FEATURE:
<223> OTHER INFORMATION: Synthetic oligonucleotide primer

<400> SEQUENCE: 47
tgcttctgac aagaagacat ctttgtactc ttcgtcatca tagacaaatt gtggcggatc    60
tgg                                                                  63

<210> SEQ ID NO 48
<211> LENGTH: 76
<212> TYPE: DNA
<213> ORGANISM: Artificial sequence
<220> FEATURE:
<223> OTHER INFORMATION: Synthetic oligonucleotide primer

<400> SEQUENCE: 48
ttttctcctt gcaagattaa tgttttcctg cgcatcacaa gcaaacgtga tgacggttat    60
catgatctgg cgtctc                                                    76

<210> SEQ ID NO 49
<211> LENGTH: 62
<212> TYPE: DNA
<213> ORGANISM: Artificial sequence
<220> FEATURE:
<223> OTHER INFORMATION: Synthetic oligonucleotide primer

<400> SEQUENCE: 49
caacatacca ctcgttggct ggacgagtga tgaaacttgc ttctgacaag aagacatctt    60
tg                                                                   62

<210> SEQ ID NO 50
<211> LENGTH: 60
<212> TYPE: DNA
<213> ORGANISM: Artificial sequence
<220> FEATURE:
<223> OTHER INFORMATION: Synthetic oligonucleotide primer

<400> SEQUENCE: 50
cgtgaagctg gtctttcacg cctcactctt ttttctcctt gcaagattaa tgttttcctg    60

<210> SEQ ID NO 51
<211> LENGTH: 61
<212> TYPE: DNA
<213> ORGANISM: Artificial sequence
<220> FEATURE:
<223> OTHER INFORMATION: Synthetic oligonucleotide primer

<400> SEQUENCE: 51
caggttgatc accaatagtg ctacctgaaa caggttcaac ataccactcg ttggctggac    60
g                                                                    61
```

<210> SEQ ID NO 52
<211> LENGTH: 63
<212> TYPE: DNA
<213> ORGANISM: Artificial sequence
<220> FEATURE:
<223> OTHER INFORMATION: Synthetic oligonucleotide primer

<400> SEQUENCE: 52
ataatagaat tcattaaaga ggagaaatta accatggatc gtgaagctgg tctttcacgc    60
ctc                                                                  63

<210> SEQ ID NO 53
<211> LENGTH: 67
<212> TYPE: DNA
<213> ORGANISM: Artificial sequence
<220> FEATURE:
<223> OTHER INFORMATION: Synthetic oligonucleotide primer

<400> SEQUENCE: 53
tattattata agcttaagac atgtcaaaag atgtagagaa ctcaggttga tcaccaatag    60
tgctacc                                                              67

<210> SEQ ID NO 54
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 54
gagcggataa caattataat agattc                                         26

<210> SEQ ID NO 55
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 55
ctccatttta gcttccttag ctcctg                                         26

<210> SEQ ID NO 56
<211> LENGTH: 37
<212> TYPE: DNA
<213> ORGANISM: Artificial sequence
<220> FEATURE:
<223> OTHER INFORMATION: Synthetic oligonucleotide primer

<400> SEQUENCE: 56
gaggagaaat taaccatgcg aattggacac ggttttg                             37

<210> SEQ ID NO 57
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 57
tattatctgc agccttgcgg tttaccgtgg agg                                 33

<210> SEQ ID NO 58
<211> LENGTH: 35
<212> TYPE: DNA

```
<213> ORGANISM: Artificial sequence
<220> FEATURE:
<223> OTHER INFORMATION: Synthetic oligonucleotide primer

<400> SEQUENCE: 58
acacagaatt cattaaagag gagaaattaa ccatg                          35

<210> SEQ ID NO 59
<211> LENGTH: 36
<212> TYPE: DNA
<213> ORGANISM: Artificial sequence
<220> FEATURE:
<223> OTHER INFORMATION: Synthetic oligonucleotide primer

<400> SEQUENCE: 59
gagaaggatc catgcgaatt ggacacggtt ttgacg                         36

<210> SEQ ID NO 60
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 60
tccatatgga tccatgtttt taaaaggata cacc                           34

<210> SEQ ID NO 61
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 61
gacctgcctg cagttatgaa ttttttaggta ttaac                         35

<210> SEQ ID NO 62
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 62
ttatttggat ccatgggtat aagaataggt caagg                          35

<210> SEQ ID NO 63
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 63
tgatccgcca tggatctttt atcaatacag g                              31

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 64
ttgaatagag gatccccgcc                                           20
```

<210> SEQ ID NO 65
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 65
ggaggatcca tgaagcaact cacc                                          24

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 66
gcgcgactct ctgcagccgg                                               20

<210> SEQ ID NO 67
<211> LENGTH: 236
<212> TYPE: PRT
<213> ORGANISM: Escherichia coli

<400> SEQUENCE: 67

Met Ala Thr Thr His Leu Asp Val Cys Ala Val Val Pro Ala Ala Gly
1               5                   10                  15

Phe Gly Arg Arg Met Gln Thr Glu Cys Pro Lys Gln Tyr Leu Ser Ile
            20                  25                  30

Gly Asn Gln Thr Ile Leu Glu His Ser Val His Ala Leu Leu Ala His
        35                  40                  45

Pro Arg Val Lys Arg Val Val Ile Ala Ile Ser Pro Gly Asp Ser Arg
    50                  55                  60

Phe Ala Gln Leu Pro Leu Ala Asn His Pro Gln Ile Thr Val Val Asp
65                  70                  75                  80

Gly Gly Asp Glu Arg Ala Asp Ser Val Leu Ala Gly Leu Lys Ala Ala
                85                  90                  95

Gly Asp Ala Gln Trp Val Leu Val His Asp Ala Ala Arg Pro Cys Leu
            100                 105                 110

His Gln Asp Asp Leu Ala Arg Leu Leu Ala Leu Ser Glu Thr Ser Arg
        115                 120                 125

Thr Gly Gly Ile Leu Ala Ala Pro Val Arg Asp Thr Met Lys Arg Ala
    130                 135                 140

Glu Pro Gly Lys Asn Ala Ile Ala His Thr Val Asp Arg Asn Gly Leu
145                 150                 155                 160

Trp His Ala Leu Thr Pro Gln Phe Phe Pro Arg Glu Leu Leu His Asp
                165                 170                 175

Cys Leu Thr Arg Ala Leu Asn Glu Gly Ala Thr Ile Thr Asp Glu Ala
            180                 185                 190

Ser Ala Leu Glu Tyr Cys Gly Phe His Pro Gln Leu Val Glu Gly Arg
        195                 200                 205

Ala Asp Asn Ile Lys Val Thr Arg Pro Glu Asp Leu Ala Leu Ala Glu
    210                 215                 220

Phe Tyr Leu Thr Arg Thr Ile His Gln Glu Asn Thr
225                 230                 235

<210> SEQ ID NO 68
<211> LENGTH: 225
<212> TYPE: PRT
<213> ORGANISM: Haemophilus influenzae

<400> SEQUENCE: 68

Met Ala Arg Ser Ile Ala Val Leu Pro Ala Ala Gly Val Gly Ser
1               5                   10                  15

Arg Met Gln Ala Asp Lys Pro Lys Gln Tyr Leu Thr Leu Leu Gly Lys
            20                  25                  30

Thr Leu Leu Glu His Thr Leu Asp Val Met Leu Ser Tyr Pro Ala Val
                35                  40                  45

Ser Lys Ile Ile Leu Ala Val Ser Lys Asp Asp Pro Tyr Ile Ser Thr
        50                  55                  60

Leu Ser Leu Asp Pro Lys Ile Gln Leu Val Glu Gly Gly Thr Thr Arg
65                  70                  75                  80

Ala Glu Ser Val Leu Asn Gly Leu Asn Ala Ile Ala Glu Lys Asn Ala
                85                  90                  95

Trp Val Leu Val His Asp Ala Ala Arg Pro Cys Leu Gln His Ala Asp
            100                 105                 110

Ile Asp Lys Leu Leu Ala Ile Glu Asp Lys Gln Gly Ala Ile Leu Ala
        115                 120                 125

Ile Pro Val Thr Asp Thr Ile Lys Arg Ala Asp Asn Gln Gln Cys Ile
    130                 135                 140

Val Lys Thr Glu Asp Arg Ser Gln Leu Trp Gln Ala Met Thr Pro Gln
145                 150                 155                 160

Phe Phe Pro Val Asp Ile Leu Arg Asp Ala Leu Ser Thr Gly Ile Gln
                165                 170                 175

Gln Gly Ala Asn Ile Thr Asp Glu Ala Ser Ala Ile Glu Leu Ala Gly
            180                 185                 190

Phe Arg Pro His Leu Val Ala Gly Arg Ser Asp Asn Leu Lys Val Thr
        195                 200                 205

Arg Pro Glu Asp Leu Ala Leu Ala Glu Phe Tyr Leu Thr Arg Asn Lys
    210                 215                 220

Leu
225

<210> SEQ ID NO 69
<211> LENGTH: 231
<212> TYPE: PRT
<213> ORGANISM: Bacillus subtilis

<400> SEQUENCE: 69

Met Ser Tyr Asp Val Val Ile Pro Ala Ala Gly Gln Gly Lys Arg Met
1               5                   10                  15

Lys Ala Gly Arg Asn Lys Leu Phe Ile Glu Leu Lys Gly Asp Pro Val
            20                  25                  30

Ile Ile His Thr Leu Arg Val Phe Asp Ser His Arg Gln Cys Asp Lys
        35                  40                  45

Ile Ile Leu Val Ile Asn Glu Gln Asp Arg Glu His Phe Gln Gln Leu
    50                  55                  60

Leu Ser Asp Tyr Pro Phe Gln Thr Ser Ile Glu Leu Val Ala Gly Gly
65                  70                  75                  80

Asp Glu Arg Gln His Ser Val Tyr Lys Gly Leu Lys Ala Val Lys Gln
                85                  90                  95

Glu Lys Ile Val Leu Val His Asp Gly Ala Arg Pro Phe Ile Lys His

```
                100             105             110
Glu Gln Ile Asp Glu Leu Ile Ala Glu Ala Gln Thr Gly Ala Ala
            115                 120                 125

Ile Leu Ala Val Pro Val Lys Asp Thr Ile Lys Arg Val Gln Asp Leu
130                 135                 140

Gln Val Ser Glu Thr Ile Glu Arg Ser Ser Leu Trp Ala Val Gln Thr
145                 150                 155                 160

Pro Gln Ala Phe Arg Leu Ser Leu Leu Met Lys Ala His Ala Glu Ala
                165                 170                 175

Glu Arg Lys Gly Phe Leu Gly Thr Asp Asp Ala Ser Leu Val Glu Gln
            180                 185                 190

Met Glu Gly Gly Ser Val Arg Val Val Glu Gly Ser Tyr Thr Asn Ile
            195                 200                 205

Lys Leu Thr Thr Pro Asp Asp Leu Thr Ser Ala Glu Ala Ile Met Glu
            210                 215                 220

Ser Glu Ser Gly Asn Lys His
225                 230

<210> SEQ ID NO 70
<211> LENGTH: 230
<212> TYPE: PRT
<213> ORGANISM: Aquifex aeolicus

<400> SEQUENCE: 70

Met His Leu Leu Ile Pro Ala Ala Gly Ser Gly Lys Arg Met Gly Ser
1               5                   10                  15

Gly His Asn Lys Leu Leu Leu Asn Val Leu Gly Gln Pro Leu Leu Ser
            20                  25                  30

Trp Thr Val Gln Ala Ala Leu Ala Ser Gln Ser Ile Glu Trp Ile Gly
            35                  40                  45

Ile Met Gly Gln Pro Tyr Asp Phe Pro Ala Phe Glu Ala Leu Leu Thr
        50                  55                  60

Pro Leu His Ser Pro Lys Pro Val Gln Leu Ile Val Gly Gly Asp Thr
65                  70                  75                  80

Arg Gln Gln Ser Val Phe Asn Gly Ile Gln Ala Leu Pro Pro Gly Ala
                85                  90                  95

Lys Phe Val Leu Ile His Asp Gly Ala Arg Cys Leu Ala Thr Pro Asp
            100                 105                 110

Leu Phe Asp Arg Cys Thr Glu Ala Leu Gln His Cys Gln Gly Leu Ile
            115                 120                 125

Ala Ala Met Pro Val Lys Asp Thr Ile Lys Ile Val Asn Ala Asp Gly
130                 135                 140

Trp Ile Thr Asp Thr Pro Asp Arg Gln Gly Leu Trp Gly Ala Gln Thr
145                 150                 155                 160

Pro Gln Gly Phe Asp Val Ala Leu Leu Lys Ala Cys His Asp Lys Gly
                165                 170                 175

Lys Gln Glu Gly Trp Glu Val Thr Asp Asp Ala Ala Leu Leu Glu Lys
            180                 185                 190

Cys Gly Gln Pro Val Lys Ile Val Pro Gly Glu Asp Thr Asn Leu Lys
            195                 200                 205

Ile Thr Thr Pro Val Asp Leu Ala Ile Ala Glu Phe Ile Leu Gly Gln
            210                 215                 220

Arg Ser Ala Lys Ser Ala
225                 230
```

```
<210> SEQ ID NO 71
<211> LENGTH: 231
<212> TYPE: PRT
<213> ORGANISM: Mycobacterium tuberculosis

<400> SEQUENCE: 71

Met Val Arg Glu Ala Gly Glu Val Val Ala Ile Val Pro Ala Ala Gly
1               5                   10                  15

Ser Gly Glu Arg Leu Ala Val Gly Val Pro Lys Ala Phe Tyr Gln Leu
            20                  25                  30

Asp Gly Gln Thr Leu Ile Glu Arg Ala Val Asp Gly Leu Leu Asp Ser
        35                  40                  45

Gly Val Val Asp Thr Val Val Ala Val Pro Ala Asp Arg Thr Asp
    50                  55                  60

Glu Ala Arg Gln Ile Leu Gly His Arg Ala Met Ile Val Ala Gly Gly
65                  70                  75                  80

Ser Asn Arg Thr Asp Thr Val Asn Leu Ala Leu Thr Val Leu Ser Gly
                85                  90                  95

Thr Ala Glu Pro Glu Phe Val Leu Val His Asp Ala Ala Arg Ala Leu
            100                 105                 110

Thr Pro Pro Ala Leu Val Ala Arg Val Glu Ala Leu Arg Asp Gly
        115                 120                 125

Tyr Ala Ala Val Val Pro Val Leu Pro Leu Ser Asp Thr Ile Lys Ala
    130                 135                 140

Val Asp Ala Asn Gly Val Val Leu Gly Thr Pro Glu Arg Ala Gly Leu
145                 150                 155                 160

Arg Ala Val Gln Thr Pro Gln Gly Phe Thr Thr Asp Leu Leu Leu Arg
                165                 170                 175

Ser Tyr Gln Arg Gly Ser Leu Asp Leu Pro Ala Ala Glu Tyr Thr Asp
            180                 185                 190

Asp Ala Ser Leu Val Glu His Ile Gly Gly Gln Val Gln Val Val Asp
        195                 200                 205

Gly Asp Pro Leu Ala Phe Lys Ile Thr Thr Lys Leu Asp Leu Leu Leu
    210                 215                 220

Ala Gln Ala Ile Val Arg Gly
225                 230

<210> SEQ ID NO 72
<211> LENGTH: 213
<212> TYPE: PRT
<213> ORGANISM: Aquifex aeolicus

<400> SEQUENCE: 72

Met Tyr Thr Ala Ile Ile Leu Ala Ala Gly Arg Gly Ser Arg Ile Gly
1               5                   10                  15

Phe Arg Lys Gln Phe Ala Thr Leu Cys Gly Lys Pro Leu Phe Met His
            20                  25                  30

Ser Leu Glu Lys Val Leu Asp Ile Phe Glu Glu Val Ile Leu Val Leu
        35                  40                  45

Pro Glu Asp Phe Leu Asp Lys Val Lys Val His Pro Lys Val Lys Lys
    50                  55                  60

Val Ala Gly Gly Pro Glu Arg Gln Asp Ser Val Phe Asn Ala Leu Leu
65                  70                  75                  80

Gln Ala Thr Gly Asp Ile Val Val Ile His Asp Ser Ala Arg Pro Leu
                85                  90                  95
```

```
Ala Thr Lys Lys Met Phe Leu Glu Val Ala Gln Leu Gly Asp Tyr His
            100                 105                 110

Gly Lys Val Val Ala Ser Pro Ala Arg Asp Thr Leu Lys Glu Val Val
            115                 120                 125

Glu Gly Lys Val Ile Lys Thr Leu Asn Arg Ser Leu Ile Trp His Ala
            130                 135                 140

Gln Thr Pro Gln Ala Phe Arg Arg Asp Ile Leu Leu Glu Cys His Met
145                 150                 155                 160

Arg Ala Lys Ala Glu Gly Phe Val Gly Thr Asp Asp Ala Ser Leu Leu
                165                 170                 175

Glu Arg Tyr Gly Tyr Ser Val Gly Val Val Gly Ser Tyr Trp Asn
            180                 185                 190

Val Lys Ile Thr Tyr Pro Glu Asp Leu Glu Met Val Lys Lys Ile Met
            195                 200                 205

Gly Cys Glu Glu Asp
    210

<210> SEQ ID NO 73
<211> LENGTH: 219
<212> TYPE: PRT
<213> ORGANISM: Chlamydia trachomatis

<400> SEQUENCE: 73

Met Asn Leu Ser Cys Ser Leu Val Leu Leu Gly Gly Lys Gly Glu
1               5                   10                  15

Arg Phe Asn Ser Leu Gln Pro Lys Gln Tyr Thr His Leu Cys Gly Glu
            20                  25                  30

Pro Leu Ile Leu His Ala Leu His Ala Tyr Gln Arg Leu Pro Phe Val
            35                  40                  45

Gln Glu Val Val Val Cys Glu Glu Gln Tyr Arg Glu Leu Phe Leu
    50                  55                  60

Pro Tyr Ser Val Lys Phe Ala Ser Pro Gly Thr Leu Arg Gln Asp Ser
65                  70                  75                  80

Val Phe Ser Gly Leu Gln Gln Val Ser Thr Pro Trp Val Cys Ile His
                85                  90                  95

Asp Gly Val Arg Pro Phe Val Tyr Ala Asp Glu Val Ile Glu Val Cys
            100                 105                 110

Ser Ala Ala Arg Lys Thr Gly Ala Ala Ala Leu Ala Ser Pro Ala Thr
            115                 120                 125

Tyr Thr Ile Lys Ser Cys Ala Pro Val Arg Thr Leu Asp Arg Asp Ala
            130                 135                 140

Leu Ala Val Ile His Thr Pro Gln Cys Leu Asp Thr Glu Val Leu Arg
145                 150                 155                 160

Glu Gly Leu Leu Leu Ala Arg Ala Met Asp Phe Ser Leu Ser Asp Asp
                165                 170                 175

Thr Glu Ala Ala Glu Leu Leu Gly Ile Glu Pro Thr Leu Val Phe Ser
            180                 185                 190

Asn Arg Val Gln Ile Lys Val Thr Tyr Pro Glu Asp Leu Leu Phe Ala
            195                 200                 205

Glu Thr Leu Leu Ser Lys Ser Ser Thr Tyr Lys
    210                 215

<210> SEQ ID NO 74
<211> LENGTH: 211
<212> TYPE: PRT
<213> ORGANISM: Chlamydia pneumoniae
```

<400> SEQUENCE: 74

```
Met Ile Lys Ser Ser Leu Ile Leu Leu Ser Gly Gln Gly Thr Arg
1               5                   10                  15

Phe Gly Ser Lys Ile Pro Lys Gln Tyr Leu Pro Leu Asn Gly Thr Pro
            20                  25                  30

Leu Val Leu His Ser Leu Lys Ile Leu Ser Ser Leu Pro Gln Ile Ala
        35                  40                  45

Glu Val Ile Val Val Cys Asp Pro Ser Tyr Gln Glu Thr Phe Gln Glu
    50                  55                  60

Tyr Pro Val Ser Phe Ala Ile Pro Gly Glu Arg Arg Gln Asp Ser Val
65                  70                  75                  80

Phe Ser Gly Leu Gln Gln Val Ser Tyr Pro Trp Val Ile Ile His Asp
                85                  90                  95

Gly Ala Arg Pro Phe Ile Tyr Pro Asp Glu Ile His Asp Leu Leu Glu
            100                 105                 110

Thr Ala Glu Lys Ile Gly Ala Thr Ala Leu Ala Ser Pro Ile Pro Tyr
        115                 120                 125

Thr Ile Lys Gln Arg Asn Pro Val Arg Thr Leu Asp Arg Asp Asn Leu
    130                 135                 140

Ala Ile Ile His Thr Pro Gln Cys Ile Lys Thr Glu Ile Leu Arg Glu
145                 150                 155                 160

Gly Leu Ala Leu Ala Lys Glu Lys Gln Leu Thr Leu Val Asp Asp Ile
                165                 170                 175

Glu Ala Ala Glu Ile Ile Gly Lys Pro Ser Gln Leu Val Phe Asn Lys
            180                 185                 190

His Pro Gln Ile Lys Ile Ser Tyr Pro Glu Asp Leu Thr Ile Ala Gln
        195                 200                 205

Ala Leu Leu
    210
```

<210> SEQ ID NO 75
<211> LENGTH: 222
<212> TYPE: PRT
<213> ORGANISM: Thermotoga maritima

<400> SEQUENCE: 75

```
Met Asn Val Ala Ile Leu Leu Ala Ala Gly Lys Gly Glu Arg Met Ser
1               5                   10                  15

Glu Asn Val Pro Lys Gln Phe Leu Glu Ile Glu Gly Arg Met Leu Phe
            20                  25                  30

Glu Tyr Pro Leu Ser Thr Phe Leu Lys Ser Glu Ala Ile Asp Gly Val
        35                  40                  45

Val Ile Val Thr Arg Arg Glu Trp Phe Glu Val Val Glu Lys Arg Val
    50                  55                  60

Phe His Glu Lys Val Leu Gly Ile Val Glu Gly Asp Thr Arg Ser
65                  70                  75                  80

Gln Ser Val Arg Ser Ala Leu Glu Phe Leu Lys Phe Ser Pro Ser
                85                  90                  95

Tyr Val Leu Val His Asp Ser Ala Arg Pro Phe Leu Arg Lys Lys His
            100                 105                 110

Val Ser Glu Val Leu Arg Arg Ala Glu Thr Gly Ala Ala Thr Leu
        115                 120                 125

Ala Leu Lys Asn Ser Asp Ala Leu Val Arg Val Glu Asn Asp Arg Ile
    130                 135                 140
```

```
Glu Tyr Ile Pro Arg Lys Gly Val Tyr Arg Ile Leu Thr Pro Gln Ala
145                 150                 155                 160

Phe Ser Tyr Glu Ile Leu Lys Lys Ala His Glu Asn Gly Gly Glu Trp
                165                 170                 175

Ala Asp Asp Thr Glu Pro Val Gln Lys Leu Gly Val Lys Ile Ala Leu
            180                 185                 190

Val Glu Gly Asp Pro Leu Cys Phe Lys Val Thr Phe Lys Glu Asp Leu
            195                 200                 205

Glu Leu Ala Arg Ile Ile Ala Arg Glu Trp Glu Arg Ile Pro
    210                 215                 220
```

<210> SEQ ID NO 76
<211> LENGTH: 229
<212> TYPE: PRT
<213> ORGANISM: Pyrococcus horikoshii

<400> SEQUENCE: 76

```
Met Val Thr Leu Ile Leu Leu Ala Gly Gly Ser Gly Thr Arg Ala Ser
1               5                   10                  15

Leu Asn Leu Pro Lys Gln Tyr Tyr Arg Ile Glu Glu Lys Met Val Ile
                20                  25                  30

Glu Tyr Thr Leu Glu Asn Val Ser Arg Val Lys Gly Val Asp Asn Ile
                35                  40                  45

Ile Leu Val Ser Asn Pro Arg Phe Met Asp Thr Ala Leu Glu Leu Lys
        50                  55                  60

Glu Ser Phe Pro Lys Ile Lys Asp Val Ala Lys Gly Gly Arg Thr Arg
65                  70                  75                  80

Asn Glu Ser Ile Tyr Asn Gly Phe Met Lys Val Pro Gln Lys Glu Ser
                85                  90                  95

Lys Ile Leu Val His Asp Ala Val Arg Pro Phe Thr Pro Arg Trp Val
            100                 105                 110

Phe Glu Arg Ile Ile Ser Leu Leu Asp Glu Arg Asp Val Ile Thr Thr
        115                 120                 125

Val Asn Pro Ile Thr Gly Asn Leu Ile Glu Leu Asp Asn Gly Lys Val
    130                 135                 140

Lys Arg Ile Tyr Asp Arg Ser Lys Phe Ala Ile Gly Glu Ala Pro Thr
145                 150                 155                 160

Gly Tyr Arg Tyr Gly Ala Leu Lys Lys Thr Leu Glu Val Ala Val Ser
                165                 170                 175

Asn Gly Thr Leu Asn Glu Ile Pro His Asp Ile Val Leu Ala Met Asn
            180                 185                 190

Ala Gly Phe Asp Val Tyr Val Leu Pro Cys Asn Cys Phe Asn Leu Lys
        195                 200                 205

Ile Thr Phe Lys Glu Asp Ile Glu Ile Ala Arg Thr Leu Ile Lys Met
    210                 215                 220

Leu Glu Glu Arg Glu
225
```

<210> SEQ ID NO 77
<211> LENGTH: 409
<212> TYPE: PRT
<213> ORGANISM: Helicobacter pylori

<400> SEQUENCE: 77

```
Met Ser Leu Ile Arg Val Asn Gly Glu Ala Phe Lys Leu Ser Leu Glu
1               5                   10                  15
```

```
Ser Leu Glu Glu Asp Pro Phe Glu Thr Lys Glu Thr Leu Thr Leu
            20                  25                  30

Glu Thr Leu Ile Lys Gln Thr Ser Val Val Leu Ala Ala Gly Glu
            35                  40                  45

Ser Lys Arg Phe Ser Arg Ala Ile Lys Lys Gln Trp Leu Arg Ser His
        50                  55                  60

His Thr Pro Leu Trp Leu Ser Val Tyr Glu Ser Phe Lys Glu Ala Leu
65                  70                  75                  80

Asp Phe Lys Glu Val Ile Leu Val Val Ser Glu Leu Asp Tyr Val Tyr
                85                  90                  95

Ile Gln Arg His Tyr Pro Lys Ile Lys Leu Val Lys Gly Gly Ala Ser
                100                 105                 110

Arg Gln Glu Ser Val Arg Asn Ala Leu Lys Val Ile Asp Ser Thr Tyr
            115                 120                 125

Thr Ile Thr Ser Asp Val Ala Arg Gly Leu Ala Asn Met Glu Ala Leu
        130                 135                 140

Lys Ser Leu Phe Leu Thr Leu Gln Gln Thr Ser His Tyr Cys Ile Ala
145                 150                 155                 160

Pro Tyr Leu Pro Cys Tyr Asp Thr Ala Ile Tyr Tyr Asn Glu Ala Leu
                165                 170                 175

Asp Arg Glu Ala Ile Lys Leu Ile Gln Thr Pro Gln Leu Ser His Thr
            180                 185                 190

Lys Thr Leu Gln Ser Ala Leu Asn Gln Gly Gly Phe Lys Asp Glu Ser
        195                 200                 205

Ser Ala Ile Leu Gln Ala Phe Pro Asn Ser Val Ser Tyr Ile Glu Gly
        210                 215                 220

Ser Lys Asp Leu His Lys Leu Thr Thr Ser Gly Asp Leu Lys Phe Phe
225                 230                 235                 240

Thr Pro Phe Phe Asn Pro Ala Lys Asp Thr Phe Ile Gly Met Gly Phe
                245                 250                 255

Asp Thr His Ala Phe Ile Lys Asp Lys Pro Met Val Leu Gly Gly Val
            260                 265                 270

Val Leu Asp Cys Glu Phe Gly Leu Lys Ala His Ser Asp Gly Asp Ala
        275                 280                 285

Leu Leu His Ala Val Ile Asp Ala Ile Leu Gly Ala Ile Lys Gly Gly
        290                 295                 300

Asp Ile Gly Glu Trp Phe Pro Asp Asn Asp Pro Lys Tyr Lys Asn Ala
305                 310                 315                 320

Ser Ser Lys Glu Leu Leu Lys Ile Val Leu Asp Phe Ser Gln Ser Ile
                325                 330                 335

Gly Phe Glu Leu Leu Glu Met Gly Ala Thr Ile Phe Ser Glu Ile Pro
            340                 345                 350

Lys Ile Thr Pro Tyr Lys Pro Ala Ile Leu Glu Asn Leu Ser Gln Leu
        355                 360                 365

Leu Gly Leu Glu Lys Ser Gln Ile Ser Leu Lys Ala Thr Thr Met Glu
        370                 375                 380

Lys Met Gly Phe Ile Gly Lys Gln Glu Gly Leu Leu Val Gln Ala His
385                 390                 395                 400

Val Ser Met Arg Tyr Lys Gln Lys Leu
                405

<210> SEQ ID NO 78
<211> LENGTH: 399
```

```
<212> TYPE: PRT
<213> ORGANISM: Treponema pallidum

<400> SEQUENCE: 78

Met Arg Arg Gly Gly Ala Cys Val Gln Lys Lys Glu Tyr Leu Pro Leu
1               5                   10                  15

Thr Ser Arg Gln Pro Gly Val Cys Leu Leu Ser Glu Ile Leu Val Arg
                20                  25                  30

Ala Leu Glu Ala Arg Ser Phe Phe Leu Val Val Thr Val Pro Ala
            35                  40                  45

Gly Glu Val Ala Tyr Ala Glu Ser Gln Val Ala Cys Asp Ser Arg Leu
    50                  55                  60

Ser Ala Phe Pro Ser Arg Thr Arg Pro Val Ile Leu Tyr Val Pro Gly
65                  70                  75                  80

Ala His Thr Arg Ser Ala Ser Val Arg Ala Gly Leu Asp Ala Met Ala
                85                  90                  95

Thr His Ala Pro Asp Val Val Leu Val His Asp Gly Ala Arg Pro Phe
            100                 105                 110

Val Ser Val Ala Leu Ile His Ser Val Leu Glu Ala Thr Cys Arg Tyr
        115                 120                 125

Gly Ala Ala Val Pro Val Ile Glu Ala Thr Asp Thr Pro Lys Gly Val
130                 135                 140

Ala Ala Asp Gly Ser Ile Glu Thr His Leu Ile Arg Ser Arg Val Arg
145                 150                 155                 160

Leu Ala Gln Thr Pro Gln Gly Phe Cys Tyr Ala Ser Leu Cys Ala Ala
                165                 170                 175

His His Arg Ala Ala Thr Asp Gly Glu Gln Tyr Thr Asp Asp Ser Glu
            180                 185                 190

Leu Tyr Ala Arg Tyr Gly Gly Thr Val His Val Cys Ala Gly Glu Arg
        195                 200                 205

Ser Asn Val Lys Ile Thr Tyr Pro Glu Asp Leu Glu Gln Arg Ala Ser
    210                 215                 220

Glu Pro Ala Leu Thr Arg Gly Ile Ser Val Leu Pro Cys Thr Glu Glu
225                 230                 235                 240

Gly Ala Leu Arg Val Gly Leu Gly Thr Asp Met His Ala Leu Cys Ala
                245                 250                 255

Gly Arg Pro Leu Ile Leu Ala Gly Ile His Ile Pro Ser Lys Lys Gly
            260                 265                 270

Ala Gln Gly His Ser Asp Ala Asp Val Leu Ala His Ala Ser Ile Asp
        275                 280                 285

Ala Leu Leu Gly Ala Ala Gly Leu Gly Asp Ile Gly Thr Phe Phe Pro
    290                 295                 300

Ser Cys Asp Gly Arg Trp Lys Asp Ala His Ser Cys Ala Leu Leu Arg
305                 310                 315                 320

His Thr Trp Gln Leu Val Arg Ala Ala Cys Trp Arg Leu Val Asn Leu
                325                 330                 335

Asp Ala Val Val Cys Leu Glu Gln Pro Ala Leu His Pro Phe Arg Glu
            340                 345                 350

Ala Met Arg Ala Ser Leu Ala Gln Ala Leu Asp Thr His Val Thr Arg
        355                 360                 365

Val Phe Val Lys Ala Lys Thr Ala Glu Arg Leu Gly Pro Val Gly Ser
    370                 375                 380

Gly Ala Ala Val Thr Ala Gln Val Val Val Leu Leu Lys Lys Ile
385                 390                 395
```

-continued

<210> SEQ ID NO 79
<211> LENGTH: 234
<212> TYPE: PRT
<213> ORGANISM: Salmonella typhi
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 79

Met Ala Ala Thr Leu Leu Asp Val Cys Ala Val Val Pro Ala Ala Gly
1 5 10 15

Phe Gly Arg Arg Met Gln Thr Glu Cys Pro Xaa Gln Tyr Leu Ser Ile
20 25 30

Gly Asn Lys Thr Ile Leu Glu His Ser Val His Ala Leu Leu Ala His
35 40 45

Pro Arg Val Thr Arg Val Val Ile Ala Ile Ser Pro Gly Asp His Arg
50 55 60

Phe Ala Gln Leu Pro Leu Ala Asn His Pro Gln Ile Thr Val Val Asp
65 70 75 80

Gly Gly Asn Glu Arg Ala Asp Ser Val Leu Ala Gly Leu Gln Ala Val
85 90 95

Ala Lys Ala Gln Trp Val Leu Xaa His Asp Ala Ala Arg Pro Cys Leu
100 105 110

His Gln Asp Asp Leu Ala Arg Leu Leu Ala Ile Ser Glu Asn Ser Arg
115 120 125

Val Gly Gly Ile Leu Ala Ser Pro Val Arg Asp Thr Met Lys Arg Gly
130 135 140

Glu Pro Gly Lys Asn Ala Ile Ala His Thr Val Glu Arg Ala Asp Leu
145 150 155 160

Trp His Ala Leu Thr Pro Gln Phe Phe Pro Arg Glu Leu Leu His Asp
165 170 175

Cys Leu Thr Arg Ala Leu Asn Glu Gly Ala Thr Ile Thr Asp Glu Ala
180 185 190

Ser Ala Leu Glu Tyr Cys Gly Phe His Pro Ala Leu Val Glu Gly Arg
195 200 205

Ala Asp Asn Ile Lys Val Thr Arg Pro Glu Asp Leu Ala Leu Ala Glu
210 215 220

Phe Tyr Leu Thr Arg Thr Ile His Gln Glu
225 230

<210> SEQ ID NO 80
<211> LENGTH: 223
<212> TYPE: PRT
<213> ORGANISM: Yersinia pestis

<400> SEQUENCE: 80

Glu Val Ile Ala Val Leu Pro Ala Ala Gly Ile Gly Ser Arg Met Leu
1 5 10 15

Val Asp Cys Pro Lys Gln Tyr Leu Thr Val Gly Gly Lys Thr Ile Ile
20 25 30

Glu His Ala Ile Phe Ser Leu Leu His His Pro Arg Ile Gln Arg Val
35 40 45

```
Ile Val Val Ile His Pro Gln Asp Thr Gln Phe Ser Arg Leu Ser Val
 50                  55                  60

Ala Gln Asp Pro Arg Ile Ser Thr Val Tyr Gly Gly Asp Gln Arg Ala
 65                  70                  75                  80

Asn Ser Val Met Ala Gly Leu Gln Leu Ala Gly Gln Ala Glu Trp Val
                 85                  90                  95

Leu Val His Asp Ala Ala Arg Pro Cys Leu His Leu Asp Asp Leu Ser
                100                 105                 110

Arg Leu Leu Ser Ile Thr Glu Cys Ser Gln Val Gly Gly Ile Leu Ala
            115                 120                 125

Ala Pro Val Arg Asp Thr Met Lys Arg Ala Glu Pro Gly Ile Gln Ala
130                 135                 140

Ile Ala His Thr Val Asp Arg Gln Asp Leu Trp His Ala Leu Thr Pro
145                 150                 155                 160

Gln Leu Phe Pro Leu Glu Leu Leu Lys Leu Cys Leu Ser Arg Ala Leu
                165                 170                 175

Arg Glu Gly Val Ala Val Thr Asp Glu Ala Ser Ala Leu Glu His Cys
            180                 185                 190

Gly Tyr His Pro Ile Leu Val Thr Gly Arg Ser Asp Asn Ile Lys Val
        195                 200                 205

Thr Arg Pro Glu Asp Leu Ala Leu Ala Glu Phe Tyr Leu Thr Gln
    210                 215                 220

<210> SEQ ID NO 81
<211> LENGTH: 227
<212> TYPE: PRT
<213> ORGANISM: Actinobacillus actinomycetemcomitans

<400> SEQUENCE: 81

Thr Ser Thr Arg Lys Ile Ile Ala Val Val Pro Ala Ala Gly Ile Gly
 1               5                  10                  15

Ser Arg Met Gln Ala Asp Lys Pro Lys Gln Tyr Leu His Ile His Gly
                 20                  25                  30

Gln Pro Ile Leu Gln His Thr Leu Asn Val Leu Leu Ala Tyr Pro His
             35                  40                  45

Ile Ser Arg Ile Val Leu Ala Val Ala Ala Asp Asp Pro Tyr Ile Asp
 50                  55                  60

Gln Leu Lys Leu Ser Gln Asn Pro Lys Ile Gln Leu Val Glu Gly Gly
 65                  70                  75                  80

Glu Thr Arg Ala Asp Ser Val Leu Asn Gly Leu Asn Ala Val Gln Asp
                 85                  90                  95

Ala Gly Ala Asp Val Trp Val Met Val His Asp Ala Ala Arg Pro Cys
                100                 105                 110

Leu Thr His Gly Asp Leu Glu Lys Leu Leu Glu Ile Gln Asp Asp Asn
            115                 120                 125

Gly Ala Ile Leu Ala Ile Pro Ala Thr Asp Thr Ile Lys Arg Ala Leu
130                 135                 140

Pro Ser Gln Gln Ile Ala His Thr Glu Asp Arg Ser Gln Leu Trp Leu
145                 150                 155                 160

Ala Gln Thr Pro Gln Phe Phe Arg Ala Asp Leu Leu Arg Asp Ala Leu
                165                 170                 175

Thr Arg Ala Lys Gln Gln Gln Phe Ala Val Thr Asp Glu Ala Ser Ala
            180                 185                 190

Met Glu Leu Ala Gly Phe Arg Pro His Leu Val Ala Gly Arg Ser Asp
        195                 200                 205
```

```
Asn Ile Lys Val Thr Arg Pro Glu Asp Leu Ala Leu Ala Glu Phe Tyr
    210                 215                 220

Leu Thr Arg
225

<210> SEQ ID NO 82
<211> LENGTH: 225
<212> TYPE: PRT
<213> ORGANISM: Vibrio cholerae

<400> SEQUENCE: 82

Asn Met Thr Ala Ile Val Pro Ala Ala Gly Val Gly Ser Arg Met Gln
1               5                   10                  15

Ala Asp Arg Pro Lys Gln Tyr Leu Thr Leu Leu Asp Lys Thr Val Leu
            20                  25                  30

Glu His Thr Val Glu His Leu Leu Glu His Pro Leu Ile Glu His Val
        35                  40                  45

Val Val Ala Val Ser Ala Asp Asp Pro Tyr Phe Ala Asn Leu Pro Leu
    50                  55                  60

Ala His His Pro Arg Val Ile Arg Val Asp Gly Gly Lys Glu Arg Ala
65                  70                  75                  80

Asp Ser Val Leu Ser Ala Leu Glu Tyr Val Cys Gln His Arg Leu Ser
                85                  90                  95

Glu Trp Val Leu Val His Asp Ala Ala Arg Pro Cys Val Thr His Ala
            100                 105                 110

Asp Ile Thr Gln Leu Ile Thr Thr Ala Leu Ala His Pro Ile Gly Ala
        115                 120                 125

Ile Leu Ala Ser Pro Val Arg Asp Thr Met Lys Arg Gly Asp His Leu
    130                 135                 140

Gln Gln Ile Val His Thr Val Asp Arg Thr Ala Leu Trp His Ala Leu
145                 150                 155                 160

Thr Pro Gln Met Phe Arg Ala Gln Ser Leu Arg Glu Arg Leu Phe Ala
                165                 170                 175

Ala Leu Gln Gln Gln Val Thr Ile Thr Asp Glu Ala Ser Ala Phe Glu
            180                 185                 190

Trp Arg Gly Glu Lys Pro Ala Leu Val Ala Gly Arg Ala Asp Asn Leu
        195                 200                 205

Lys Ile Thr Gln Pro Glu Asp Leu Ala Leu Ala Glu Phe Tyr Leu Ser
    210                 215                 220

Arg
225

<210> SEQ ID NO 83
<211> LENGTH: 222
<212> TYPE: PRT
<213> ORGANISM: Shewanella putrefaciens

<400> SEQUENCE: 83

Asn Val Val Ala Ile Val Pro Ala Ala Gly Ile Gly Ser Arg Met Gly
1               5                   10                  15

Ala Gly Lys Pro Lys Gln Tyr Leu Pro Leu Leu Gly Gln Ser Ile Leu
            20                  25                  30

Ala His Thr Leu Asp Lys Leu Leu Ser His Pro Leu Ile Ser Gln Val
        35                  40                  45

Ile Val Ala Leu His Pro Glu Asp Ala Asp Phe Tyr Ala Leu Pro Gln
    50                  55                  60
```

-continued

```
Ala Lys His Pro Lys Leu Lys Thr Val Ile Gly Gly Ser Glu Arg Ala
 65                  70                  75                  80

Asn Ser Val Leu Ala Ala Leu Asp Lys Ala Pro Asp Asn Ser Trp Ala
                 85                  90                  95

Leu Val His Asp Ala Ala Arg Pro Cys Leu Met Ala Ser Asp Ile Asp
            100                 105                 110

Lys Leu Leu Thr Ser Arg Val Gln Phe Pro Gln Gly Ala Ile Leu Ala
        115                 120                 125

Met Pro Val Arg Asp Thr Met Lys Arg Ala Asn Ser Leu Gly Glu Ile
    130                 135                 140

Asn Ser Thr Val Cys Arg Asp Asn Leu Trp His Ala Leu Thr Pro Gln
145                 150                 155                 160

Leu Phe Pro Thr Ser Leu Leu Arg Leu His Leu Gln Gly Ala Leu Asn
                165                 170                 175

Ala Gly Ala Val Val Thr Asp Glu Ala Ser Ala Met Glu Trp Ala Gly
            180                 185                 190

Ile Ser Pro Gly Leu Val Ala Gly Arg Ala Asp Asn Ile Lys Val Thr
        195                 200                 205

His Pro Asp Asp Leu Glu Leu Ala Glu Leu Phe Leu Met Arg
    210                 215                 220

<210> SEQ ID NO 84
<211> LENGTH: 225
<212> TYPE: PRT
<213> ORGANISM: Pasteurella multocida

<400> SEQUENCE: 84

Ile Val Ala Val Val Pro Ala Ala Gly Ile Gly Ser Arg Met Gln Met
  1               5                  10                  15

Asp Lys Pro Lys Gln Tyr Leu His Ile His Gly Lys Thr Ile Leu Glu
                 20                  25                  30

His Thr Leu Ser Val Leu Leu Gly Tyr Pro Leu Ile Glu Lys Ile Ile
            35                  40                  45

Ala Val Ala Ala Asn Asp Pro Tyr Ile Ser Thr Cys Pro Leu Leu Thr
        50                  55                  60

His Pro Lys Ile Gln Leu Val Glu Gly Gly Ser Ser Arg Ala Asp Ser
 65                  70                  75                  80

Val Leu Asn Gly Leu Asn Ala Val Lys Ser Ala Val Gln Asn Ser Glu
                 85                  90                  95

Asp Phe Trp Val Met Val His Asp Ala Ala Arg Pro Cys Leu Thr His
            100                 105                 110

Gln Asp Leu Asp Lys Leu Val Gln Val Glu Asp Gln Asn Gly Ala Ile
        115                 120                 125

Leu Ala Ile Pro Ala Thr Asp Thr Ile Lys Arg Ala Leu His Asn Gln
    130                 135                 140

Gln Ile His Tyr Thr Glu Asp Arg Ser Gln Leu Trp Leu Ala Gln Thr
145                 150                 155                 160

Pro Gln Phe Phe Pro Ile Ala Thr Leu Ala Gln Ala Leu Glu Gln Ala
                165                 170                 175

Leu Ala Gln Gly Leu Gln Val Thr Asp Glu Ala Ser Ala Met Glu Phe
            180                 185                 190

Ala Gly Phe Arg Pro His Leu Val Ala Gly Arg Ser Asp Asn Ile Lys
        195                 200                 205

Val Thr Arg Pro Glu Asp Phe Ala Leu Ala Glu Phe Tyr Leu Ser Arg
```

```
                    210                 215                 220

Thr
225

<210> SEQ ID NO 85
<211> LENGTH: 214
<212> TYPE: PRT
<213> ORGANISM: Pseudomonas aeruginosa

<400> SEQUENCE: 85

Val Ile Pro Ala Ala Gly Val Gly Ser Arg Met Arg Ala Asp Arg Pro
1               5                   10                  15

Lys Gln Tyr Leu Asp Leu Ala Gly Arg Thr Val Ile Glu Arg Thr Leu
            20                  25                  30

Asp Cys Phe Leu Glu His Pro Met Leu Arg Gly Leu Val Val Cys Leu
        35                  40                  45

Ala Glu Asp Asp Pro Tyr Trp Pro Gly Leu Asp Cys Ala Ala Ser Arg
    50                  55                  60

His Val Gln Arg Ala Ala Gly Ala Glu Arg Ala Gly Ser Val Leu
65                  70                  75                  80

Asn Gly Leu Leu Arg Leu Leu Glu Leu Gly Ala Gln Ala Asp Trp
                85                  90                  95

Val Leu Val His Asp Ala Ala Arg Pro Asn Leu Thr Arg Gly Asp Leu
            100                 105                 110

Asp Arg Leu Leu Glu Glu Leu Ala Glu Asp Pro Val Gly Gly Leu Leu
        115                 120                 125

Ala Val Pro Ala Arg Asp Thr Leu Lys Arg Ser Asp Arg Asp Gly Arg
    130                 135                 140

Val Ser Glu Thr Ile Asp Arg Ser Val Val Trp Leu Ala Tyr Thr Pro
145                 150                 155                 160

Gln Met Phe Arg Leu Gly Ala Leu His Arg Ala Leu Ala Asp Ala Leu
                165                 170                 175

Val Ala Gly Val Ala Ile Thr Asp Glu Ala Ser Ala Met Glu Trp Ala
            180                 185                 190

Gly Tyr Ala Pro Lys Leu Val Glu Gly Arg Ala Asp Asn Leu Lys Ile
        195                 200                 205

Thr Thr Pro Glu Asp Leu
    210

<210> SEQ ID NO 86
<211> LENGTH: 220
<212> TYPE: PRT
<213> ORGANISM: Neisseria gonorrhoeae

<400> SEQUENCE: 86

Ala Leu Ile Pro Ala Ala Gly Ile Gly Val Arg Phe Gly Ala Asp Lys
1               5                   10                  15

Pro Lys Gln Tyr Val Glu Ile Gly Ser Lys Thr Val Leu Glu His Val
            20                  25                  30

Leu Gly Ile Phe Glu Arg His Glu Ala Val Asp Leu Val Val Val
        35                  40                  45

Val Ser Pro Glu Asp Thr Phe Ala Asp Lys Val Gln Thr Ala Phe Pro
    50                  55                  60

Gln Val Arg Val Trp Lys Asn Gly Gly Gln Thr Arg Ala Glu Thr Val
65                  70                  75                  80

Arg Asn Gly Val Ala Lys Leu Leu Glu Thr Gly Leu Ala Ala Glu Thr
```

-continued

```
                85                  90                  95
Asp Asn Ile Leu Val His Asp Ala Ala Arg Cys Cys Leu Pro Ser Glu
            100                 105                 110
Ala Leu Ala Arg Leu Ile Glu Gln Ala Gly Asn Ala Ala Glu Gly Gly
        115                 120                 125
Ile Leu Ala Val Pro Val Ala Asp Thr Leu Lys Arg Ala Glu Ser Gly
    130                 135                 140
Gln Ile Ser Ala Thr Val Asp Arg Ser Gly Leu Trp Gln Ala Gln Thr
145                 150                 155                 160
Pro Gln Leu Phe Gln Ala Gly Leu Leu His Arg Ala Leu Ala Ala Glu
                165                 170                 175
Asn Leu Gly Gly Ile Thr Asp Glu Ala Ser Ala Val Glu Lys Leu Gly
            180                 185                 190
Val Arg Pro Leu Leu Ile Gln Gly Asp Ala Arg Asn Leu Lys Leu Thr
        195                 200                 205
Gln Pro Gln Asp Ala Tyr Ile Val Arg Leu Leu Leu
    210                 215                 220

<210> SEQ ID NO 87
<211> LENGTH: 221
<212> TYPE: PRT
<213> ORGANISM: Bordetella pertussis
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid

<400> SEQUENCE: 87

Ala Ile Val Pro Ala Ala Gly Ile Gly Ala Arg Ala Ser Leu Pro Gly
1               5                   10                  15
Glu Ala Ala Val Pro Lys Gln Tyr Arg Pro Leu Ala Gly Gln Pro Met
                20                  25                  30
Leu Arg His Ala Val Arg Ala Leu Leu Ala Asp Pro Arg Ile Val Gln
            35                  40                  45
Val Arg Val Ala Val Ser Ala Gly Asp Gly Xaa Val Glu Gln Ala Leu
        50                  55                  60
Ala Gly Leu Pro Arg Thr Val Trp Arg Pro Cys Gly Gly Pro Asn Arg
65                  70                  75                  80
Ala Asp Thr Val Ala Xaa Ala Leu Ala Asp Ser Gly Ala Ala Ala Asp
                85                  90                  95
Asp Trp Ile Xaa Val His Asp Ala Ala Arg Pro Gly Leu Pro Ala Ala
            100                 105                 110
```

```
Ala Xaa Ala Arg Leu Ile Asp Ala Cys Xaa Xaa Asp Ala Val Gly Gly
        115                 120                 125

Leu Leu Ala Leu Pro Val Ala Asp Thr Val Xaa Ala Gly Arg Gln Arg
130                 135                 140

Val Ser Arg Thr Val Asp Arg Asp Gly Leu Trp Leu Ala Gln Thr Pro
145                 150                 155                 160

Gln Met Phe Arg Ala Gly Leu Leu Arg Asp Ala Leu Ala Arg Ala Arg
                165                 170                 175

Ala Ala Gly Leu Ala Val Thr Asp Glu Ala Ser Ala Val Glu Ala Ala
            180                 185                 190

Gly His Ala Pro Arg Leu Val Ala Gly Ala Leu Arg Asn Phe Lys Val
        195                 200                 205

Thr Trp Pro Asp Asp Phe Glu Leu Met Glu Lys Trp Leu
210                 215                 220
```

<210> SEQ ID NO 88
<211> LENGTH: 220
<212> TYPE: PRT
<213> ORGANISM: Neisseria meningitidis

<400> SEQUENCE: 88

```
Ala Leu Ile Pro Ala Gly Ile Gly Ala Arg Phe Gly Ala Asp Lys
1               5                   10                  15

Pro Lys Gln Tyr Val Glu Ile Gly Ser Lys Thr Val Leu Glu His Thr
                20                  25                  30

Ile Gly Ile Phe Glu Arg His Glu Ala Val Asp Leu Thr Val Val Val
            35                  40                  45

Val Ser Pro Glu Asp Thr Phe Ala Asp Lys Val Gln Thr Ala Phe Pro
50                  55                  60

Gln Val Arg Val Trp Lys Asn Gly Gly Gln Thr Arg Ala Glu Thr Val
65                  70                  75                  80

Arg Asn Gly Val Ala Lys Leu Leu Glu Thr Gly Leu Ala Ala Glu Thr
                85                  90                  95

Asp Asn Ile Leu Val His Asp Ala Ala Arg Cys Cys Leu Pro Ser Glu
            100                 105                 110

Ala Leu Thr Arg Leu Ile Glu Gln Ala Gly Asn Ala Ala Glu Gly Gly
        115                 120                 125

Ile Leu Ala Ile Pro Val Ala Asp Thr Leu Lys Cys Ala Asp Gly Gly
130                 135                 140

Asn Ile Ser Ala Thr Val Glu Arg Thr Ser Leu Trp Gln Ala Gln Thr
145                 150                 155                 160

Pro Gln Leu Phe Arg Ala Gly Leu Leu His Arg Ala Leu Ala Ala Glu
                165                 170                 175

Asn Leu Asp Gly Ile Thr Asp Glu Ala Ser Ala Val Glu Lys Leu Gly
            180                 185                 190

Ile Arg Pro Leu Leu Val Gln Gly Asp Ala Arg Asn Leu Lys Leu Thr
        195                 200                 205

Gln Pro Gln Asp Ala Tyr Ile Val Arg Leu Leu Leu
210                 215                 220
```

<210> SEQ ID NO 89
<211> LENGTH: 197
<212> TYPE: PRT
<213> ORGANISM: Thiobacillus ferrooxidans

<400> SEQUENCE: 89

```
Asp Arg Pro Val Ile Ala His Thr Leu Ala Ala Phe Leu Gly Glu Pro
1               5                   10                  15

Arg Ile Ala Gly Ile Gln Leu Val Leu Pro Gly Glu Asp Ile Ala Thr
            20                  25                  30

Gly Ala Trp Arg Glu Leu Leu Gly Pro Met Pro Ala Pro Leu Leu Pro
        35                  40                  45

Pro Val Val Gly Gly Gly Leu Arg Ala Asp Ser Val Arg Leu Gly Leu
    50                  55                  60

Glu Ala Leu Leu Arg Gln Gly Ala Val Pro Ser Asp Trp Val Leu Val
65                  70                  75                  80

His Asp Ala Ala Arg Pro Cys Leu Arg Arg Glu Asp Leu Leu Arg Leu
                85                  90                  95

Leu Glu Ser Leu Ala Asn Ala Pro Gln Gly Ala Leu Leu Ala Val Pro
                100                 105                 110

Val Ala Asp Thr Leu Lys Arg Gly Glu Asp Gly Cys Ser Ser Gly Thr
            115                 120                 125

Val Asp Arg Glu Gly Leu Trp Arg Ala Leu Thr Pro Gln Ala Phe Pro
    130                 135                 140

Leu Gly Ala Leu Leu Ala Ala Leu Glu Ala Ala Arg Ala Gly Asn Arg
145                 150                 155                 160

Gln Ile Thr Asp Glu Ala Ser Ala Met Glu Ala Gln Gly Trp Arg Pro
                165                 170                 175

Arg Leu Ile Pro Gly His Gly Asp Asn Ile Lys Val Thr Leu Ser Asp
                180                 185                 190

Asp Leu Met Leu Ala
            195

<210> SEQ ID NO 90
<211> LENGTH: 202
<212> TYPE: PRT
<213> ORGANISM: Deinococcus radiodurans

<400> SEQUENCE: 90

Ala Leu Ile Pro Ala Ala Gly Ser Gly Thr Arg Leu Gly Leu Gly Pro
1               5                   10                  15

Lys Ala Phe Val Glu Val Ala Gly Arg Ser Leu Leu Ala Arg Ser Val
            20                  25                  30

Ala Ala Leu Ala Pro Phe Val Asp Glu Val Val Val Ala Leu Pro Ala
        35                  40                  45

Gly Met Asp Leu Pro Ala Gly Val Pro Ala Arg Ala Ile Val Gly Gly
    50                  55                  60

Glu Thr Arg Gln Gly Ser Val Arg Arg Leu Leu Glu Ala Thr Glu Ala
65                  70                  75                  80

Gly Thr Val Leu Ile His Asp Ala Ala Arg Pro Phe Val Pro Pro Pro
                85                  90                  95

Val Ile Leu Ala Leu Leu Asp Ala Ile Ala Ala Thr Gly Ala Ala Thr
                100                 105                 110

Val Ala Leu Pro Val Ala Asp Thr Leu Val Arg Ala Glu Gly Gln Ser
            115                 120                 125

Trp Gly Gln Leu Val Pro Arg Glu Gly Leu Trp Ala Val Gln Thr Pro
    130                 135                 140

Gln Gly Phe Arg Arg Glu Leu Leu Gln Ala His Ala Arg Ala Glu
145                 150                 155                 160

Ala Glu Gln Tyr Ala Ala Thr Asp Asp Ala Gly Leu Leu Ala Arg Leu
                165                 170                 175
```

-continued

```
Gly Val Gln Val Arg Leu Val Pro Gly Asp Ala Arg Leu Phe Lys Val
            180                 185                 190

Thr Thr Pro Gly Asp Leu Ala Leu Ala Glu
        195                 200

<210> SEQ ID NO 91
<211> LENGTH: 225
<212> TYPE: PRT
<213> ORGANISM: Clostridium acetobutylicum

<400> SEQUENCE: 91

Cys Ala Ile Ile Met Ala Ala Gly Arg Gly Ser Arg Met Lys Val Asn
1               5                   10                  15

Lys Asn Lys Gln Phe Ile Leu Ile Gln Gly Lys Pro Ile Leu Ala Tyr
            20                  25                  30

Thr Ile Asp Lys Phe Gln Arg Ser Pro Leu Ile Asp Glu Ile Ile Ile
        35                  40                  45

Val Ala Ala Glu Ser Glu Ile Asn Phe Cys Met Gln Glu Ile Val Tyr
    50                  55                  60

Lys Tyr Lys Phe Asn Lys Val Lys Asn Ile Val Ser Gly Gly Ser Glu
65                  70                  75                  80

Arg Gln Gln Ser Val Met Asn Gly Leu Lys Ala Val Lys Ser Ala Asn
                85                  90                  95

Ile Val Leu Ile His Asp Gly Ala Arg Pro Phe Val Asp Asn Lys Ile
            100                 105                 110

Ile Glu Asn Gly Ile Lys Tyr Ala Glu Lys Tyr Gly Gly Ala Ala Cys
        115                 120                 125

Gly Val Gln Pro Lys Asp Thr Ile Lys Ile Lys Ser Glu Asp Gly Phe
    130                 135                 140

Ser Glu Lys Thr Ile Asp Arg Ser Lys Leu Phe Cys Val Gln Thr Pro
145                 150                 155                 160

Gln Cys Phe Lys Tyr Asp Ser Ile Leu Lys Ala His Ile Asn Ala Glu
                165                 170                 175

Lys Glu Gly Ile Leu Ala Thr Asp Asp Thr Met Ile Phe Glu Met Ser
            180                 185                 190

Gly Asn Lys Val Tyr Leu Tyr Asp Gly Ser Tyr Glu Asn Leu Lys Ile
        195                 200                 205

Thr Thr Pro Asp Asp Leu Tyr Ala Ala Glu Thr Leu Leu Lys Lys Asn
    210                 215                 220

Ser
225

<210> SEQ ID NO 92
<211> LENGTH: 219
<212> TYPE: PRT
<213> ORGANISM: Mycobacterium avium

<400> SEQUENCE: 92

Val Ala Ala Val Val Pro Ala Ala Gly Ser Gly Glu Arg Leu Ala Ala
1               5                   10                  15

Gly Ile Pro Lys Ala Phe Cys Glu Ile Asp Gly Ala Ser Met Leu Ala
            20                  25                  30

Arg Ala Val Ala Gly Leu Leu Asp Ser Lys Val Val Asp His Val Val
        35                  40                  45

Val Ala Val Pro Ala Asp Arg Val Asp Glu Ala Lys Arg Leu Leu Ala
    50                  55                  60
```

-continued

```
Ala Gln Ala Thr Val Val Ala Gly Gly Ala Asp Arg Thr Ala Ser Val
65                  70                  75                  80

Arg Leu Ala Leu Ala Ala Val Pro Gly Asn Pro Ala Phe Val Leu Val
                85                  90                  95

His Asp Ala Ala Arg Ala Leu Thr Pro Pro Ala Leu Ile Ala Arg Val
            100                 105                 110

Val Gln Ala Leu Arg Asp Gly His Arg Ala Val Val Pro Ala Leu Pro
        115                 120                 125

Leu His Asp Thr Val Lys Ala Val Asp Ala Asn Gly Val Val Leu Gly
    130                 135                 140

Thr Pro Glu Arg Asp Gly Leu Arg Ala Val Gln Thr Pro Gln Gly Phe
145                 150                 155                 160

Ala Thr Asp Leu Leu Leu Arg Ala Tyr Ala Ala Gly Ala Gly Thr Ala
                165                 170                 175

Gly Phe Thr Asp Asp Ala Ser Leu Val Glu His Val Gly Gly Gln Val
            180                 185                 190

Gln Val Val Asp Gly Asp Pro Leu Ala Phe Lys Ile Thr Thr Gln Leu
        195                 200                 205

Asp Leu Leu Leu Ala Glu Thr Ile Val Arg Arg
    210                 215

<210> SEQ ID NO 93
<211> LENGTH: 223
<212> TYPE: PRT
<213> ORGANISM: Mycobacterium bovis

<400> SEQUENCE: 93

Glu Val Val Ala Ile Val Pro Ala Ala Gly Ser Gly Glu Arg Leu Ala
1               5                   10                  15

Val Gly Val Pro Lys Ala Phe Tyr Gln Leu Asp Gly Gln Thr Leu Ile
            20                  25                  30

Glu Arg Ala Val Asp Gly Leu Leu Asp Ser Gly Val Val Asp Thr Val
        35                  40                  45

Val Val Ala Val Pro Ala Asp Arg Thr Asp Glu Ala Arg Gln Ile Leu
    50                  55                  60

Gly His Arg Ala Met Ile Val Ala Gly Gly Ser Asn Arg Thr Asp Thr
65                  70                  75                  80

Val Asn Leu Ala Leu Ala Val Leu Ser Gly Thr Ala Glu Pro Glu Phe
                85                  90                  95

Val Leu Val His Asp Ala Ala Arg Ala Leu Thr Pro Pro Ala Leu Val
            100                 105                 110

Ala Arg Val Val Glu Ala Leu Arg Asp Gly Tyr Ala Ala Val Val Pro
        115                 120                 125

Val Leu Pro Leu Ser Asp Thr Ile Lys Ala Val Asp Ala Asn Gly Val
    130                 135                 140

Val Leu Gly Thr Pro Glu Arg Ala Gly Leu Arg Ala Val Gln Thr Pro
145                 150                 155                 160

Gln Gly Phe Thr Thr Asp Leu Leu Leu Arg Ser Tyr Gln Arg Gly Ser
                165                 170                 175

Leu Asp Leu Pro Ala Ala Glu Tyr Thr Asp Asp Ala Ser Leu Val Glu
            180                 185                 190

His Ile Gly Gly Gln Val Gln Val Val Asp Gly Asp Pro Leu Ala Phe
        195                 200                 205

Lys Ile Thr Thr Lys Leu Asp Leu Leu Leu Ala Gln Ala Ile Val
```

```
           210                 215                 220

<210> SEQ ID NO 94
<211> LENGTH: 243
<212> TYPE: PRT
<213> ORGANISM: Chlorobium tepidum
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid

<400> SEQUENCE: 94

Met Lys Thr Val Val Ile Ile Ala Ala Ser Gly Val Gly Lys Arg Met
1               5                   10                  15

Lys Leu Asp Gly Gly Arg Ser Lys Gln Met Leu Glu Ile Gly Gly Gln
            20                  25                  30

Pro Val Ile Trp His Thr Met Lys Ala Phe Gln Glu Ala Ser Thr Val
        35                  40                  45

Glu Ser Val Tyr Ile Ala Thr Leu Pro Asp Ser Ile Pro Val Phe Lys
    50                  55                  60

Glu Ile Ala Lys Ala Asn Gly Phe Thr Lys Ile Thr Ala Ile Ile Glu
65                  70                  75                  80

Gly Gly Lys Glu Arg Gln Asp Ser Ile Gly Asn Cys Met Lys Leu Ile
                85                  90                  95

Glu Gln Glu Ile Glu Asn Ser Gly Val Met Pro Asp Ala Ile Leu Val
            100                 105                 110

His Asp Gly Ala Arg Pro Phe Ile Gln Pro Glu Glu Ile Asp Asp Ile
        115                 120                 125

Ala Arg Leu Ser Ala Thr His Gly Ala Cys Val Pro Ala Thr Lys Pro
    130                 135                 140

Lys Asp Thr Ile Lys Tyr Val Gly Cys Asn Pro Glu Ile Phe Gly Glu
145                 150                 155                 160

Thr Leu Asp Arg Ser Arg Leu Leu Gln Val Gln Thr Pro Gln Gly Phe
                165                 170                 175

Ala Pro Ala Lys Leu Ile Glu Ala His Arg Leu Ala Gly Glu Glu Gln
            180                 185                 190

Trp Tyr Ala Xaa Asp Asp Ala Ala Leu Val Glu Arg Tyr Phe Pro Gln
        195                 200                 205

Gln Ala Ile Xaa Ile Tyr Glu Thr Gly Tyr His Asn Ile Lys Ile Thr
    210                 215                 220

Thr Pro Glu Asp Val Phe Ile Gly Glu Ala Ile Leu Ala Gly Leu Lys
225                 230                 235                 240

Ala Arg Lys

<210> SEQ ID NO 95
<211> LENGTH: 216
<212> TYPE: PRT
<213> ORGANISM: Porphyromonas gingivalis

<400> SEQUENCE: 95

Ala Leu Ile Val Ala Gly Gly His Gly Leu Arg Met Gly Ala Asp Arg
1               5                   10                  15

Pro Lys Gln Phe Leu Leu Leu Ala Gly Leu Pro Val Leu Met His Thr
            20                  25                  30
```

-continued

```
Leu Asn Arg Phe Ala Pro His Val Asp Ala Ile Val Leu Val Leu Pro
         35                  40                  45

Thr Asp His His Ala Tyr Trp Gln Glu Leu Cys Arg Lys Tyr Asp Phe
 50                  55                  60

Ser Val Ser His Arg Val Val Ala Gly Gly Asn Thr Arg Phe Ala Ser
65                  70                  75                  80

Val Arg Asn Gly Leu Gln Val Val Pro Asp Gly Val Leu Val Ala Val
                 85                  90                  95

His Asp Gly Val Arg Pro Leu Val Ser Ala Glu Thr Ile Asp Ala Cys
            100                 105                 110

Phe Asp Leu Ala Glu Leu Lys Gly Ala Val Ala Pro Cys Arg Pro Met
        115                 120                 125

Thr Glu Ser Leu Arg Tyr Tyr Ala Thr Asp Gly Asn Tyr Ala Val Asp
    130                 135                 140

Arg Ser Arg Tyr Val Thr Val Gln Thr Pro Gln Thr Phe Arg Ser Glu
145                 150                 155                 160

Trp Leu Arg Glu Ala Tyr Arg Gln Pro Tyr Glu Tyr Phe Thr Asp
                165                 170                 175

Asp Cys Ser Val Tyr Glu His His Phe Gly Arg Pro Val Ala Leu Ile
                180                 185                 190

Val Gly Asn Ile Glu Asn Ile Lys Leu Thr Thr Pro Leu Asp Leu Ser
            195                 200                 205

Leu Ala Lys Leu Leu Leu Thr Ser
        210                 215

<210> SEQ ID NO 96
<211> LENGTH: 227
<212> TYPE: PRT
<213> ORGANISM: Enterococcus faecalis

<400> SEQUENCE: 96

Ile Thr Ala Leu Ile Ile Ala Gly Gly Val Gly Lys Arg Met Gly Gln
1               5                   10                  15

Glu Ile Pro Lys Gln Phe Ile Met Val Glu Glu Lys Pro Ile Ile Ile
            20                  25                  30

Tyr Thr Leu Glu Ser Phe Gln Lys His Pro Leu Ile Asp Arg Ile Leu
        35                  40                  45

Val Val Cys Lys Lys Gly Trp Glu Gln Thr Leu Asp Ala Tyr Ala Lys
    50                  55                  60

Glu Tyr His Ile Asp Lys Leu Gln Trp Ile Ile Pro Gly Gly Asn Ser
65                  70                  75                  80

Gly Gln Glu Ser Ile Asn Asn Gly Val Asn Phe Leu Lys Glu His Ser
                85                  90                  95

Asn Pro Glu Asp Thr Ile Val Ile His Asp Gly Ile Arg Pro Leu Val
            100                 105                 110

Asp Glu Leu Val Leu Ser Asp Val Ile Val Lys Cys Gln Glu Tyr Gly
        115                 120                 125

Asn Ala Val Thr Ser Leu Pro Tyr Asn Glu Gln Ile Phe Val Lys Glu
    130                 135                 140

Thr Glu Glu Thr Thr Arg Gln Tyr Ile Asn Arg Glu Thr Leu Arg Arg
145                 150                 155                 160

Val Ser Thr Pro Gln Ala Tyr Lys Phe Glu Lys Leu Thr Trp Ala Tyr
                165                 170                 175

Glu Lys Ala Phe Arg Glu Asn Ile Gly Ile Ser Glu Ser Ser Tyr Thr
            180                 185                 190
```

```
Asn Thr Met Met Val Asp Leu Gly Glu Thr Leu His Phe Ala Leu Gly
        195                 200                 205

Ser Asp Lys Asn Ile Lys Leu Thr Thr Gln Asp Asp Leu Gln Leu Phe
        210                 215                 220

Lys Phe Leu
225

<210> SEQ ID NO 97
<211> LENGTH: 234
<212> TYPE: PRT
<213> ORGANISM: Streptococcus pneumoniae

<400> SEQUENCE: 97

Ile Tyr Ala Gly Ile Leu Ala Gly Gly Thr Gly Thr Arg Met Gly Ile
1               5                   10                  15

Ser Asn Leu Pro Lys Gln Phe Leu Glu Leu Gly Asp Arg Pro Ile Leu
            20                  25                  30

Ile His Thr Ile Glu Lys Phe Val Leu Glu Pro Ser Ile Glu Lys Ile
        35                  40                  45

Val Val Gly Val His Gly Asp Trp Val Ser His Ala Glu Asp Leu Val
    50                  55                  60

Asp Lys Tyr Leu Pro Leu Tyr Lys Glu Arg Ile Ile Ile Thr Lys Gly
65                  70                  75                  80

Gly Ala Asp Arg Asn Thr Ser Ile Lys Asn Ile Ile Glu Ala Ile Asp
                85                  90                  95

Ala Tyr Arg Pro Leu Thr Pro Glu Asp Ile Val Val Thr His Asp Ser
            100                 105                 110

Val Arg Pro Phe Ile Thr Leu Arg Met Ile Gln Asp Asn Ile Gln Leu
        115                 120                 125

Ala Gln Asn His Asp Ala Val Asp Thr Val Val Glu Ala Val Asp Thr
    130                 135                 140

Ile Val Glu Ser Thr Asn Gly Gln Phe Ile Thr Asp Ile Pro Asn Arg
145                 150                 155                 160

Ala His Leu Tyr Gln Gly Gln Thr Pro Gln Thr Phe Arg Cys Lys Asp
                165                 170                 175

Phe Met Asp Leu Tyr Gly Ser Leu Ser Asp Glu Glu Lys Glu Ile Leu
            180                 185                 190

Thr Asp Ala Cys Lys Ile Phe Val Ile Lys Gly Lys Asp Val Ala Leu
        195                 200                 205

Ala Lys Gly Glu Tyr Ser Asn Leu Lys Ile Thr Thr Val Thr Asp Leu
    210                 215                 220

Lys Ile Ala Lys Ser Met Ile Glu Lys Asp
225                 230

<210> SEQ ID NO 98
<211> LENGTH: 229
<212> TYPE: PRT
<213> ORGANISM: Staphylococcus aureus

<400> SEQUENCE: 98

Ile Leu Ala Gly Gly Ile Gly Ser Arg Met Gly Asn Val Pro Leu Pro
1               5                   10                  15

Lys Gln Phe Leu Asp Ile Asp Asn Lys Pro Ile Leu Ile His Thr Ile
            20                  25                  30

Glu Lys Phe Ile Leu Val Ser Glu Phe Asn Glu Ile Ile Ile Ala Thr
        35                  40                  45
```

```
Pro Ala Gln Trp Ile Ser His Thr Gln Asp Ile Leu Lys Lys Tyr Asn
    50                  55                  60

Ile Thr Asp Gln Arg Val Lys Val Val Ala Gly Thr Asp Arg Asn
65                  70                  75                  80

Glu Thr Ile Met Asn Ile Ile Asp His Ile Arg Asn Val Asn Gly Ile
                85                  90                  95

Asn Asn Asp Asp Val Ile Val Thr His Asp Ala Val Arg Pro Phe Leu
                100                 105                 110

Thr Gln Arg Ile Ile Lys Glu Asn Ile Glu Val Ala Ala Lys Tyr Gly
            115                 120                 125

Ala Val Asp Thr Val Ile Glu Ala Ile Asp Thr Ile Val Met Ser Lys
        130                 135                 140

Asp Lys Gln Asn Ile His Ser Ile Pro Val Arg Asn Glu Met Tyr Gln
145                 150                 155                 160

Gly Gln Thr Pro Gln Ser Phe Asn Ile Lys Leu Leu Gln Asp Ser Tyr
                165                 170                 175

Arg Ala Leu Ser Ser Glu Gln Lys Glu Ile Leu Ser Asp Ala Cys Lys
            180                 185                 190

Ile Ile Val Glu Ser Gly His Ala Val Lys Leu Val Arg Gly Glu Leu
        195                 200                 205

Tyr Asn Ile Lys Val Thr Thr Pro Tyr Asp Leu Lys Val Ala Asn Ala
    210                 215                 220

Ile Ile Gln Gly Asp
225

<210> SEQ ID NO 99
<211> LENGTH: 69
<212> TYPE: PRT
<213> ORGANISM: Plasmodium falciparum

<400> SEQUENCE: 99

Asp Glu Val Val Ile Val Val Ala Pro Gly Glu Asp Ala Arg Ala Val
1               5                   10                  15

Asp Val Leu Ala Gly Leu Ser Asn Trp Arg Ser Val Thr Gly Gly Asp
            20                  25                  30

Ala Arg Ala Asp Ser Val Arg Ala Gly Leu Thr Ala Leu Thr Cys Pro
        35                  40                  45

Ala Asp Gln Pro Val Met Ile His Asp Ala Ala Arg Pro Leu Leu Ser
    50                  55                  60

Gln Thr Val Ile Glu
65

<210> SEQ ID NO 100
<211> LENGTH: 379
<212> TYPE: PRT
<213> ORGANISM: Rhodobacter capsulatus

<400> SEQUENCE: 100

Met Thr Val Ala Val Ile Ile Val Ala Ala Gly Arg Gly Thr Arg Ala
1               5                   10                  15

Gly Glu Gly Leu Pro Lys Gln Trp Arg Asp Leu Ala Gly Arg Pro Val
            20                  25                  30

Leu Ala Gln Thr Val Ala Ala Phe Ala Gly Leu Gly Arg Ile Leu Val
        35                  40                  45

Val Leu His Pro Asp Asp Met Gly Leu Gly Met Asp Leu Leu Gly Gly
    50                  55                  60
```

Ser Val Val Leu Val Ala Gly Gly Ser Thr Arg Ser Glu Ser Val Lys
65                  70                  75                  80

Asn Ala Leu Glu Ala Leu Glu Gly Ser Asp Val Thr Arg Val Leu Ile
            85                  90                  95

His Asp Gly Ala Arg Pro Leu Val Pro Ala Ser Val Thr Ala Ala Val
        100                 105                 110

Leu Ala Ala Leu Glu Thr Thr Pro Gly Ala Ala Pro Ala Leu Ala Val
            115                 120                 125

Thr Asp Ala Leu Trp Arg Gly Glu Ala Gly Leu Val Ala Gly Thr Gln
130                 135                 140

Asp Arg Glu Gly Leu Tyr Arg Ala Gln Thr Pro Gln Gly Phe Arg Phe
145                 150                 155                 160

Pro Glu Ile Leu Ala Ala His Arg Ala His Pro Gly Gly Ala Ala Asp
                165                 170                 175

Asp Val Glu Val Ala Arg His Ala Gly Leu Ser Val Ala Ile Val Pro
            180                 185                 190

Gly His Glu Asp Asn Leu Lys Ile Thr Tyr Ala Pro Asp Phe Ala Arg
        195                 200                 205

Ala Glu Ala Ile Leu Arg Glu Arg Lys Gly Leu Thr Met Asp Val Arg
210                 215                 220

Leu Gly Asn Gly Tyr Asp Val His Ala Phe Cys Glu Gly Asp His Val
225                 230                 235                 240

Val Leu Cys Gly Val Lys Val Pro His Val Lys Ala Leu Leu Gly His
                245                 250                 255

Ser Asp Ala Asp Val Gly Met His Ala Leu Thr Asp Ala Ile Tyr Gly
            260                 265                 270

Ala Leu Ala Glu Gly Asp Ile Gly Arg His Phe Pro Pro Ser Asp Pro
        275                 280                 285

Gln Trp Lys Gly Ala Ala Ser Trp Ile Phe Leu Asp His Ala Ala Lys
290                 295                 300

Leu Ala Lys Ser Arg Gly Phe Arg Ile Gly Asn Ala Asp Val Thr Leu
305                 310                 315                 320

Ile Cys Glu Arg Pro Lys Val Gly Pro His Ala Val Ala Met Ala Ala
                325                 330                 335

Glu Leu Ala Arg Ile Met Glu Ile Glu Pro Ser Arg Val Ser Val Lys
            340                 345                 350

Ala Thr Thr Ser Glu Arg Leu Gly Phe Thr Gly Arg Glu Glu Gly Ile
        355                 360                 365

Ala Ser Ile Ala Thr Val Thr Leu Ile Gly Ala
    370                 375

<210> SEQ ID NO 101
<211> LENGTH: 378
<212> TYPE: PRT
<213> ORGANISM: Caulobacter crescentus

<400> SEQUENCE: 101

Met Thr Phe Ser Val Val Ile Val Ala Ala Gly Ser Gly Thr Arg Ala
1               5                   10                  15

Gly Pro Gly Gln Ala Lys Gln Trp Arg Val Leu Ala Gly Arg Pro Val
            20                  25                  30

Leu Arg Trp Ser Val Glu Ala Phe Leu Ala Ala Gly Ala Ala Glu Val
        35                  40                  45

Val Val Val Thr Thr Ala Asp Gly Glu Ala Phe Leu Pro Arg Met Leu

```
                50                   55                    60
Glu Gly Leu Gln Gly Trp Arg Ser Thr Leu Gly Gly Ala Thr Arg Ala
 65                  70                   75                   80

Leu Ser Val Gln Ala Gly Leu Ala Ala Leu Ser Glu Arg Pro Gly Ala
                 85                   90                   95

Glu Pro Val Met Ile His Asp Ala Ala Arg Pro Phe Val Ser Arg Asn
                100                  105                  110

Val Ile Leu Ala Leu Leu Gly Ala Leu Ser Asp Ala Asp Leu Ala Leu
                115                  120                  125

Pro Ala Leu Ala Val Ala Asp Thr Leu Lys Arg Gln Pro Thr Gly Glu
130                  135                  140

Ala Ala Gln Thr Val Ser Arg Glu His Leu Trp Arg Ala Gln Thr Pro
145                  150                  155                  160

Gln Ala Ala Arg Arg Asp Thr Leu Ile Ala Ala Tyr Ala Ala Trp Thr
                165                  170                  175

His Gly Glu Pro Thr Asp Ala Gln Val Tyr Glu His His Phe Gly
                180                  185                  190

Arg Ile Ala Leu Thr Ala Gly Asp Pro Leu Leu Thr Lys Leu Thr Tyr
                195                  200                  205

Pro Glu Asp Phe Ala Met Ala Glu His Leu Ala Gly Val Ala Arg Val
                210                  215                  220

Thr Arg Val Gly Gln Gly Phe Asp Ala His Arg Trp Gly Pro Gly Glu
225                  230                  235                  240

Glu Val Trp Leu Cys Gly Val Ala Ile Lys His Asp Glu Thr Leu Val
                245                  250                  255

Gly His Ser Asp Ala Asp Ala Gly Leu His Ala Leu Thr Asp Ala Ile
                260                  265                  270

Leu Gly Ala Ile Gly Glu Gly Asp Ile Gly Asp His Phe Pro Pro Thr
                275                  280                  285

Asp Pro Lys Trp Lys Gly Ala Ala Ser Asp Gln Phe Leu Lys His Ala
                290                  295                  300

Val Asp Leu Val Thr Ala Lys Gly Gly Ala Leu Val Asn Val Asp Val
305                  310                  315                  320

Thr Leu Ile Cys Glu Arg Pro Lys Ile Lys Pro His Arg Gln Ala Met
                325                  330                  335

Arg Glu Arg Leu Ala Glu Ile Leu Ser Ile Pro Val Asp Arg Val Ser
                340                  345                  350

Val Lys Ala Thr Thr Thr Glu Lys Met Gly Phe Thr Gly Arg Gly Glu
                355                  360                  365

Gly Leu Ala Ala Ser Ala Val Val Ala Val
                370                  375

<210> SEQ ID NO 102
<211> LENGTH: 362
<212> TYPE: PRT
<213> ORGANISM: Campylobacter jejuni

<400> SEQUENCE: 102

Met Ser Leu Ile Met Leu Ala Ala Gly Asn Ser Thr Arg Phe Asn Thr
 1                5                   10                   15

Lys Val Lys Lys Gln Phe Leu Arg Leu Gly Asn Asp Pro Leu Trp Leu
                 20                   25                   30

Tyr Ala Thr Lys Asn Leu Ser Ser Phe Tyr Pro Phe Lys Lys Ile Val
                 35                   40                   45
```

Val Thr Ser Ser Asn Ile Thr Tyr Met Lys Lys Phe Thr Lys Asn Tyr
 50                  55                  60

Glu Phe Ile Glu Gly Gly Asp Thr Arg Ala Glu Ser Leu Lys Lys Ala
 65                  70                  75                  80

Leu Glu Leu Ile Asp Ser Glu Phe Val Met Val Ser Asp Val Ala Arg
                 85                  90                  95

Val Leu Val Ser Lys Asn Leu Phe Asp Arg Leu Ile Glu Asn Leu Asp
                100                 105                 110

Lys Ala Asp Cys Ile Thr Pro Ala Leu Lys Val Ala Asp Thr Thr Leu
            115                 120                 125

Phe Asp Asn Glu Ala Leu Gln Arg Glu Lys Ile Lys Leu Ile Gln Thr
    130                 135                 140

Pro Gln Ile Ser Lys Thr Lys Leu Leu Lys Lys Ala Leu Asp Gln Asn
145                 150                 155                 160

Leu Glu Phe Thr Asp Asp Ser Thr Ala Ile Ala Ala Met Gly Gly Lys
                165                 170                 175

Ile Trp Phe Val Glu Gly Gly Glu Asn Ala Arg Lys Leu Thr Phe Lys
                180                 185                 190

Glu Asp Leu Lys Lys Leu Asp Leu Pro Thr Pro Ser Phe Glu Ile Phe
            195                 200                 205

Thr Gly Asn Gly Phe Asp Val His Glu Phe Gly Glu Asn Arg Pro Leu
    210                 215                 220

Leu Leu Ala Gly Val Gln Ile His Pro Thr Met Gly Leu Lys Ala His
225                 230                 235                 240

Ser Asp Gly Asp Val Leu Ala His Ser Leu Thr Asp Ala Ile Leu Gly
                245                 250                 255

Ala Ala Gly Leu Gly Asp Ile Gly Glu Leu Tyr Pro Asp Thr Asp Met
                260                 265                 270

Lys Phe Lys Asn Ala Asn Ser Met Glu Leu Leu Lys Gln Ala Tyr Asp
            275                 280                 285

Lys Val Arg Glu Ile Gly Phe Glu Leu Ile Asn Ile Asp Ile Cys Val
    290                 295                 300

Met Ala Gln Ser Pro Lys Leu Lys Asp Phe Lys Gln Ala Met Gln Ser
305                 310                 315                 320

Asn Ile Ala His Thr Leu Asp Leu Asp Glu Phe Arg Ile Asn Val Lys
                325                 330                 335

Ala Thr Thr Thr Glu Lys Leu Gly Phe Ile Gly Arg Lys Glu Gly Met
                340                 345                 350

Ala Val Leu Ser Ser Val Asn Leu Lys Tyr
            355                 360

<210> SEQ ID NO 103
<211> LENGTH: 159
<212> TYPE: PRT
<213> ORGANISM: Escherichia coli

<400> SEQUENCE: 103

Met Arg Ile Gly His Gly Phe Asp Val His Ala Phe Gly Gly Glu Gly
 1                   5                  10                  15

Pro Ile Ile Ile Gly Gly Val Arg Ile Pro Tyr Glu Lys Gly Leu Leu
                 20                  25                  30

Ala His Ser Asp Gly Asp Val Ala Leu His Ala Leu Thr Asp Ala Leu
             35                  40                  45

Leu Gly Ala Ala Ala Leu Gly Asp Ile Gly Lys Leu Phe Pro Asp Thr
 50                  55                  60

Asp Pro Ala Phe Lys Gly Ala Asp Ser Arg Glu Leu Leu Arg Glu Ala
65                  70                  75                  80

Trp Arg Arg Ile Gln Ala Lys Gly Tyr Thr Leu Gly Asn Val Asp Val
                85                  90                  95

Thr Ile Ile Ala Gln Ala Pro Lys Met Leu Pro His Ile Pro Gln Met
            100                 105                 110

Arg Val Phe Ile Ala Glu Asp Leu Gly Cys His Met Asp Asp Val Asn
        115                 120                 125

Val Lys Ala Thr Thr Thr Glu Lys Leu Gly Phe Thr Gly Arg Gly Glu
    130                 135                 140

Gly Ile Ala Cys Glu Ala Val Ala Leu Leu Ile Lys Ala Thr Lys
145                 150                 155

<210> SEQ ID NO 104
<211> LENGTH: 158
<212> TYPE: PRT
<213> ORGANISM: Haemophilus influenzae

<400> SEQUENCE: 104

Met Ile Arg Ile Gly His Gly Phe Asp Val His Ala Phe Gly Glu Asp
1               5                   10                  15

Arg Pro Leu Ile Ile Gly Gly Val Glu Val Pro Tyr His Thr Gly Phe
                20                  25                  30

Ile Ala His Ser Asp Gly Asp Val Ala Leu His Ala Leu Thr Asp Ala
            35                  40                  45

Ile Leu Gly Ala Ala Ala Leu Gly Asp Ile Gly Lys Leu Phe Pro Asp
        50                  55                  60

Thr Asp Met Gln Tyr Lys Asn Ala Asp Ser Arg Gly Leu Leu Arg Glu
65                  70                  75                  80

Ala Phe Arg Gln Val Gln Glu Lys Gly Tyr Lys Ile Gly Asn Val Asp
                85                  90                  95

Ile Thr Ile Ile Ala Gln Ala Pro Lys Met Arg Pro His Ile Asp Ala
            100                 105                 110

Met Arg Ala Lys Ile Ala Glu Asp Leu Gln Cys Asp Ile Glu Gln Val
        115                 120                 125

Asn Val Lys Ala Thr Thr Thr Glu Lys Leu Gly Phe Thr Gly Arg Gln
    130                 135                 140

Glu Gly Ile Ala Cys Glu Ala Val Ala Leu Leu Ile Arg Gln
145                 150                 155

<210> SEQ ID NO 105
<211> LENGTH: 158
<212> TYPE: PRT
<213> ORGANISM: Bacillus subtilis

<400> SEQUENCE: 105

Met Phe Arg Ile Gly Gln Gly Phe Asp Val His Gln Leu Val Glu Gly
1               5                   10                  15

Arg Pro Leu Ile Ile Gly Gly Ile Glu Ile Pro Tyr Glu Lys Gly Leu
                20                  25                  30

Leu Gly His Ser Asp Ala Asp Val Leu Leu His Thr Val Ala Asp Ala
            35                  40                  45

Cys Leu Gly Ala Val Gly Glu Gly Asp Ile Gly Lys His Phe Pro Asp
        50                  55                  60

Thr Asp Pro Glu Phe Lys Asp Ala Asp Ser Phe Lys Leu Leu Gln His
65                  70                  75                  80

Val Trp Gly Ile Val Lys Gln Lys Gly Tyr Val Leu Gly Asn Ile Asp
            85                  90                  95

Cys Thr Ile Ile Ala Gln Lys Pro Lys Met Leu Pro Tyr Ile Glu Asp
            100                 105                 110

Met Arg Lys Arg Ile Ala Glu Gly Leu Glu Ala Asp Val Ser Gln Val
            115                 120                 125

Asn Val Lys Ala Thr Thr Glu Lys Leu Gly Phe Thr Gly Arg Ala
    130                 135                 140

Glu Gly Ile Ala Ala Gln Ala Thr Val Leu Ile Gln Lys Gly
145                 150                 155

<210> SEQ ID NO 106
<211> LENGTH: 161
<212> TYPE: PRT
<213> ORGANISM: Synchocystis sp.

<400> SEQUENCE: 106

Met Thr Ala Leu Arg Ile Gly Asn Gly Tyr Asp Ile His Arg Leu Val
1               5                   10                  15

Gly Asp Arg Pro Leu Ile Leu Gly Gly Val Thr Ile Ala His His Leu
            20                  25                  30

Gly Leu Asp Gly His Ser Asp Ala Asp Val Leu Thr His Ala Leu Met
        35                  40                  45

Asp Ala Leu Leu Gly Ala Leu Ser Leu Gly Asp Ile Gly His Tyr Phe
    50                  55                  60

Pro Pro Ser Asp Ala Arg Trp Gln Gly Ala Asp Ser Leu Lys Leu Leu
65                  70                  75                  80

Ala Gln Val His Gln Leu Ile Leu Glu Arg Gly Trp Arg Ile Asn Asn
                85                  90                  95

Leu Asp Asn Val Ile Val Ala Glu Gln Pro Lys Leu Lys Pro His Ile
            100                 105                 110

Gln Ala Met Lys Glu Asn Leu Ala Lys Val Leu Thr Ile Asp Pro Asp
        115                 120                 125

Leu Ile Gly Ile Lys Ala Thr Thr Asn Glu Arg Leu Gly Pro Thr Gly
    130                 135                 140

Arg Glu Glu Gly Ile Ala Ala Tyr Ser Val Ala Leu Leu Ile Lys Glu
145                 150                 155                 160

Gly

<210> SEQ ID NO 107
<211> LENGTH: 159
<212> TYPE: PRT
<213> ORGANISM: Mycobacterium tuberculosis

<400> SEQUENCE: 107

Met Asn Gln Leu Pro Arg Val Gly Leu Gly Thr Asp Val His Pro Ile
1               5                   10                  15

Glu Pro Gly Arg Pro Cys Trp Leu Val Gly Leu Leu Phe Pro Ser Ala
            20                  25                  30

Asp Gly Cys Ala Gly His Ser Asp Gly Asp Val Ala Val His Ala Leu
        35                  40                  45

Cys Asp Ala Val Leu Ser Ala Ala Gly Leu Gly Asp Ile Gly Glu Val
    50                  55                  60

Phe Gly Val Asp Asp Pro Arg Trp Gln Gly Val Ser Gly Ala Asp Met
65                  70                  75                  80

```
Leu Arg His Val Val Leu Ile Thr Gln His Gly Tyr Arg Val Gly
                85                  90                  95

Asn Ala Val Val Gln Val Ile Gly Asn Arg Pro Lys Ile Gly Trp Arg
            100                 105                 110

Arg Leu Glu Ala Gln Ala Val Leu Ser Arg Leu Asn Ala Pro Val
        115                 120                 125

Ser Val Ser Ala Thr Thr Thr Asp Gly Leu Gly Leu Thr Gly Arg Gly
    130                 135                 140

Glu Gly Leu Ala Ala Ile Ala Thr Ala Leu Val Val Ser Leu Arg
145                 150                 155

<210> SEQ ID NO 108
<211> LENGTH: 156
<212> TYPE: PRT
<213> ORGANISM: Aquifex aeolicus

<400> SEQUENCE: 108

Met Glu Leu Arg Ile Gly Phe Gly Phe Asp Ser His Glu Phe Val Glu
1               5                   10                  15

Gly Lys Leu Leu Ile Leu Gly Gly Val Glu Ile Glu Lys Asp Tyr Gly
            20                  25                  30

Leu Lys Gly His Ser Asp Gly Asp Ala Leu Leu His Ala Ile Thr Asp
        35                  40                  45

Ala Ile Leu Gly Ala Leu Gly Glu Arg Asp Ile Gly Glu Ile Phe Lys
    50                  55                  60

Asp Thr Asp Pro Arg Trp Lys Asn Ala Pro Ser Arg Ile Phe Leu Glu
65                  70                  75                  80

Lys Ala Leu Glu Val Met Ser Glu Lys Gly Phe Asn Ile Ser Asn Ile
                85                  90                  95

Asp Cys Val Ile Val Ala Asp Arg Pro Lys Ile Ala Pro His Lys Glu
            100                 105                 110

Arg Ile Lys Glu Ser Leu Ser Lys Leu Leu Gly Ile Pro Lys Glu Arg
        115                 120                 125

Ile Ser Leu Lys Gly Lys Arg Arg Glu Gly Phe Cys Glu Gly Asn Gly
    130                 135                 140

Leu Val Cys Met Cys Thr Val Leu Leu Val Lys Met
145                 150                 155

<210> SEQ ID NO 109
<211> LENGTH: 178
<212> TYPE: PRT
<213> ORGANISM: Chlamydia trachomatis

<400> SEQUENCE: 109

Met Thr Glu Ile Pro Ser Ser Phe Val Leu Pro Asp Pro Glu Trp Ile
1               5                   10                  15

Tyr Arg Val Gly Ile Gly Gln Asp Ser His Arg Phe Leu Pro Asp Glu
            20                  25                  30

Asp Pro Lys Pro Cys Ile Leu Gly Gly Ile Ile Phe Glu Asn Thr Pro
        35                  40                  45

Gly Phe Glu Ala Asn Ser Asp Gly Asp Val Val Phe His Ala Ile Cys
    50                  55                  60

Asn Ala Phe Ser Ser Val Thr His Lys Gly Ile Leu Gly Gly Leu Ala
65                  70                  75                  80

Asp Glu Leu Leu Lys Thr Lys Gly Ile Thr Asp Ser Val Val Tyr Leu
                85                  90                  95
```

```
Gln Glu Ala Val Ala Ser Leu Lys Pro Thr Gln Arg Val Ser His Leu
                100                 105                 110

Ala Ile Thr Ile Glu Gly Lys Arg Pro Lys Leu Leu Pro Gln Leu Pro
            115                 120                 125

Ser Met Arg Lys Arg Ile Ala Glu Val Leu His Ile Pro Leu Asp Ser
        130                 135                 140

Ile Asn Ile Thr Ala Thr Ser Gly Glu Gly Leu Thr Ala Met Gly Gln
145                 150                 155                 160

Gly Tyr Gly Val Gln Cys Phe Cys Val Leu Thr Ile Met Glu Tyr Cys
                165                 170                 175

Arg Tyr

<210> SEQ ID NO 110
<211> LENGTH: 176
<212> TYPE: PRT
<213> ORGANISM: Chlamydia pneumoniae

<400> SEQUENCE: 110

Met Asp Arg Asp Asn Glu Val Pro Leu Pro Lys Pro Lys Trp Ile Tyr
1               5                   10                  15

Arg Thr Gly Ile Gly Gln Asp Ser His Arg Phe Leu Pro Glu Ser Ser
            20                  25                  30

Thr Lys Pro Cys Ile Leu Gly Gly Ile Phe Asp His Cys Pro Gly
        35                  40                  45

Phe Gln Ala Asn Ser Asp Gly Asp Ile Ile Phe His Ala Ile Cys Asn
    50                  55                  60

Ala Ile Ser Ser Val Thr Asn Lys Ile Ile Leu Gly Lys Val Ala Asp
65                  70                  75                  80

Glu Leu Leu Gln Thr Arg Gly Ile Thr Asp Ser Gly Ile Tyr Leu Glu
                85                  90                  95

Glu Ala Leu Lys Ser Leu Lys Pro Asn Gln Lys Ile Ser His Val Ala
                100                 105                 110

Ile Thr Ile Glu Gly Ser Arg Pro Lys Phe Leu Cys Lys Leu Ser Ala
            115                 120                 125

Leu Arg Gln Asn Ile Ala Gln Val Met Asn Leu Thr Pro Thr Asp Ile
        130                 135                 140

Gly Ile Thr Ala Thr Ser Gly Glu Gly Leu Ser Asp Phe Gly Cys Gly
145                 150                 155                 160

Asp Gly Val Gln Cys Phe Cys Val Leu Thr Val Met Glu Tyr Cys Asp
                165                 170                 175

<210> SEQ ID NO 111
<211> LENGTH: 165
<212> TYPE: PRT
<213> ORGANISM: Thermotoga maritima

<400> SEQUENCE: 111

Met Glu Ser Asp Pro Met Phe Ile Gly Phe Gly Tyr Asp Arg His Pro
1               5                   10                  15

Leu Val Glu Gly Arg Arg Leu Val Leu Ala Gly Val Glu Ile Asp Ala
            20                  25                  30

Pro Leu Gly Ser Leu Gly His Ser Asp Gly Asp Val Leu Ser His Ala
        35                  40                  45

Ile Ile Asp Ala Leu Leu Gly Ala Gly Cys Leu Gly Asp Ile Gly Thr
    50                  55                  60

Trp Phe Pro Glu Thr Lys Glu Tyr Lys Asp Ala Asn Ser Leu Asp Leu
```

```
                65                  70                  75                  80
Leu Lys Glu Thr Val Lys Ile Leu Glu Glu Arg Gly Phe Ser Val Val
                        85                  90                  95

Asn Val Asp Ala Thr Val Val Ala Ser Ile Val Lys Leu Ser Pro Tyr
                100                 105                 110

Arg Glu Lys Ile Val Glu Asn Leu Lys Ser Ala Leu Glu Thr Ser Arg
            115                 120                 125

Val Asn Val Lys Phe Lys Ser Gly Asn Thr Leu Gly Phe Glu Gly Glu
        130                 135                 140

Glu Arg Gly Ile Ser Ala Tyr Ala Val Cys Leu Val Glu Glu Lys Gly
145                 150                 155                 160

Cys Thr Lys Ser Thr
                165

<210> SEQ ID NO 112
<211> LENGTH: 160
<212> TYPE: PRT
<213> ORGANISM: Haemophilus ducreyi

<400> SEQUENCE: 112

Met Ile Arg Ile Gly His Gly Phe Asp Val His Ala Phe Gly Glu Lys
1               5                   10                  15

Arg Pro Leu Ile Ile Gly Gly Val Thr Ile Pro Tyr His Thr Gly Phe
            20                  25                  30

Ile Ala His Ser Asp Gly Asp Val Ala Leu His Ala Leu Thr Asp Ala
        35                  40                  45

Leu Leu Gly Ala Ala Ala Leu Gly Asp Ile Gly Lys Leu Phe Pro Asp
    50                  55                  60

Thr Asp Gln Gln Tyr Lys Asn Ile Asp Ser Arg Lys Leu Leu Ile Glu
65                  70                  75                  80

Ala Tyr Arg Gln Val Gln Thr Lys Gly Tyr Gln Ile Ser Asn Ile Asp
                85                  90                  95

Ile Thr Ile Ile Ala Gln Ala Pro Lys Met Arg Pro His Ile Asp Asn
            100                 105                 110

Met Arg Gln Leu Ile Ala Asn Asp Leu Asn Cys Asp Ile Asp Gln Ile
        115                 120                 125

Asn Ile Lys Ala Thr Thr Thr Glu Lys Leu Gly Phe Thr Gly Arg Gly
    130                 135                 140

Glu Gly Ile Ala Cys Glu Ala Val Ala Leu Leu Ser Lys Lys Thr Val
145                 150                 155                 160

<210> SEQ ID NO 113
<211> LENGTH: 148
<212> TYPE: PRT
<213> ORGANISM: Salmonella typhi
<220> FEATURE:
<221> NAME/KEY: misc_feature
<222> LOCATION: (89)..(89)
<223> OTHER INFORMATION: Xaa can be any naturally occurring amino acid

<400> SEQUENCE: 113

Ile Gly His Gly Phe Asp Val His Ala Phe Gly Gly Glu Gly Pro Ile
1               5                   10                  15

Ile Ile Gly Gly Val Arg Ile Pro Tyr Glu Lys Gly Leu Leu Ala His
            20                  25                  30

Ser Asp Gly Asp Val Ala Leu His Ala Leu Thr Asp Ala Leu Leu Gly
        35                  40                  45
```

```
Ala Ala Ala Leu Gly Asp Ile Gly Lys Leu Phe Pro Asp Thr Asp Pro
        50                  55                  60

Ala Phe Lys Gly Ala Asp Ser Arg Glu Leu Leu Arg Glu Ala Trp Arg
 65                  70                  75                  80

Arg Ile Gln Ala Lys Gly Tyr Thr Xaa Gly Asn Val Asp Val Thr Ile
                 85                  90                  95

Ile Ala Gln Ala Pro Lys Met Leu Pro His Ile Pro Gln Met Arg Val
                100                 105                 110

Phe Ile Ala Glu Asp Leu Gly Cys His Met Asp Val Asn Val Lys
                115                 120                 125

Ala Thr Thr Glu Lys Leu Gly Phe Thr Gly Arg Gly Glu Gly Ile
        130                 135                 140

Ala Cys Glu Ala
145

<210> SEQ ID NO 114
<211> LENGTH: 152
<212> TYPE: PRT
<213> ORGANISM: Yersinia pestis

<400> SEQUENCE: 114

Ile Gly His Gly Phe Asp Val His Lys Phe Gly Glu Asn Gly Ser Gly
 1               5                  10                  15

Pro Leu Ile Ile Gly Gly Val Arg Ile Pro Tyr Glu Lys Gly Leu Leu
                20                  25                  30

Ala His Ser Asp Gly Asp Val Ala Leu His Ala Ala Thr Asp Ala Leu
            35                  40                  45

Leu Gly Ala Ala Ala Leu Gly Asp Ile Gly Lys Leu Phe Pro Asp Thr
        50                  55                  60

Asp Pro Ala Phe Lys Gly Ala Asp Ser Arg Gly Leu Leu Arg Glu Ala
 65                  70                  75                  80

Tyr Arg Arg Ile Leu Ala Lys Gly Tyr Lys Leu Gly Asn Leu Asp Ile
                 85                  90                  95

Thr Ile Ile Ala Gln Ala Pro Lys Met Ala Pro His Ile Pro Gln Met
                100                 105                 110

Arg Val Asn Leu Ala Glu Asp Leu Gln Cys His Met Asp Asp Ile Asn
                115                 120                 125

Val Lys Ala Thr Thr Thr Glu Gln Leu Gly Phe Thr Gly Arg Gly Glu
        130                 135                 140

Gly Ile Ala Cys Glu Ala Val Val
145                 150

<210> SEQ ID NO 115
<211> LENGTH: 148
<212> TYPE: PRT
<213> ORGANISM: Actinobacillus actinomycetemcomitans

<400> SEQUENCE: 115

Ile Gly His Gly Phe Asp Val His Ala Phe Gly Thr Asn Asn Pro Leu
 1               5                  10                  15

Ile Ile Gly Gly Val Thr Ile Pro Phe Asp Lys Gly Phe Ile Ala His
                20                  25                  30

Ser Asp Gly Asp Val Ala Leu His Ala Leu Thr Asp Ala Leu Leu Gly
            35                  40                  45

Ala Ala Ala Leu Gly Asp Ile Gly Lys Leu Phe Pro Asp Thr Asp Met
        50                  55                  60
```

-continued

```
Gln Tyr Lys Gly Ala Asp Ser Arg Val Leu Leu Arg Glu Ala Tyr Arg
 65                  70                  75                  80

Gln Val Gln Glu Lys Gly Tyr Cys Val Gly Asn Val Asp Val Thr Ile
                 85                  90                  95

Ile Ala Gln Ala Pro Lys Met Arg Pro His Ile Asp Ala Met Arg Ala
            100                 105                 110

Leu Ile Ala Gln Asp Leu Ala Cys Asp Ile Glu Gln Val Asn Val Lys
        115                 120                 125

Ala Thr Thr Thr Glu Lys Leu Gly Phe Thr Gly Arg Gly Glu Gly Ile
    130                 135                 140

Ala Cys Glu Ala
145

<210> SEQ ID NO 116
<211> LENGTH: 153
<212> TYPE: PRT
<213> ORGANISM: Vibrio cholerae

<400> SEQUENCE: 116

Ile Gly His Gly Phe Asp Val His Arg Phe Gly Gly Glu Gly Pro Ile
 1               5                  10                  15

Ile Ile Gly Gly Val Lys Ile Pro Tyr Glu Gln Gly Leu Ile Ala His
            20                  25                  30

Ser Asp Gly Asp Val Ala Leu His Ala Leu Ser Asp Ala Leu Leu Gly
        35                  40                  45

Ala Ile Ala Ala Gly Asp Ile Gly Arg His Phe Pro Asp Thr Asp Asp
    50                  55                  60

Lys Trp Lys Gly Ala Asp Ser Arg Glu Leu Leu Lys Asp Val Tyr Arg
 65                  70                  75                  80

Arg Val Lys Ala Gln Gly Tyr Val Leu Gly Asn Ala Asp Val Thr Ile
                 85                  90                  95

Ile Ala Gln Ala Pro Lys Met Ala Pro Tyr Ile Gln Ala Met Cys Ala
            100                 105                 110

Ala Ile Ala Glu Asp Leu Glu Thr Asp Leu Gly Asn Ile Asn Val Lys
        115                 120                 125

Ala Thr Thr Thr Glu Lys Leu Gly Phe Thr Gly Arg Lys Glu Gly Ile
    130                 135                 140

Ala Cys Glu Ala Val Val Leu Leu Arg
145                 150

<210> SEQ ID NO 117
<211> LENGTH: 144
<212> TYPE: PRT
<213> ORGANISM: Shewanella putrefaciens

<400> SEQUENCE: 117

Ile Gly His Gly Phe Asp Val His Lys Phe Gly Glu Pro Arg Pro Leu
 1               5                  10                  15

Ile Leu Cys Gly Val Glu Val Pro Tyr Glu Thr Gly Leu Val Ala His
            20                  25                  30

Ser Asp Gly Asp Val Val Leu His Ala Ile Ser Asp Ala Ile Leu Gly
        35                  40                  45

Ala Met Ala Leu Gly Asp Ile Gly Lys His Phe Pro Asp Thr Asp Ala
    50                  55                  60

Ala Tyr Lys Gly Ala Asp Ser Arg Val Leu Leu Arg His Cys Tyr Ala
 65                  70                  75                  80
```

```
Leu Ala Lys Ala Lys Gly Phe Glu Leu Gly Asn Leu Asp Val Thr Ile
                85                  90                  95

Ile Ala Gln Ala Pro Lys Met Ala Pro His Ile Glu Asp Met Arg Gln
            100                 105                 110

Val Leu Ala Ala Asp Leu Asn Ala Asp Val Ala Asp Ile Asn Val Lys
        115                 120                 125

Ala Thr Thr Thr Glu Lys Leu Gly Phe Thr Gly Arg Lys Glu Ala Leu
    130                 135                 140
```

<210> SEQ ID NO 118
<211> LENGTH: 148
<212> TYPE: PRT
<213> ORGANISM: Pasteurella multocida

<400> SEQUENCE: 118

```
Ile Gly His Gly Phe Asp Val His Ala Phe Gly Gly Glu Gly Pro Ile
1               5                   10                  15

Ile Ile Gly Gly Val Ala Ile Pro Tyr Glu Lys Gly Leu Leu Ala His
            20                  25                  30

Ser Asp Gly Asp Val Ala Leu His Ala Leu Thr Asp Ala Leu Leu Gly
        35                  40                  45

Ala Val Ala Leu Gly Asp Ile Gly Lys Leu Phe Pro Asp Thr Asp Met
    50                  55                  60

Gln Tyr Lys Gly Ala Asp Ser Arg Gly Leu Leu Arg Glu Ala Tyr Thr
65                  70                  75                  80

Gln Val Gln Ala Lys Gly Tyr Lys Val Gly Asn Val Ala Val Thr Ile
                85                  90                  95

Ile Ala Gln Ala Pro Lys Met Arg Pro His Ile Asp Ala Met Arg Ala
            100                 105                 110

Ala Ile Ala Glu Asp Leu Ala Cys Asp Ile Glu Gln Val Asn Val Lys
        115                 120                 125

Ala Thr Thr Ser Glu Arg Leu Gly Phe Thr Gly Arg Gly Glu Gly Ile
    130                 135                 140

Ala Cys Glu Ala
145
```

<210> SEQ ID NO 119
<211> LENGTH: 148
<212> TYPE: PRT
<213> ORGANISM: Pseudomonas aeruginosa

<400> SEQUENCE: 119

```
Ile Gly His Gly Tyr Asp Val His Arg Phe Gly Glu Gly Asp Phe Ile
1               5                   10                  15

Thr Leu Gly Gly Val Arg Ile Pro His Lys His Gly Leu Val Ala His
            20                  25                  30

Ser Asp Gly Asp Val Leu Leu His Ala Leu Ser Asp Ala Leu Leu Gly
        35                  40                  45

Ala Ala Ala Leu Gly Asp Ile Gly Lys His Phe Pro Asp Thr Asp Pro
    50                  55                  60

Arg Phe Lys Gly Ala Asp Ser Arg Ala Leu Leu Arg His Val Val Ala
65                  70                  75                  80

Ile Val Ala Glu Lys Gly Trp Lys Val Gly Asn Val Asp Ala Thr Ile
                85                  90                  95

Val Ala Gln Ala Pro Lys Met Ala Pro His Ile Glu Thr Met Arg Gly
            100                 105                 110
```

```
Leu Ile Ala Glu Asp Leu Gly Val Ala Val Asp Gln Val Asn Val Lys
        115                 120                 125
Ala Thr Thr Glu Arg Leu Gly Phe Thr Gly Arg Glu Glu Gly Ile
130                 135                 140
Ala Val His Ala
145

<210> SEQ ID NO 120
<211> LENGTH: 150
<212> TYPE: PRT
<213> ORGANISM: Neisseria gonorrhoeae

<400> SEQUENCE: 120

Ile Gly Gln Gly Tyr Asp Val His Gln Leu Thr Glu Gly Arg Lys Leu
1               5                   10                  15
Ile Leu Gly Gly Val Glu Ile Pro Phe Glu Lys Gly Leu Leu Gly His
            20                  25                  30
Ser Asp Ala Asp Ala Leu Leu His Ala Val Thr Asp Ala Leu Leu Gly
        35                  40                  45
Ala Ala Gly Leu Gly Asp Ile Gly Ser His Phe Pro Asp Thr Ala Ala
    50                  55                  60
Glu Phe Lys Asp Ala Asp Ser Arg Val Leu Leu Arg Ala Ala Tyr Gln
65                  70                  75                  80
Ser Val Gln Ala Gln Gly Trp Gln Val Val Asn Val Asp Thr Thr Val
                85                  90                  95
Ile Ala Gln Lys Pro Lys Leu Ala Pro His Ile Pro Gln Met Arg Ala
            100                 105                 110
Asn Ile Ala Ala Asp Leu Gly Ile Asp Ile Ser Cys Val Asn Ile Lys
        115                 120                 125
Gly Lys Thr Asn Glu Lys Leu Gly Tyr Leu Gly Arg Met Glu Gly Ile
    130                 135                 140
Glu Ala Gln Ala Ala Val
145                 150

<210> SEQ ID NO 121
<211> LENGTH: 144
<212> TYPE: PRT
<213> ORGANISM: Bordetella pertussis

<400> SEQUENCE: 121

Val Gly Gln Gly Phe Asp Val His Ala Leu Val Glu Gly Arg Pro Leu
1               5                   10                  15
Ile Ile Gly Gly Val Thr Ile Ala His Thr His Gly Leu Leu Gly His
            20                  25                  30
Ser Asp Ala Asp Val Leu Leu His Ala Val Thr Asp Ala Leu Leu Gly
        35                  40                  45
Gly Ala Gly Leu Gly Asp Ile Gly Arg His Phe Pro Asp Thr Asp Pro
    50                  55                  60
Ala Tyr Arg Gly Ala Asp Ser Arg Val Leu Leu Arg Ala Ala Phe Asp
65                  70                  75                  80
Lys Val Arg Ala Ala Gly Trp Ala Pro Val Asn Val Asp Ala Thr Ile
                85                  90                  95
His Ala Gln Ala Pro Lys Ile Gly Pro His Ala Ala Ala Met Val Ala
            100                 105                 110
Asn Ile Ala Ala Asp Leu Ala Leu Asp Ala Gly Ala Val Asn Ile Lys
        115                 120                 125
```

Ala Lys Thr Asn Glu Gly Leu Gly Tyr Leu Gly Arg Lys Glu Gly Ile
    130                 135                 140

<210> SEQ ID NO 122
<211> LENGTH: 139
<212> TYPE: PRT
<213> ORGANISM: Neisseria meningitidis

<400> SEQUENCE: 122

Leu Ile Leu Gly Gly Val Glu Ile Pro Phe Glu Lys Gly Leu Leu Gly
1               5                   10                  15

His Ser Asp Ala Asp Ala Leu Leu His Ala Val Thr Asp Ala Leu Leu
            20                  25                  30

Gly Ala Ala Gly Leu Gly Asp Ile Gly Ser His Phe Pro Asp Thr Ala
        35                  40                  45

Ala Glu Phe Lys Asp Ala Asp Ser Arg Val Leu Leu Arg Ala Ala Tyr
    50                  55                  60

Gln Ser Val Gln Ala Gln Gly Trp Gln Ala Val Asn Val Asp Thr Thr
65                  70                  75                  80

Val Ile Ala Gln Lys Pro Thr Leu Ala Pro His Ile Pro Gln Met Arg
                85                  90                  95

Ala Asn Ile Ala Ala Asp Leu Gly Ile Asp Ile Ser Cys Val Asn Ile
            100                 105                 110

Lys Gly Lys Thr Asn Glu Lys Leu Gly Tyr Leu Gly Arg Met Glu Gly
        115                 120                 125

Ile Glu Ala Gln Ala Ala Val Leu Leu Val Arg
    130                 135

<210> SEQ ID NO 123
<211> LENGTH: 150
<212> TYPE: PRT
<213> ORGANISM: Neisseria meningitidis

<400> SEQUENCE: 123

Ile Gly Gln Gly Tyr Asp Val His Gln Leu Thr Glu Gly Arg Lys Leu
1               5                   10                  15

Ile Leu Gly Gly Val Glu Ile Pro Phe Glu Lys Gly Leu Leu Gly His
            20                  25                  30

Ser Asp Ala Asp Ala Leu Leu His Ala Val Thr Asp Ala Leu Leu Gly
        35                  40                  45

Ala Ala Gly Leu Gly Asp Ile Gly Ser His Phe Pro Asp Thr Ala Ala
    50                  55                  60

Glu Phe Lys Asp Ala Asp Ser Arg Val Leu Leu Arg Ala Ala Tyr Gln
65                  70                  75                  80

Ser Val Gln Ala Gln Gly Trp Gln Ala Val Asn Val Asp Thr Thr Val
                85                  90                  95

Ile Ala Gln Lys Pro Lys Leu Ala Pro His Ile Pro Gln Met Arg Ala
            100                 105                 110

Asn Ile Ala Ala Asp Leu Gly Ile Asp Ile Ser Cys Val Asn Ile Lys
        115                 120                 125

Gly Lys Thr Asn Glu Lys Leu Gly Tyr Leu Gly Arg Met Glu Gly Ile
    130                 135                 140

Glu Ser Gln Ala Ala Val
145                 150

<210> SEQ ID NO 124
<211> LENGTH: 154

```
<212> TYPE: PRT
<213> ORGANISM: Thiobacillus ferrooxidans

<400> SEQUENCE: 124

Ile Gly His Gly Phe Asp Val His Ala Leu Val Pro Gly Arg Ala Leu
1               5                   10                  15

Ile Leu Gly Gly Val Ser Val Pro Tyr Glu Arg Gly Leu Ala Gly His
            20                  25                  30

Ser Asp Ala Asp Val Leu Leu His Ser Ile Cys Asp Ala Leu Leu Gly
        35                  40                  45

Ala Ala Ala Leu Gly Asp Ile Gly Arg His Phe Pro Asp Thr Asp Ala
    50                  55                  60

Arg Phe Glu Gly Ala Asp Ser Arg Leu Leu Arg His Cys Arg Gln
65                  70                  75                  80

Leu Val Gln Gly Lys Gly Phe Ser Val Gly Asn Val Asp Ala Thr Ile
                85                  90                  95

Val Cys Gln Arg Pro Lys Leu Ala Asp His Ile Pro Gln Met Arg Ala
            100                 105                 110

His Ile Ala Ala Asp Leu Ala Val Glu Leu Asp Ala Val Asn Ile Lys
        115                 120                 125

Ala Thr Thr Thr Glu Gln Leu Gly Tyr Thr Gly Arg Gly Glu Gly Ile
    130                 135                 140

Ala Ala His Ala Val Val Leu Ile Gln His
145                 150

<210> SEQ ID NO 125
<211> LENGTH: 134
<212> TYPE: PRT
<213> ORGANISM: Deinococcus radiodurans

<400> SEQUENCE: 125

Ile Gly Tyr Gly Glu Asp Ala His Arg Leu Ala Pro Gly Leu Pro Leu
1               5                   10                  15

Val Leu Gly Gly Val Ala Ile Pro His Ala Glu Leu Gly Ala Val Ala
            20                  25                  30

His Ser Asp Gly Asp Ala Val Leu His Ala Val Ala Asp Ala Leu Leu
        35                  40                  45

Ser Gly Leu Ala Leu Gly Asp Ile Gly Gln Tyr Phe Pro Asp Thr Ala
    50                  55                  60

Ala Glu Trp Lys Gly Met Asp Ser Arg Arg Ile Leu Ala Lys Ala Leu
65                  70                  75                  80

Glu Leu Val Glu Glu Arg Gly Tyr Arg Pro Val Asn Val Ala Leu Val
                85                  90                  95

Val Thr Leu Asp Arg Pro Lys Leu Gly Pro Leu Arg Ala Asp Ile Ala
            100                 105                 110

Ala Ser Val Ala Glu Leu Leu Gly Leu Pro Ala Gly Glu Val Gly Val
        115                 120                 125

Ser Phe Lys Thr Ser Glu
    130

<210> SEQ ID NO 126
<211> LENGTH: 148
<212> TYPE: PRT
<213> ORGANISM: Clostridium acetobutylicum

<400> SEQUENCE: 126

Val Gly Ile Gly Tyr Asp Val His Lys Leu Val Glu Asn Arg Lys Leu
```

```
                 1               5                  10                 15
Ile Leu Gly Gly Val Glu Ile Gln Tyr Ser Lys Gly Leu Leu Gly His
                    20                 25                 30

Ser Asp Ala Asp Val Leu Val His Ala Ile Ile Asp Ser Ile Leu Gly
                    35                 40                 45

Ala Ala Gly Leu Gly Asp Ile Gly Lys Leu Phe Pro Asp Ser Asp Asn
                50                 55                 60

Lys Tyr Lys Gly Ile Ser Ser Leu Lys Leu Leu Lys Glu Val Asn Ala
 65                  70                 75                  80

Leu Ile Lys Asp Lys Gly Tyr Lys Ile Gly Asn Ile Asp Ser Thr Ile
                 85                 90                 95

Ile Ala Gln Lys Pro Lys Ile Ser Pro Tyr Ile Glu Asp Ile Lys Lys
                100                105                110

Ser Leu Cys Asn Val Leu Asp Ile Asp Leu Gly Ser Ile Asn Ile Lys
                115                120                125

Ala Thr Thr Glu Glu Gly Leu Gly Phe Thr Gly Arg Gly Glu Gly Ile
                130                135                140

Ser Ser Gln Ser
145

<210> SEQ ID NO 127
<211> LENGTH: 141
<212> TYPE: PRT
<213> ORGANISM: Mycobacterium avium

<400> SEQUENCE: 127

Ile Gly Leu Gly Val Asp Val His Pro Ile Gln Pro Gly Arg Pro Cys
 1               5                  10                 15

Arg Leu Leu Gly Leu Leu Phe Asp Asp Ala Asp Gly Cys Ala Gly His
                    20                 25                 30

Ser Asp Gly Asp Val Gly Ala His Ala Leu Cys Asp Ala Val Leu Ser
                    35                 40                 45

Ala Ala Gly Leu Gly Asp Val Gly Ala Val Phe Gly Val Asp Asp Pro
                50                 55                 60

Arg Trp Ala Gly Val Ser Gly Ala Asp Met Leu Arg His Val Ala Asp
 65                  70                 75                  80

Leu Thr Ala Arg His Gly Phe Arg Val Gly Asn Ala Ala Val Gln Val
                 85                 90                 95

Ile Gly Asn Arg Pro Lys Val Gly Pro Arg Ala Glu Ala Gln Arg
                100                105                110

Val Leu Ser Glu Leu Leu Gly Ala Pro Val Ser Val Ala Ala Thr Thr
                115                120                125

Thr Asp Gly Leu Gly Leu Thr Gly Arg Gly Glu Gly Leu
                130                135                140

<210> SEQ ID NO 128
<211> LENGTH: 141
<212> TYPE: PRT
<213> ORGANISM: Mycobacterium bovis

<400> SEQUENCE: 128

Val Gly Leu Gly Thr Asp Val His Pro Ile Glu Pro Gly Arg Pro Cys
 1               5                  10                 15

Trp Leu Val Gly Leu Leu Phe Pro Ser Ala Asp Gly Cys Ala Gly His
                    20                 25                 30

Ser Asp Gly Asp Val Ala Val His Ala Leu Cys Asp Ala Val Leu Ser
```

-continued

```
                35                  40                  45
Ala Ala Gly Leu Gly Asp Ile Gly Glu Val Phe Gly Val Asp Pro
    50                  55                  60

Arg Trp Gln Gly Val Ser Gly Ala Asp Met Leu Arg His Val Val
 65                  70                  75                  80

Leu Ile Thr Gln His Gly Tyr Arg Val Gly Asn Ala Val Val Gln Val
                85                  90                  95

Ile Gly Asn Arg Pro Lys Ile Gly Trp Arg Arg Leu Glu Ala Gln Ala
                100                 105                 110

Val Leu Ser Arg Leu Leu Asn Ala Pro Val Ser Val Ser Ala Thr Thr
                115                 120                 125

Thr Asp Gly Leu Gly Leu Thr Gly Arg Gly Glu Gly Leu
    130                 135                 140

<210> SEQ ID NO 129
<211> LENGTH: 143
<212> TYPE: PRT
<213> ORGANISM: Chlorobium tepidum

<400> SEQUENCE: 129

Ile Gly Ile Gly Ile Asp Val His Gln Phe Ala Glu Gly Arg Lys Leu
 1               5                  10                  15

Ile Ile Gly Gly Val Glu Val Pro Ser Pro Ile Gly Leu Leu Gly His
                20                  25                  30

Ser Asp Ala Asp Val Leu Leu His Ala Ile Ser Asp Ala Leu Leu Gly
                35                  40                  45

Ala Ala Ala Leu Gly Asp Ile Gly Lys His Phe Pro Asp Thr Ser Pro
    50                  55                  60

Asp Tyr Lys Asp Ala Asp Ser Met Glu Leu Leu Arg His Val Cys Lys
 65                  70                  75                  80

Leu Leu Glu Gln Glu Gly Tyr Lys Pro Val Asn Val Asp Thr Met Leu
                85                  90                  95

Leu Leu Glu Lys Pro Lys Ile Ala Pro Tyr Ile Asp Gln Met Arg Arg
                100                 105                 110

Asn Ile Ala Arg Cys Leu Gly Leu Glu Ile Asn Ala Val Ser Val Lys
                115                 120                 125

Ala Thr Thr Asn Glu Lys Leu Gly Tyr Val Gly Arg Gln Glu Gly
    130                 135                 140

<210> SEQ ID NO 130
<211> LENGTH: 148
<212> TYPE: PRT
<213> ORGANISM: Porphyromonas gingivalis

<400> SEQUENCE: 130

Ile Gly Phe Gly Phe Asp Val His Arg Leu Ser Glu Gly Tyr Pro Leu
 1               5                  10                  15

Trp Met Gly Gly Val Arg Leu Glu His Ser Lys Gly Leu Glu Gly His
                20                  25                  30

Ser Asp Ala Asp Val Leu Ile His Ala Ile Cys Asp Ala Leu Leu Gly
                35                  40                  45

Ala Ala Ala Leu Arg Asp Ile Gly Tyr His Phe Pro Pro Ser Asp Pro
    50                  55                  60

Gln Tyr Lys Gly Ile Asp Ser Lys Ile Leu Leu Ala Arg Val Met Glu
 65                  70                  75                  80

Leu Val Arg Ser Gln Gly Tyr Glu Leu Gly Asn Ile Asp Ala Thr Ile
```

```
                    85                  90                  95
Ala Ala Glu Gln Pro Lys Leu Asn Pro His Ile Pro Asp Met Gln Arg
            100                 105                 110

Val Leu Ala Glu Val Ile Gln Val Glu Val Ser Asp Ile Ser Leu Lys
            115                 120                 125

Ala Thr Thr Thr Glu Lys Leu Gly Phe Thr Gly Arg Glu Glu Gly Ile
            130                 135                 140

Ser Ala Tyr Ala
145

<210> SEQ ID NO 131
<211> LENGTH: 144
<212> TYPE: PRT
<213> ORGANISM: Enterococcus faecalis

<400> SEQUENCE: 131

Ile Gly Gln Gly Phe Asp Val His Gln Leu Val Pro Gln Arg Pro Leu
1               5                   10                  15

Ile Ile Gly Gly Val Thr Leu Pro Tyr Glu Lys Gly Leu Leu Gly His
            20                  25                  30

Ser Asp Ala Asp Val Leu Thr His Ala Ile Ile Asp Ala Ile Leu Gly
        35                  40                  45

Ala Ala Gly Leu Gly Asp Ile Gly Gln Leu Phe Pro Glu Thr Asp Pro
    50                  55                  60

Gln Phe Lys Asn Ala Asn Ser Val Asn Leu Leu Lys Lys Val Asn Glu
65                  70                  75                  80

Lys Val Gly Arg Ser Gly Phe Thr Ile Gly Asn Ile Asp Cys Thr Ile
                85                  90                  95

Leu Ala Glu Glu Pro Lys Met Ser Pro Tyr Leu Ala Glu Met Lys Lys
            100                 105                 110

Asn Leu Ala Ala Ser Cys His Leu Ala Val Thr Gln Val Asn Ile Lys
            115                 120                 125

Ala Thr Thr Met Glu Thr Met Gly Phe Val Gly Lys Lys Glu Gly Ile
            130                 135                 140

<210> SEQ ID NO 132
<211> LENGTH: 240
<212> TYPE: PRT
<213> ORGANISM: Plasmodium falciparum

<400> SEQUENCE: 132

Met Phe Leu Lys Gly Tyr Thr Ser Asn Val Val Leu Ile Ile Leu Thr
1               5                   10                  15

Phe Phe Ile Leu Leu Thr Lys Glu Glu Lys Asn Ile Lys Asn Asn Ile
            20                  25                  30

Ser Gly Tyr Cys Phe Leu Asn Phe Gly Leu Lys Lys Asn Ala Ile Ile
        35                  40                  45

Lys Lys Arg Glu Lys Gln Asn Leu Lys Leu Phe Cys Tyr Asn Gly Ile
    50                  55                  60

Arg Ile Gly Gln Gly Tyr Asp Ile His Lys Ile Lys Val Leu Asp Glu
65                  70                  75                  80

Glu Tyr Asn Thr Tyr Ala Asn Asn Asp Phe Asn Lys Asn Glu Gln Ser
                85                  90                  95

Phe Lys Thr Leu Thr Leu Gly Gly Val Lys Ile Asn Asn Val Leu Val
            100                 105                 110

Leu Ser His Ser Asp Gly Asp Ile Ile Tyr His Ser Ile Val Asp Ser
```

```
            115                 120                 125
Ile Leu Gly Ala Leu Gly Ser Leu Asp Ile Gly Thr Leu Phe Pro Asp
        130                 135                 140

Lys Asp Glu Lys Asn Lys Asn Lys Asn Ser Ala Ile Phe Leu Arg Tyr
145                 150                 155                 160

Ala Arg Leu Leu Ile Tyr Lys Lys Asn Tyr Asp Ile Gly Asn Val Asp
                165                 170                 175

Ile Asn Val Ile Ala Gln Val Pro Lys Ile Ser Asn Ile Arg Lys Asn
                180                 185                 190

Ile Ile Lys Asn Ile Ser Thr Val Leu Asn Ile Asp Glu Ser Gln Ile
            195                 200                 205

Ser Val Lys Gly Lys Thr His Glu Lys Leu Gly Val Ile Gly Glu Lys
        210                 215                 220

Lys Ala Ile Glu Cys Phe Ala Asn Ile Leu Leu Ile Pro Lys Asn Ser
225                 230                 235                 240

<210> SEQ ID NO 133
<211> LENGTH: 283
<212> TYPE: PRT
<213> ORGANISM: Escherichia coli

<400> SEQUENCE: 133

Met Arg Thr Gln Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Ile Ser Ile Glu Leu Arg Asp Asp
        35                  40                  45

Gly Asp Ile Arg Leu Leu Thr Pro Val Glu Gly Val Glu His Glu Asp
    50                  55                  60

Asn Leu Ile Val Arg Ala Ala Arg Leu Leu Met Lys Thr Ala Ala Asp
65                  70                  75                  80

Ser Gly Arg Leu Pro Thr Gly Ser Gly Ala Asn Ile Ser Ile Asp Lys
                85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Met
        115                 120                 125

Asp Glu Leu Ala Glu Met Gly Leu Thr Leu Gly Ala Asp Val Pro Val
    130                 135                 140

Phe Val Arg Gly His Ala Ala Phe Ala Glu Gly Val Gly Glu Ile Leu
145                 150                 155                 160

Thr Pro Val Asp Pro Pro Glu Lys Trp Tyr Leu Val Ala His Pro Gly
                165                 170                 175

Val Ser Ile Pro Thr Pro Val Ile Phe Lys Asp Pro Glu Leu Pro Arg
            180                 185                 190

Asn Thr Pro Lys Arg Ser Ile Glu Thr Leu Leu Lys Cys Glu Phe Ser
        195                 200                 205

Asn Asp Cys Glu Val Ile Ala Arg Lys Arg Phe Arg Glu Val Asp Ala
    210                 215                 220

Val Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Glu Ala Arg Gln
                245                 250                 255
```

```
Val Leu Glu Gln Ala Pro Glu Trp Leu Asn Gly Phe Val Ala Lys Gly
            260                 265                 270

Ala Asn Leu Ser Pro Leu His Arg Ala Met Leu
            275                 280

<210> SEQ ID NO 134
<211> LENGTH: 313
<212> TYPE: PRT
<213> ORGANISM: Haemophilus influenzae

<400> SEQUENCE: 134

Met Lys Ser His Gln Phe Ser Thr Ala Leu Cys Gln Asn Thr Thr Glu
1               5                   10                  15

Ser Asn Gly Gln Pro Leu Arg Phe Pro Ser Pro Ala Lys Leu Asn Leu
            20                  25                  30

Phe Leu Tyr Ile Asn Gly Lys Phe Pro Asn Gly Tyr His Glu Leu Gln
        35                  40                  45

Thr Leu Phe Gln Phe Leu Asp Phe Gly Asp Trp Leu Asp Ile Ser Ile
    50                  55                  60

Arg Glu Gln Asp Asn Gln Ile Val Leu Thr Pro Glu Ile Pro Asn Leu
65                  70                  75                  80

Lys Thr Glu Asn Asn Leu Ile Tyr Arg Ala Ala Lys Leu Leu Gln Glu
                85                  90                  95

Lys Ala Asn Ile Gln Leu Gly Ala Asn Ile His Leu Asp Lys Ile Leu
            100                 105                 110

Pro Met Gly Gly Gly Val Gly Gly Gly Ser Ser Asn Ala Ala Thr Ala
        115                 120                 125

Leu Val Ser Leu Asn Tyr Leu Trp Gln Ala Asn Leu Ser Ile Asp Glu
    130                 135                 140

Leu Ala Lys Leu Gly Leu Thr Leu Gly Ala Asp Val Pro Ile Phe Val
145                 150                 155                 160

His Gly His Ala Ala Phe Ala Glu Gly Val Gly Glu Lys Ile Thr Tyr
                165                 170                 175

Cys Glu Pro Ala Glu Lys Trp Phe Val Ile Leu Lys Pro Asp Asp Ser
            180                 185                 190

Ile Ser Thr Ala Val Ile Phe Gln Asp Pro Asn Leu Pro Arg Asn Thr
        195                 200                 205

Pro Lys Lys Ser Leu Ala Gln Leu Leu Ser Glu Pro Tyr Lys Asn Asp
    210                 215                 220

Cys Glu Lys Val Val Ile Asn His Tyr Ser Asn Val Glu Lys Ala Leu
225                 230                 235                 240

Asn Trp Leu Leu Gln Tyr Ala Pro Ala Arg Leu Thr Gly Thr Gly Ala
                245                 250                 255

Cys Val Phe Ala Glu Phe Asp His Glu Ala Glu Ala Gln Ala Val Phe
            260                 265                 270

Arg Gln Lys Pro Glu Ala Phe Phe Gly Phe Val Ala Lys Gly Leu Asn
            275                 280                 285

Val Ser Pro Leu His Ala Met Leu Lys Gln Leu Ser Ser Thr His Thr
        290                 295                 300

His Arg Gln Ser Lys Pro Glu Val Leu
305                 310

<210> SEQ ID NO 135
<211> LENGTH: 289
<212> TYPE: PRT
<213> ORGANISM: Bacillus subtilis
```

<400> SEQUENCE: 135

Met Arg Ile Leu Glu Lys Ala Pro Ala Lys Ile Asn Leu Ser Leu Asp
1               5                   10                  15

Val Thr Arg Lys Arg Pro Asp Gly Tyr His Glu Val Glu Met Ile Met
            20                  25                  30

Thr Thr Ile Asp Leu Ala Asp Arg Ile Glu Leu Thr Glu Leu Ala Glu
        35                  40                  45

Asp Glu Val Arg Val Ser Ser His Asn Arg Phe Val Pro Asp Asp Gln
50                  55                  60

Arg Asn Leu Ala Tyr Gln Ala Ala Lys Leu Ile Lys Asp Arg Tyr Asn
65                  70                  75                  80

Val Lys Lys Gly Val Ser Ile Met Ile Thr Lys Val Ile Pro Val Ala
                85                  90                  95

Ala Gly Leu Ala Gly Gly Ser Ser Asp Ala Ala Thr Leu Arg Gly
            100                 105                 110

Leu Asn Arg Leu Trp Asn Leu Asn Leu Ser Ala Glu Thr Leu Ala Glu
            115                 120                 125

Leu Gly Ala Glu Ile Gly Ser Asp Val Ser Phe Cys Val Tyr Gly Gly
130                 135                 140

Thr Ala Leu Ala Thr Gly Arg Gly Glu Lys Ile Lys His Ile Ser Thr
145                 150                 155                 160

Pro Pro His Cys Trp Val Ile Leu Ala Lys Pro Thr Ile Gly Val Ser
                165                 170                 175

Thr Ala Glu Val Tyr Arg Ala Leu Lys Leu Asp Gly Ile Glu His Pro
            180                 185                 190

Asp Val Gln Gly Met Ile Glu Ala Ile Glu Glu Lys Ser Phe Gln Lys
            195                 200                 205

Met Cys Ser Arg Leu Gly Asn Val Leu Glu Ser Val Thr Leu Asp Met
210                 215                 220

His Pro Glu Val Ala Met Ile Lys Asn Gln Met Lys Arg Phe Gly Ala
225                 230                 235                 240

Asp Ala Val Leu Met Ser Gly Ser Gly Pro Thr Val Phe Gly Leu Val
                245                 250                 255

Gln Tyr Glu Ser Lys Val Gln Arg Ile Tyr Asn Gly Leu Arg Gly Phe
            260                 265                 270

Cys Asp Gln Val Tyr Ala Val Arg Met Ile Gly Glu Gln Asn Ala Leu
        275                 280                 285

Asp

<210> SEQ ID NO 136
<211> LENGTH: 315
<212> TYPE: PRT
<213> ORGANISM: Synechocystis sp.

<400> SEQUENCE: 136

Met His Ser Tyr Thr Leu His Ala Pro Ala Lys Ile Asn Leu Phe Leu
1               5                   10                  15

Glu Ile Leu Gly Asp Arg Pro Asp Gly Phe His Glu Leu Val Met Val
            20                  25                  30

Leu Gln Ser Ile Ala Leu Gly Asp Lys Ile Thr Val Arg Ala Asn Gly
        35                  40                  45

Thr Asp Asp Ile Arg Leu Ser Cys Gly Asp Ser Pro Leu Ala Asn Asp
50                  55                  60

```
Ala Thr Asn Leu Ala Tyr Arg Ala Ala Gln Leu Met Ile Asn Asn Phe
 65                  70                  75                  80

Pro Gln Ala His Asp Asn Tyr Gly Gly Val Asp Ile Thr Leu Thr Lys
                 85                  90                  95

His Ile Pro Met Ala Ala Gly Leu Ala Gly Ser Ala Asp Ala Ala
            100                 105                 110

Ala Val Leu Val Gly Leu Asp Leu Leu Trp Asn Leu Gly Leu Thr Arg
        115                 120                 125

Pro Glu Leu Glu Gln Leu Ala Ala Gln Leu Gly Ser Asp Ile Pro Phe
    130                 135                 140

Cys Ile Gly Gly Gly Thr Ala Ile Ala Thr Gly Arg Gly Glu Ile Leu
145                 150                 155                 160

Asp Pro Leu Pro Asp Gly Asn Cys Phe Trp Val Val Leu Ala Lys His
                165                 170                 175

Arg Ser Ile Glu Val Ser Thr Pro Trp Ala Tyr Gln Thr Tyr Arg Gln
            180                 185                 190

Lys Phe Gly Lys Asn Tyr Leu Asn Asp Asp Gln Ser Gln Arg Ala Arg
        195                 200                 205

Arg Lys Thr Ile His Ala Gly Pro Leu Leu Gln Gly Ile Gln His Arg
    210                 215                 220

Asn Pro Gly Gln Ile Ala Ser His Ile His Asn Asp Leu Glu Lys Val
225                 230                 235                 240

Val Leu Pro Ala His Gln Pro Val Ala Gln Leu Arg Gln Val Leu Gln
                245                 250                 255

Ser Ala Gly Gly Leu Gly Thr Met Met Ser Gly Ser Gly Pro Ser Val
            260                 265                 270

Phe Thr Leu Cys Arg Glu Gln Ala Glu Ala Glu Gln Val Leu Ala Ile
        275                 280                 285

Ala Lys Glu Lys Leu Asn Asp Pro Asp Val Asp Phe Trp Leu Thr His
    290                 295                 300

Thr Ile Gly His Gly Ile Gln Ile Met Asn Asn
305                 310                 315

<210> SEQ ID NO 137
<211> LENGTH: 306
<212> TYPE: PRT
<213> ORGANISM: Mycobacterium tuberculosis

<400> SEQUENCE: 137

Met Pro Thr Gly Ser Val Thr Val Arg Val Pro Gly Lys Val Asn Leu
  1               5                  10                  15

Tyr Leu Ala Val Gly Asp Arg Arg Glu Asp Gly Tyr His Glu Leu Thr
             20                  25                  30

Thr Val Phe His Ala Val Ser Leu Val Asp Glu Val Thr Val Arg Asn
         35                  40                  45

Ala Asp Val Leu Ser Leu Glu Leu Val Gly Glu Gly Ala Asp Gln Leu
     50                  55                  60

Pro Thr Asp Glu Arg Asn Leu Ala Trp Gln Ala Ala Glu Leu Met Ala
 65                  70                  75                  80

Glu His Val Gly Arg Ala Pro Asp Val Ser Ile Met Ile Asp Lys Ser
                 85                  90                  95

Ile Pro Val Ala Gly Gly Met Ala Gly Gly Ser Ala Asp Ala Ala Ala
            100                 105                 110

Val Leu Val Ala Met Asn Ser Leu Trp Glu Leu Asn Val Pro Arg Arg
        115                 120                 125
```

```
Asp Leu Arg Met Leu Ala Ala Arg Leu Gly Ser Asp Val Pro Phe Ala
    130                 135                 140

Leu His Gly Gly Thr Ala Leu Gly Thr Gly Arg Gly Glu Glu Leu Ala
145                 150                 155                 160

Thr Val Leu Ser Arg Asn Thr Phe His Trp Val Leu Ala Phe Ala Asp
                165                 170                 175

Ser Gly Leu Leu Thr Ser Ala Val Tyr Asn Glu Leu Asp Arg Leu Arg
            180                 185                 190

Glu Val Gly Asp Pro Pro Arg Leu Gly Glu Pro Gly Pro Val Leu Ala
        195                 200                 205

Ala Leu Ala Ala Gly Asp Pro Asp Gln Leu Ala Pro Leu Leu Gly Asn
    210                 215                 220

Glu Met Gln Ala Ala Val Ser Leu Asp Pro Ala Leu Ala Arg Ala
225                 230                 235                 240

Leu Arg Ala Gly Val Glu Ala Gly Ala Leu Ala Gly Ile Val Ser Gly
                245                 250                 255

Ser Gly Pro Thr Cys Ala Phe Leu Cys Thr Ser Ala Ser Ser Ala Ile
            260                 265                 270

Asp Val Gly Ala Gln Leu Ser Gly Ala Gly Val Cys Arg Thr Val Arg
        275                 280                 285

Val Ala Thr Gly Pro Val Pro Gly Ala Arg Val Val Ser Ala Pro Thr
    290                 295                 300

Glu Val
305

<210> SEQ ID NO 138
<211> LENGTH: 268
<212> TYPE: PRT
<213> ORGANISM: Aquifex aeolicus

<400> SEQUENCE: 138

Met Ile Lys Val Leu Ser Pro Ala Lys Ile Asn Leu Gly Leu Trp Val
1               5                   10                  15

Leu Gly Arg Leu Pro Ser Gly Tyr His Glu Ile Leu Thr Leu Tyr Gln
            20                  25                  30

Glu Ile Pro Phe Tyr Asp Glu Ile Tyr Ile Arg Glu Gly Val Leu Arg
        35                  40                  45

Val Glu Thr Asn Ile Gly Ile Pro Gln Glu Glu Asn Leu Val Tyr Lys
    50                  55                  60

Gly Leu Arg Glu Phe Glu Arg Ile Thr Gly Ile Glu Ile Asn Tyr Ser
65                  70                  75                  80

Ile Phe Ile Gln Lys Asn Ile Pro Pro Gly Ala Gly Leu Gly Gly Gly
                85                  90                  95

Ser Ser Asn Leu Ala Val Val Leu Lys Lys Val Asn Glu Leu Leu Gly
            100                 105                 110

Ser Pro Leu Ser Glu Glu Glu Leu Arg Glu Leu Val Gly Ser Ile Ser
        115                 120                 125

Ala Asp Ala Pro Phe Phe Leu Leu Gly Lys Ser Ala Ile Gly Arg Gly
    130                 135                 140

Lys Gly Glu Val Leu Glu Pro Val Glu Thr Glu Ile Ser Gly Lys Ile
145                 150                 155                 160

Thr Leu Val Ile Pro Gln Val Ser Ser Ser Thr Gly Arg Val Tyr Ser
                165                 170                 175

Ser Leu Arg Glu Glu His Phe Val Thr Pro Glu Tyr Ala Glu Glu Lys
```

```
                180                 185                 190
Ile Gln Arg Ile Ile Ser Gly Glu Val Glu Ile Glu Asn Val Leu
            195                 200                 205

Gly Asp Ile Ala Arg Glu Leu Tyr Pro Glu Ile Asn Glu Val Tyr Arg
210                 215                 220

Phe Val Glu Tyr Leu Gly Phe Lys Pro Phe Val Ser Gly Ser Gly Ser
225                 230                 235                 240

Thr Val Tyr Phe Phe Gly Gly Ala Ser Glu Leu Lys Lys Ala Ala
                245                 250                 255

Lys Met Arg Gly Trp Lys Val Val Glu Leu Glu Leu
            260                 265

<210> SEQ ID NO 139
<211> LENGTH: 288
<212> TYPE: PRT
<213> ORGANISM: Chlamydia trachomatis

<400> SEQUENCE: 139

Met His Phe Leu Ser Pro Ala Lys Leu Asn Leu Phe Leu Gln Ile Leu
1               5                   10                  15

Gly Arg Arg Glu Asp Asp Phe His Glu Ile Val Thr Arg Tyr Gln Ala
            20                  25                  30

Ile Ala Phe Gly Asp Gln Leu Ser Leu Ser Ile Ser Ser Arg Asp Ser
        35                  40                  45

Leu Gln Val Ile Asn Ala Cys His Leu Glu Thr Pro Ser Asn Ser Ile
    50                  55                  60

Trp Lys Ser Val Ala Leu Phe Arg Arg Tyr Thr Gly Ile Thr Thr Pro
65                  70                  75                  80

Val Ser Trp Arg Val Val Lys Gln Ile Pro Val Gly Ala Gly Leu Ala
                85                  90                  95

Gly Gly Ser Ser Asn Ala Ala Thr Ala Leu Phe Ala Leu Asn Gln Ile
            100                 105                 110

Phe Lys Thr Gly Leu Ser Asp Glu Glu Met Arg Ser Leu Ala Glu Gln
        115                 120                 125

Leu Gly Val Asp Thr Pro Phe Phe Ser Thr Gly Ala Ala Leu Gly
    130                 135                 140

Val Ala Arg Gly Glu Lys Ile Ile Ala Leu Glu Glu Ser Val Ser Asp
145                 150                 155                 160

Arg Tyr Val Leu Tyr Phe Ser Ser Glu Gly Val Leu Thr Ser Arg Ala
                165                 170                 175

Phe Ala Ala Val Gln Pro Ser Asp Cys Ser Ser Arg Lys Asn Leu Glu
            180                 185                 190

Tyr Thr Gln Asn Asp Leu Glu Lys Pro Val Phe Arg Leu Arg Leu Asp
        195                 200                 205

Leu Lys Glu Lys Lys His Trp Leu Glu Asn Leu Trp Ala Glu Leu Pro
    210                 215                 220

Val His Ile Gly Leu Thr Gly Ser Gly Ala Thr Leu Phe Val Arg Tyr
225                 230                 235                 240

Pro Glu Ile Leu Glu Glu Asp Leu Ser Tyr Ala Ala Gln Ile Gln Arg
                245                 250                 255

Ala Val Thr Leu Ser Gly Gly Leu Leu Thr Ser Pro Ile Arg Arg Asp
            260                 265                 270

Pro Thr Ala Trp Tyr Ser Ile Tyr Ser Glu Ser Ala Leu Ala Ala Thr
        275                 280                 285
```

<210> SEQ ID NO 140
<211> LENGTH: 280
<212> TYPE: PRT
<213> ORGANISM: Chlamydia pneumoniae

<400> SEQUENCE: 140

Met Gln Tyr Phe Ser Pro Ala Lys Leu Asn Leu Phe Leu Lys Ile Trp
1               5                   10                  15

Gly Lys Arg Phe Asp Asn Phe His Glu Leu Thr Thr Leu Tyr Gln Ala
            20                  25                  30

Ile Asp Phe Gly Asp Thr Leu Ser Leu Lys Asn Ser Met Lys Asp Ser
        35                  40                  45

Leu Ser Ser Asn Val Asn Glu Leu Leu Ser Pro Ser Asn Leu Ile Trp
    50                  55                  60

Lys Ser Leu Glu Ile Phe Arg Arg Glu Thr Gln Ile His Gln Pro Val
65                  70                  75                  80

Ser Trp His Leu Asn Lys Ser Ile Pro Leu Gln Ser Gly Leu Gly Gly
                85                  90                  95

Gly Ser Ser Asn Ala Ala Thr Ala Leu Tyr Ala Leu Asn Glu His Phe
            100                 105                 110

Gln Thr His Ile Pro Ile Thr Thr Leu Gln Leu Trp Ala Arg Glu Ile
        115                 120                 125

Gly Ser Asp Val Pro Phe Phe Phe Ser Ser Gly Thr Ala Leu Gly Lys
    130                 135                 140

Gly Arg Gly Glu His Leu Phe Ser Ile Lys Lys Leu Asn His Lys His
145                 150                 155                 160

Lys Tyr Val Leu Tyr Leu Asp His Gln Gly Ile Pro Thr Glu Lys Ala
                165                 170                 175

Tyr Gln Ser Leu Leu Pro Gln Asp Tyr Ser Thr Gly Asn His Asn Ala
            180                 185                 190

Cys Phe Tyr Gly Glu Asn Asp Leu Glu Lys Ser Val Phe Arg Ile Arg
        195                 200                 205

Thr Asp Leu Lys Asn Lys Lys His Met Leu Glu Arg Met Trp Ser Pro
    210                 215                 220

Phe Glu Ser His Val Leu Met Ser Gly Ser Gly Ala Thr Leu Phe Val
225                 230                 235                 240

Cys Tyr Leu Glu Glu Leu Glu Gln Asp Ser Lys Val Ser Ser Gln Ile
                245                 250                 255

His Ser Leu Ile Lys Gln Thr Gln Gly Ile Pro Val Ser Arg Leu Tyr
            260                 265                 270

Arg Glu Pro His Trp Tyr Ser Leu
        275                 280

<210> SEQ ID NO 141
<211> LENGTH: 271
<212> TYPE: PRT
<213> ORGANISM: Thermotoga maritima

<400> SEQUENCE: 141

Met Val Glu Asn Ile Gly Ser Gly Ser Ala Glu Leu Val Ser Tyr Ala
1               5                   10                  15

Lys Leu Asn Leu Tyr Leu Asp Val Leu Gly Lys Arg Ser Asp Gly Tyr
            20                  25                  30

His Glu Ile Val Gly Leu Phe Gln Thr Ile Ser Leu His Asp Thr Leu
        35                  40                  45

```
Thr Val Glu Ile Cys Asp Arg Gly Phe Tyr Leu Glu Ser Ser Val Ala
 50                  55                  60

Leu Pro Ser Asp Asn Thr Ile Lys Arg Ala Trp Glu Met Phe Arg Lys
 65                  70                  75                  80

Asn Thr Gly Lys Glu Phe Gly Leu Lys Val Thr Leu Lys Lys Glu Ile
                 85                  90                  95

Pro Val Gly Ser Gly Leu Gly Gly Ser Ser Asn Ala Ala Ala Val
             100                 105                 110

Leu Arg Tyr Leu Gly Glu Val Phe Lys Ile Pro Leu Glu Asp Leu Leu
             115                 120                 125

Asn Ile Ala Ala Gln Val Gly Ser Asp Val Pro Phe Phe Leu Tyr Gly
130                 135                 140

Gly Thr Ala Leu Val Arg Gly Arg Gly Glu Ile Val Glu Lys Leu Glu
145                 150                 155                 160

Asp Ile Glu Gly Tyr Ser Val Asp Leu Phe Phe Pro Gly Ile His Ser
                165                 170                 175

Ser Thr Lys Glu Met Tyr Leu Ser Leu Thr Pro Glu Met Tyr Arg Lys
                180                 185                 190

Gly Pro Gly Arg Val Glu Glu Leu His Arg Ala Tyr Leu Glu Arg Asn
                195                 200                 205

Tyr Glu Lys Ile Lys Glu Leu Ser Tyr Asn Val Phe Glu Lys Val Phe
210                 215                 220

Leu Glu Lys His Pro Glu Val Met Asp Gly Leu Arg Asn Phe Gly Asp
225                 230                 235                 240

Gly Ser Ile Val Lys Met Met Thr Gly Ser Gly Ser Val Phe Phe Ala
                245                 250                 255

Leu Tyr Pro Leu Asp Lys Gly Asn Tyr Ser Phe Val Gly Gly Val
                260                 265                 270

<210> SEQ ID NO 142
<211> LENGTH: 268
<212> TYPE: PRT
<213> ORGANISM: Helicobacter pylori

<400> SEQUENCE: 142

Met Thr His Val Phe Glu Val Tyr Pro Lys Val Asn Ile Phe Leu Lys
 1               5                  10                  15

Ile Leu His Lys Glu Gly Ala Tyr His Lys Leu Ile Ser Arg Met Cys
                 20                  25                  30

Leu Val Lys Asp Lys Leu Lys Asp Ile Ile Ser Val Lys Ser Ala Leu
             35                  40                  45

Ser Phe Ser Leu Lys Gly Asp Phe Asp Cys Pro Leu Glu Glu Asn Ser
 50                  55                  60

Leu Phe Lys Ala Leu Gln Ile Leu Lys Asn Phe Leu Lys Ser Lys Asn
 65                  70                  75                  80

Phe Ser His Ser Val Ile Lys Ser Leu Asp Thr Leu Ala Ile Glu Val
                 85                  90                  95

Glu Lys Asn Ile Pro Thr Gln Ala Gly Leu Gly Gly Ser Thr Asp
             100                 105                 110

Ala Gly Gly Leu Leu Tyr His Leu Asn Gln Ile Phe Asp Trp Arg Leu
             115                 120                 125

Ser Leu Glu Glu Leu Tyr Ser Met Gly Ser Leu Val Gly Ala Asp Thr
130                 135                 140

Asn Phe Phe Ile Ser Gln Tyr Lys Ser Thr Asn Ala Thr Ser Tyr Gly
145                 150                 155                 160
```

Glu Val Ile Glu Asn Phe Glu Glu Pro Leu Glu Asn Arg Leu Glu
            165                 170                 175

Ile Tyr Ala Pro Asn His Val Phe Cys Ser Thr Lys Ala Val Tyr Gln
        180                 185                 190

Ala Tyr Lys Pro Glu Thr Cys Phe Ser Gln Ala Lys Glu Trp Leu Lys
        195                 200                 205

Lys Pro Ser Leu Glu Cys Leu Lys Thr Tyr Asp Arg Asn Gly Leu Asn
        210                 215                 220

Asp Leu Leu Lys Pro Ala Leu Leu Thr Asn Gln Ala Leu Lys Asp Ile
225                 230                 235                 240

Glu Ser Glu Leu Gly Lys Glu Trp Phe Phe Ser Gly Ser Gly Ser Ala
                245                 250                 255

Phe Phe Arg Leu Lys Pro Met Gln Lys Gly Gly Glu
            260                 265

<210> SEQ ID NO 143
<211> LENGTH: 291
<212> TYPE: PRT
<213> ORGANISM: Treponema pallidum
<220> FEATURE:
<221> NAME/KEY: misc_feature
<222> LOCATION: (259)..(259)
<223> OTHER INFORMATION: Xaa can be any naturally occurring amino acid

<400> SEQUENCE: 143

Met Gln Ser Leu Ser Leu Arg Ala His Ala Lys Val Asn Met His Leu
1               5                   10                  15

Trp Val Gly Ala Arg Arg Ala Asp Gly Leu His Ser Ile Glu Ser Val
            20                  25                  30

Met Gln Arg Ile Thr Leu Ala Asp Ser Leu Ser Leu Ser Arg Leu Asp
        35                  40                  45

Ile Pro Gly Arg Cys Glu Val Cys Ser Pro Tyr Met Ala Leu Pro Arg
    50                  55                  60

Glu Asn Thr Leu Thr Arg Ala Tyr Ala Arg Phe Cys Gln Val Thr Gly
65                  70                  75                  80

Val His Asp Gly Val Arg Val Arg Val Lys Arg Ile Pro Ala Gly
                85                  90                  95

Ser Gly Leu Gly Gly Gly Ser Ala Asp Ala Ala Ala Leu Leu Cys Gly
            100                 105                 110

Leu Asp Thr Leu Phe Gly Thr Thr Leu Ser Ala Arg Val Leu Arg Glu
        115                 120                 125

Val Ala Tyr Ser Val Gly Ser Asp Val Pro Phe Phe Leu Ala Ser Gln
    130                 135                 140

Ala Ala Cys Val Leu Gly Gly Gly Glu Gln Leu Val Pro Leu Val Pro
145                 150                 155                 160

Lys Thr Gly Tyr Leu Gly Leu Leu Val Trp Pro Gly Leu His Ser Gly
                165                 170                 175

Ser Ala Gln Ala Tyr Glu Asp Leu Asp Arg Leu Arg Ala Cys Gly Val
            180                 185                 190

His Ala Ala Asp Gly Glu Gln Tyr Ser Leu Arg Gly Ala Thr Ala Leu
        195                 200                 205

Ser Ala His Tyr Ala Gln Asp Cys Ala Arg Trp Arg Phe Phe Asn Ser
    210                 215                 220

Leu Asp Ala Pro Val Gln Arg Arg Tyr Pro Val Val Ala Leu Ala Arg
225                 230                 235                 240

```
Trp Asp Leu Ala Arg Ala Gly Ala Cys Phe Thr Ala Met Ser Gly Ser
            245                 250                 255

Gly Ser Xaa Val Phe Gly Leu Tyr Arg Asp Glu Glu Leu Arg Arg
        260                 265                 270

Ala His Lys Leu Leu Ala Lys Arg Trp Cys Trp Cys Val Arg Val Arg
        275                 280                 285

Leu Cys Gly
    290

<210> SEQ ID NO 144
<211> LENGTH: 283
<212> TYPE: PRT
<213> ORGANISM: Salmonella typhimurium

<400> SEQUENCE: 144

Met Met Thr His Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Leu His Ile Glu Pro Arg His Asp
        35                  40                  45

Gly Glu Ile His Leu Leu Thr Pro Val Asn Gly Val Glu Asn Glu Asp
    50                  55                  60

Asn Leu Ile Val Arg Ala Ala Arg Leu Leu Met Lys Val Ala Ser Glu
65                  70                  75                  80

Ser Gly Arg Leu Pro Ala Gly Ser Gly Ala Asp Ile Ser Ile Glu Lys
                85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Ile
        115                 120                 125

Asp Glu Leu Ala Thr Leu Gly Leu Thr Leu Gly Ala Asp Val Pro Val
    130                 135                 140

Phe Val Arg Gly His Ala Ala Phe Ala Glu Gly Val Gly Glu Ile Leu
145                 150                 155                 160

Thr Pro Val Asn Pro Pro Glu Lys Trp Tyr Leu Val Ala His Pro Gly
                165                 170                 175

Val Ser Ile Pro Thr Pro Val Ile Phe Lys Asp Pro Gln Leu Pro Arg
            180                 185                 190

Asn Thr Pro Lys Arg Ser Ile Asp Thr Leu Leu Lys Cys Glu Phe Ser
        195                 200                 205

Asn Asp Cys Glu Val Ile Ala Arg Lys Arg Phe Arg Glu Val Asp Ala
    210                 215                 220

Ala Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Cys Ala Arg Gln
                245                 250                 255

Val Leu Glu Gln Ala Pro Glu Trp Leu Asn Ala Phe Val Ala Lys Gly
            260                 265                 270

Val Asn Leu Ser Pro Leu His Arg Glu Leu Leu
        275                 280

<210> SEQ ID NO 145
<211> LENGTH: 282
<212> TYPE: PRT
<213> ORGANISM: Zymomonas mobilis
```

<400> SEQUENCE: 145

```
Met Pro Lys Leu Thr Glu Ile Ala Tyr Ala Lys Ile Asn Leu Ala Leu
1               5                   10                  15

His Val Arg Gly Lys Met Pro Asn Gly Tyr His Ala Leu Glu Thr Ile
            20                  25                  30

Phe Ala Phe Ala Lys Asp Gly Asp Ile Leu Gln Ala Glu Ala Asn Asp
        35                  40                  45

Thr Glu Asp Asn Leu Thr Ile Thr Gly Pro Phe Ser Glu Gly Leu Glu
    50                  55                  60

Ala Asn Lys Asp Asn Leu Val Leu Arg Ala Val Thr Ala Leu Arg Gln
65                  70                  75                  80

Ala Cys Pro Asn Lys Ile Pro Ala Gly Phe Ser Ile Ile Leu Asp Lys
                85                  90                  95

Arg Leu Pro Val Ala Ala Gly Ile Gly Gly Ser Ala Asp Ala Ala
            100                 105                 110

Ala Met Leu Arg Met Ile Gly Gln His Tyr Gln Ile Pro His Glu Leu
            115                 120                 125

Ile Leu Ser Leu Ala Asn Ser Leu Gly Ala Asp Val Pro Ala Cys Val
        130                 135                 140

Asp Ser Cys Leu Val Arg Gly Glu Gly Val Gly Glu Lys Leu Thr Gln
145                 150                 155                 160

Ile Gly Asp Arg Ser Leu Glu Glu Lys Pro Leu Leu Val Asn Pro
                165                 170                 175

Arg Val Ser Cys Ser Thr Pro Met Ile Phe Lys Asn Trp Asp Gly Val
            180                 185                 190

Asp Arg Gly Ala Leu Asp Ser Asp Gly Ser Ile Leu Gly Ala Ala Arg
        195                 200                 205

Ser Gly Arg Asn Asp Leu Glu Pro Pro Ala Arg Lys Ile Leu Pro Ile
    210                 215                 220

Ile Gly Glu Val Val Glu Trp Leu Gln Gln Gln Lys Gly Val Ser Phe
225                 230                 235                 240

Ser Arg Met Ser Gly Ser Gly Ala Thr Cys Phe Ala Leu Phe Asp Glu
                245                 250                 255

Ile Glu Asp Arg Asp Thr Ala Tyr Lys Lys Leu Asn Ile Asp His Pro
            260                 265                 270

Glu Trp Trp Ala Leu Ser Ser Leu Leu Arg
        275                 280
```

<210> SEQ ID NO 146
<211> LENGTH: 283
<212> TYPE: PRT
<213> ORGANISM: Salmonella typhi

<400> SEQUENCE: 146

```
Met Met Thr His Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Leu His Ile Glu Pro Arg His Asp
        35                  40                  45

Gly Glu Ile His Leu Leu Thr Pro Val Thr Gly Val Glu Asn Glu Asp
    50                  55                  60

Asn Leu Ile Val Arg Ala Ala Arg Leu Leu Met Lys Val Ala Ser Glu
65                  70                  75                  80
```

Ser Gly Arg Leu Pro Ala Gly Ser Gly Ala Asp Ile Ser Ile Glu Lys
            85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Ile
            115                 120                 125

Asp Glu Leu Ala Thr Leu Gly Leu Thr Leu Gly Ala Asp Val Pro Val
            130                 135                 140

Phe Val Arg Gly His Ala Ala Phe Ala Glu Gly Val Gly Glu Ile Leu
145                 150                 155                 160

Thr Pro Val Asn Pro Pro Glu Lys Trp Tyr Leu Val Ala His Pro Gly
            165                 170                 175

Val Ser Ile Pro Thr Pro Val Ile Phe Lys Asp Pro Gln Leu Pro Arg
            180                 185                 190

Asn Thr Pro Lys Arg Ser Ile Asp Thr Leu Leu Lys Cys Glu Phe Ser
            195                 200                 205

Asn Asp Cys Glu Val Ile Ala Arg Lys Arg Phe Arg Glu Val Asp Ala
            210                 215                 220

Ala Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Cys Ala Arg Gln
            245                 250                 255

Val Leu Glu Gln Ala Pro Glu Trp Leu Asn Ala Phe Val Ala Lys Gly
            260                 265                 270

Val Asn Leu Ser Pro Leu His Arg Glu Leu Leu
            275                 280

<210> SEQ ID NO 147
<211> LENGTH: 282
<212> TYPE: PRT
<213> ORGANISM: Salmonella paratyphi

<400> SEQUENCE: 147

Met Met Thr His Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Leu His Ile Glu Pro Arg Arg Asp
            35                  40                  45

Gly Glu Ile His Leu Leu Thr Pro Val Asn Gly Val Glu Asn Glu Asp
        50                  55                  60

Asn Leu Ile Val Arg Ala Ala Gln Leu Leu Met Lys Ile Ala Ser Glu
65                  70                  75                  80

Ser Gly Arg Leu Pro Ala Gly Ser Gly Ala Asp Ile Ser Ile Glu Lys
            85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Ile
            115                 120                 125

Asp Glu Leu Ala Thr Leu Gly Leu Thr Leu Gly Ala Asp Val Pro Val
            130                 135                 140

Phe Val Arg Gly His Ala Ala Phe Ala Glu Gly Val Gly Glu Ile Leu
145                 150                 155                 160

Thr Pro Val Asn Pro Pro Glu Lys Trp Tyr Leu Val Ala His Pro Gly

-continued

```
                165                 170                 175

Val Ser Ile Pro Thr Pro Val Ile Phe Lys Asp Pro Gln Leu Pro Asn
            180                 185                 190

Thr Pro Lys Arg Ser Ile Asp Thr Leu Leu Lys Cys Glu Phe Ser Asn
        195                 200                 205

Asp Cys Glu Val Ile Ala Arg Lys Arg Phe Arg Glu Val Asp Ala Ala
    210                 215                 220

Leu Ser Trp Leu Leu Glu Tyr Ala Pro Ser Arg Leu Thr Gly Thr Gly
225                 230                 235                 240

Ala Cys Val Phe Ala Glu Phe Asp Thr Glu Ser Cys Ala Arg Gln Val
                245                 250                 255

Leu Glu Gln Ala Pro Glu Trp Leu Asn Ala Phe Val Ala Lys Gly Val
            260                 265                 270

Asn Leu Ser Pro Leu His Arg Glu Leu Leu
        275                 280

<210> SEQ ID NO 148
<211> LENGTH: 274
<212> TYPE: PRT
<213> ORGANISM: Yersinia pestis

<400> SEQUENCE: 148

Lys Trp Pro Ser Pro Ala Lys Leu Asn Leu Phe Leu Tyr Ile Thr Gly
1               5                   10                  15

Gln Arg Ala Asp Gly Tyr His Gln Leu Gln Thr Leu Phe Gln Phe Leu
            20                  25                  30

Asp Tyr Gly Asp Gln Leu Thr Ile Glu Pro Arg Asp Asp Asn Gln Ile
        35                  40                  45

Arg Leu Leu Thr Pro Ile Ala Gly Val Glu Asn Glu Gln Asn Leu Ile
    50                  55                  60

Val Arg Ala Ala Lys Met Leu Gln Lys His Pro Gly Asn Thr Pro Val
65                  70                  75                  80

Pro Arg Gly Ala Asp Ile Ser Ile Asp Lys Cys Leu Pro Met Gly Gly
                85                  90                  95

Gly Leu Gly Gly Gly Ser Ser Asn Ala Ala Thr Val Leu Val Ala Leu
            100                 105                 110

Asn Leu Leu Trp Gln Cys Gly Leu Thr Asp Glu Gln Leu Ala Asp Leu
        115                 120                 125

Gly Leu Thr Leu Gly Ala Asp Val Pro Val Phe Val Arg Gly His Ala
    130                 135                 140

Ala Phe Ala Glu Gly Ile Gly Glu Lys Leu Gln Pro Ala Glu Pro Val
145                 150                 155                 160

Glu Lys Trp Tyr Leu Val Ile His Pro Gly Val Asn Ile Pro Thr Pro
                165                 170                 175

Ile Ile Phe Ser Asp Pro Glu Leu Lys Arg Asn Thr Pro Ile Arg Pro
            180                 185                 190

Leu Ala Ala Leu Leu Ser Thr Pro Tyr Ala Asn Asp Cys Glu Pro Ile
        195                 200                 205

Ala Arg Lys Arg Phe Arg Glu Val Glu Gln Ala Leu Ser Trp Leu Leu
    210                 215                 220

Glu Tyr Ala Pro Ser Arg Leu Thr Gly Thr Gly Ala Cys Val Phe Ala
225                 230                 235                 240

Glu Phe Asp Thr Glu Ser Ser Ala Arg Gln Val Leu Ser Ile Ala Pro
                245                 250                 255
```

Glu Trp Leu His Gly Phe Val Ala Arg Gly Val Asn Val Ser Pro Leu
            260                 265                 270

His Arg

<210> SEQ ID NO 149
<211> LENGTH: 273
<212> TYPE: PRT
<213> ORGANISM: Actinobacillus actinomycetemcomitans

<400> SEQUENCE: 149

Arg Phe Pro Cys Pro Ala Lys Leu Asn Leu Phe Leu Tyr Ile Asn Gly
1               5                   10                  15

Lys Arg Ala Thr Gly Tyr His Glu Leu Gln Thr Leu Phe Gln Phe Val
            20                  25                  30

Asp Phe Gly Asp Trp Leu His Ile Lys Val Arg Pro Asp Gly Lys Ile
        35                  40                  45

Arg Leu Thr Ser Val Ile Ala Asp Leu Lys Ala Glu Asp Asn Leu Ile
    50                  55                  60

Tyr Arg Ala Ala Lys Leu Leu Gln Gln Tyr Thr Gly Cys Thr Leu Gly
65                  70                  75                  80

Thr Glu Leu Thr Leu Asp Lys Ile Leu Pro Ile Gly Gly Val Gly
                85                  90                  95

Gly Gly Ser Ser Asn Ala Ala Thr Thr Leu Val Ala Leu Asn His Leu
            100                 105                 110

Trp Lys Thr Gly Leu Ser Thr Gly Gln Leu Ala Glu Leu Gly Leu Thr
        115                 120                 125

Leu Gly Ala Asp Val Pro Ile Phe Val His Gly Lys Ala Ala Phe Ala
    130                 135                 140

Glu Gly Ile Gly Glu Lys Ile Thr Tyr Cys Glu Pro Pro Glu Lys Trp
145                 150                 155                 160

Tyr Leu Val Leu Lys Pro Asn Val Ser Ile Ser Thr Ala Val Val Phe
                165                 170                 175

Ser Asp Pro His Leu Pro Arg Asn Thr Pro Lys Lys Ser Leu Ala Gln
            180                 185                 190

Leu Leu Ala Gly Lys Tyr Ala Asn Asp Cys Glu Lys Val Val Arg Asp
        195                 200                 205

His Tyr Ser Glu Val Glu Glu Ser Leu Asn Trp Leu Val Lys Tyr Ala
    210                 215                 220

Pro Ala Arg Leu Thr Gly Thr Gly Ala Cys Val Phe Ala Glu Phe Asp
225                 230                 235                 240

Asp Lys Lys Ser Ala Gln Ser Val Leu Gln Ala Lys Pro Lys Asn Cys
                245                 250                 255

Phe Gly Phe Val Ala Lys Gly Leu Asn His Ser Pro Leu His Glu Met
            260                 265                 270

Leu

<210> SEQ ID NO 150
<211> LENGTH: 275
<212> TYPE: PRT
<213> ORGANISM: Vibrio cholerae
<220> FEATURE:
<221> NAME/KEY: misc_feature
<222> LOCATION: (165)..(167)
<223> OTHER INFORMATION: Xaa can be any naturally occurring amino acid

<400> SEQUENCE: 150

Thr Val Trp Pro Ser Pro Ala Lys Leu Asn Leu Phe Leu Tyr Ile Thr

```
                1               5                   10                  15
        Gly Arg Arg Ala Asn Gly Tyr His Asp Leu Gln Thr Leu Phe Gln Phe
                        20                  25                  30

Leu Asp His Gly Asp Glu Leu Thr Ile Thr Ala Asn Asn Ser Gly Asn
                        35                  40                  45

Ile Thr Leu Ser Pro Ala Leu Ala Asp Val Ala Leu Glu Asp Asn Leu
                50                  55                  60

Ile Tyr Lys Ala Ala Met Ala Leu Lys Asn Ala Ala Gln Ser Pro Leu
        65                  70                  75                  80

Gly Ala Asp Ile Gln Leu His Lys Val Leu Pro Met Gly Gly Gly Ile
                        85                  90                  95

Gly Gly Gly Ser Ser Asn Ala Ala Thr Thr Leu Val Ala Leu Asn Tyr
                        100                 105                 110

Leu Trp Gln Thr Gly Leu Ser Asp Asp Gln Leu Ala Glu Ile Gly Leu
                        115                 120                 125

Ala Leu Gly Ala Asp Val Pro Val Phe Thr Arg Gly Phe Ala Ala Phe
                        130                 135                 140

Ala Glu Gly Val Gly Glu Glu Leu Ser Ala Val Glu Pro Glu Lys
        145                 150                 155                 160

Trp Tyr Leu Val Xaa Xaa Xaa Pro Ala Val Ser Ile Ala Thr Lys Asp
                        165                 170                 175

Ile Phe Thr His Pro Gln Leu Met Arg Asn Thr Pro Lys Arg Asp Leu
                        180                 185                 190

Ala Ser Leu Leu Thr Thr Pro Tyr Glu Asn Asp Cys Glu Lys Ile Val
                        195                 200                 205

Arg Ser Leu Tyr Pro Glu Val Asp Lys Gln Leu Ser Trp Leu Leu Gln
                        210                 215                 220

Tyr Ala Pro Ser Arg Leu Thr Gly Thr Gly Ser Cys Val Phe Ala Glu
        225                 230                 235                 240

Phe Ser Ser Arg Lys Asp Ala Gln Ala Val Phe Ala Gln Leu Ser Asp
                        245                 250                 255

Asn Val Leu Ala Phe Val Ala Gln Gly Arg Asn Val Ser Pro Leu Arg
                        260                 265                 270

Lys Thr Leu
                275

<210> SEQ ID NO 151
<211> LENGTH: 269
<212> TYPE: PRT
<213> ORGANISM: Shewanella putrefaciens

<400> SEQUENCE: 151

Trp Pro Ala Pro Ala Lys Leu Asn Leu Phe Leu His Ile Asn Gly Arg
1               5                   10                  15

Arg Ser Asp Gly Tyr His Glu Leu Gln Thr Leu Phe Gln Phe Val Asp
                20                  25                  30

Cys Cys Asp Gln Leu Asp Phe Arg Val Thr Asp Thr Pro Glu Leu Ile
            35                  40                  45

Leu His Ser Thr Met Ser Ala Val Val Ala Asp Ser Asp Asn Leu Ile
        50                  55                  60

Leu Arg Ala Ala Lys Ser Leu Gln Gln Ala Thr Gly Phe Asn Gly Gly
65                  70                  75                  80

Ala Glu Ile Trp Leu Asp Lys Arg Leu Pro Met Gly Gly Gly Leu Gly
                85                  90                  95
```

-continued

```
Gly Gly Ser Ser Asp Ala Ala Thr Thr Leu Val Ala Leu Asn Arg Leu
            100                 105                 110

Trp Asn Thr Gln Leu Ser His Asp Glu Leu Ala Ala Ile Gly Leu Lys
        115                 120                 125

Leu Gly Ala Asp Ile Pro Val Phe Ile His Gly Phe Ala Ala Phe Ala
    130                 135                 140

Gln Gly Val Gly Glu Arg Leu Gln Ala Val Asn Pro Ala Glu Leu Trp
145                 150                 155                 160

Tyr Leu Val Ile Ala Pro Asp Ala His Val Ser Thr Ala Ala Val Phe
                165                 170                 175

Gln Asp Pro Leu Leu Pro Arg Asn Thr Pro Lys Leu Gly Leu Asp Thr
            180                 185                 190

Leu Leu Ser Gln Pro Trp Ala Asn Asp Cys Gln Glu Leu Val Val Ser
        195                 200                 205

Lys Tyr Pro Gln Val Ala Lys Ala Leu Gly Trp Leu Leu Glu Tyr Ala
    210                 215                 220

Pro Ser Arg Met Thr Gly Thr Gly Ala Cys Val Phe Gly Glu Phe Ser
225                 230                 235                 240

Ser Gln Gln Gln Ala Leu Ala Ala Leu Ala Lys Leu Pro Ser Asp Met
                245                 250                 255

Gln Gly Phe Val Ala Lys Gly Met Asn Ile Ser Pro Leu
            260                 265

<210> SEQ ID NO 152
<211> LENGTH: 273
<212> TYPE: PRT
<213> ORGANISM: Pasteurella multocida

<400> SEQUENCE: 152

Arg Phe Pro Cys Pro Ala Lys Leu Asn Leu Phe Leu Tyr Ile Asn Gly
1               5                   10                  15

Lys Arg Gln Asp Gly Tyr His Glu Leu Gln Thr Leu Phe Gln Phe Val
            20                  25                  30

Asp Phe Gly Asp Trp Leu Asp Ile Glu Val Arg Glu Asp Asn Glu Ile
        35                  40                  45

Cys Leu Thr Pro Glu Leu Pro Ser Leu Lys Asn Glu Asp Asn Leu Val
    50                  55                  60

Tyr Arg Ala Ala Lys Leu Leu Gln Gln Lys Thr Asn Cys Ala Leu Gly
65                  70                  75                  80

Ala Asn Leu Thr Leu Asp Lys Ile Leu Pro Met Gly Ser Gly Leu Gly
                85                  90                  95

Gly Gly Ser Ser Asn Ala Ala Thr Ala Leu Val Ala Leu Asn Tyr Leu
            100                 105                 110

Trp Asn Thr Gln Leu Ser Thr Lys Gln Leu Ala Lys Leu Gly Leu Met
        115                 120                 125

Leu Gly Ala Asp Val Pro Ile Phe Val His Gly His Ala Ala Phe Ala
    130                 135                 140

Glu Gly Val Gly Glu Lys Ile Thr Tyr Cys Glu Pro Lys Glu Lys Trp
145                 150                 155                 160

Tyr Val Val Leu Lys Pro Asn Val Ser Ile Ser Thr Ala Thr Val Phe
                165                 170                 175

Ser Asp Pro Asp Leu Ile Arg Asn Thr Pro Lys Gln Ser Leu Glu Gln
            180                 185                 190

Leu Leu Asn Gln Lys Tyr Ala Asn Asp Cys Glu Lys Val Val Leu Asn
        195                 200                 205
```

His Tyr Pro Glu Val Glu Ile Leu His Arg Leu Leu Gln Tyr Ala
    210                 215                 220

Pro Ser Arg Leu Thr Gly Thr Gly Ala Cys Val Phe Ala Glu Phe Asn
225                 230                 235                 240

Asp Glu Glu Ser Ala Gln Leu Ala Phe Gln Thr Ile Pro Lys Asn Tyr
                245                 250                 255

Phe Gly Phe Val Ala Gln Gly Leu Asn Lys Ser Pro Leu His Asn Met
            260                 265                 270

Leu

<210> SEQ ID NO 153
<211> LENGTH: 276
<212> TYPE: PRT
<213> ORGANISM: Pseudomonas aeruginosa

<400> SEQUENCE: 153

Val Arg Leu Ser Leu Pro Ala Pro Ala Lys Leu Asn Leu Phe Leu His
1               5                   10                  15

Ile Leu Gly Arg Arg Asp Asp Gly Tyr His Glu Leu Gln Thr Leu Phe
            20                  25                  30

Gln Phe Leu Asp His Gly Asp Glu Leu His Phe Glu Ala Arg Gln Asp
        35                  40                  45

Gly Gln Val Arg Leu His Thr Glu Ile Ala Gly Val Pro His Asp Ser
    50                  55                  60

Asn Leu Ile Val Arg Ala Ala Arg Gly Leu Gln Glu Ala Ser Gly Ser
65                  70                  75                  80

Pro Gln Gly Val Asp Ile Trp Leu Asp Lys Arg Leu Pro Met Gly Gly
                85                  90                  95

Gly Ile Gly Gly Gly Ser Ser Asp Ala Ala Thr Thr Leu Leu Ala Leu
            100                 105                 110

Asn His Leu Trp Gln Leu Gly Trp Asp Glu Asp Arg Ile Ala Ala Leu
        115                 120                 125

Gly Leu Arg Leu Gly Ala Asp Val Pro Val Phe Thr Arg Gly Arg Ala
    130                 135                 140

Ala Phe Ala Glu Gly Val Gly Glu Lys Leu Thr Pro Val Asp Ile Pro
145                 150                 155                 160

Glu Pro Trp Tyr Leu Val Val Pro Gln Val Leu Val Ser Thr Ala
                165                 170                 175

Glu Ile Phe Ser Asp Pro Leu Leu Thr Arg Asp Ser Pro Ala Ile Lys
            180                 185                 190

Val Arg Thr Val Leu Glu Gly Asp Ser Arg Asn Asp Cys Gln Pro Val
        195                 200                 205

Val Glu Arg Arg Tyr Pro Glu Val Arg Asn Ala Leu Ile Leu Leu Asn
    210                 215                 220

Lys Phe Val Ser Ala Arg Leu Thr Gly Thr Gly Gly Cys Val Phe Gly
225                 230                 235                 240

Ser Phe Pro Asn Lys Ala Glu Ala Asp Lys Val Ser Ala Leu Leu Pro
                245                 250                 255

Asp His Leu Gln Arg Phe Val Ala Lys Gly Ser Asn Ile Ser Met Leu
            260                 265                 270

His Arg Lys Leu
        275

<210> SEQ ID NO 154

<211> LENGTH: 272
<212> TYPE: PRT
<213> ORGANISM: Neisseria gonorrhoeae

<400> SEQUENCE: 154

```
Arg Gln Ala Phe Pro Ala Pro Ala Lys Leu Asn Leu Asp Leu Arg Ile
1               5                   10                  15

Thr Gly Arg Arg Glu Asp Gly Tyr His Asn Ile Glu Ser Ile Phe Cys
            20                  25                  30

Leu Ile Asp Leu Gln Asp Thr Val Tyr Leu Lys Pro Arg Asp Asp Gly
        35                  40                  45

Lys Ile Ile Leu His Asn Pro Val Asp Gly Met Pro Gln Glu Ala Asp
    50                  55                  60

Leu Ser Tyr Arg Ala Ala Ser Leu Leu Gln Lys Tyr Ala Arg Thr Pro
65                  70                  75                  80

Thr Gly Val Glu Ile Trp Leu Asp Lys Lys Ile Pro Thr Gly Ala Gly
                85                  90                  95

Leu Gly Gly Gly Ser Ser Asp Ala Ala Thr Val Leu Leu Val Leu Asn
            100                 105                 110

Arg Trp Trp Gln Cys Gly Leu Thr Gln Arg Gln Leu Ile Asp Ser Gly
        115                 120                 125

Ala Ala Leu Gly Ala Asp Val Pro Phe Phe Ile Phe Gly Lys Asn Ala
    130                 135                 140

Phe Ala Arg Gly Ile Gly Asp Arg Leu Asp Glu Met Asp Ile Pro Lys
145                 150                 155                 160

Gln Trp Tyr Val Ile Val Lys Pro Pro Val His Val Ser Thr Ala Lys
                165                 170                 175

Ile Phe Thr His Glu Gly Leu Thr Arg Asn Ser Ala Ser Ser Ile Met
            180                 185                 190

Pro Thr Phe Gln Asn Leu Gln Pro Phe Arg Asn Asp Met Gln Ala Val
        195                 200                 205

Val Phe Lys Glu Tyr Pro Glu Val Trp Lys Ala Tyr Ser Glu Leu Ser
    210                 215                 220

Arg Tyr Gly Phe Ala Leu Met Thr Gly Ser Gly Ala Cys Val Phe Thr
225                 230                 235                 240

Ala Cys Gln Asp Arg Asn Ser Ala Tyr Asn Ile Tyr Arg Gln Val Ser
                245                 250                 255

Asp Leu Tyr Glu Ala Tyr Leu Ala Glu Gly Leu Ser Lys His Pro Leu
            260                 265                 270
```

<210> SEQ ID NO 155
<211> LENGTH: 248
<212> TYPE: PRT
<213> ORGANISM: Bordetella pertussis

<400> SEQUENCE: 155

```
Pro Ala Pro Ala Lys Leu Asn Leu Phe Leu His Val Val Gly Arg Arg
1               5                   10                  15

Ala Asp Gly Tyr His Leu Leu Gln Thr Ala Phe Arg Phe Ile Asp Leu
            20                  25                  30

Ala Asp Thr Leu His Phe Glu Ala Arg Ala Asp Gly Ala Ile Gly Arg
        35                  40                  45

Ala Tyr Glu Leu Pro Gly Val Ala Glu Ser Asp Asp Leu Val Met Arg
    50                  55                  60

Ala Ala Arg Ser Leu Gln Arg Ala Thr Gly Thr Arg Gln Gly Ala Gln
65                  70                  75                  80
```

```
Ile Gly Leu His Lys Arg Ile Pro Gln Gly Gly Leu Gly Gly
            85                  90                  95

Ser Ser Asp Ala Ala Thr Thr Leu Ile Ala Leu Asn Arg Leu Trp Gly
            100                 105                 110

Thr Gly Leu Ser Arg Ser Gln Leu Met Gln Leu Ala Leu Pro Leu Gly
            115                 120                 125

Ala Asp Val Pro Val Phe Val Phe Gly Gln Ser Ala Phe Ala Gln Gly
            130                 135                 140

Val Gly Glu Asp Leu Thr Ala Val Ala Leu Ser Pro Ala Ala Tyr Leu
145                 150                 155                 160

Val Val Gln Pro Asp Ala Gly Val Pro Thr Ala Val Ile Phe Ser Asp
            165                 170                 175

Pro Asp Leu Thr Arg Asp Cys Ala Ser Val Thr Ile Ala Asp Phe Leu
            180                 185                 190

Ala Leu Pro Thr Ser Cys Phe Gly Arg Asn Asp Leu Glu Pro Val Val
            195                 200                 205

Leu Arg Arg Tyr Pro Glu Val Ser Gly Ala Val Arg Trp Leu Phe Glu
            210                 215                 220

His Gly Leu Arg Val Arg Met Ser Gly Ser Gly Ala Cys Leu Phe Ala
225                 230                 235                 240

Glu Phe Pro Thr Leu Pro Glu Ala
            245

<210> SEQ ID NO 156
<211> LENGTH: 272
<212> TYPE: PRT
<213> ORGANISM: Neisseria meningitidis

<400> SEQUENCE: 156

Arg Gln Ala Phe Pro Ala Pro Ala Lys Leu Asn Leu Asp Leu Arg Ile
1               5                   10                  15

Thr Gly Arg Arg Glu Asp Gly Tyr His Asn Ile Glu Ser Ile Phe Cys
            20                  25                  30

Leu Ile Asp Leu Gln Asp Thr Val Tyr Leu Lys Pro Arg Asp Asp Gly
            35                  40                  45

Lys Ile Ile Leu His Asn Pro Val Asp Gly Met Pro Gln Glu Ala Asp
        50                  55                  60

Leu Ser Tyr Arg Ala Ala Ser Leu Leu Gln Lys Tyr Ala Arg Thr Pro
65              70                  75                  80

Thr Gly Val Glu Ile Trp Leu Asp Lys Lys Ile Pro Thr Gly Ala Gly
            85                  90                  95

Leu Gly Gly Gly Ser Ser Asp Ala Ala Thr Val Leu Leu Val Leu Asn
            100                 105                 110

Arg Trp Trp Gln Cys Gly Leu Thr Gln Arg Gln Leu Ile Asp Ser Gly
            115                 120                 125

Ala Ala Leu Gly Ala Asp Val Pro Phe Phe Ile Phe Gly Lys Asn Ala
            130                 135                 140

Phe Ala Arg Gly Ile Gly Asp Arg Leu Asp Glu Met Asp Ile Pro Lys
145                 150                 155                 160

Gln Trp Tyr Val Ile Val Lys Pro Pro Val His Val Ser Thr Ala Lys
            165                 170                 175

Ile Phe Thr His Glu Gly Leu Thr Arg Asn Ser Ala Ser Ser Ile Met
            180                 185                 190

Pro Thr Phe Gln Asn Leu Gln Pro Phe Arg Asn Asp Met Gln Ala Val
```

```
                 195                 200                 205
Val Phe Lys Glu Tyr Pro Glu Val Trp Lys Ala Tyr Ser Glu Leu Ser
    210                 215                 220

Arg Tyr Gly Phe Ala Leu Met Thr Gly Ser Gly Ala Cys Val Phe Thr
225                 230                 235                 240

Ala Cys Gln Asp Arg Asn Ser Ala Tyr Asn Ile Tyr Arg Gln Val Ser
                245                 250                 255

Asp Leu Tyr Glu Ala Tyr Leu Ala Glu Gly Leu Ser Lys His Pro Leu
            260                 265                 270

<210> SEQ ID NO 157
<211> LENGTH: 129
<212> TYPE: PRT
<213> ORGANISM: Klebsiella pneumoniae
<220> FEATURE:
<221> NAME/KEY: misc_feature
<222> LOCATION: (9)..(9)
<223> OTHER INFORMATION: Xaa can be any naturally occurring amino acid

<400> SEQUENCE: 157

Gly Val Gly Glu Ile Leu Thr Pro Xaa Lys Pro Glu Lys Lys Trp Tyr
1               5                   10                  15

Leu Trp Pro His Arg Gly Ser Ser Ile Pro Thr Pro Ile Ile Phe Arg
            20                  25                  30

Asp Pro Glu Leu Pro Arg Asn Thr Pro Arg Arg Ser Ile Asn Thr Leu
        35                  40                  45

Leu Asn Cys Glu Phe Ser Asn Asp Cys Glu Leu Ile Ala Arg Lys Arg
    50                  55                  60

Phe Arg Glu Val Asp Ala Ala Leu Ser Trp Leu Leu Glu Tyr Ala Pro
65                  70                  75                  80

Ser Arg Leu Thr Gly Thr Gly Ala Cys Val Phe Ala Glu Phe Asn Thr
                85                  90                  95

Glu Ser Ala Ala Arg Gln Val Leu Asp Thr Ala Pro Ala Trp Leu Asn
            100                 105                 110

Gly Phe Val Ala Arg Gly Val Asn Leu Ser Pro Leu Lys Gln Ala Leu
        115                 120                 125

Leu

<210> SEQ ID NO 158
<211> LENGTH: 168
<212> TYPE: PRT
<213> ORGANISM: Deinococcus radiodurans

<400> SEQUENCE: 158

Ala Pro Ala Lys Ile Asn Leu Gly Leu Ser Val Leu Gly Val Arg Glu
1               5                   10                  15

Asn Gly Tyr His Asp Leu His Ser Leu Met Val Pro Leu Thr Val Gly
            20                  25                  30

Asp Glu Leu Glu Ile Arg Pro Ala Gly Ala Leu Thr Leu Arg Val Glu
        35                  40                  45

Gly Ala Asp Leu Pro Thr Asp Glu Arg Asn Leu Val Tyr Arg Ala Ala
    50                  55                  60

Arg Ala Tyr Leu Asp Ala Gly Ala Ala Gly Gly Ala Asp Leu Val
65                  70                  75                  80

Leu His Lys Arg Leu Pro Leu Ala Ser Gly Leu Gly Gly Gly Ser Ser
                85                  90                  95

Asp Ala Ala Ser Thr Leu Leu Ala Leu Ala Glu Leu Tyr Pro Ala Pro
```

```
                    100                 105                 110
Asp His Arg Pro Val Asp Leu Pro Ala Leu Ala Leu Thr Leu Gly Ala
            115                 120                 125

Asp Val Pro Phe Phe Leu Leu Gly Gly Ala Ala Leu Ala Glu Gly Val
        130                 135                 140

Gly Glu Arg Leu Thr Pro Val Asp Asp Leu Pro Pro Val His Leu Val
145                 150                 155                 160

Leu Ala Asn Ala Gly Ala Glu Val
                165
```

<210> SEQ ID NO 159
<211> LENGTH: 220
<212> TYPE: PRT
<213> ORGANISM: Bordetella bronchiseptica
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 159

```
Thr Ile Tyr Xaa Lys Ala Arg Xaa Asp Gly Ile Ile Ala Arg Ala Xaa
1               5                   10                  15

Lys Leu Pro Gly Val Pro Glu Ser Thr Asn Leu Val Val Arg Ala Ala
            20                  25                  30

Arg Ser Leu Gln Arg Ala Thr Gly Thr Ala Lys Gly Ala Gln Ile Ala
        35                  40                  45

Cys Asn Lys Arg Ile Pro Gln Ala Phe Gly Leu Ala Ser Gly Ser Arg
    50                  55                  60

Asn Ala Ala Thr Thr Leu Ile Ala Leu Thr Arg Leu Trp Gly Thr Gly
65                  70                  75                  80

Leu Ser Arg Ser Gln Leu Met Gln Leu Ala Leu Pro Leu Gly Ala Asp
                85                  90                  95

Val Pro Val Phe Val Phe Gly Gln Ser Ala Phe Ala Gln Gly Val Gly
            100                 105                 110

Glu Asp Leu Thr Ala Val Ala Leu Pro Pro Ala Tyr Leu Val Val
        115                 120                 125

Gln Pro Asp Ala Gly Val Pro Thr Ala Ala Ile Phe Ser Asp Pro Asp
    130                 135                 140

Leu Thr Arg Asp Cys Ala Ser Val Thr Ile Ala Asp Phe Leu Ala Leu
145                 150                 155                 160

Pro Thr Phe Cys Phe Gly Arg Asn Asp Leu Glu Pro Val Val Leu Arg
                165                 170                 175

Arg Tyr Pro Glu Val Ser Gly Ala Val Arg Trp Leu Phe Glu His Gly
            180                 185                 190

Leu Arg Val Arg Met Ser Gly Ser Gly Ala Cys Leu Phe Ala Glu Phe
        195                 200                 205

Pro Thr Leu Pro Glu Ala Val Leu Ala Gln Asp Pro
    210                 215                 220
```

<210> SEQ ID NO 160
<211> LENGTH: 258

```
<212> TYPE: PRT
<213> ORGANISM: Clostridium difficile
<220> FEATURE:
<221> NAME/KEY: misc_feature
<222> LOCATION: (107)..(107)
<223> OTHER INFORMATION: Xaa can be any naturally occurring amino acid

<400> SEQUENCE: 160

Ser Arg Ala Lys Ile Asn Leu Ser Ile Asp Val Leu Gly Lys Arg Gln
1               5                   10                  15

Asp Gly Tyr His Phe Val Glu Met Ile Met Gln Thr Ile Asp Leu Tyr
                20                  25                  30

Asp Ile Val Lys Ile Lys Glu Leu Asp Glu Asp Ile Lys Val Lys
            35                  40                  45

Ser Thr Ser Leu Asp Ile Pro Leu Asp Glu Asp Asn Ile Val Tyr Lys
50                  55                  60

Ala Ala Lys Ile Leu Lys Asn Lys Phe Tyr Ile Lys Lys Gly Val Glu
65                  70                  75                  80

Ile Phe Ile Glu Lys Asn Ile Pro Val Ala Ala Gly Met Ala Gly Gly
                85                  90                  95

Ser Ser Asn Ala Ala Val Leu Val Gly Xaa Asn His Leu Trp Glu
            100                 105                 110

Leu Arg Leu Ser Glu Asp Glu Leu Lys Glu Ile Gly Leu Asn Leu Gly
            115                 120                 125

Ala Asp Val Pro Phe Cys Ile Ser Gly Arg Pro Ala Leu Ala Gln Gly
130                 135                 140

Ile Gly Glu Lys Leu Thr Asn Ile Lys Gly Leu Pro Cys Asp Thr Asn
145                 150                 155                 160

Ile Leu Ile Cys Lys Pro Asp Leu Phe Val Ser Thr Lys Glu Val Tyr
                165                 170                 175

Gln Gly Leu Asp Leu Asn Asn Ile Lys Lys Arg Pro Asn Asn Lys Tyr
            180                 185                 190

Leu Ile Glu Cys Leu Lys Ser Glu Asp Ile Lys Ala Val Ser Glu Ser
            195                 200                 205

Met Val Asn Ile Leu Glu Asn Val Thr Ile Gly Lys His Lys Glu Ile
        210                 215                 220

Ser Asp Ile Lys Gln Val Met Met Lys Asn Asn Ala Leu Gly Ser Met
225                 230                 235                 240

Met Ser Gly Ser Gly Pro Thr Val Phe Gly Leu Phe Lys Asn Lys Glu
                245                 250                 255

Asp Ala

<210> SEQ ID NO 161
<211> LENGTH: 272
<212> TYPE: PRT
<213> ORGANISM: Clostridium acetobutylicum

<400> SEQUENCE: 161

Ala Lys Val Asn Ile Ser Leu Asp Val Ile Gly Lys Arg Glu Asp Gly
1               5                   10                  15

Tyr His Leu Leu Lys Met Ile Met Gln Ser Ile Asn Leu Tyr Asp Val
                20                  25                  30

Leu Asp Ile Arg Ile Ile Asp Gly Gly Ile Lys Ile Thr Ser Asn Arg
            35                  40                  45

Arg Asn Ile Pro Thr Asn Asp Lys Asn Ile Ala Tyr Arg Ala Ala Lys
50                  55                  60
```

```
Leu Phe Met Asp Thr Tyr Lys Ile Asp Lys Gly Ile Ser Ile His Ile
 65                  70                  75                  80

Asn Lys Arg Ile Pro Val Ala Ala Gly Leu Ala Gly Gly Ser Ala Asp
                 85                  90                  95

Gly Ala Ala Val Leu Lys Ala Met Arg Asp Ile Phe Lys Lys Asp Val
            100                 105                 110

Ser Asp Glu Glu Leu Ile Asn Leu Gly Val Lys Ile Gly Ala Asp Ile
        115                 120                 125

Pro Phe Cys Ile Val Gly Gly Thr Ala Phe Cys Glu Gly Ile Gly Glu
    130                 135                 140

Lys Ile Thr Lys Leu Arg Ser Met Asn Gly Lys Ile Ile Val Leu Val
145                 150                 155                 160

Lys Pro Asp Phe Gly Val Ser Thr Lys Met Val Tyr Thr Glu Tyr Asp
                165                 170                 175

Lys Cys Leu Asp Val Lys His Pro Asp Ser Glu Gly Leu Val Lys Ala
            180                 185                 190

Val Asn Asn Gly His Phe Lys Phe Val Val Asn Asn Met Val Asn Val
        195                 200                 205

Leu Glu Asn Val Thr Ala Val Lys Tyr Lys Glu Ile Asn Glu Ile Lys
    210                 215                 220

Glu Lys Ala Leu Glu Tyr Asn Ser Ile Gly Thr Met Met Ser Gly Ser
225                 230                 235                 240

Gly Pro Thr Val Phe Ser Phe Phe Asp Asn Thr Lys Glu Ala Glu Lys
                245                 250                 255

Tyr Phe Tyr Glu Met Lys Lys Glu Tyr Asn Lys Val Phe Ile Thr Arg
            260                 265                 270

<210> SEQ ID NO 162
<211> LENGTH: 152
<212> TYPE: PRT
<213> ORGANISM: Mycobacterium avium

<400> SEQUENCE: 162

Pro Gly Lys Val Asn Leu Tyr Leu Ala Val Gly Asp Arg Arg Glu Asp
  1               5                  10                  15

Gly Tyr His Glu Leu Thr Thr Ile Phe Gln Ala Val Ser Leu Leu Asp
                 20                  25                  30

Glu Val Thr Val Arg Asn Ala Asp Val Leu Ser Leu Asp Ile Val Gly
             35                  40                  45

Glu Gly Ala Asp Lys Leu Pro Thr Asp Glu Arg Asn Leu Ala Trp Gln
         50                 55                  60

Ala Ala Glu Leu Met Ala Glu His Val Gly Arg Ala Pro Asp Val Ser
 65                 70                  75                  80

Ile Met Ile Asp Lys Ser Ile Pro Val Ala Gly Gly Met Ala Gly Gly
                 85                  90                  95

Ser Ala Asp Ala Ala Val Leu Val Ala Met Asn Ser Leu Trp Glu
            100                 105                 110

Leu Asn Val Pro Arg Arg Asp Leu Arg Met Leu Ala Ala Gln Leu Gly
        115                 120                 125

Ser Asp Val Pro Phe Ala Leu His Gly Gly Thr Ala Leu Gly Thr Gly
    130                 135                 140

Arg Gly Glu Glu Leu Ala Thr Val
145                 150

<210> SEQ ID NO 163
```

<211> LENGTH: 152
<212> TYPE: PRT
<213> ORGANISM: Mycobacterium bovis

<400> SEQUENCE: 163

```

<400> SEQUENCE: 165

Ala Lys Ile Asn Leu Gly Leu Leu Ile Thr Ser Arg Arg Ala Asp Gly
1               5                   10                  15

Tyr His Thr Leu Glu Thr Ile Phe Ala Pro Ile Asp Trp Phe Asp Thr
            20                  25                  30

Leu Glu Phe Thr Glu Ser Asp Ala Ile Ser Met Glu Cys Ser Asn Leu
        35                  40                  45

Asp Leu Leu Val Asp Asp Ser Asn Leu Cys Ile Arg Ala Ala Lys Ala
    50                  55                  60

Leu Gln Glu His Thr Gly Val Lys Arg Gly Ala Thr Ile Lys Leu Leu
65                  70                  75                  80

Lys Arg Val Pro Phe Gly Ala Gly Leu Gly Gly Ser Ser Asp Ala
                85                  90                  95

Ala Ala Thr Leu Asn Ala Leu Cys Lys Leu Trp Gln Ile Asp Val Pro
            100                 105                 110

Ser Ala Glu Leu His Lys Leu Ala Val Lys Leu Gly Ala Asp Val Pro
        115                 120                 125

Tyr Phe Leu Glu Met Lys Gly Leu Ala Tyr Ala Ala Gly Ile Gly Glu
    130                 135                 140

Glu Leu Glu Asp Leu Asn Leu Ala Leu Pro Trp His Val Val Thr Val
145                 150                 155                 160

Phe Pro Glu Val Gln Val Pro Thr Ala Trp Ala Tyr Lys Asn Phe His
                165                 170                 175

Arg Gln Phe Glu Arg Pro Val Pro Asp Leu Lys Thr Leu Val Arg Arg
            180                 185                 190

Leu Cys His Glu Arg Asp Ile Ser Val Phe Gly Val Phe Glu Asn Asp
        195                 200                 205

Phe Ala Ser Val Val Phe Glu His Tyr Pro Val Val Arg Glu Val Arg
    210                 215                 220

Asp Ala Leu Ala Ala Ser Gly Ala Gln Phe Val Ser Leu Ser Gly Ser
225                 230                 235                 240

Gly Ser Ala Val Tyr Ala Leu Tyr Glu Gly Arg Ala Asp Ala Val Lys
                245                 250                 255

Ala Ala Glu

<210> SEQ ID NO 166
<211> LENGTH: 150
<212> TYPE: PRT
<213> ORGANISM: Porphyromonas gingivalis

<400> SEQUENCE: 166

Ala Lys Ile Asn Leu Gly Leu Gln Val Val Ala Lys Arg Ala Asp Gly
1               5                   10                  15

Tyr His Asn Ile Glu Thr Val Phe Tyr Pro Ile Pro Leu Thr Asp Ala
            20                  25                  30

Leu Glu Ile Glu Val Arg Glu Asp Thr Cys Asp Arg Leu Ser Val His
        35                  40                  45

Gly Val Pro Ile Asp Ala Ala Thr Glu Asp Asn Leu Val Met Lys Ala
    50                  55                  60

Val Met Ala Leu Arg Arg Lys Phe Asp Phe Pro Pro Leu Thr Ile Glu
65                  70                  75                  80

Leu Ile Lys His Ile Pro Ser Gly Ala Gly Leu Gly Gly Gly Ser Ser
                85                  90                  95

-continued

Asn Ala Ser Phe Met Leu Lys Leu Val Arg Asp Tyr Phe Ser Leu Pro
                100                 105                 110

Ile Asp Asp Glu Glu Leu Ala Ala Ile Ala Leu Thr Ile Gly Ala Asp
            115                 120                 125

Cys Pro Phe Phe Val Gly Asn Arg Pro Val Leu Ala Thr Asp Leu Gly
        130                 135                 140

Gln Val Phe Thr Pro Leu
145                 150

<210> SEQ ID NO 167
<211> LENGTH: 259
<212> TYPE: PRT
<213> ORGANISM: Enterococcus faecalis

<400> SEQUENCE: 167

Ala Pro Ala Lys Ile Asn Leu Gly Leu Asp Val Leu His Lys Arg Val
1               5                   10                  15

Asp Gly Tyr His Glu Val Glu Ser Ile Phe Ala Ser Val Asp Leu Ala
            20                  25                  30

Asp His Leu Thr Phe Glu Asn Leu Glu Glu Asp Ile Ile Arg Ile Glu
        35                  40                  45

Thr Asp Ser Ser Phe Leu Pro Val Asp Arg Arg Asn His Val Tyr Gln
    50                  55                  60

Ala Val Asp Leu Leu Lys Arg Thr Tyr Asn Ile His Lys Gly Ile Lys
65                  70                  75                  80

Ile Tyr Ile Glu Lys Arg Ile Pro Val Ala Ala Gly Leu Ala Gly Gly
                85                  90                  95

Ser Ser Asp Cys Ala Ala Ala Leu Arg Gly Leu Asn Lys Leu Trp Asn
            100                 105                 110

Leu Gly Leu Thr Met Asp Glu Leu Cys Glu Ile Gly Ser Gln Ile Gly
        115                 120                 125

Met Asp Val Pro Tyr Cys Leu Arg Gly Gly Thr Ala Phe Ala Asn Gly
    130                 135                 140

Arg Gly Glu Lys Ile Glu Ala Leu Pro Thr Met Pro Gln Cys Trp Ile
145                 150                 155                 160

Val Leu Val Lys Pro Arg Ile Ser Val Ser Thr Ser Thr Val Phe Asn
                165                 170                 175

Asp Leu Ala Val Asp Glu Leu His His Pro Asp Ile Ala Gly Leu Arg
            180                 185                 190

Ile Ala Ile Glu Asn Gly Asp Tyr Thr Gly Met Thr Gln Thr Val Gly
        195                 200                 205

Asn Ala Leu Glu Ser Val Thr Ile Ala Arg His Pro Ile Val Gln Gln
    210                 215                 220

Ile Lys Asp Arg Met Leu Lys Tyr Gly Ala Asp Ala Ala Leu Met Ser
225                 230                 235                 240

Gly Ser Gly Pro Thr Val Phe Ala Leu Cys Glu Lys Lys Thr Arg Ala
                245                 250                 255

Gln Arg Ile

<210> SEQ ID NO 168
<211> LENGTH: 260
<212> TYPE: PRT
<213> ORGANISM: Streptococcus mutans

<400> SEQUENCE: 168

Ala Pro Ala Lys Ile Asn Leu Gly Leu Asp Ile Ala Gly Lys Tyr Gln

```
                1               5                   10                  15
Asp Gly Phe His Glu Leu Ser Met Ile Met Ala Ser Val Asp Leu Asn
                20                  25                  30

Asp Tyr Leu Thr Ile Thr Glu Ile Ala Glu Asp Lys Ile Val Val Glu
                35                  40                  45

Ser Asn Asn Cys Lys Leu Pro Leu Asn Arg Lys Asn Asp Val Tyr Lys
    50                  55                  60

Ala Ala His Leu Leu Lys Arg Arg Tyr His Ile Ser Thr Gly Leu Lys
65                  70                  75                  80

Ile Ser Leu Gln Lys Lys Ile Pro Ile Cys Ala Gly Leu Gly Gly Gly
                85                  90                  95

Ser Ser Asp Ala Ala Ala Thr Leu Arg Ala Leu Asn Cys Leu Trp Lys
            100                 105                 110

Leu Asn Leu Ser Pro Lys Glu Leu Ile Asp Val Gly Phe Glu Ile Gly
                115                 120                 125

Ser Asp Val Pro Tyr Cys Ile Glu Ala Gly Cys Ala Leu Ile Ser Gly
            130                 135                 140

Lys Gly Glu Ile Val Glu Pro Leu Ala Thr Thr Leu Ser Thr Trp Val
145                 150                 155                 160

Val Leu Val Lys Pro Asp Phe Gly Ile Ser Thr Lys Thr Ile Phe Lys
                165                 170                 175

Glu Ile Asp Met Ala Thr Ile Ser Arg Val Asp Ile Pro Ala Leu Lys
            180                 185                 190

Glu Ala Leu Leu Ala Asn Tyr Tyr Glu Asp Ala Leu Gln Phe Met Gly
            195                 200                 205

Asn Ser Leu Glu Asp Ile Thr Ile Ala Lys Lys Pro Phe Ile Gln Lys
    210                 215                 220

Ile Lys Gly Arg Met Ile Lys Cys Gly Ala Asp Ile Ala Leu Met Thr
225                 230                 235                 240

Gly Ser Gly Pro Thr Val Phe Ala Leu Cys Arg Thr Glu Lys Arg Ala
                245                 250                 255

Asp Arg Val Val
            260

<210> SEQ ID NO 169
<211> LENGTH: 252
<212> TYPE: PRT
<213> ORGANISM: Streptococcus pyogenes
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid

<400> SEQUENCE: 169

Lys Ile Lys Leu Gly Leu Asp Thr Lys Asn Lys Arg Xaa Asp Gly Tyr
1               5                   10                  15

His Asp Leu Ser Met Val Met Met Ser Ile Asp Leu Cys Asp Tyr Val
                20                  25                  30

Thr Val Asp His Ile Asp Asp Asn Lys Ile Val Phe Ala Ser Asn Cys
            35                  40                  45
```

```
Pro Lys Ile Pro Ile Asn Xaa Asp Asn Asp Val Tyr Lys Ile Val Gln
 50                  55                  60

Leu Met Lys His Arg Phe Gln Val Lys Arg Gly Val Ser Val Tyr Leu
 65                  70                  75                  80

Glu Lys Arg Ile Pro Met Cys Ala Gly Met Gly Gly Ser Ser Asp
                 85                  90                  95

Ala Val Thr Ile Arg Ala Leu Asn Gln Met Trp Leu Leu Thr Leu Ser
                100                 105                 110

Arg Lys Asp Met Met Asp Ile Gly Ile Pro Ile Gly Ser Asp Val Pro
            115                 120                 125

Tyr Cys Leu Leu Ser Gly Cys Ala Gln Val Thr Gly Lys Gly Glu Val
        130                 135                 140

Val Cys Arg Ile Leu Gly Leu Leu Ser Ser Trp Val Val Leu Val Lys
145                 150                 155                 160

Pro Asp Phe Gly Ile Ser Thr Xaa Thr Phe Phe Leu Asp Ile Asn Cys
                165                 170                 175

Lys Ile Ile Ser Arg Val Ser Thr Thr His Leu Val Ala Ala Ile Glu
                180                 185                 190

Ala Gly Asn Tyr Asn Asp Gly Ile Leu Thr Glu Met Asn Asn Leu Leu
            195                 200                 205

Glu Asp Ile Phe Ile Ala Lys Arg Pro Phe Ile Gln Lys Ile Lys Glu
        210                 215                 220

Lys Thr Leu Gln Ala Gly Ala Ala Asn Ala Leu Met Thr Gly Ser Gly
225                 230                 235                 240

Pro Thr Val Phe Ala Leu Cys Gln Thr Glu Lys Gln
                245                 250

<210> SEQ ID NO 170
<211> LENGTH: 259
<212> TYPE: PRT
<213> ORGANISM: Staphylococcus aureus

<400> SEQUENCE: 170

Ala Pro Ala Lys Ile Asn Phe Thr Leu Asp Thr Leu Phe Lys Arg Asn
 1               5                  10                  15

Asp Gly Tyr His Glu Ile Glu Met Ile Met Thr Thr Val Asp Leu Asn
                20                  25                  30

Asp Arg Leu Thr Phe His Lys Arg Lys Asp Arg Lys Ile Val Val Glu
            35                  40                  45

Ile Glu His Asn Tyr Val Pro Ser Asn His Lys Asn Leu Ala Tyr Arg
 50                  55                  60

Ala Ala Gln Leu Phe Ile Glu Gln Tyr Gln Leu Lys Gln Gly Val Thr
 65                  70                  75                  80

Ile Ser Ile Asp Lys Glu Ile Pro Val Ser Ala Gly Leu Ala Gly Gly
                85                  90                  95

Ser Ala Asp Ala Ala Thr Leu Arg Gly Leu Asn Arg Leu Phe Asp
                100                 105                 110

Ile Gly Ala Ser Leu Glu Glu Leu Ala Leu Leu Gly Ser Lys Ile Gly
        115                 120                 125

Thr Asp Ile Pro Phe Cys Ile Tyr Asn Lys Thr Ala Leu Cys Thr Gly
    130                 135                 140

Arg Gly Glu Lys Ile Glu Phe Leu Asn Lys Pro Ser Ala Trp Val
145                 150                 155                 160

Ile Leu Ala Lys Pro Asn Leu Gly Ile Ser Ser Pro Asp Ile Phe Lys
                165                 170                 175
```

```
Leu Ile Asn Leu Asp Lys Arg Tyr Asp Val His Thr Lys Met Cys Tyr
            180                 185                 190

Glu Ala Leu Glu Asn Arg Asp Tyr Gln Gln Leu Cys Gln Ser Leu Ser
            195                 200                 205

Asn Arg Leu Glu Pro Ile Ser Val Ser Lys His Pro Gln Ile Asp Lys
            210                 215                 220

Leu Lys Asn Asn Met Leu Lys Ser Gly Ala Asp Gly Ala Leu Met Ser
225                 230                 235                 240

Gly Ser Gly Pro Thr Val Tyr Gly Leu Ala Arg Lys Glu Ser Gln Ala
                245                 250                 255

Lys Asn Ile

<210> SEQ ID NO 171
<211> LENGTH: 259
<212> TYPE: PRT
<213> ORGANISM: Staphylococcus aureus

<400> SEQUENCE: 171

Ala Pro Ala Lys Ile Asn Phe Thr Leu Asp Thr Leu Phe Lys Arg Asn
1               5                   10                  15

Asp Gly Tyr His Glu Ile Glu Met Ile Met Thr Thr Val Asp Leu Asn
            20                  25                  30

Asp Arg Leu Thr Phe His Lys Arg Lys Asp Arg Lys Ile Val Val Glu
        35                  40                  45

Ile Glu His Asn Tyr Val Pro Ser Asn His Lys Asn Leu Ala Tyr Arg
    50                  55                  60

Ala Ala Gln Leu Phe Ile Glu Gln Tyr Gln Leu Lys Gln Gly Val Thr
65                  70                  75                  80

Ile Ser Ile Asp Lys Glu Ile Pro Val Ser Ala Gly Leu Ala Gly Gly
                85                  90                  95

Ser Ala Asp Ala Ala Thr Leu Arg Gly Leu Asn Arg Leu Phe Asp
            100                 105                 110

Ile Gly Ala Ser Leu Glu Glu Leu Ala Leu Leu Gly Ser Lys Ile Gly
        115                 120                 125

Thr Asp Ile Pro Phe Cys Ile Tyr Asn Lys Thr Ala Leu Cys Thr Gly
130                 135                 140

Arg Gly Glu Lys Ile Glu Phe Leu Asn Lys Pro Pro Ser Ala Trp Val
145                 150                 155                 160

Ile Leu Ala Lys Pro Asn Leu Gly Ile Ser Ser Pro Asp Ile Phe Lys
                165                 170                 175

Leu Ile Asn Leu Asp Lys Arg Tyr Asp Val His Thr Lys Met Cys Tyr
            180                 185                 190

Glu Ala Leu Glu Asn Arg Asp Tyr Gln Gln Leu Cys Gln Ser Leu Ser
            195                 200                 205

Asn Arg Leu Glu Pro Ile Ser Val Ser Lys His Pro Gln Ile Asp Lys
            210                 215                 220

Leu Lys Asn Asn Met Leu Lys Ser Gly Ala Asp Gly Ala Leu Met Asn
225                 230                 235                 240

Gly Ser Gly Pro Thr Val Tyr Gly Leu Ala Arg Lys Glu Ser Gln Ala
                245                 250                 255

Lys Asn Ile

<210> SEQ ID NO 172
<211> LENGTH: 383
```

<212> TYPE: PRT
<213> ORGANISM: Arabidopsis thaliana

<400> SEQUENCE: 172

```
Met Ala Thr Ala Ser Pro Pro Phe Ile Ser Thr Leu Ser Phe Thr His
1               5                   10                  15

Ser Ser Phe Lys Thr Ser Ser Ser Ser Phe Ser Pro Lys Leu Leu
            20                  25                  30

Arg Pro Leu Leu Ser Phe Ser Val Lys Ala Ser Arg Lys Gln Val Glu
            35                  40                  45

Ile Val Phe Asp Pro Asp Glu Arg Leu Asn Lys Ile Gly Asp Asp Val
50                  55                  60

Asp Lys Glu Ala Pro Leu Ser Arg Leu Lys Leu Phe Ser Pro Cys Lys
65                  70                  75                  80

Ile Asn Val Phe Leu Arg Ile Thr Gly Lys Arg Glu Asp Gly Phe His
                85                  90                  95

Asp Leu Ala Ser Leu Phe His Val Ile Ser Leu Gly Asp Thr Ile Lys
            100                 105                 110

Phe Ser Leu Ser Pro Ser Lys Ser Lys Asp Arg Leu Ser Thr Asn Val
        115                 120                 125

Gln Gly Val Pro Val Asp Gly Arg Asn Leu Ile Ile Lys Ala Leu Asn
130                 135                 140

Leu Tyr Arg Lys Lys Thr Gly Ser Asn Arg Phe Phe Trp Ile His Leu
145                 150                 155                 160

Asp Lys Lys Val Pro Thr Gly Ala Gly Leu Gly Gly Ser Ser Asn
                165                 170                 175

Ala Ala Thr Ala Leu Trp Ala Ala Asn Glu Leu Asn Gly Gly Leu Val
            180                 185                 190

Thr Glu Asn Glu Leu Gln Asp Trp Ser Ser Glu Ile Gly Ser Asp Ile
        195                 200                 205

Pro Phe Phe Ser His Gly Ala Ala Tyr Cys Thr Gly Arg Gly Glu
210                 215                 220

Ile Val Gln Asp Leu Pro Pro Phe Pro Leu Asp Leu Pro Met Val
225                 230                 235                 240

Leu Ile Lys Pro Arg Glu Ala Cys Ser Thr Ala Glu Val Tyr Lys Arg
                245                 250                 255

Leu Arg Leu Asp Gln Thr Ser Asn Ile Asn Pro Leu Thr Leu Leu Glu
            260                 265                 270

Asn Val Thr Ser Asn Gly Val Ser Gln Ser Ile Cys Val Asn Asp Leu
        275                 280                 285

Glu Pro Pro Ala Phe Ser Val Leu Pro Ser Leu Lys Arg Leu Lys Gln
290                 295                 300

Arg Ile Ile Ala Ser Gly Arg Gly Glu Tyr Asp Ala Val Phe Met Ser
305                 310                 315                 320

Gly Ser Gly Ser Thr Ile Ile Gly Ile Gly Ser Pro Asp Pro Pro Gln
                325                 330                 335

Phe Ile Tyr Asp Asp Glu Glu Tyr Lys Asn Val Phe Leu Ser Glu Ala
            340                 345                 350

Asn Phe Met Thr Arg Glu Ala Asn Glu Trp Tyr Lys Glu Pro Ala Ser
        355                 360                 365

Ala Asn Ala Thr Thr Ser Ser Ala Glu Ser Arg Met Asp Phe Gln
370                 375                 380
```

<210> SEQ ID NO 173

<211> LENGTH: 401
<212> TYPE: PRT
<213> ORGANISM: Solanum lycopersicum

<400> SEQUENCE: 173

```
Leu Trp Leu Pro Val Ile Phe Phe Val Val Ser Asn Pro Lys Leu Ile
1               5                   10                  15

Leu Leu Lys Arg Val Val Phe Phe Gln Ser Trp Ser Asn Arg Pro His
            20                  25                  30

Gly Ser Ser Tyr Phe Asn Lys Asn Ile Gln Phe Arg Arg Asn Ser Phe
        35                  40                  45

Val Ile Val Lys Ala Ser Gly Ser Arg Thr Ser Lys Lys Gln Val Glu
    50                  55                  60

Ile Thr Tyr Asn Pro Glu Glu Lys Phe Asn Lys Leu Ala Asp Glu Val
65                  70                  75                  80

Asp Arg Glu Ala Gly Leu Ser Arg Leu Thr Leu Phe Ser Pro Cys Lys
                85                  90                  95

Ile Asn Val Phe Leu Arg Ile Thr Ser Lys Arg Asp Asp Gly Tyr His
            100                 105                 110

Asp Leu Ala Ser Leu Phe His Val Ile Ser Leu Gly Asp Lys Ile Lys
        115                 120                 125

Phe Ser Leu Ser Pro Ser Lys Ser Lys Asp Arg Leu Ser Thr Asn Val
    130                 135                 140

Ala Gly Val Pro Leu Asp Glu Arg Asn Leu Ile Ile Lys Ala Leu Asn
145                 150                 155                 160

Leu Tyr Arg Lys Lys Thr Gly Thr Asp Asn Tyr Phe Trp Ile His Leu
                165                 170                 175

Asp Lys Lys Val Pro Thr Gly Ala Gly Leu Gly Gly Gly Ser Ser Asn
            180                 185                 190

Ala Ala Thr Thr Leu Trp Ala Ala Asn Gln Phe Ser Gly Cys Val Ala
        195                 200                 205

Thr Glu Lys Glu Leu Gln Glu Trp Ser Gly Glu Ile Gly Ser Asp Ile
    210                 215                 220

Pro Phe Phe Phe Ser His Gly Ala Ala Tyr Cys Thr Gly Arg Gly Glu
225                 230                 235                 240

Val Val Gln Asp Ile Pro Ser Pro Ile Pro Phe Asp Ile Pro Met Val
                245                 250                 255

Leu Ile Lys Pro Gln Gln Ala Cys Ser Thr Ala Glu Val Tyr Lys Arg
            260                 265                 270

Phe Gln Leu Asp Leu Ser Ser Lys Val Asp Pro Leu Ser Leu Leu Glu
        275                 280                 285

Lys Ile Ser Thr Ser Gly Ile Ser Gln Asp Val Cys Val Asn Asp Leu
    290                 295                 300

Glu Pro Pro Ala Phe Glu Val Leu Pro Ser Leu Lys Arg Leu Lys Gln
305                 310                 315                 320

Arg Val Ile Ala Ala Gly Arg Gly Gln Tyr Asp Ala Val Phe Met Ser
                325                 330                 335

Gly Ser Gly Ser Thr Ile Val Gly Val Gly Ser Pro Asp Pro Pro Gln
            340                 345                 350

Phe Val Tyr Asp Asp Glu Glu Tyr Lys Asp Val Phe Leu Ser Glu Ala
        355                 360                 365

Ser Phe Ile Thr Arg Pro Ala Asn Glu Trp Tyr Val Glu Pro Val Ser
    370                 375                 380

Gly Ser Thr Ile Gly Asp Gln Pro Glu Phe Ser Thr Ser Phe Asp Met
```

<210> SEQ ID NO 174
<211> LENGTH: 186
<212> TYPE: PRT
<213> ORGANISM: Sinrhizobium meliloti
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid

<400> SEQUENCE: 174

```
Leu Glu Lys Asn Leu Pro Ile Ala Ser Gly Met Gly Gly Gly Ser Ala
1               5                   10                  15

Asp Ala Ala Thr Leu Arg Gly Leu Xaa Ser Leu Trp Gly Ala Thr
            20                  25                  30

Val Glu Ala Ala Ser Leu Asn Ser Pro Ala Leu Gln Leu Gly Ala Asp
        35                  40                  45

Val Pro Met Cys Leu Asp Arg Gly Pro Leu Val Ala Arg Gly Ile Gly
    50                  55                  60

Glu Glu Ile Thr Pro Leu Pro Asp Leu Pro Pro Xaa Xaa Val Val Leu
65                  70                  75                  80

Val Asn Pro Leu Val Ala Val Ser Thr Pro Val Ile Phe Arg Ser Leu
                85                  90                  95

Val Arg Lys Thr Asn Pro Pro Leu Val Leu Pro Glu Asp Ala Arg Ser
            100                 105                 110

Thr Ala Glu Trp Leu Thr Ala Met Ala Ala Met Arg Asn Asp Leu Glu
        115                 120                 125

Pro Pro Ala Arg Ala His Glu Pro Met Ile Glu Thr Val Ser Asn Ala
    130                 135                 140

Leu Arg Asp Ala Gly Ala Ala Leu Val Arg Met Ser Gly Ser Gly Ala
145                 150                 155                 160

Thr Cys Phe Gly Leu Phe Thr Gly Met Lys Ser Ala Glu Arg Ala Ala
                165                 170                 175

Glu Thr Ile Ser Ala Gly His Pro Arg Trp
            180                 185
```

<210> SEQ ID NO 175
<211> LENGTH: 147
<212> TYPE: PRT
<213> ORGANISM: Caulobacter crescentus

<400> SEQUENCE: 175

```
Met Arg Leu Ser Ala Phe Ala Pro Ala Lys Val Asn Leu Phe Leu His
1               5                   10                  15

Val Gly Gly Pro Asp Gly Glu Gly Tyr His Pro Ile Ser Ser Leu Met
            20                  25                  30

Val Phe Ala Asp Val Gly Asp Arg Val Asn Leu Gln Pro Ala Asp Ala
        35                  40                  45

Pro Ala Phe Glu Thr Ser Gly Pro Ile Gly Asp Gln Ile Pro Ala Gly
    50                  55                  60

Gly Asp Asn Leu Val Val Arg Ala Gly Gln Ala Phe His Arg Arg Leu
65                  70                  75                  80
```

-continued

```
Gly Gly Pro Val Pro Pro Tyr Arg Leu Ile Leu Glu Lys His Leu Pro
            85                  90                  95

Ile Ala Ala Gly Leu Gly Gly Ser Ser Asp Ala Gly Ala Ala Leu
            100                 105                 110

Lys Leu Met Arg Asp Ala Leu Ala Pro Ala Leu Ser Asp Asp Leu
            115                 120                 125

Glu Ala Leu Ala Ala Ser Leu Gly Ala Asp Gly Ala Ala Cys Leu Arg
            130                 135                 140

Ala Arg Ala
145

<210> SEQ ID NO 176
<211> LENGTH: 185
<212> TYPE: PRT
<213> ORGANISM: Campylobacter jejuni

<400> SEQUENCE: 176

Gln Met Lys Ala Tyr Ala Lys Ala Asn Ile Phe Leu Lys Leu Thr Gly
1               5                   10                  15

Phe Asp Ser Arg Lys Tyr His Leu Leu Glu Ser Arg Phe Ile Leu Leu
            20                  25                  30

Lys Asp Val Phe Asp Glu Leu Glu Leu Val Asp Lys Glu Ser Asp Ser
            35                  40                  45

Lys Lys Glu Phe Glu Ile Ile Ser Asn Phe Lys Cys Glu Asn Asn Ile
    50                  55                  60

Ile Gln Lys Ala Tyr Leu Leu Leu Ser Arg Arg Tyr Asn Asn Glu Leu
65                  70                  75                  80

Lys Glu Leu Phe Ser Lys Lys Ser Leu Lys Leu Thr Lys Asn Ile Pro
            85                  90                  95

Val Cys Ala Gly Leu Gly Gly Ser Ser Asp Cys Ala Ser Phe Leu
            100                 105                 110

Leu Leu Ile Asn Glu Thr Leu Asn Leu Lys Leu Asn Leu Gln Glu Leu
            115                 120                 125

Ile Asn Leu Ser Ile Gln Leu Gly Ser Asp Ile Ala Phe Phe Leu Ser
            130                 135                 140

Gly Phe His Ser Ala Asn Val Ser Ser Cys Gly Glu Ile Ile Glu Glu
145                 150                 155                 160

Phe Glu Asp Asp Ile Pro Asn Leu Lys Trp Thr Phe Pro Gln Ile Ser
                165                 170                 175

Cys Gln Thr Lys Ala Val Tyr Asp Glu
            180                 185
```